US010266837B2

(12) United States Patent
Jang et al.

(10) Patent No.: US 10,266,837 B2
(45) Date of Patent: Apr. 23, 2019

(54) TERPENE SYNTHASES FROM YLANG YLANG (*CANANGA ODORATA* VAR. *FRUTICOSA*)

(71) Applicant: TEMASEK LIFE SCIENCES LABORATORY LIMITED, Singapore (SG)

(72) Inventors: In-cheol Jang, Singapore (SG); Mi Jung Kim, Singapore (SG)

(73) Assignee: TEMASEK LIFE SCIENCES LABORATORY LIMITED, Singapore (SG)

( * ) Notice: Subject to any disclaimer, the term of this patent is extended or adjusted under 35 U.S.C. 154(b) by 0 days.

(21) Appl. No.: 15/519,595

(22) PCT Filed: Oct. 19, 2015

(86) PCT No.: PCT/SG2015/050400
§ 371 (c)(1),
(2) Date: Apr. 17, 2017

(87) PCT Pub. No.: WO2016/064347
PCT Pub. Date: Apr. 28, 2016

(65) Prior Publication Data
US 2017/0253885 A1 Sep. 7, 2017

Related U.S. Application Data

(60) Provisional application No. 62/067,191, filed on Oct. 22, 2014.

(51) Int. Cl.
*C12N 9/18* (2006.01)
*C12N 15/82* (2006.01)
*C12N 9/88* (2006.01)
*C12P 7/04* (2006.01)
*C12P 5/00* (2006.01)

(52) U.S. Cl.
CPC .......... *C12N 15/8243* (2013.01); *C12N 9/18* (2013.01); *C12N 9/88* (2013.01); *C12P 5/007* (2013.01); *C12P 7/04* (2013.01); *C12Y 402/03* (2013.01)

(58) Field of Classification Search
None
See application file for complete search history.

(56) References Cited

U.S. PATENT DOCUMENTS 6,451,576 B1  9/2002  Croteau et al.
7,790,413 B2 *  9/2010  Schalk ............... C12N 9/88
                                               435/134
2014/0081058 A1  5/2014  Kutchan et al.

FOREIGN PATENT DOCUMENTS

WO  9937139 A1  7/1999
WO  2006134523 A2  12/2006
WO  2011050432 A9  5/2011
WO  2012058636 A1  5/2012
WO  2013166320 A1  11/2013
WO  2013170265 A1  11/2013

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
Search Report and Written Opinion dated Nov. 16, 2015 in PCT/SG2015/050400.
Brokl, M. et al. "Improvement of ylang-ylang essential oil characterization by GCxGC-TOFMS", Molecules, Jan. 2013, pp. 1783-1797, vol. 18, No. 2.
Database GenBank, Aug. 28, 2013, Database accession No. CCM43930.
Database GenBank, Jan. 4, 2013, Database accession No. JN882024.
Jin, J. et al. "The floral transcriptome of ylang ylang (*Cananga odorata* var. *fruticosa*) uncovers biosynthetic pathways for volatile organic compounds and a multifunctional and novel sesquiterpene synthase", Journal of Experimental Biology, May 2015, pp. 3959-3975, vol. 66, No. 13.
The partial supplementary European Search Report issued in Application No. 15853076.6 dated May 2, 2018, 14 pages.
Gaydou, Emile M. et al., "Composition of the essential oil of Ylang-Ylang (*Cananga odorata* Hook Fil. et Thomson forma genuina) from Madagascar", Journal of Agricultural and Food Chemistry, vol. 34, No. 3, May 1, 1986, XP0055468220, 7 pages.
Lücker, Joost et al., "Monoterpene biosynthesis in lemon (*Citrus limon*). cDNA isolation and functional analysis of four monoterpene synthases", European Journal of Biochemistry, Wiley-Blackwell Publishing Ltd, GB, vol. 269, No. 13, Jul. 1, 2002, XP002557522, pp. 3160-3171.
European Communication with a Supplementary European Search Report issued in Application No. 15853076.6 dated Aug. 30, 2018, 12 pages.

* cited by examiner

*Primary Examiner* — Richard G Hutson
(74) *Attorney, Agent, or Firm* — Rothwell, Figg, Ernst & Manbeck, P.C.

(57) ABSTRACT

The present invention relates to the field of plant molecular biology. More particularly, the present invention relates to the isolation of nucleic acids encoding terpene synthases (TPSs), including a novel, multifunctional TPS identified herein as CoTPS2.

22 Claims, 26 Drawing Sheets
Specification includes a Sequence Listing.

Retention time (min)

```
CoHMGS    1  MDSQ-KDVGILAMDIYFPPTCVLDDALEDRDGASKGKYTIGLGQDCMAPCTEVEDVISMS
NtHMGS    1  METKAKDVGILAVDIYFPPTCVQQAELEAYDGASKGKYTIGLGQDCLAPCTELEDVISMS
GsHMGS    1  MA---KNVGILAIDIYFPPTCIQQELLEAHDGASKGKYTIGLGQDCMAPCTEVEDVISMS
PnHMGS    1  MASQ-KNVGILAMEIYFPPTCIQQRVLEAHDGASKGKYTIGLGQDCMGPCTEVEDVISMS

CoHMGS   60  LTVVTSLLEKYGVDPKQIGRLEVGSETVIDKSKSIKTWLMQIPEKHGNTDIEGVDSTNAC
NtHMGS   61  LTVVTSLLEKYQIDPKMIGRLEVGTETVIDKSKSIKTWLMQIPEEHGNTDIEGVDSTNAC
GsHMGS   58  LTVVSSLLEKYAIDPKQIGRLEVGSETVIDKSKSIKTPIMQIPEKYGNTDIEGVDSTNAC
PnHMGS   60  LTTVTSLLEKYKIDPKQIGRLEVGSETVIDKSKSIETFLMQIPEKCQNTDIEGVDSTNAC

CoHMGS  120  YGGTAALPNCVNWVESSSWDGPPGLVVCADSAVYAEGPARPTGGAAAVAMLIGPHAPIVP
NtHMGS  121  YGGTAALPNCVNWVRSNSWDGRYGLVVCTDSAVYAEGPARPTGGAAAIAMLIGPHAPIAP
GsHMGS  118  YGGTAALPNCVNWVESSSWDGRYGLVVCTDSAVYAEGPARPTGGAAAVAMLIGPDAPISP
PnHMGS  120  YGGTAALPNCVNWVESSSWDGRYGLVVCTDSAVYAEGPARPTGGAATIAMLIGTDAPITP

CoHMGS  180  ENKYPGTHMAHVYDPYKPNLASEYPVVDGKLSQTCYLMALDSCYKRPSSKYEKLEKKPPS
NtHMGS  181  ESKYPGTHMSHVYDPYKPNLASEYPVVDGKLSQTCYLMALDSCYKPPCAKYEKPEGKQPS
GsHMGS  178  ESKLRGSKMAHAYDPYKPNLASEYPVGDGQLSQTCYLMALDSCYNHLSHKYEKQRGKQPS
PnHMGS  180  ESKFRGSHMSHAYDPYKPNLAGEYPVVDGKLSQTCYLMALDSCYPRYCKATEKLRGKQPS

CoHMGS  240  ISDADYPVFHSPYNKLVQKSFARLYYNDPLRNPSPVENDARIKLSPSSLSGDESYQNRD
NtHMGS  241  ISDADYFVFHSPYNKLVQKSFARLYFNDFMRNSSSVDKEAREKLEPPSSLSGNRSYQSRD
GsHMGS  238  ISDAEYFVFHSPYNKLVQKSFARLVFNDFLKNASPVDEAAKEKLEPPATLSGDESYQSRD
PnHMGS  240  MDDADYFVFHSPYNKLVQKSFARLMFNDFLRNASSVDESAKEKLAPPSTLTGDESYASRD

CoHMGS  300  LEKVSQQVAKQLVDAKVQPSTLLPKQVGNMYTASLYAAPATVLHNKHSTLEGKRVMPSY
NtHMGS  301  LEKVSQQVAKNLVDEKVQPATLVPKQVGNMYTASLYAAPASVLEDKHSTLAGQRIVMPSY
GsHMGS  298  LERASQQVAKPQVDAYAAPISLIEKHSTLDGKRVILPSY... (partial)
PnHMGS  300  LEKATQQVALSQIDVKVQPTTLIPKQVGNMYTASLYAAFASLIENKHSTLAGKRVMMPSY CoHMGS  360  GSGLSSTMPSFGLQRGQHPPSLSNIVSLLDVYRKLESKHTPPPEKPVETHKLMRHRYGGK
NtHMGS  361  GSGLSSSMFGLRIQDGQHPPSLSNIDNVMNVSGKLEARHVPPPEKPVRTMKVMRHRYGAK
GsHMGS  358  GSGLTSTMPSLLLREGQHPPSLSHIDKMMDVAGKLIKSRHEPPPEKPVETMKLMRHRYGGK
PnHMGS  360  GSGLSATMPSLRLREGQHPPSLSHIANVMNVAEKLKSRNEPPPEKPVEIMKLMRHRYGAK CoHMGS  420  DPVIDIKGTSLLSPGTFYLTKVDSMYERYYAKEAGEKPSTISYENGSLPNGH
NtHMGS  421  DPVT-AKDTSLLSPGTFYLTQVDSMYREPYSRK-GLNEKSSAVAMGTLANGH
GsHMGS  418  EPVT-SKDTSLLSPGTFYLTEVDSMYRRFYAKK-TS------EHGLVTNGH
PnHMGS  420  DPVT-SKDCSLLSPGTYYLTEVDSMYRRPYAKK-AVDKTTIGTENGTLANGH CoPMK     1  MAEVYISAPGKVLVTGGYLVLERSNPGIVLSTTARPYAIVKELYEAVDPNSWAWAWTDVK
PnPMK     1  -MAIVASAPGKVLMTGGTLILERPNEGLVLSTNARPYAIVKFPLCDELKPDSWAKAWTDVE
ZmPMK     1  -MEVVASAPGKVLIAGGTILVLERPNAGLVLSTTARPYAVVRPLRDSLPADSWTWAWTDVK
AePMK     1  -MAVVASAPGKVLMTGGYLVLERPNAGIVLSTNARPYSVVKEIYDEVKPDSWAWAWADVK CoPMK    61  LSSPQLFRETSYELSLRNLTLQCISPRDPRNPFIRQAVQYSVAAAHSMCSDKGMKDGLHK
PnPMK    60  LTSPQMARETTYKMSLKHLLDQCAESSNSRNPFVRYAVQYSVAAAYATL-DNDKKNALHK
ZmPMK    60  VTSPQLSRVATYKLSLNKTTLQLTSSRESTNPFVEQAIQFSVAAAKATIIDKERKDVVDK
AePMK    60  LTSPQMSREKTYELSLKYLTLQSVSLSDSRNPFVEYAVQYVTAAAYSRL-SSSGKDALTK CoPMK   121  LLLQGLDITAIGCNDFYSYRNQIEANGIPLAPDVLASIPPFSPINFNKENSSGTIVREQS
PnPMK   119  LLLQGLDITILGCNQFYSYRNQIEALGLPLSPESFATLKKETEITPNAGESNG----ENS
ZmPMK   120  LLLQGLNITIIGHNDFYSYRNKQIEARGLPLITPEVLLSLPPPSSITPNSEVANGTMTGEKC
AePMK   119  LLLRGLDITILGCNEFYSYRNQIEARGLPLTPESLSSSLPPFTSITFNKEESGG----QNS CoPMK   181  KPEVAKTGLGSSAAMTTAVVLAAVLQYLGVVDLSSTAGNPHGTICNPDLDLVHAVAQTAHC
PnPMK   175  KPEVAKTGLGSSAAMTTVVVAALLSYLGVVNLSSLSEDQNQEMDTADLDVVHVIAQTAHK
ZmPMK   180  KPEVAKTGLGSSAAMTTSVVAALLHYLGAVNLSCPGQSSGDNASGRELDLVETIAQSAHC
AePMK   175  KPEVAKTGLGSSAAMTAVVASLLHYLGVVNLSSVKDN------SEDLDTVEMIAQTAHC CoPMK   241  IAQGKVGSGPDVSSAAVYGSQRYIKPSPSPSVLSPAQVATGQPLDEVISHILEFKWDHEKIQ
PnPMK   235  IAQGKVGSGPDVSSAVYGSQRYVRPSPEVLSSSAQGAVGGQPLDEVITDVLKGKWDHERTK
ZmPMK   240  LAQGKIGSGPDVSAAVYGSQRYVRPSPEILSSAQ-AIGGTVLPDVVSDVLTQRWDHENKQ
AePMK   229  IAQGEVGSGPDVSSAVYGSQRYVRFSPGVISSAQDAVKAAPLEEVINDVLKAEWDHEK-D CoPMK   301  PSLPPLMTLLLGEPGTGGSSTPSMVGAVKQWQRSEPQKEAETWTRLAKANSMPEIQLAAL
PnPMK   295  PSLPPLMMLLGEPGPTRGSSTPSMVGAVKEWQKSDPQKSRDTWTKELSNANSALETQLNLL
ZmPMK   299  PSLPPLMTLLLGEPGTGGSSTPSMVGSVKRRLKSDPEKSRDTWSKLAIANSTLENQLRIL
AePMK   288  MSHAPLMTSIR-EPGTGGSSTPSMVGAVKKWQKADPQTSVETKRKLSEGHAALEMQLNTL CoPMK   361  KKYAQEKMETYKIVIGSCSAHSHEKWLEQATDPCQEGIIRSLLAVRDAMLDIEFHMRQMG
PnPMK   355  RKLAEEHWDAYKCVISSCNMCKSEEWMGQASEPSQVQIVKALLGSRDATLEIRCQMRQMG
ZmPMK   359  NGLSENHHEAYESMVRSCSHLTYGKWAEVATNQHQELIIRSLLAARDACLEIRLHMREHG
AePMK   347  SNLARMSFDVYKDVINNCSTLPSEKWLEVATEPSRTDIVKALLGAKDVMLEIRYQMEKMG CoPMK   421  QAAGAPIEPESQTLLLLDATMNLEGVLPAGVPGAGGPDAIPVTVLGDTR-NNVANVMCSQG
PnPMK   415  DAAGIPIEPESQTRLLDATMKMEGVLLAGVPGAGGPDAIPAVTLGDASSTNLTKAMSSHN
ZmPMK   419  IAAGVPIEPDSQTRLLLDATMNMEGVLLAGVPGAGGPDAVPSVVLGDAS-NAVAHAWSSVG
AePMK   407  EAAGIPIEPRSQTLLLLDSTMNMEGVLLAGVPGAGGPDAVPATTLGDAS-DKVIKSWSRQN CoPMK   480  VLPMLVREDPRGLCLESGDPRTKEISSAPSAIQV-
PnPMK   475  VLAMLVREDPRGVSLQSSDPRATEITSGISAVHIE
ZmPMK   478  VLPLPVREDCRGVSLEDADPRTREVSAAVWSIQIN
AePMK   466  VLALLVREDPNGVLLENNDSRAKEVTSGVSAIQIQ
```

```
CoTPS3    1  ---------------------------------------MNPVSLLSLSGERRGANWKPSSWDS
LcTOS     1  MSLIIQSLPHWSRIPPRPPQLSQFQNSSRPKPLIQAGQVQHNALQIARRSANYHPSIWDP
LaBERS    1  ----------------------------------------------MEARRSGNPESSIWDD
LdTPS7    1  ----------------------------------------------MEARRSGNFKASIWDD

CoTPS3   26  NQIHQSLKSDPNDLQEKWHTEIIQAVEQMLEAVAEPLQKETIIDDIQRLGVAKRFEKQTD
LcTOS    61  QYIESLKSPTGDECFGTRLEYLIFEAKRLLEATIEPLSWDELVDSIQRLGVAYHPEDEIK
LaBERS   17  DYIQSLTSSYTGKMYVDKSEKLIIEVKMMMDEATDELEQLELINDLQRLGISYHPKDGIA
LdTPS7   17  DPLQSLTSPYTAKEYLEQADKLNWQVEVIIKETKQRLDQLDLIDNIQRLGISHHPRDEIQ

CoTPS3   86  DALSSIWSN----YAAEVSSKKDLLAASLYPRLLRQHGCYVSPIIIQPKDEAGQFKASL
LcTOS   121  EGLDGVTG------VGAHAGDDLYTAALQPRLLRQHGYGVTPDIFNKPLEKERTPKACT
LaBERS   77  KMLNNITK------SDSKYMEKDLHLTALKFRLLRQHGYRVPQDVFSSPMDDEGNPEAWV
LdTPS7   77  RVEQNIYEKMRVECPDRMLMEKDLYSTSLQPRLLRQHGYEVSQBVECSPMDGAGNPQA--

CoTPS3  142  GDDVEGLLSLYEASYLGIKGETILDDAKAPSTSTDENLMPHV-ERDIASRISHALRLPLH
LcTOS   174  SLDAKGLLSLYEASHTMIHGREVLEDAKEPSVKELNYLMGNLQN-NLREQVQHALEMPLH
LaBERS  131  VEDVSVLVSLYEASHISVEGESILDMAKDPSSHHITEMVEQIGEACLAEQVERTLELRLH
LdTPS7  135  VDDLKGILALYEASFLSREGENILGSARDPETRHLKQKLEEITDPILAEKIRRALELPLH

CoTPS3  201  WNMRRMEARLYIDVYRENEKRRNDNLLEFARLDFNMLQVIHQRDLKDVSPWDFLDLPRK
LcTOS   233  WRMPRLEAKHYIDVN-GRSDERNMVLLELARLDFNPVQSKHQEELIEVSRWWRDLGLAKK
LaBERS  191  WRVGRLEARWFVQAY-ETRPNSHPTLVELAKLDFNMVQAKYQDELLRCSRWYEETGLPEK
LdTPS7  195  WRLQKLEAIWFINIY-ESRFDANLILLQLAKLEPNMVQAQYQEDLLWLSRWYKETGLPEK
                                                              DDXXD
CoTPS3  261  LGFIRDRLMESFIFSVGLNFEPQFSECREAATEDILLITVLDDIYDITGSMDEVEIPNNA
LcTOS   292  LGFSRDRLVENYLWAVGIAFSPKFSNCRKGLTKLISILTVIDDIYDVVGSLDELELFTEA
LaBERS  250  MSPARHRLAECPLWSLGFIPDPHHGYSREIMTHIAVLITITDDIYDIYGALEELQEPTEA
LdTPS7  254  MNFARDRLAECPLWALGFIPEAHLGQARKILTKIAVLIVIMDDFYDIYGTLDEIKVPTEE

CoTPS3  321  VNEWDLGAVDELPEYMQLQYLGLLNSVNELAVVTMFDTGRNVLDFLKFLWKRHFNAAVKE
LcTOS   352  VKRWDIEALETDPEYMKICYLALFNFVHEVSVDTLKDYGWNILPFIREEWERLCMSYLVE
LaBERS  310  FERWDINSLDLLPEYMQICPLAIFNSANELGVQILRDQGLNIIPNLKRSWAELSFAIYLE
LdTPS7  314  LQRWDINALDNLPETMRICFLAIFNTANEIAYDILPRDQGINIISNLRRLWAELGRVIYTE

CoTPS3  381  SRWPHRQTTPTLEDTMENAQESIGAELVLTHAFVKMLKYMPNEDVNHVDKYLKLISMMCY
LcTOS   412  AEWPGNGNKPALDEYLRNGWISVGGPVAMVHAYFLQGRPIRKDSINFLDHGSELIYWSSV
LaBERS  370  ARWFHNGFVPTTDQYLNTAWESISGPLLLSYGVLTTTNPINNKELKSLEKHPSIIRWPSM
LdTPS7  374  AKWYHSGYFPSTEEYLNVAWISITGPVLLFEAYFSIMNPIDMKELQYLEQTFGIIRWPST
             NSE/DTE
CoTPS3  441  VFRLYDDWGTSKAEIENGDVPKAIQCYMHEAKVSEEIARBHIKNIINERWRELNEBCLKA
LcTOS   472  ATRLNDDLGTSKAEMKRGDVPRAVECYMIQTGESYEDAREHIQGLVRDCWEKMNEBCLKC
LaBERS  430  VLRLADDLGTSSEEIKRGDVSKSIQCYMNETGCCEGDARHHVKSLIEVALKRMNDEILME
LdTPS7  434  VLRLADDLGTASDEIKRGDVPKSIQCTMHETGCSEEEARSYVEQLIDTTLEKMNFEILME

CoTPS3  501  TDLNRKPVAAVLDALHAAAFPYHDRDGFGEPDHKPKSQAMALFSQQV-----
LcTOS   532  CLPK-SYVETVLNMVRTAQCIHQEGDGIETSTGVTQDRVISLICEPVPSQWP
LaBERS  490  KPFK-SFDTNAMNLARISLCPYQYGDGPGKPHSDTIKNLVGLIVLPFHMP--
LdTPS7  494  KPTN-DFGATAMNLARISLFFYQYGDGPGVPHNQTKENLVGLIVKPICLT--
```

Figure 17D

```
CoTPS4    1   MAATR-NLSLLAQS-SQPWAGIYGSHGSPRPISSWLRRQSIAKTSYICMCTPLSMSQLIA
OeGES1    1   MDCTMTSISLFSQS-------ENGISGTARSPFQWPINHRFSSGQRDFICKSLPVSSPSA
ObGES     1   MSCARITVTLPYRR---------AKTSIQRGITHYPALIRPRFSACTPLASAMPLS---S
CrGES     1   MAATISNLSFLAKSRALSRPSSSSLSWLERPKTSSTICMSMPSSSSSSSS--SMSLPLA

CoTPS4   59   TPLTDIE-SLLKYLRQPQVLPHEIDDSTKRRS-GLERTRRELQT-TLEPLQAMYMIDTL
OeGES1   54   TPLPAENGAMYNYIRQPVIVTPEVDDGTKHSE-LVEPTRRELQR-STKPVETLELIDNL
ObGES    49   TPLINGDN-SQRKNTRQ-----EMEESSSKRRSYLLEETTRKLQRNDTESVEKLELIDNI
CrGES    59   TPLKDNE-SLIKPLRQPLVLPHEVDDSTKRRS-LLERTRKELELNAEKPLEALKMIDTI

CoTPS4  116   QRLGLAYHPEDDINSLETG-PS---NGQPDEDSLEASSRPPLLRHNGHRINPNIPQKPMDK
OeGES1  112   QRLGIAYYFEDDTNAILDQ-PS--DGLPDEDLFTTALCFRLLRDQRLQTGSDVPLKPMEK
ObGES   103   QQLGIGIYFRDAINAVLRSPPS----TGREDLFTAALRPRLLRHNGIEISPEIFLKFKDE
CrGES   117   QRLGLSIHPEDDINSILTG-PSNISSQTEEDLLEASLCFRLLRHNGHKINPDIPQKPMDN

CoTPS4  173   QGETIDSLKEDTRGLFSLYRASYLGANGIDTILQALRPTKAHLKEGLPSLAPPLAKKVSQ
OeGES1  169   NMKPKEHLAQDTIGLVSLYRASMGANGEPISEAKEFTEMHLRQSMPQLAPQLRRQVSS
ObGES   159   RGYPDE---SDTLGLLSLYRASNLGVAGEEILEEAMEPAEARLRESLSEPAAPLHGEVAQ
CrGES   176   NGKPKDSLKDDTLGMLSLYRASYLGANGEEILMERQEETKTHLKNSLPAMAPSLSKKVSQ

CoTPS4  233   ALELPRRREKARLEARSYIEEYGGENGSSPDELELAKSLDYNKVQSLHQLELSEISRWWKQ
OeGES1  229   ALELPRHLRMARLEARRYIEEYGNESDHDPALLELAPLDYNKVQLQHQWELAEITRWWKQ
ObGES   216   ALDVPRHLRMAPLEARPFIRQYGKQSDEDGDLLELAILDYNQVQAQHQSELTEIIRWWKE
CrGES   236   ALEQPRHRRMLRLEARSFIEEYGAENDLNFDLLELAKLDYNKVQSLHQMELSEITRWWKQ

DDXXD
CoTPS4  293   LGLVDKITFARDRPLECPLWTVGILPEPKYSSCRIELAKTIAILLVIDDIFDTHGTLDEL
OeGES1  289   LGLVERLSFARDRPLECPLWTVGLLPEPKYSSCRIELAETIAILLVIDDIFDTYGKMEEL
ObGES   276   LGLVDKLSPGRDRPLECPLWTVGLLPEPKYSSVRIELAKAISILLVIDDIFDTYGEMDDL
CrGES   296   LGLVDKITFARDRPLECPLWTVGILPEPKYSGCRIELAKTIAILLVIDDIFDTHGTLDEL

CoTPS4  353   ILPTNAIRWDLEAMEDLPEYMRICYMALYNTTNEICYRILKQNGWSVLPYLRATWIDMI
OeGES1  349   VLPTEARQRWDLDELETLIPYMRICYMALYNTTNEICYEILKEYGPCVLPYLKSTWIDMI
ObGES   336   ILFTDAIERWDLEAMECLPEYMRICYMALYNTTNEVCYEVLRDTGRIVLLNLKSTWIDMI
CrGES   356   LLFTNAIRKWDLEAMEDLPEYMRICYMALYNTTNEICYRVLKENGWSVLPYLRATWIDMI

CoTPS4  413   EGPMLERSWLNTGYVPNMEETVENGVTTAGAYMALVHLPPLIGQQVTEEN-VKLLVKPYP
OeGES1  409   EGPMVEANWFNGCHGPNLEETIRNGVSTAGAYMALVHLPPLIGEGVTNENIAKLLRKPYP
ObGES   396   EGPMEEAKWFNGGSAPKLEEVIRNGVSTAGAFMAFHIPPLIGEGVTHQNSQLFTQKPYP
CrGES   415   EGPMVEAEWFNSDYVPNMEETVENGVRTAGSYMALVHLPPLIGQQVTEDN-VKLLIKPYP

NSE/DTE
CoTPS4  472   KLFTSYSGRILRLWDDLGTAKEEQERGDLASSIDLFMPENNITSDEECRECTLKITDNLWK
OeGES1  469   KLFSAAGRILRLWDDLGTAKEEHERGDLASCMQILMPEKNIDCENECENYTLKAINGLWK
ObGES   456   KVPSAAGRILRLWDDLGTAKEEBERGDLASCVQLPMKBKSLT-EEEARSRLLEEIKGLWR
CrGES   475   KLFSSSGRILRLWDELGTAKEEQERGDLASSIQLFMPEKEIKSEEEGRKCILEIIENLWK

CoTPS4  532   ELNGELVSRHALPLAITIAASFNMARASQVVTQHEEDSTPSSVDNTVQALFFTPFN
OeGES1  529   DLNDELISPNAMPLAITKVALNMARASFEVVTKEEDSYPSSVDNYVQALFFTPIN
ObGES   515   DLNGELVYNKNLPLSIIKVILNMARASQVVTKEDQDTYPSSVDNYVDALFFTQ--
CrGES   535   ELNGELVYREEMPLAIITKAFNMARASQVVTQEEEDTYPSSVDNYVKALFFTPCF
```

SEQUENCE LISTING

```
<160> NUMBER OF SEQ ID NOS: 158

<210> SEQ ID NO 1
<211> LENGTH: 11
<212> TYPE: PRT
<213> ORGANISM: Artificial Sequence
<220> FEATURE:
<223> OTHER INFORMATION: protein motif
<220> FEATURE:
<221> NAME/KEY: misc_feature
<222> LOCATION: (3)..(10)
<223> OTHER INFORMATION: Xaa can be any naturally occurring amino acid

<400> SEQUENCE: 1

Arg Arg Xaa Xaa Xaa Xaa Xaa Xaa Xaa Xaa Trp
1               5                   10

<210> SEQ ID NO 2
<211> LENGTH: 5
<212> TYPE: PRT
<213> ORGANISM: Artificial Sequence
<220> FEATURE:
<223> OTHER INFORMATION: Asp-rich domain
<220> FEATURE:
<221> NAME/KEY: misc_feature
```

```
<222> LOCATION: (3)..(4)
<223> OTHER INFORMATION: Xaa can be any naturally occurring amino acid

<400> SEQUENCE: 2

Asp Asp Xaa Xaa Asp
1               5

<210> SEQ ID NO 3
<211> LENGTH: 3
<212> TYPE: PRT
<213> ORGANISM: Artificial Sequence
<220> FEATURE:
<223> OTHER INFORMATION: protein motif

<400> SEQUENCE: 3

Asn Ser Glu
1

<210> SEQ ID NO 4
<211> LENGTH: 3
<212> TYPE: PRT
<213> ORGANISM: Artificial Sequence
<220> FEATURE:
<223> OTHER INFORMATION: protein motif

<400> SEQUENCE: 4

Asp Thr Glu
1

<210> SEQ ID NO 5
<211> LENGTH: 1644
<212> TYPE: DNA
<213> ORGANISM: Cananga odorata
<220> FEATURE:
<221> NAME/KEY: CDS
<222> LOCATION: (1)..(1641)

<400> SEQUENCE: 5 atg aat cct gtt tct ctt ttg agc tta tca gga gag cgc cgc tca gcc      48
Met Asn Pro Val Ser Leu Leu Ser Leu Ser Gly Glu Arg Arg Ser Ala
1               5                   10                  15 aac tgg aaa ccc agc agt tgg gac agc aac caa att cac cag tcc ctc      96
Asn Trp Lys Pro Ser Ser Trp Asp Ser Asn Gln Ile His Gln Ser Leu
            20                  25                  30 aaa agc gat ttc aat gat tta caa gag aaa tgg cat acg gaa ctc aaa     144
Lys Ser Asp Phe Asn Asp Leu Gln Glu Lys Trp His Thr Glu Leu Lys
        35                  40                  45 cag gca gtt gaa cag atg ttg gag gct gtg gct gaa cct cta caa aag     192
Gln Ala Val Glu Gln Met Leu Glu Ala Val Ala Glu Pro Leu Gln Lys
    50                  55                  60 ctt act ttg atc gac gac atc caa agg ctt ggt gtg gcc tac cga ttt     240
Leu Thr Leu Ile Asp Asp Ile Gln Arg Leu Gly Val Ala Tyr Arg Phe
65                  70                  75                  80 gaa aag cag ata gat gat gct ttg agt agc att tac tcg aat tat gct     288
Glu Lys Gln Ile Asp Asp Ala Leu Ser Ser Ile Tyr Ser Asn Tyr Ala
                85                  90                  95 gct gaa gta tcc agc aag aag gat ctg ctt gca gcc agt ctc tac ttc     336
Ala Glu Val Ser Ser Lys Lys Asp Leu Leu Ala Ala Ser Leu Tyr Phe
            100                 105                 110 aga cta ctc agg caa cat ggt tgc tac gtt tcg cca gat ata ttc atc     384
Arg Leu Leu Arg Gln His Gly Cys Tyr Val Ser Pro Asp Ile Phe Ile
        115                 120                 125 caa ttc aag gat gaa gct ggt caa ttc aag gcc agc cta ggc gat gat     432
Gln Phe Lys Asp Glu Ala Gly Gln Phe Lys Ala Ser Leu Gly Asp Asp
```

```
                130              135              140
gtg gaa ggt ctg tta agc ctg tac gaa gcc tca tat ctt ggg atc aag      480
Val Glu Gly Leu Leu Ser Leu Tyr Glu Ala Ser Tyr Leu Gly Ile Lys
145              150              155              160 ggt gaa act atc ttg gat gac gct aag gct ttc tcc acg tca acc ctc      528
Gly Glu Thr Ile Leu Asp Asp Ala Lys Ala Phe Ser Thr Ser Thr Leu
                 165              170              175 gag aat ttg atg ccc cat gtc gag gca gat att gca agc agg ata tca      576
Glu Asn Leu Met Pro His Val Glu Ala Asp Ile Ala Ser Arg Ile Ser
             180              185              190 cat gca ttg cat ctt ccc ctg cac tgg aac atg aga agg atg gaa gct      624
His Ala Leu His Leu Pro Leu His Trp Asn Met Arg Arg Met Glu Ala
         195              200              205 aga ctt tac ata gat gtt tat aga gag aac aag aaa agg agg aat gat      672
Arg Leu Tyr Ile Asp Val Tyr Arg Glu Asn Lys Lys Arg Arg Asn Asp
     210              215              220 aat ttg cta gag ttt gca agg ttg gat ttc aac atg cta caa gtc ata      720
Asn Leu Leu Glu Phe Ala Arg Leu Asp Phe Asn Met Leu Gln Val Ile
225              230              235              240 cac caa aga gac ctc aaa gat gtg tcc ttc tgg tgg gat ttt ctc gat      768
His Gln Arg Asp Leu Lys Asp Val Ser Phe Trp Trp Asp Phe Leu Asp
                 245              250              255 tta cca agg aag ttg gga ttt atc cgt gac aga ctg atg gag agt ttc      816
Leu Pro Arg Lys Leu Gly Phe Ile Arg Asp Arg Leu Met Glu Ser Phe
             260              265              270 ata ttc tca gtt gga ttg aat ttc gag cca cag ttc agt gaa tgc aga      864
Ile Phe Ser Val Gly Leu Asn Phe Glu Pro Gln Phe Ser Glu Cys Arg
         275              280              285 aaa gca gct act aaa gac atc ctt ctt att aca gtc ctc gat gac ata      912
Lys Ala Ala Thr Lys Asp Ile Leu Leu Ile Thr Val Leu Asp Asp Ile
     290              295              300 tat gac att tat ggt tca atg gat gaa gtg gaa att ttc aac aac gca      960
Tyr Asp Ile Tyr Gly Ser Met Asp Glu Val Glu Ile Phe Asn Asn Ala
305              310              315              320 gtc aac aga tgg gac ttg ggg gct gtt gat gag ctc cca gag tat atg     1008
Val Asn Arg Trp Asp Leu Gly Ala Val Asp Glu Leu Pro Glu Tyr Met
                 325              330              335 cag ctt tgt tac tta ggt ttg tta aac agc gtg aac gag ctt gca tac     1056
Gln Leu Cys Tyr Leu Gly Leu Leu Asn Ser Val Asn Glu Leu Ala Tyr
             340              345              350 gtt acc atg aaa gat acg gga cgc aat gtg ctg gac ttc ctt aaa aaa     1104
Val Thr Met Lys Asp Thr Gly Arg Asn Val Leu Asp Phe Leu Lys Lys
         355              360              365 ttg tgg aaa agg cac ttc aat gct gcc gtc aag gag tct cgc tgg ttc     1152
Leu Trp Lys Arg His Phe Asn Ala Ala Val Lys Glu Ser Arg Trp Phe
     370              375              380 cac agg caa tac aca cca acg ttg gag gaa tac atg gaa aat gcc caa     1200
His Arg Gln Tyr Thr Pro Thr Leu Glu Glu Tyr Met Glu Asn Ala Gln
385              390              395              400 att tca att ggg gct ccc ctc gta ctc aca cat gca tat gta aaa atg     1248
Ile Ser Ile Gly Ala Pro Leu Val Leu Thr His Ala Tyr Val Lys Met
                 405              410              415 ctc aag tac atg ccc aac gag gat gtc aat cac gtt gac aaa tat ctg     1296
Leu Lys Tyr Met Pro Asn Glu Asp Val Asn His Val Asp Lys Tyr Leu
             420              425              430 aag ctc ata tca atg atg tgt tac gtc ttt cgg ctc tat gat gac tgg     1344
Lys Leu Ile Ser Met Met Cys Tyr Val Phe Arg Leu Tyr Asp Asp Trp
         435              440              445 ggc act tca aag gcg gag ata gaa cgc ggg gat gta cct aaa gca atc     1392
```

```
Gly Thr Ser Lys Ala Glu Ile Glu Arg Gly Asp Val Pro Lys Ala Ile
    450                 455                 460 caa tgt tac atg cat gaa gcc aaa gtt tcg gaa gag att gca agg gaa       1440
Gln Cys Tyr Met His Glu Ala Lys Val Ser Glu Glu Ile Ala Arg Glu
465                 470                 475                 480 cac att aag aat atc atc aat gaa cgt tgg aag gaa cta aac gaa gag       1488
His Ile Lys Asn Ile Ile Asn Glu Arg Trp Lys Glu Leu Asn Glu Glu
                485                 490                 495 tgt ctg aaa gca aca gat ctc aat cga aaa ttt gta gct gct gtc ctc       1536
Cys Leu Lys Ala Thr Asp Leu Asn Arg Lys Phe Val Ala Ala Val Leu
            500                 505                 510 gat gct ctg aga gct gct gca ttt ttc tat cat gac aga gat ggt ttt       1584
Asp Ala Leu Arg Ala Ala Ala Phe Phe Tyr His Asp Arg Asp Gly Phe
        515                 520                 525 ggg gag cca gac cat aag ttc aag agt caa gcc atg gct cta ttt tcc       1632
Gly Glu Pro Asp His Lys Phe Lys Ser Gln Ala Met Ala Leu Phe Ser
    530                 535                 540 caa caa gtt taa                                                        1644
Gln Gln Val
545

<210> SEQ ID NO 6
<211> LENGTH: 547
<212> TYPE: PRT
<213> ORGANISM: Cananga odorata

<400> SEQUENCE: 6

Met Asn Pro Val Ser Leu Leu Ser Leu Ser Gly Glu Arg Arg Ser Ala
1               5                   10                  15

Asn Trp Lys Pro Ser Ser Trp Asp Ser Asn Gln Ile His Gln Ser Leu
            20                  25                  30

Lys Ser Asp Phe Asn Asp Leu Gln Glu Lys Trp His Thr Glu Leu Lys
        35                  40                  45

Gln Ala Val Glu Gln Met Leu Glu Ala Val Ala Glu Pro Leu Gln Lys
    50                  55                  60

Leu Thr Leu Ile Asp Asp Ile Gln Arg Leu Gly Val Ala Tyr Arg Phe
65                  70                  75                  80

Glu Lys Gln Ile Asp Asp Ala Leu Ser Ser Ile Tyr Ser Asn Tyr Ala
                85                  90                  95

Ala Glu Val Ser Ser Lys Lys Asp Leu Leu Ala Ala Ser Leu Tyr Phe
            100                 105                 110

Arg Leu Leu Arg Gln His Gly Cys Tyr Val Ser Pro Asp Ile Phe Ile
        115                 120                 125

Gln Phe Lys Asp Glu Ala Gly Gln Phe Lys Ala Ser Leu Gly Asp Asp
    130                 135                 140

Val Glu Gly Leu Leu Ser Leu Tyr Glu Ala Ser Tyr Leu Gly Ile Lys
145                 150                 155                 160

Gly Glu Thr Ile Leu Asp Asp Ala Lys Ala Phe Ser Thr Ser Thr Leu
                165                 170                 175

Glu Asn Leu Met Pro His Val Glu Ala Asp Ile Ala Ser Arg Ile Ser
            180                 185                 190

His Ala Leu His Leu Pro Leu His Trp Asn Met Arg Arg Met Glu Ala
        195                 200                 205

Arg Leu Tyr Ile Asp Val Tyr Arg Glu Asn Lys Lys Arg Arg Asn Asp
    210                 215                 220

Asn Leu Leu Glu Phe Ala Arg Leu Asp Phe Asn Met Leu Gln Val Ile
225                 230                 235                 240
```

```
His Gln Arg Asp Leu Lys Asp Val Ser Phe Trp Trp Asp Phe Leu Asp
                245                 250                 255

Leu Pro Arg Lys Leu Gly Phe Ile Arg Asp Arg Leu Met Glu Ser Phe
            260                 265                 270

Ile Phe Ser Val Gly Leu Asn Phe Glu Pro Gln Phe Ser Glu Cys Arg
        275                 280                 285

Lys Ala Ala Thr Lys Asp Ile Leu Leu Ile Thr Val Leu Asp Asp Ile
    290                 295                 300

Tyr Asp Ile Tyr Gly Ser Met Asp Glu Val Glu Ile Phe Asn Asn Ala
305                 310                 315                 320

Val Asn Arg Trp Asp Leu Gly Ala Val Asp Glu Leu Pro Glu Tyr Met
                325                 330                 335

Gln Leu Cys Tyr Leu Gly Leu Leu Asn Ser Val Asn Glu Leu Ala Tyr
            340                 345                 350

Val Thr Met Lys Asp Thr Gly Arg Asn Val Leu Asp Phe Leu Lys Lys
        355                 360                 365

Leu Trp Lys Arg His Phe Asn Ala Ala Val Lys Glu Ser Arg Trp Phe
    370                 375                 380

His Arg Gln Tyr Thr Pro Thr Leu Glu Glu Tyr Met Glu Asn Ala Gln
385                 390                 395                 400

Ile Ser Ile Gly Ala Pro Leu Val Leu Thr His Ala Tyr Val Lys Met
                405                 410                 415

Leu Lys Tyr Met Pro Asn Glu Asp Val Asn His Val Asp Lys Tyr Leu
            420                 425                 430

Lys Leu Ile Ser Met Met Cys Tyr Val Phe Arg Leu Tyr Asp Asp Trp
        435                 440                 445

Gly Thr Ser Lys Ala Glu Ile Glu Arg Gly Asp Val Pro Lys Ala Ile
    450                 455                 460

Gln Cys Tyr Met His Glu Ala Lys Val Ser Glu Ile Ala Arg Glu
465                 470                 475                 480

His Ile Lys Asn Ile Ile Asn Glu Arg Trp Lys Glu Leu Asn Glu Glu
                485                 490                 495

Cys Leu Lys Ala Thr Asp Leu Asn Arg Lys Phe Val Ala Ala Val Leu
            500                 505                 510

Asp Ala Leu Arg Ala Ala Ala Phe Phe Tyr His Asp Arg Asp Gly Phe
        515                 520                 525

Gly Glu Pro Asp His Lys Phe Lys Ser Gln Ala Met Ala Leu Phe Ser
    530                 535                 540

Gln Gln Val
545

<210> SEQ ID NO 7
<211> LENGTH: 1773
<212> TYPE: DNA
<213> ORGANISM: Cananga odorata
<220> FEATURE:
<221> NAME/KEY: CDS
<222> LOCATION: (1)..(1770)

<400> SEQUENCE: 7 atg gcc ttg aat acg ttc ttg cat ttt cct ccc tgc agt ctt tcg agt    48
Met Ala Leu Asn Thr Phe Leu His Phe Pro Pro Cys Ser Leu Ser Ser
1               5                   10                  15 ttt tca tgt gct gtt cct aag ctc ccg cta gcc att ttc cac aag act    96
Phe Ser Cys Ala Val Pro Lys Leu Pro Leu Ala Ile Phe His Lys Thr
            20                  25                  30
```

```
atg gca agg cag atc agg tgt ccg cgg gca agc tct caa acc agc gag         144
Met Ala Arg Gln Ile Arg Cys Pro Arg Ala Ser Ser Gln Thr Ser Glu
         35                  40                  45 ccc gct ctg gca agg cga tca gca aat ttc caa ccc acc atc tgg acc         192
Pro Ala Leu Ala Arg Arg Ser Ala Asn Phe Gln Pro Thr Ile Trp Thr
 50                  55                  60 aat gac ttc ata cag tct cta aac agc gat tac tcg agt gac gtc tat         240
Asn Asp Phe Ile Gln Ser Leu Asn Ser Asp Tyr Ser Ser Asp Val Tyr
 65                  70                  75                  80 gta caa cgg atc gaa aag cta aag aaa tca gtg agg caa agt ctt gaa         288
Val Gln Arg Ile Glu Lys Leu Lys Lys Ser Val Arg Gln Ser Leu Glu
                     85                  90                  95 gaa gca gat ggg cca ctg gcc cag ctg gaa ctg atc gat gat ctc cag         336
Glu Ala Asp Gly Pro Leu Ala Gln Leu Glu Leu Ile Asp Asp Leu Gln
                 100                 105                 110 cgt ctg gga gta ggc cgc ctc ttc gag cgg gag atc aac gag atg ctg         384
Arg Leu Gly Val Gly Arg Leu Phe Glu Arg Glu Ile Asn Glu Met Leu
             115                 120                 125 aat ggt ata tac atg gat tac aaa gaa acg cag gcc caa tgg aat ctc         432
Asn Gly Ile Tyr Met Asp Tyr Lys Glu Thr Gln Ala Gln Trp Asn Leu
         130                 135                 140 cat ttt acg tca atg tac ttc agg ctc ctg agg gcg cgt ggg ttt gac         480
His Phe Thr Ser Met Tyr Phe Arg Leu Leu Arg Ala Arg Gly Phe Asp
145                 150                 155                 160 gtc tca cca gaa ata ttc agt aga ttc atg gac gag acg ggt aat ttc         528
Val Ser Pro Glu Ile Phe Ser Arg Phe Met Asp Glu Thr Gly Asn Phe
                     165                 170                 175 caa aca agc att agc aat gat cca att ggg atg ttg agc ctg tat gaa         576
Gln Thr Ser Ile Ser Asn Asp Pro Ile Gly Met Leu Ser Leu Tyr Glu
                 180                 185                 190 gct tct tac ctt tgc atg cct ggc gag acc acc ttg gat gaa gct caa         624
Ala Ser Tyr Leu Cys Met Pro Gly Glu Thr Thr Leu Asp Glu Ala Gln
             195                 200                 205 gcc ttc aca tgc aag cat ctc aaa tac tgg aag gaa aag gac gta cac         672
Ala Phe Thr Cys Lys His Leu Lys Tyr Trp Lys Glu Lys Asp Val His
         210                 215                 220 ccc acc att gca ttg cag ata gaa cac gca ttg gag ctt cca atc cat         720
Pro Thr Ile Ala Leu Gln Ile Glu His Ala Leu Glu Leu Pro Ile His
225                 230                 235                 240 tgg agg atg cca agg ttg gac tcc cga tgg tat ata aag ctg tat gaa         768
Trp Arg Met Pro Arg Leu Asp Ser Arg Trp Tyr Ile Lys Leu Tyr Glu
                     245                 250                 255 gag aag gaa ggg aca agg cct ctc ttg ctt gaa cta gct aag ctg gat         816
Glu Lys Glu Gly Thr Arg Pro Leu Leu Leu Glu Leu Ala Lys Leu Asp
                 260                 265                 270 ttc aac atg gtg caa agc gct cat cag act gag ctt agg aag gtg tca         864
Phe Asn Met Val Gln Ser Ala His Gln Thr Glu Leu Arg Lys Val Ser
             275                 280                 285 agg tgg tgg agc gaa ttc ggc ctt gct gag aag gcg agc ttt gca aga         912
Arg Trp Trp Ser Glu Phe Gly Leu Ala Glu Lys Ala Ser Phe Ala Arg
         290                 295                 300 gat cgc ctc atg gag ggt tac caa tgg gcc atc gga aca gtc ttc gag         960
Asp Arg Leu Met Glu Gly Tyr Gln Trp Ala Ile Gly Thr Val Phe Glu
305                 310                 315                 320 cca gag ttt gga caa tgt agg gaa gtg ctt gca aaa ctc gcc caa ctc        1008
Pro Glu Phe Gly Gln Cys Arg Glu Val Leu Ala Lys Leu Ala Gln Leu
                     325                 330                 335 att gca gtc att gat gat atg tac gat gtt tat ggt tcg ccg gat gag        1056
Ile Ala Val Ile Asp Asp Met Tyr Asp Val Tyr Gly Ser Pro Asp Glu
```

```
                    340                 345                 350
ttg gag ctt ttc aca gat gca gtt gat agg tgg aac att aat acc atc     1104
Leu Glu Leu Phe Thr Asp Ala Val Asp Arg Trp Asn Ile Asn Thr Ile
            355                 360                 365 gag ggc ctt cca gat tac atg aag cta tgc ttt ctg tct atc tac aac     1152
Glu Gly Leu Pro Asp Tyr Met Lys Leu Cys Phe Leu Ser Ile Tyr Asn
370                 375                 380 acc acc aac caa gga gga tac gag ttt ctc aag gac cat ggg gtg gac     1200
Thr Thr Asn Gln Gly Gly Tyr Glu Phe Leu Lys Asp His Gly Val Asp
385                 390                 395                 400 atc ata ccc cat ctc agg aaa gcg tgg gca gat tac tgc aaa gct ctc     1248
Ile Ile Pro His Leu Arg Lys Ala Trp Ala Asp Tyr Cys Lys Ala Leu
                405                 410                 415 cga act gag gca aga tgg gtc aat agc aag tac act cca acg ctc gac     1296
Arg Thr Glu Ala Arg Trp Val Asn Ser Lys Tyr Thr Pro Thr Leu Asp
            420                 425                 430 gag tac ctg aac aat gca tac acc tca gca tca ggt ccc ctc atc ctt     1344
Glu Tyr Leu Asn Asn Ala Tyr Thr Ser Ala Ser Gly Pro Leu Ile Leu
435                 440                 445 atc cac gca ttt ttc ttc agc gga cag gag cca tgg aag gaa gcc atc     1392
Ile His Ala Phe Phe Phe Ser Gly Gln Glu Pro Trp Lys Glu Ala Ile
450                 455                 460 gat tgc ttc gtg agt agt aat aaa gat ata atc cga tta tcg gct act     1440
Asp Cys Phe Val Ser Ser Asn Lys Asp Ile Ile Arg Leu Ser Ala Thr
465                 470                 475                 480 att ttc cgg ctc acg gat gat ttg gaa act tct gcg gaa gaa ata gaa     1488
Ile Phe Arg Leu Thr Asp Asp Leu Glu Thr Ser Ala Glu Glu Ile Glu
                485                 490                 495 aga ggc gac gtg cca aaa tcc att caa tgt tac atg cat gaa gcc gga     1536
Arg Gly Asp Val Pro Lys Ser Ile Gln Cys Tyr Met His Glu Ala Gly
            500                 505                 510 gcg tcg gag gca gtc tct aga gcc cac atc aga ggc aaa att agt gag     1584
Ala Ser Glu Ala Val Ser Arg Ala His Ile Arg Gly Lys Ile Ser Glu
515                 520                 525 gtg tgg agg aag atg aac aaa tat ttg acc gct cct gct aca cgg cat     1632
Val Trp Arg Lys Met Asn Lys Tyr Leu Thr Ala Pro Ala Thr Arg His
530                 535                 540 aag act ttc aat gca gct gct ttc aat ttg gca cgg acg tcg act tgt     1680
Lys Thr Phe Asn Ala Ala Ala Phe Asn Leu Ala Arg Thr Ser Thr Cys
545                 550                 555                 560 gtt tac ctt tat gga gat gga tat ggc gta cca aac ggg aag aac aag     1728
Val Tyr Leu Tyr Gly Asp Gly Tyr Gly Val Pro Asn Gly Lys Asn Lys
                565                 570                 575 gaa aac atc acg tca ctt acc gtt gaa ccc atc gtg ctt gag taa         1773
Glu Asn Ile Thr Ser Leu Thr Val Glu Pro Ile Val Leu Glu
            580                 585                 590

<210> SEQ ID NO 8
<211> LENGTH: 590
<212> TYPE: PRT
<213> ORGANISM: Cananga odorata

<400> SEQUENCE: 8

Met Ala Leu Asn Thr Phe Leu His Phe Pro Pro Cys Ser Leu Ser Ser
1               5                   10                  15

Phe Ser Cys Ala Val Pro Lys Leu Pro Leu Ala Ile Phe His Lys Thr
            20                  25                  30

Met Ala Arg Gln Ile Arg Cys Pro Arg Ala Ser Ser Gln Thr Ser Glu
        35                  40                  45
```

```
Pro Ala Leu Ala Arg Arg Ser Ala Asn Phe Gln Pro Thr Ile Trp Thr
 50                  55                  60

Asn Asp Phe Ile Gln Ser Leu Asn Ser Asp Tyr Ser Ser Asp Val Tyr
 65                  70                  75                  80

Val Gln Arg Ile Glu Lys Leu Lys Lys Ser Val Arg Gln Ser Leu Glu
                 85                  90                  95

Glu Ala Asp Gly Pro Leu Ala Gln Leu Glu Leu Ile Asp Asp Leu Gln
            100                 105                 110

Arg Leu Gly Val Gly Arg Leu Phe Glu Arg Glu Ile Asn Glu Met Leu
        115                 120                 125

Asn Gly Ile Tyr Met Asp Tyr Lys Glu Thr Gln Ala Gln Trp Asn Leu
130                 135                 140

His Phe Thr Ser Met Tyr Phe Arg Leu Leu Arg Ala Arg Gly Phe Asp
145                 150                 155                 160

Val Ser Pro Glu Ile Phe Ser Arg Phe Met Asp Glu Thr Gly Asn Phe
                165                 170                 175

Gln Thr Ser Ile Ser Asn Asp Pro Ile Gly Met Leu Ser Leu Tyr Glu
            180                 185                 190

Ala Ser Tyr Leu Cys Met Pro Gly Glu Thr Thr Leu Asp Glu Ala Gln
        195                 200                 205

Ala Phe Thr Cys Lys His Leu Lys Tyr Trp Lys Glu Lys Asp Val His
210                 215                 220

Pro Thr Ile Ala Leu Gln Ile Glu His Ala Leu Glu Leu Pro Ile His
225                 230                 235                 240

Trp Arg Met Pro Arg Leu Asp Ser Arg Trp Tyr Ile Lys Leu Tyr Glu
                245                 250                 255

Glu Lys Glu Gly Thr Arg Pro Leu Leu Leu Glu Leu Ala Lys Leu Asp
            260                 265                 270

Phe Asn Met Val Gln Ser Ala His Gln Thr Glu Leu Arg Lys Val Ser
        275                 280                 285

Arg Trp Trp Ser Glu Phe Gly Leu Ala Glu Lys Ala Ser Phe Ala Arg
290                 295                 300

Asp Arg Leu Met Glu Gly Tyr Gln Trp Ala Ile Gly Thr Val Phe Glu
305                 310                 315                 320

Pro Glu Phe Gly Gln Cys Arg Glu Val Leu Ala Lys Leu Ala Gln Leu
                325                 330                 335

Ile Ala Val Ile Asp Asp Met Tyr Asp Val Tyr Gly Ser Pro Asp Glu
            340                 345                 350

Leu Glu Leu Phe Thr Asp Ala Val Asp Arg Trp Asn Ile Asn Thr Ile
        355                 360                 365

Glu Gly Leu Pro Asp Tyr Met Lys Leu Cys Phe Leu Ser Ile Tyr Asn
370                 375                 380

Thr Thr Asn Gln Gly Gly Tyr Glu Phe Leu Lys Asp His Gly Val Asp
385                 390                 395                 400

Ile Ile Pro His Leu Arg Lys Ala Trp Ala Asp Tyr Cys Lys Ala Leu
                405                 410                 415

Arg Thr Glu Ala Arg Trp Val Asn Ser Lys Tyr Thr Pro Thr Leu Asp
            420                 425                 430

Glu Tyr Leu Asn Asn Ala Tyr Thr Ser Ala Ser Gly Pro Leu Ile Leu
        435                 440                 445

Ile His Ala Phe Phe Phe Ser Gly Gln Glu Pro Trp Lys Glu Ala Ile
450                 455                 460

Asp Cys Phe Val Ser Ser Asn Lys Asp Ile Ile Arg Leu Ser Ala Thr
```

```
        465                 470                 475                 480
Ile Phe Arg Leu Thr Asp Asp Leu Glu Thr Ser Ala Glu Glu Ile Glu
                    485                 490                 495

Arg Gly Asp Val Pro Lys Ser Ile Gln Cys Tyr Met His Glu Ala Gly
                500                 505                 510

Ala Ser Glu Ala Val Ser Arg Ala His Ile Arg Gly Lys Ile Ser Glu
            515                 520                 525

Val Trp Arg Lys Met Asn Lys Tyr Leu Thr Ala Pro Ala Thr Arg His
        530                 535                 540

Lys Thr Phe Asn Ala Ala Ala Phe Asn Leu Ala Arg Thr Ser Thr Cys
545                 550                 555                 560

Val Tyr Leu Tyr Gly Asp Gly Tyr Gly Val Pro Asn Gly Lys Asn Lys
                565                 570                 575

Glu Asn Ile Thr Ser Leu Thr Val Glu Pro Ile Val Leu Glu
            580                 585                 590

<210> SEQ ID NO 9
<211> LENGTH: 1686
<212> TYPE: DNA
<213> ORGANISM: Cananga odorata
<220> FEATURE:
<221> NAME/KEY: CDS
<222> LOCATION: (1)..(1683)

<400> SEQUENCE: 9 atg gca ctt ata ttt gca aat ggc cac tct gat gtt ccc tct acc cag      48
Met Ala Leu Ile Phe Ala Asn Gly His Ser Asp Val Pro Ser Thr Gln
1               5                   10                  15 cct cca ata ggc aag cag aaa aag gag att ggt cgt gaa tcc gta aac      96
Pro Pro Ile Gly Lys Gln Lys Lys Glu Ile Gly Arg Glu Ser Val Asn
            20                  25                  30 tac cac cct agt gtt tgg ggt gat cgg ttc gcc att ttg aca gcc cat     144
Tyr His Pro Ser Val Trp Gly Asp Arg Phe Ala Ile Leu Thr Ala His
        35                  40                  45 gaa att gag gtc gat gaa ata acc aag caa agg gct gaa aag ctg aag     192
Glu Ile Glu Val Asp Glu Ile Thr Lys Gln Arg Ala Glu Lys Leu Lys
    50                  55                  60 cat gat gtg ctg aag atg cta cat aat gtc agt gtt tct ttg caa gat     240
His Asp Val Leu Lys Met Leu His Asn Val Ser Val Ser Leu Gln Asp
65                  70                  75                  80 ctg aat ctg atc gat gaa atc caa cgg cta ggg gtt ggt tac cac ttt     288
Leu Asn Leu Ile Asp Glu Ile Gln Arg Leu Gly Val Gly Tyr His Phe
                85                  90                  95 gag act gag att gaa aat gca atg aag aga atc tac aat tca aga gat     336
Glu Thr Glu Ile Glu Asn Ala Met Lys Arg Ile Tyr Asn Ser Arg Asp
            100                 105                 110 aat gat gat gat gac ctt cat gcg gtg gct cta cga ttt cgg ctt cta     384
Asn Asp Asp Asp Asp Leu His Ala Val Ala Leu Arg Phe Arg Leu Leu
        115                 120                 125 aga cag cat ggt tat aac gtg tca tct gat gtg ttt aaa aag ttt aaa     432
Arg Gln His Gly Tyr Asn Val Ser Ser Asp Val Phe Lys Lys Phe Lys
    130                 135                 140 gat gag aaa gga gaa ttt aag gca tca ttg aga gaa aat gta cgg gga     480
Asp Glu Lys Gly Glu Phe Lys Ala Ser Leu Arg Glu Asn Val Arg Gly
145                 150                 155                 160 ttg ctg agc ttt tat gaa gca gca tat ctt ggc aca gct gat gac acc     528
Leu Leu Ser Phe Tyr Glu Ala Ala Tyr Leu Gly Thr Ala Asp Asp Thr
                165                 170                 175 att ttg gat caa gcc att gac ttc act acc gac caa ctt aag tct gtg     576
Ile Leu Asp Gln Ala Ile Asp Phe Thr Thr Asp Gln Leu Lys Ser Val
```

```
Ile Leu Asp Gln Ala Ile Asp Phe Thr Thr Asp Gln Leu Lys Ser Val
            180                 185                 190 ttg cca aac ttg aac cct cca ctt tca gag tta gta aag ctc gct ttg    624
Leu Pro Asn Leu Asn Pro Pro Leu Ser Glu Leu Val Lys Leu Ala Leu
            195                 200                 205 gat gta ccg ctg cat aaa cgc att gag aga ctt cag tca aga tat ttc    672
Asp Val Pro Leu His Lys Arg Ile Glu Arg Leu Gln Ser Arg Tyr Phe
        210                 215                 220 atc tct atc tac caa gaa gaa aag gag aga aac gaa gta ctc cta gag    720
Ile Ser Ile Tyr Gln Glu Glu Lys Glu Arg Asn Glu Val Leu Leu Glu
225                 230                 235                 240 ttc gcc aag ttg gat ttc aat gtt ttg cag tct ttg cac aag gag gag    768
Phe Ala Lys Leu Asp Phe Asn Val Leu Gln Ser Leu His Lys Glu Glu
                245                 250                 255 ctc agt caa ctc tca agg tgg tgg aaa gac aat gat ttt gct aga aag    816
Leu Ser Gln Leu Ser Arg Trp Trp Lys Asp Asn Asp Phe Ala Arg Lys
            260                 265                 270 ttg cca ttc atc aga gac aga ctc gtt gag tgc tat ttt tgg ata tta    864
Leu Pro Phe Ile Arg Asp Arg Leu Val Glu Cys Tyr Phe Trp Ile Leu
        275                 280                 285 ggc gtg tat tat gaa cca cgt tat tcc aga ggt aga atg atg aca act    912
Gly Val Tyr Tyr Glu Pro Arg Tyr Ser Arg Gly Arg Met Met Thr Thr
290                 295                 300 aaa gta ata tca tta aca tcg atc atg gat gac aca tat gat gtg tat    960
Lys Val Ile Ser Leu Thr Ser Ile Met Asp Asp Thr Tyr Asp Val Tyr
305                 310                 315                 320 ggt aaa cta gat gag ctc gaa ctc ctt aca act gca ata gaa agg tgg   1008
Gly Lys Leu Asp Glu Leu Glu Leu Leu Thr Thr Ala Ile Glu Arg Trp
                325                 330                 335 gag tgg gca gcc atg gat gag ctg cca gat tac atg aaa ttg cat ttc   1056
Glu Trp Ala Ala Met Asp Glu Leu Pro Asp Tyr Met Lys Leu His Phe
            340                 345                 350 agt gcc ctt ctg act gct gtt gag aat ttt gag gag gaa ttg agc aaa   1104
Ser Ala Leu Leu Thr Ala Val Glu Asn Phe Glu Glu Glu Leu Ser Lys
        355                 360                 365 gaa gga aaa gcc tat cgc att tcc tac ttc aag aac gct tat aca aaa   1152
Glu Gly Lys Ala Tyr Arg Ile Ser Tyr Phe Lys Asn Ala Tyr Thr Lys
370                 375                 380 ttg gct aaa gcc tac ttg gaa gaa gct aga tgg gcg agt gca gat tac   1200
Leu Ala Lys Ala Tyr Leu Glu Glu Ala Arg Trp Ala Ser Ala Asp Tyr
385                 390                 395                 400 gtt cct act tta gaa gag tac atg aaa cat gcc caa gtt agt tct gcc   1248
Val Pro Thr Leu Glu Glu Tyr Met Lys His Ala Gln Val Ser Ser Ala
                405                 410                 415 tac cct gtg ctt act ttg tcc tct ctt ctt gga atg gga gcc act gca   1296
Tyr Pro Val Leu Thr Leu Ser Ser Leu Leu Gly Met Gly Ala Thr Ala
            420                 425                 430 aca aag gaa gca ttt gag tgg gcc att aac atg ccc aat gct atc aat   1344
Thr Lys Glu Ala Phe Glu Trp Ala Ile Asn Met Pro Asn Ala Ile Asn
        435                 440                 445 gcg att tct gtt gtt tgc cga cta aag gat gac atc act tca gct gag   1392
Ala Ile Ser Val Val Cys Arg Leu Lys Asp Asp Ile Thr Ser Ala Glu
450                 455                 460 ctg gag caa cag aga gtt cat gtg gca aca gca gtt gag tgc tac ata   1440
Leu Glu Gln Gln Arg Val His Val Ala Thr Ala Val Glu Cys Tyr Ile
465                 470                 475                 480 aaa gag aat ggc acc aca tat gag gaa aca tgt aag ctt ttc aaa cag   1488
Lys Glu Asn Gly Thr Thr Tyr Glu Glu Thr Cys Lys Leu Phe Lys Gln
                485                 490                 495
```

```
aaa gtt gat agt gct tgg aaa gaa atc aac aag gag tgg atg gat ccc    1536
Lys Val Asp Ser Ala Trp Lys Glu Ile Asn Lys Glu Trp Met Asp Pro
            500                 505                 510 ctt caa gtt cca agg gaa ata atc aag cgt gca gtg aac ttt gca cgt    1584
Leu Gln Val Pro Arg Glu Ile Ile Lys Arg Ala Val Asn Phe Ala Arg
        515                 520                 525 gtg ata gaa ttc ctg tac cgt tac aag gac atg tac acc gag tca gct    1632
Val Ile Glu Phe Leu Tyr Arg Tyr Lys Asp Met Tyr Thr Glu Ser Ala
    530                 535                 540 ggc gag act aaa gaa tgt att gcg atg gtg cta gtg gac cgt ttt gtt    1680
Gly Glu Thr Lys Glu Cys Ile Ala Met Val Leu Val Asp Arg Phe Val
545                 550                 555                 560 gat taa                                                             1686
Asp

<210> SEQ ID NO 10
<211> LENGTH: 561
<212> TYPE: PRT
<213> ORGANISM: Cananga odorata

<400> SEQUENCE: 10

Met Ala Leu Ile Phe Ala Asn Gly His Ser Asp Val Pro Ser Thr Gln
1               5                   10                  15

Pro Pro Ile Gly Lys Gln Lys Lys Glu Ile Gly Arg Glu Ser Val Asn
            20                  25                  30

Tyr His Pro Ser Val Trp Gly Asp Arg Phe Ala Ile Leu Thr Ala His
        35                  40                  45

Glu Ile Glu Val Asp Glu Ile Thr Lys Gln Arg Ala Glu Lys Leu Lys
    50                  55                  60

His Asp Val Leu Lys Met Leu His Asn Val Ser Val Ser Leu Gln Asp
65                  70                  75                  80

Leu Asn Leu Ile Asp Glu Ile Gln Arg Leu Gly Val Gly Tyr His Phe
                85                  90                  95

Glu Thr Glu Ile Glu Asn Ala Met Lys Arg Ile Tyr Asn Ser Arg Asp
            100                 105                 110

Asn Asp Asp Asp Asp Leu His Ala Val Ala Leu Arg Phe Arg Leu Leu
        115                 120                 125

Arg Gln His Gly Tyr Asn Val Ser Ser Asp Val Phe Lys Lys Phe Lys
    130                 135                 140

Asp Glu Lys Gly Glu Phe Lys Ala Ser Leu Arg Glu Asn Val Arg Gly
145                 150                 155                 160

Leu Leu Ser Phe Tyr Glu Ala Ala Tyr Leu Gly Thr Ala Asp Asp Thr
                165                 170                 175

Ile Leu Asp Gln Ala Ile Asp Phe Thr Thr Asp Gln Leu Lys Ser Val
            180                 185                 190

Leu Pro Asn Leu Asn Pro Pro Leu Ser Glu Leu Val Lys Leu Ala Leu
        195                 200                 205

Asp Val Pro Leu His Lys Arg Ile Glu Arg Leu Gln Ser Arg Tyr Phe
    210                 215                 220

Ile Ser Ile Tyr Gln Glu Glu Lys Glu Arg Asn Glu Val Leu Glu
225                 230                 235                 240

Phe Ala Lys Leu Asp Phe Asn Val Leu Gln Ser Leu His Lys Glu Glu
                245                 250                 255

Leu Ser Gln Leu Ser Arg Trp Trp Lys Asp Asn Asp Phe Ala Arg Lys
            260                 265                 270

Leu Pro Phe Ile Arg Asp Arg Leu Val Glu Cys Tyr Phe Trp Ile Leu
```

```
                275                 280                 285
Gly Val Tyr Tyr Glu Pro Arg Tyr Ser Arg Gly Arg Met Met Thr Thr
290                 295                 300

Lys Val Ile Ser Leu Thr Ser Ile Met Asp Asp Thr Tyr Asp Val Tyr
305                 310                 315                 320

Gly Lys Leu Asp Glu Leu Glu Leu Leu Thr Thr Ala Ile Glu Arg Trp
                325                 330                 335

Glu Trp Ala Ala Met Asp Glu Leu Pro Asp Tyr Met Lys Leu His Phe
                340                 345                 350

Ser Ala Leu Leu Thr Ala Val Glu Asn Phe Glu Glu Glu Leu Ser Lys
            355                 360                 365

Glu Gly Lys Ala Tyr Arg Ile Ser Tyr Phe Lys Asn Ala Tyr Thr Lys
        370                 375                 380

Leu Ala Lys Ala Tyr Leu Glu Glu Ala Arg Trp Ala Ser Ala Asp Tyr
385                 390                 395                 400

Val Pro Thr Leu Glu Glu Tyr Met Lys His Ala Gln Val Ser Ser Ala
                405                 410                 415

Tyr Pro Val Leu Thr Leu Ser Ser Leu Leu Gly Met Gly Ala Thr Ala
                420                 425                 430

Thr Lys Glu Ala Phe Glu Trp Ala Ile Asn Met Pro Asn Ala Ile Asn
            435                 440                 445

Ala Ile Ser Val Val Cys Arg Leu Lys Asp Asp Ile Thr Ser Ala Glu
450                 455                 460

Leu Glu Gln Gln Arg Val His Val Ala Thr Ala Val Glu Cys Tyr Ile
465                 470                 475                 480

Lys Glu Asn Gly Thr Thr Tyr Glu Glu Thr Cys Lys Leu Phe Lys Gln
                485                 490                 495

Lys Val Asp Ser Ala Trp Lys Glu Ile Asn Lys Glu Trp Met Asp Pro
                500                 505                 510

Leu Gln Val Pro Arg Glu Ile Ile Lys Arg Ala Val Asn Phe Ala Arg
            515                 520                 525

Val Ile Glu Phe Leu Tyr Arg Tyr Lys Asp Met Tyr Thr Glu Ser Ala
530                 535                 540

Gly Glu Thr Lys Glu Cys Ile Ala Met Val Leu Val Asp Arg Phe Val
545                 550                 555                 560

Asp

<210> SEQ ID NO 11
<211> LENGTH: 1761
<212> TYPE: DNA
<213> ORGANISM: Cananga odorata
<220> FEATURE:
<221> NAME/KEY: CDS
<222> LOCATION: (1)..(1758)

<400> SEQUENCE: 11 atg gct gct acg aga aac ctt tct tta ctt gca caa tct tca caa cct    48
Met Ala Ala Thr Arg Asn Leu Ser Leu Leu Ala Gln Ser Ser Gln Pro
1               5                   10                  15 tgg gca ggt att tat ggt tct cat gga tct cca agg cct att agt tca    96
Trp Ala Gly Ile Tyr Gly Ser His Gly Ser Pro Arg Pro Ile Ser Ser
            20                  25                  30 tgg tta aga agg cag tca ata gct aaa act tca tat att tgc atg tgc    144
Trp Leu Arg Arg Gln Ser Ile Ala Lys Thr Ser Tyr Ile Cys Met Cys
        35                  40                  45 acc ccg tta tct atg tct cag ctc att gca act cca ttg atc aca gac    192
```

```
Thr Pro Leu Ser Met Ser Gln Leu Ile Ala Thr Pro Leu Ile Thr Asp
    50              55                  60 att gag tct ctt cta aaa tat ttg cgc caa cct cag gtg ctt cct cat      240
Ile Glu Ser Leu Leu Lys Tyr Leu Arg Gln Pro Gln Val Leu Pro His
 65              70                  75                  80 gaa atc gat gat agc acc aaa agg agg gaa ttg ttg gaa agg aca aga      288
Glu Ile Asp Asp Ser Thr Lys Arg Arg Glu Leu Leu Glu Arg Thr Arg
                 85                  90                  95 aga gaa ctg caa aca act tta gaa cct ttg caa gcc atg aag atg ata      336
Arg Glu Leu Gln Thr Thr Leu Glu Pro Leu Gln Ala Met Lys Met Ile
            100                 105                 110 gat aca ctt cag aga ctg gga tta gca tat cat ttt gaa gat gat att      384
Asp Thr Leu Gln Arg Leu Gly Leu Ala Tyr His Phe Glu Asp Asp Ile
            115                 120                 125 aac tca ttg ctg act gga ttt tca aat ggc caa cct gat gaa gat ctc      432
Asn Ser Leu Leu Thr Gly Phe Ser Asn Gly Gln Pro Asp Glu Asp Leu
        130                 135                 140 ctc act gct tcc cta cgc ttc cga ttg ctt cga cac aat ggc cac agg      480
Leu Thr Ala Ser Leu Arg Phe Arg Leu Leu Arg His Asn Gly His Arg
145                 150                 155                 160 att aat cct aat att ttc cag aag ttc atg gac aaa cag gga aag ttt      528
Ile Asn Pro Asn Ile Phe Gln Lys Phe Met Asp Lys Gln Gly Lys Phe
                165                 170                 175 att gac tct ttg aag gaa gac aca cga ggt ttg ttc agc tta tat gaa      576
Ile Asp Ser Leu Lys Glu Asp Thr Arg Gly Leu Phe Ser Leu Tyr Glu
            180                 185                 190 gca tcc tac tta gga gca aat gga gaa gat ata ctg ttg cag gcc tta      624
Ala Ser Tyr Leu Gly Ala Asn Gly Glu Asp Ile Leu Leu Gln Ala Leu
            195                 200                 205 gag ttc acc aaa gcc cac ctg aaa gaa tcg ctg cct agc ttg gca cct      672
Glu Phe Thr Lys Ala His Leu Lys Glu Ser Leu Pro Ser Leu Ala Pro
        210                 215                 220 cca ctt gct aag aag gtc tct cag gcc ttg gag ctt cca aga cac cga      720
Pro Leu Ala Lys Lys Val Ser Gln Ala Leu Glu Leu Pro Arg His Arg
225                 230                 235                 240 aga atg gcg agg tta gaa gcc aga agg tat att gaa gaa tat ggt ggt      768
Arg Met Ala Arg Leu Glu Ala Arg Arg Tyr Ile Glu Glu Tyr Gly Gly
                245                 250                 255 gaa aat ggc cac agc cct gat ctt ctt gag ctt gca aaa ttg gat tat      816
Glu Asn Gly His Ser Pro Asp Leu Leu Glu Leu Ala Lys Leu Asp Tyr
            260                 265                 270 aac aaa gtc cag tca ctt cac caa ttg gaa ttg tct gag att tcg agg      864
Asn Lys Val Gln Ser Leu His Gln Leu Glu Leu Ser Glu Ile Ser Arg
            275                 280                 285 tgg tgg aaa cag tta ggc ctg gtt gat aag ctt act ttt gct cga gat      912
Trp Trp Lys Gln Leu Gly Leu Val Asp Lys Leu Thr Phe Ala Arg Asp
        290                 295                 300 aga ccc ctg gag tgc ttt ctc tgg aca gtt gga att tta ccg gaa ccc      960
Arg Pro Leu Glu Cys Phe Leu Trp Thr Val Gly Ile Leu Pro Glu Pro
305                 310                 315                 320 aag tat tct tcc tgc aga att gag cta gcc aaa acc ata gcc atc tta     1008
Lys Tyr Ser Ser Cys Arg Ile Glu Leu Ala Lys Thr Ile Ala Ile Leu
                325                 330                 335 ctg gtg att gac gac att ttt gat act cat ggc acc tta gat gag ctt     1056
Leu Val Ile Asp Asp Ile Phe Asp Thr His Gly Thr Leu Asp Glu Leu
            340                 345                 350 att cta ttt aca aat gca att cga aga tgg gat ctt gaa gct atg gaa     1104
Ile Leu Phe Thr Asn Ala Ile Arg Arg Trp Asp Leu Glu Ala Met Glu
        355                 360                 365
```

| | | | | | | | | | | | | | | | | |
|---|---|---|---|---|---|---|---|---|---|---|---|---|---|---|---|---|
| gat | tta | cca | gaa | tat | atg | aga | att | tgt | tac | atg | gca | ttg | tac | aac | act | 1152 |
| Asp | Leu | Pro | Glu | Tyr | Met | Arg | Ile | Cys | Tyr | Met | Ala | Leu | Tyr | Asn | Thr | |
| | | 370 | | | | 375 | | | | | 380 | | | | | |
| act | aat | gaa | att | tgc | tac | aag | atc | ctc | aag | caa | aat | ggt | tgg | agt | gtc | 1200 |
| Thr | Asn | Glu | Ile | Cys | Tyr | Lys | Ile | Leu | Lys | Gln | Asn | Gly | Trp | Ser | Val | |
| 385 | | | | | 390 | | | | | 395 | | | | | 400 | |
| ctc | cca | tac | cta | aag | gca | acg | tgg | att | gat | atg | att | gaa | ggc | ttc | atg | 1248 |
| Leu | Pro | Tyr | Leu | Lys | Ala | Thr | Trp | Ile | Asp | Met | Ile | Glu | Gly | Phe | Met | |
| | | | | 405 | | | | | 410 | | | | | 415 | | |
| ctt | gaa | gca | agc | tgg | ttg | aac | acc | ggt | tat | gta | cca | aac | atg | gaa | gaa | 1296 |
| Leu | Glu | Ala | Ser | Trp | Leu | Asn | Thr | Gly | Tyr | Val | Pro | Asn | Met | Glu | Glu | |
| | | | 420 | | | | | 425 | | | | | 430 | | | |
| tat | gta | gaa | aat | ggt | gtt | aca | aca | gcg | gga | gca | tac | atg | gcc | tta | gtg | 1344 |
| Tyr | Val | Glu | Asn | Gly | Val | Thr | Thr | Ala | Gly | Ala | Tyr | Met | Ala | Leu | Val | |
| | | 435 | | | | | 440 | | | | | 445 | | | | |
| cat | ctg | ttc | ttt | cta | ata | gga | cag | gga | gtc | act | gaa | gag | aat | gta | aaa | 1392 |
| His | Leu | Phe | Phe | Leu | Ile | Gly | Gln | Gly | Val | Thr | Glu | Glu | Asn | Val | Lys | |
| | | | | 450 | | | | | 455 | | | | | 460 | | |
| ttg | tta | gta | aaa | ccc | tat | cca | aag | ctc | ttc | tcc | tat | tcg | gga | aga | atc | 1440 |
| Leu | Leu | Val | Lys | Pro | Tyr | Pro | Lys | Leu | Phe | Ser | Tyr | Ser | Gly | Arg | Ile | |
| 465 | | | | | 470 | | | | | 475 | | | | | 480 | |
| ctt | cga | ctt | tgg | gac | gat | ttg | gga | acc | gca | aag | gag | gag | caa | gaa | aga | 1488 |
| Leu | Arg | Leu | Trp | Asp | Asp | Leu | Gly | Thr | Ala | Lys | Glu | Glu | Gln | Glu | Arg | |
| | | | | 485 | | | | | 490 | | | | | 495 | | |
| ggt | gat | ctt | gca | tca | agt | att | gat | cta | ttc | atg | aga | gag | aac | aac | ata | 1536 |
| Gly | Asp | Leu | Ala | Ser | Ser | Ile | Asp | Leu | Phe | Met | Arg | Glu | Asn | Asn | Ile | |
| | | | 500 | | | | | 505 | | | | | 510 | | | |
| aca | tca | gat | gaa | gaa | ggc | agg | aaa | tgc | atc | ttg | aaa | att | ata | gac | aac | 1584 |
| Thr | Ser | Asp | Glu | Glu | Gly | Arg | Lys | Cys | Ile | Leu | Lys | Ile | Ile | Asp | Asn | |
| | | 515 | | | | | 520 | | | | | 525 | | | | |
| cta | tgg | aaa | gag | ctg | aat | gga | gaa | ctg | gtg | tct | aga | cat | gcc | cta | cct | 1632 |
| Leu | Trp | Lys | Glu | Leu | Asn | Gly | Glu | Leu | Val | Ser | Arg | His | Ala | Leu | Pro | |
| | | | | 530 | | | | | 535 | | | | | 540 | | |
| ctt | gca | atc | atc | aag | gct | gca | ttt | aac | atg | gcc | aga | gct | tcc | caa | gtt | 1680 |
| Leu | Ala | Ile | Ile | Lys | Ala | Ala | Phe | Asn | Met | Ala | Arg | Ala | Ser | Gln | Val | |
| 545 | | | | | 550 | | | | | 555 | | | | | 560 | |
| gtg | tac | caa | cat | gaa | gaa | gat | agc | tac | ttt | tca | agc | gta | gat | aat | tat | 1728 |
| Val | Tyr | Gln | His | Glu | Glu | Asp | Ser | Tyr | Phe | Ser | Ser | Val | Asp | Asn | Tyr | |
| | | | | 565 | | | | | 570 | | | | | 575 | | |
| gtg | caa | gct | ttg | ttt | ttc | acg | cct | ttc | aat | tga | | | | | | 1761 |
| Val | Gln | Ala | Leu | Phe | Phe | Thr | Pro | Phe | Asn | | | | | | | |
| | | | 580 | | | | | 585 | | | | | | | | |

<210> SEQ ID NO 12
<211> LENGTH: 586
<212> TYPE: PRT
<213> ORGANISM: Cananga odorata

<400> SEQUENCE: 12

Met Ala Ala Thr Arg Asn Leu Ser Leu Leu Ala Gln Ser Ser Gln Pro
1               5                   10                  15

Trp Ala Gly Ile Tyr Gly Ser His Gly Ser Pro Arg Pro Ile Ser Ser
            20                  25                  30

Trp Leu Arg Arg Gln Ser Ile Ala Lys Thr Ser Tyr Ile Cys Met Cys
        35                  40                  45

Thr Pro Leu Ser Met Ser Gln Leu Ile Ala Thr Pro Leu Ile Thr Asp
    50                  55                  60

Ile Glu Ser Leu Leu Lys Tyr Leu Arg Gln Pro Gln Val Leu Pro His
65                  70                  75                  80

-continued

```
Glu Ile Asp Asp Ser Thr Lys Arg Arg Glu Leu Leu Glu Arg Thr Arg
                85                  90                  95
Arg Glu Leu Gln Thr Thr Leu Glu Pro Leu Gln Ala Met Lys Met Ile
            100                 105                 110
Asp Thr Leu Gln Arg Leu Gly Leu Ala Tyr His Phe Glu Asp Asp Ile
            115                 120                 125
Asn Ser Leu Leu Thr Gly Phe Ser Asn Gly Gln Pro Asp Glu Asp Leu
130                 135                 140
Leu Thr Ala Ser Leu Arg Phe Arg Leu Leu Arg His Asn Gly His Arg
145                 150                 155                 160
Ile Asn Pro Asn Ile Phe Gln Lys Phe Met Asp Lys Gln Gly Lys Phe
                165                 170                 175
Ile Asp Ser Leu Lys Glu Asp Thr Arg Gly Leu Phe Ser Leu Tyr Glu
            180                 185                 190
Ala Ser Tyr Leu Gly Ala Asn Gly Glu Asp Ile Leu Leu Gln Ala Leu
            195                 200                 205
Glu Phe Thr Lys Ala His Leu Lys Glu Ser Leu Pro Ser Leu Ala Pro
210                 215                 220
Pro Leu Ala Lys Lys Val Ser Gln Ala Leu Glu Leu Pro Arg His Arg
225                 230                 235                 240
Arg Met Ala Arg Leu Glu Ala Arg Arg Tyr Ile Glu Glu Tyr Gly Gly
                245                 250                 255
Glu Asn Gly His Ser Pro Asp Leu Leu Glu Leu Ala Lys Leu Asp Tyr
            260                 265                 270
Asn Lys Val Gln Ser Leu His Gln Leu Glu Leu Ser Glu Ile Ser Arg
            275                 280                 285
Trp Trp Lys Gln Leu Gly Leu Val Asp Lys Leu Thr Phe Ala Arg Asp
290                 295                 300
Arg Pro Leu Glu Cys Phe Leu Trp Thr Val Gly Ile Leu Pro Glu Pro
305                 310                 315                 320
Lys Tyr Ser Ser Cys Arg Ile Glu Leu Ala Lys Thr Ile Ala Ile Leu
                325                 330                 335
Leu Val Ile Asp Asp Ile Phe Asp Thr His Gly Thr Leu Asp Glu Leu
            340                 345                 350
Ile Leu Phe Thr Asn Ala Ile Arg Arg Trp Asp Leu Glu Ala Met Glu
            355                 360                 365
Asp Leu Pro Glu Tyr Met Arg Ile Cys Tyr Met Ala Leu Tyr Asn Thr
            370                 375                 380
Thr Asn Glu Ile Cys Tyr Lys Ile Leu Lys Gln Asn Gly Trp Ser Val
385                 390                 395                 400
Leu Pro Tyr Leu Lys Ala Thr Trp Ile Asp Met Ile Glu Gly Phe Met
                405                 410                 415
Leu Glu Ala Ser Trp Leu Asn Thr Gly Tyr Val Pro Asn Met Glu Glu
            420                 425                 430
Tyr Val Glu Asn Gly Val Thr Thr Ala Gly Ala Tyr Met Ala Leu Val
            435                 440                 445
His Leu Phe Phe Leu Ile Gly Gln Gly Val Thr Glu Glu Asn Val Lys
            450                 455                 460
Leu Leu Val Lys Pro Tyr Pro Lys Leu Phe Ser Tyr Ser Gly Arg Ile
465                 470                 475                 480
Leu Arg Leu Trp Asp Asp Leu Gly Thr Ala Lys Glu Glu Gln Glu Arg
                485                 490                 495
Gly Asp Leu Ala Ser Ser Ile Asp Leu Phe Met Arg Glu Asn Asn Ile
```

-continued

```
                  500             505               510
Thr Ser Asp Glu Glu Gly Arg Lys Cys Ile Leu Lys Ile Ile Asp Asn
        515                 520                 525
Leu Trp Lys Glu Leu Asn Gly Glu Leu Val Ser Arg His Ala Leu Pro
        530                 535                 540
Leu Ala Ile Ile Lys Ala Ala Phe Asn Met Ala Arg Ala Ser Gln Val
545                 550                 555                 560
Val Tyr Gln His Glu Glu Asp Ser Tyr Phe Ser Ser Val Asp Asn Tyr
                565                 570                 575
Val Gln Ala Leu Phe Phe Thr Pro Phe Asn
                580                 585

<210> SEQ ID NO 13
<211> LENGTH: 20
<212> TYPE: DNA
<213> ORGANISM: Cananga odorata

<400> SEQUENCE: 13
tttgattggg ggtgagagag                                            20

<210> SEQ ID NO 14
<211> LENGTH: 20
<212> TYPE: DNA
<213> ORGANISM: Cananga odorata

<400> SEQUENCE: 14
gccatcaagg gacatgaact                                            20

<210> SEQ ID NO 15
<211> LENGTH: 20
<212> TYPE: DNA
<213> ORGANISM: Cananga odorata

<400> SEQUENCE: 15
ggggatcaca aaatccattg                                            20

<210> SEQ ID NO 16
<211> LENGTH: 20
<212> TYPE: DNA
<213> ORGANISM: Cananga odorata

<400> SEQUENCE: 16
tgggtagcct tttcccttttt                                           20

<210> SEQ ID NO 17
<211> LENGTH: 20
<212> TYPE: DNA
<213> ORGANISM: Cananga odorata

<400> SEQUENCE: 17
cttctgcaag cccctagatg                                            20

<210> SEQ ID NO 18
<211> LENGTH: 20
<212> TYPE: DNA
<213> ORGANISM: Cananga odorata

<400> SEQUENCE: 18
gttgcagcaa tgtgcctaga                                            20

<210> SEQ ID NO 19
```

```
<211> LENGTH: 20
<212> TYPE: DNA
<213> ORGANISM: Cananga odorata

<400> SEQUENCE: 19
aaggggagaa tccttgcagt                                              20

<210> SEQ ID NO 20
<211> LENGTH: 20
<212> TYPE: DNA
<213> ORGANISM: Cananga odorata

<400> SEQUENCE: 20
tgttcttggc aaagcttcct                                              20

<210> SEQ ID NO 21
<211> LENGTH: 20
<212> TYPE: DNA
<213> ORGANISM: Cananga odorata

<400> SEQUENCE: 21
gttctgagtg cagccaatga                                              20

<210> SEQ ID NO 22
<211> LENGTH: 20
<212> TYPE: DNA
<213> ORGANISM: Cananga odorata

<400> SEQUENCE: 22
caagaacagg tcgcagatca                                              20

<210> SEQ ID NO 23
<211> LENGTH: 20
<212> TYPE: DNA
<213> ORGANISM: Cananga odorata

<400> SEQUENCE: 23
aggagcgtgt cagtggttct                                              20

<210> SEQ ID NO 24
<211> LENGTH: 20
<212> TYPE: DNA
<213> ORGANISM: Cananga odorata

<400> SEQUENCE: 24
tggcaaattt caggtcaaca                                              20

<210> SEQ ID NO 25
<211> LENGTH: 20
<212> TYPE: DNA
<213> ORGANISM: Cananga odorata

<400> SEQUENCE: 25
tcggttctga ttgtcccttc                                              20

<210> SEQ ID NO 26
<211> LENGTH: 20
<212> TYPE: DNA
<213> ORGANISM: Cananga odorata

<400> SEQUENCE: 26
cgaaggcgct tgtaaacttc                                              20
```

```
<210> SEQ ID NO 27
<211> LENGTH: 20
<212> TYPE: DNA
<213> ORGANISM: Cananga odorata

<400> SEQUENCE: 27
acgcaagcaa aaactctcgt                                               20

<210> SEQ ID NO 28
<211> LENGTH: 20
<212> TYPE: DNA
<213> ORGANISM: Cananga odorata

<400> SEQUENCE: 28
cggtagcgtt atcagcatca                                               20

<210> SEQ ID NO 29
<211> LENGTH: 20
<212> TYPE: DNA
<213> ORGANISM: Cananga odorata

<400> SEQUENCE: 29
gtggctccat ttgaggaaaa                                               20

<210> SEQ ID NO 30
<211> LENGTH: 20
<212> TYPE: DNA
<213> ORGANISM: Cananga odorata

<400> SEQUENCE: 30
aatccacagt ggcaagatcc                                               20

<210> SEQ ID NO 31
<211> LENGTH: 20
<212> TYPE: DNA
<213> ORGANISM: Cananga odorata

<400> SEQUENCE: 31
actgtacaag gccccatctg                                               20

<210> SEQ ID NO 32
<211> LENGTH: 20
<212> TYPE: DNA
<213> ORGANISM: Cananga odorata

<400> SEQUENCE: 32
cccaccattt cagaaggaaa                                               20

<210> SEQ ID NO 33
<211> LENGTH: 20
<212> TYPE: DNA
<213> ORGANISM: Cananga odorata

<400> SEQUENCE: 33
catgagttgc tccttcagca                                               20

<210> SEQ ID NO 34
<211> LENGTH: 20
<212> TYPE: DNA
<213> ORGANISM: Cananga odorata

<400> SEQUENCE: 34
aagcttcctt tgtgcagcat                                               20
```

<210> SEQ ID NO 35
<211> LENGTH: 20
<212> TYPE: DNA
<213> ORGANISM: Cananga odorata

<400> SEQUENCE: 35
tgcagtgaag tctgctggtc                                          20

<210> SEQ ID NO 36
<211> LENGTH: 20
<212> TYPE: DNA
<213> ORGANISM: Cananga odorata

<400> SEQUENCE: 36
caacagagtt gccacacagc                                          20

<210> SEQ ID NO 37
<211> LENGTH: 20
<212> TYPE: DNA
<213> ORGANISM: Cananga odorata

<400> SEQUENCE: 37
caagacttgg ctgatgcaaa                                          20

<210> SEQ ID NO 38
<211> LENGTH: 20
<212> TYPE: DNA
<213> ORGANISM: Cananga odorata

<400> SEQUENCE: 38
aacaacaagc ccaaatcgtc                                          20

<210> SEQ ID NO 39
<211> LENGTH: 20
<212> TYPE: DNA
<213> ORGANISM: Cananga odorata

<400> SEQUENCE: 39
caggctgatt tccctgacat                                          20

<210> SEQ ID NO 40
<211> LENGTH: 20
<212> TYPE: DNA
<213> ORGANISM: Cananga odorata

<400> SEQUENCE: 40
ctggcatgtg cattgtatcc                                          20

<210> SEQ ID NO 41
<211> LENGTH: 20
<212> TYPE: DNA
<213> ORGANISM: Cananga odorata

<400> SEQUENCE: 41
ggtgtttcgg agagagcttg                                          20

<210> SEQ ID NO 42
<211> LENGTH: 20
<212> TYPE: DNA
<213> ORGANISM: Cananga odorata

<400> SEQUENCE: 42
acccccatgc actgaagtag                                          20

<210> SEQ ID NO 43
<211> LENGTH: 20
<212> TYPE: DNA
<213> ORGANISM: Cananga odorata

<400> SEQUENCE: 43
tgctcctcga tgctacaatg                                              20

<210> SEQ ID NO 44
<211> LENGTH: 20
<212> TYPE: DNA
<213> ORGANISM: Cananga odorata

<400> SEQUENCE: 44
agggtcttct ctgaccagca                                              20

<210> SEQ ID NO 45
<211> LENGTH: 20
<212> TYPE: DNA
<213> ORGANISM: Cananga odorata

<400> SEQUENCE: 45
cccatcaatg acagcatcag                                              20

<210> SEQ ID NO 46
<211> LENGTH: 20
<212> TYPE: DNA
<213> ORGANISM: Cananga odorata

<400> SEQUENCE: 46
cgtattcgga tctccctcaa                                              20

<210> SEQ ID NO 47
<211> LENGTH: 20
<212> TYPE: DNA
<213> ORGANISM: Cananga odorata

<400> SEQUENCE: 47
atcctccatc ttccctgctt                                              20

<210> SEQ ID NO 48
<211> LENGTH: 20
<212> TYPE: DNA
<213> ORGANISM: Cananga odorata

<400> SEQUENCE: 48
ttcttggatt tccagccatc                                              20

<210> SEQ ID NO 49
<211> LENGTH: 20
<212> TYPE: DNA
<213> ORGANISM: Cananga odorata

<400> SEQUENCE: 49
cctttccttc cgctttctct                                              20

<210> SEQ ID NO 50
<211> LENGTH: 20
<212> TYPE: DNA
<213> ORGANISM: Cananga odorata

<400> SEQUENCE: 50
ttccatgaac atgcctttga                                                  20

<210> SEQ ID NO 51
<211> LENGTH: 20
<212> TYPE: DNA
<213> ORGANISM: Cananga odorata

<400> SEQUENCE: 51
tgatcagcta gagcgcagaa                                                  20

<210> SEQ ID NO 52
<211> LENGTH: 20
<212> TYPE: DNA
<213> ORGANISM: Cananga odorata

<400> SEQUENCE: 52
ccatctgttc gacggatttt                                                  20

<210> SEQ ID NO 53
<211> LENGTH: 20
<212> TYPE: DNA
<213> ORGANISM: Cananga odorata

<400> SEQUENCE: 53
caccgttccg aagatttgtt                                                  20

<210> SEQ ID NO 54
<211> LENGTH: 20
<212> TYPE: DNA
<213> ORGANISM: Cananga odorata

<400> SEQUENCE: 54
ccagacccca tcataccaac                                                  20

<210> SEQ ID NO 55
<211> LENGTH: 20
<212> TYPE: DNA
<213> ORGANISM: Cananga odorata

<400> SEQUENCE: 55
gctgctggaa gttcttttgg                                                  20

<210> SEQ ID NO 56
<211> LENGTH: 20
<212> TYPE: DNA
<213> ORGANISM: Cananga odorata

<400> SEQUENCE: 56
tctgtcctgg cctccttcta                                                  20

<210> SEQ ID NO 57
<211> LENGTH: 20
<212> TYPE: DNA
<213> ORGANISM: Cananga odorata

<400> SEQUENCE: 57
aatctctcag ggggaaggaa                                                  20

<210> SEQ ID NO 58
<211> LENGTH: 20
<212> TYPE: DNA
<213> ORGANISM: Cananga odorata

<400> SEQUENCE: 58 caacccagc gagtttacat                    20

<210> SEQ ID NO 59
<211> LENGTH: 20
<212> TYPE: DNA
<213> ORGANISM: Cananga odorata

<400> SEQUENCE: 59
ttaacggcag gaagagccta                    20

<210> SEQ ID NO 60
<211> LENGTH: 20
<212> TYPE: DNA
<213> ORGANISM: Cananga odorata

<400> SEQUENCE: 60
atcacggcct tcatttcttg                    20

<210> SEQ ID NO 61
<211> LENGTH: 20
<212> TYPE: DNA
<213> ORGANISM: Cananga odorata

<400> SEQUENCE: 61
ttctgttcct caagcggagt                    20

<210> SEQ ID NO 62
<211> LENGTH: 20
<212> TYPE: DNA
<213> ORGANISM: Cananga odorata

<400> SEQUENCE: 62
cggaagtagc ccacattcat                    20

<210> SEQ ID NO 63
<211> LENGTH: 20
<212> TYPE: DNA
<213> ORGANISM: Cananga odorata

<400> SEQUENCE: 63
catgagcatg gtcaggaaga                    20

<210> SEQ ID NO 64
<211> LENGTH: 20
<212> TYPE: DNA
<213> ORGANISM: Cananga odorata

<400> SEQUENCE: 64
gcacagcaac tcactttcca                    20

<210> SEQ ID NO 65
<211> LENGTH: 20
<212> TYPE: DNA
<213> ORGANISM: Cananga odorata

<400> SEQUENCE: 65
tatctctggt ggggatcgac                    20

<210> SEQ ID NO 66
<211> LENGTH: 20
<212> TYPE: DNA
<213> ORGANISM: Cananga odorata

```
<400> SEQUENCE: 66
ctgcttctcc ctgaagatgg                                                    20

<210> SEQ ID NO 67
<211> LENGTH: 20
<212> TYPE: DNA
<213> ORGANISM: Cananga odorata

<400> SEQUENCE: 67
gcaatggtga ttggtcctct                                                    20

<210> SEQ ID NO 68
<211> LENGTH: 20
<212> TYPE: DNA
<213> ORGANISM: Cananga odorata

<400> SEQUENCE: 68
gaagcggaat tgatgggtaa                                                    20

<210> SEQ ID NO 69
<211> LENGTH: 20
<212> TYPE: DNA
<213> ORGANISM: Cananga odorata

<400> SEQUENCE: 69
acccacaagc ttccctacct                                                    20

<210> SEQ ID NO 70
<211> LENGTH: 20
<212> TYPE: DNA
<213> ORGANISM: Cananga odorata

<400> SEQUENCE: 70
aggtaccagg cattcaccag                                                    20

<210> SEQ ID NO 71
<211> LENGTH: 20
<212> TYPE: DNA
<213> ORGANISM: Cananga odorata

<400> SEQUENCE: 71
gttgcacctg cagaacttga                                                    20

<210> SEQ ID NO 72
<211> LENGTH: 20
<212> TYPE: DNA
<213> ORGANISM: Cananga odorata

<400> SEQUENCE: 72
accttccgca gtctcttgaa                                                    20

<210> SEQ ID NO 73
<211> LENGTH: 20
<212> TYPE: DNA
<213> ORGANISM: Cananga odorata

<400> SEQUENCE: 73
ggagcgatct ggactactgc                                                    20

<210> SEQ ID NO 74
<211> LENGTH: 20
<212> TYPE: DNA
<213> ORGANISM: Cananga odorata
```

<400> SEQUENCE: 74
gaacatcgac gtaggcctgt                                               20

<210> SEQ ID NO 75
<211> LENGTH: 20
<212> TYPE: DNA
<213> ORGANISM: Cananga odorata

<400> SEQUENCE: 75
gcatgctcac tcattctgga                                               20

<210> SEQ ID NO 76
<211> LENGTH: 20
<212> TYPE: DNA
<213> ORGANISM: Cananga odorata

<400> SEQUENCE: 76
cccaaagact ttttccgtga                                               20

<210> SEQ ID NO 77
<211> LENGTH: 20
<212> TYPE: DNA
<213> ORGANISM: Cananga odorata

<400> SEQUENCE: 77
acgctccagg agaagtacga                                               20

<210> SEQ ID NO 78
<211> LENGTH: 20
<212> TYPE: DNA
<213> ORGANISM: Cananga odorata

<400> SEQUENCE: 78
cacacggtcc aattcctctt                                               20

<210> SEQ ID NO 79
<211> LENGTH: 20
<212> TYPE: DNA
<213> ORGANISM: Cananga odorata

<400> SEQUENCE: 79
actctccagt gcctgtgctt                                               20

<210> SEQ ID NO 80
<211> LENGTH: 20
<212> TYPE: DNA
<213> ORGANISM: Cananga odorata

<400> SEQUENCE: 80
agctgcccgt tgtctagtgt                                               20

<210> SEQ ID NO 81
<211> LENGTH: 20
<212> TYPE: DNA
<213> ORGANISM: Cananga odorata

<400> SEQUENCE: 81
ttggatacca gcgtctaccc                                               20

<210> SEQ ID NO 82
<211> LENGTH: 20
<212> TYPE: DNA

<213> ORGANISM: Cananga odorata

<400> SEQUENCE: 82
ctcacggttg atgtccattg                                       20

<210> SEQ ID NO 83
<211> LENGTH: 20
<212> TYPE: DNA
<213> ORGANISM: Cananga odorata

<400> SEQUENCE: 83
aaagtgggaa caacgaatgc                                       20

<210> SEQ ID NO 84
<211> LENGTH: 20
<212> TYPE: DNA
<213> ORGANISM: Cananga odorata

<400> SEQUENCE: 84
accgacctct ttgaccacac                                       20

<210> SEQ ID NO 85
<211> LENGTH: 24
<212> TYPE: DNA
<213> ORGANISM: Cananga odorata

<400> SEQUENCE: 85
agggccttcc agattacatg aagc                                  24

<210> SEQ ID NO 86
<211> LENGTH: 24
<212> TYPE: DNA
<213> ORGANISM: Cananga odorata

<400> SEQUENCE: 86
agcgttggag tgtacttgct attg                                  24

<210> SEQ ID NO 87
<211> LENGTH: 27
<212> TYPE: DNA
<213> ORGANISM: Cananga odorata

<400> SEQUENCE: 87
catcgatcat ggatgacaca tatgatg                               27

<210> SEQ ID NO 88
<211> LENGTH: 23
<212> TYPE: DNA
<213> ORGANISM: Cananga odorata

<400> SEQUENCE: 88
ctcaacagca gtcagaaggg cac                                   23

<210> SEQ ID NO 89
<211> LENGTH: 20
<212> TYPE: DNA
<213> ORGANISM: Cananga odorata

<400> SEQUENCE: 89
aggctgtggc tgaacctcta                                       20

<210> SEQ ID NO 90
<211> LENGTH: 20

```
<212> TYPE: DNA
<213> ORGANISM: Cananga odorata

<400> SEQUENCE: 90
agcagatcct tcttgctgga                                              20

<210> SEQ ID NO 91
<211> LENGTH: 24
<212> TYPE: DNA
<213> ORGANISM: Cananga odorata

<400> SEQUENCE: 91
tagccatctt actggtgatt gacg                                         24

<210> SEQ ID NO 92
<211> LENGTH: 25
<212> TYPE: DNA
<213> ORGANISM: Cananga odorata

<400> SEQUENCE: 92
gtagtgttgt acaatgccat gtaac                                        25

<210> SEQ ID NO 93
<211> LENGTH: 23
<212> TYPE: DNA
<213> ORGANISM: Cananga odorata

<400> SEQUENCE: 93
ctggacgtga cctcacagat gct                                          23

<210> SEQ ID NO 94
<211> LENGTH: 24
<212> TYPE: DNA
<213> ORGANISM: Cananga odorata

<400> SEQUENCE: 94
tcttctcaac agaggagctg ctct                                         24

<210> SEQ ID NO 95
<211> LENGTH: 33
<212> TYPE: DNA
<213> ORGANISM: Cananga odorata

<400> SEQUENCE: 95
caccatggcc ttgaatacgt tcttgcattt tcc                               33

<210> SEQ ID NO 96
<211> LENGTH: 30
<212> TYPE: DNA
<213> ORGANISM: Cananga odorata

<400> SEQUENCE: 96
ctcaagcacg atgggttcaa cggtaagtga                                   30

<210> SEQ ID NO 97
<211> LENGTH: 36
<212> TYPE: DNA
<213> ORGANISM: Cananga odorata

<400> SEQUENCE: 97
caccatggca cttatatttg caaatggcca ctctga                            36

<210> SEQ ID NO 98
```

```
<211> LENGTH: 31
<212> TYPE: DNA
<213> ORGANISM: Cananga odorata

<400> SEQUENCE: 98
atcaacaaaa cggtccacta gcaccatcgc a                              31

<210> SEQ ID NO 99
<211> LENGTH: 38
<212> TYPE: DNA
<213> ORGANISM: Cananga odorata

<400> SEQUENCE: 99
caccatgaat cctgtttctc ttttgagctt atcaggag                       38

<210> SEQ ID NO 100
<211> LENGTH: 31
<212> TYPE: DNA
<213> ORGANISM: Cananga odorata

<400> SEQUENCE: 100
aacttgttgg gaaaatagag ccatggcttg a                              31

<210> SEQ ID NO 101
<211> LENGTH: 34
<212> TYPE: DNA
<213> ORGANISM: Cananga odorata

<400> SEQUENCE: 101
caccatggct gctacgagaa acctttcttt actt                           34

<210> SEQ ID NO 102
<211> LENGTH: 29
<212> TYPE: DNA
<213> ORGANISM: Cananga odorata

<400> SEQUENCE: 102
attgaaaggc gtgaaaaaca aagcttgca                                 29

<210> SEQ ID NO 103
<211> LENGTH: 37
<212> TYPE: DNA
<213> ORGANISM: Cananga odorata

<400> SEQUENCE: 103
aaggatccga tggccttgaa tacgttcttg cattttc                        37

<210> SEQ ID NO 104
<211> LENGTH: 34
<212> TYPE: DNA
<213> ORGANISM: Cananga odorata

<400> SEQUENCE: 104
aagcggccgc ttactcaagc acgatgggtt caac                           34

<210> SEQ ID NO 105
<211> LENGTH: 41
<212> TYPE: DNA
<213> ORGANISM: Cananga odorata

<400> SEQUENCE: 105
aacgtcgaca tggcacttat atttgcaaat ggccactctg a                   41
```

<210> SEQ ID NO 106
<211> LENGTH: 37
<212> TYPE: DNA
<213> ORGANISM: Cananga odorata

<400> SEQUENCE: 106
aaagcggccg cttaatcaac aaaacggtcc actagca        37

<210> SEQ ID NO 107
<211> LENGTH: 44
<212> TYPE: DNA
<213> ORGANISM: Cananga odorata

<400> SEQUENCE: 107
aacggatccg atgaatcctg tttctctttt gagcttatca ggag        44

<210> SEQ ID NO 108
<211> LENGTH: 37
<212> TYPE: DNA
<213> ORGANISM: Cananga odorata

<400> SEQUENCE: 108
aacgtcgaca acttgttggg aaaatagagc catggct        37

<210> SEQ ID NO 109
<211> LENGTH: 40
<212> TYPE: DNA
<213> ORGANISM: Cananga odorata

<400> SEQUENCE: 109
aaaggatcct atggctgcta cgagaaacct ttctttactt        40

<210> SEQ ID NO 110
<211> LENGTH: 38
<212> TYPE: DNA
<213> ORGANISM: Cananga odorata

<400> SEQUENCE: 110
aaagtcgaca ttgaaaggcg tgaaaaacaa agcttgca        38

<210> SEQ ID NO 111
<211> LENGTH: 478
<212> TYPE: PRT
<213> ORGANISM: Cananga odorata

<400> SEQUENCE: 111

Met Pro Leu Ser Leu Cys Thr Ala Met Ala Leu Lys Phe Ser Phe Ser
1               5                   10                  15

Pro Glu Ile Ser Gly Ile Ser Phe Lys Gly Ser Ser Arg Gly Asn Leu
            20                  25                  30

His Lys Leu Gln Gly Gly Phe Ala Phe Lys Gly Lys Glu Ser Arg Thr
        35                  40                  45

Ser Val Arg Val Gly Ile Ser Cys Leu Ala Lys Ala Pro Pro Ala
    50                  55                  60

Trp Pro Gly Arg Ala Val Pro Glu Pro Ser Lys Arg Thr Trp Val Gly
65                  70                  75                  80

Pro Lys Pro Ile Ser Ile Val Gly Ser Thr Gly Ser Ile Gly Thr Gln
                85                  90                  95

Thr Leu Asp Ile Val Ala Glu Asn Pro Asp Lys Phe Lys Val Val Ala
            100                 105                 110

Leu Ala Ala Gly Ser Asn Val Thr Leu Leu Ala Asp Gln Val Lys Thr

```
                115                 120                 125
Phe Arg Pro Gln Leu Val Ser Ile Arg Asn Glu Ser Leu Ile Gly Glu
130                 135                 140

Leu Lys Glu Ala Leu Ala Asp Ala Asp Tyr Lys Pro Glu Ile Ile Pro
145                 150                 155                 160

Gly Glu Glu Gly Leu Ile Glu Val Ala Arg His Pro Asp Ala Met Thr
                165                 170                 175

Val Val Thr Gly Ile Val Gly Cys Ala Gly Leu Lys Pro Thr Val Ala
            180                 185                 190

Ala Ile Glu Ala Gly Lys Asp Ile Ala Leu Ala Asn Lys Glu Thr Leu
        195                 200                 205

Ile Ala Gly Gly Pro Phe Val Leu Pro Leu Ala His Lys His Lys Val
    210                 215                 220

Lys Ile Leu Pro Ala Asp Ser Glu His Ser Ala Ile Phe Gln Cys Ile
225                 230                 235                 240

Gln Gly Leu Pro Glu Gly Ala Leu Arg Arg Ile Ile Leu Thr Ala Ser
                245                 250                 255

Gly Gly Ala Phe Arg Asp Leu Pro Val Glu Lys Leu Lys Glu Val Lys
            260                 265                 270

Val Ala Asp Ala Leu Lys His Pro Asn Trp Ser Met Gly Lys Lys Ile
        275                 280                 285

Thr Val Asp Ser Ala Thr Leu Phe Asn Lys Gly Leu Glu Val Ile Glu
    290                 295                 300

Ala His Tyr Leu Phe Gly Ala Glu Tyr Asp Asn Ile Glu Ile Val Ile
305                 310                 315                 320

His Ala Gln Ser Ile Ile His Ser Met Ile Glu Thr Gln Asp Ser Ser
                325                 330                 335

Val Leu Ala Gln Leu Gly Leu Pro Asp Met Arg Leu Pro Ile Leu Tyr
            340                 345                 350

Thr Leu Ser Trp Pro Glu Arg Ile Phe Cys Ser Glu Val Thr Trp Pro
        355                 360                 365

Arg Leu Asp Leu Cys Lys Leu Gly Ser Leu Thr Phe Arg Ala Pro Asp
370                 375                 380

Asn Ala Lys Tyr Pro Ser Met Glu Leu Ala Tyr Ala Ala Gly Arg Ala
385                 390                 395                 400

Gly Gly Thr Met Thr Gly Val Leu Ser Ala Ala Asn Glu Lys Ala Val
                405                 410                 415

Glu Met Phe Ile Asp Glu Lys Ile Ser Tyr Leu Asp Ile Phe Lys Thr
            420                 425                 430

Val Glu Ala Thr Cys Asp Ala His Cys Ser Glu Leu Val Thr Ser Pro
        435                 440                 445

Ser Leu Glu Glu Ile Val His Tyr Asp Leu Trp Ala Arg Asp Tyr Ala
    450                 455                 460

Ala Ser Leu Gln Pro Ser Ser Asp Leu Arg Pro Val Leu Ala
465                 470                 475

<210> SEQ ID NO 112
<211> LENGTH: 467
<212> TYPE: PRT
<213> ORGANISM: Ricinus communis

<400> SEQUENCE: 112

Met Ala Leu Asn Leu Leu Ser Pro Ala Glu Leu Lys Ser Val Ser Phe
1               5                   10                  15
```

Leu Asp Ser Thr Arg Ser Ser Gln Leu Pro Lys Leu Pro Gly Ser Phe
            20                  25                  30

Ser Leu Lys Arg Lys Glu Phe Gly Arg Lys Val Gln Cys Ser Ala Gln
        35                  40                  45

Ala Pro Pro Ala Trp Pro Gly Arg Ala Val Ala Glu Pro Gly Arg
50                  55                  60

Lys Thr Trp Asp Gly Pro Lys Pro Ile Ser Ile Val Gly Ser Thr Gly
65                  70                  75                  80

Ser Ile Gly Thr Gln Thr Leu Asp Ile Val Ala Glu Asn Pro Asp Lys
                85                  90                  95

Phe Arg Val Val Ala Leu Ala Ala Gly Ser Asn Val Thr Leu Leu Ala
            100                 105                 110

Asp Gln Val Lys Thr Phe Lys Pro Gln Leu Val Ser Val Arg Asp Glu
            115                 120                 125

Ser Leu Val Asp Glu Leu Lys Glu Ala Leu Ala Asp Val Asp Glu Lys
        130                 135                 140

Pro Glu Ile Ile Pro Gly Glu Gln Gly Ile Val Glu Val Ala Arg His
145                 150                 155                 160

Pro Asp Ala Val Ser Val Val Thr Gly Ile Val Gly Cys Ala Gly Leu
                165                 170                 175

Lys Pro Thr Val Ala Ala Ile Glu Ala Gly Lys Asp Ile Cys Leu Ala
            180                 185                 190

Asn Lys Glu Thr Leu Ile Ala Gly Gly Pro Phe Val Leu Pro Leu Ala
        195                 200                 205

His Lys Tyr Asn Val Lys Ile Leu Pro Ala Asp Ser Glu His Ser Ala
210                 215                 220

Ile Phe Gln Cys Ile Gln Gly Leu Pro Glu Gly Ala Leu Arg Arg Ile
225                 230                 235                 240

Ile Leu Thr Ala Ser Gly Gly Ala Phe Arg Asp Trp Pro Val Glu Lys
                245                 250                 255

Leu Lys Asp Val Lys Val Ala Asp Ala Leu Lys His Pro Asn Trp Asn
            260                 265                 270

Met Gly Lys Lys Ile Thr Val Asp Ser Ala Thr Leu Phe Asn Lys Gly
        275                 280                 285

Leu Glu Val Ile Glu Ala His Tyr Leu Phe Gly Ala Asp Tyr Asp Asn
290                 295                 300

Ile Glu Ile Val Ile His Pro Gln Ser Ile Ile His Ser Met Val Glu
305                 310                 315                 320

Thr Glu Asp Ser Ser Val Leu Ala Gln Leu Gly Trp Pro Asp Met Arg
                325                 330                 335

Ile Pro Ile Leu Tyr Thr Met Ser Trp Pro Asp Arg Ile Tyr Cys Ser
            340                 345                 350

Glu Ile Thr Trp Pro Arg Leu Asp Leu Cys Lys Leu Gly Ser Leu Thr
        355                 360                 365

Phe Lys Ala Pro Asp Asn Val Lys Tyr Pro Ser Met Glu Leu Ala Tyr
370                 375                 380

Ala Ala Gly Arg Ala Gly Gly Thr Met Thr Gly Val Leu Ser Ala Ala
385                 390                 395                 400

Asn Glu Lys Ala Val Glu Met Phe Ile Asp Glu Gln Ile Ser Tyr Leu
                405                 410                 415

Asp Ile Phe Lys Ile Val Glu Leu Thr Cys Asp Lys His Arg Ala Glu
            420                 425                 430

Leu Val Thr Ser Pro Ser Leu Glu Glu Ile Ile His Tyr Asp Leu Trp

```
            435                 440                 445
Ala Arg Glu Tyr Ala Ala Ser Leu Gln Pro Ser Ser Gly Leu Ser Pro
    450                 455                 460

Val Leu Ala
465

<210> SEQ ID NO 113
<211> LENGTH: 478
<212> TYPE: PRT
<213> ORGANISM: Eucommia ulmoides

<400> SEQUENCE: 113

Met Ala Leu Asn Leu Leu Pro Arg Thr Glu Phe Asn Pro Val Ser Phe
1               5                   10                  15

Phe His Thr Ser Lys Ser Asn Arg Asn Leu Phe Asn Leu Gln Gly Gly
                20                  25                  30

Phe Ala Phe Lys Arg Lys Asp Ile Gly Ala Thr Asn Gly Leu Arg Val
            35                  40                  45

His Cys Ser Ala Glu Glu Val Gly Val Ala Val Ala Pro Pro Pro Ala
        50                  55                  60

Trp Pro Gly Arg Ala Val Val Glu Pro Gly Arg Lys Ser Trp Asp Gly
65                  70                  75                  80

Pro Lys Pro Ile Ser Ile Val Gly Ser Thr Gly Ser Ile Gly Thr Gln
                85                  90                  95

Thr Leu Asp Ile Val Ala Glu Asn Pro Asp Lys Phe Lys Val Val Ala
                100                 105                 110

Leu Ala Ala Gly Ser Asn Val Thr Leu Leu Ala Asp Gln Val Lys Thr
            115                 120                 125

Phe Lys Pro Gln Leu Val Ala Val Arg Asn Glu Ser Leu Val Asp Glu
        130                 135                 140

Leu Lys Glu Ala Leu Ala Asp Ala Glu Tyr Thr Pro Glu Ile Ile Pro
145                 150                 155                 160

Gly Glu Gln Gly Val Ile Glu Val Ala Arg His Pro Asp Ala Val Thr
                165                 170                 175

Val Val Thr Gly Ile Val Gly Cys Ala Gly Leu Lys Pro Thr Val Ala
                180                 185                 190

Ala Ile Glu Ala Gly Lys Asp Ile Ala Leu Ala Asn Lys Glu Thr Leu
            195                 200                 205

Ile Ala Gly Gly Pro Phe Val Leu Pro Leu Ala His Lys His Asn Val
210                 215                 220

Lys Ile Leu Pro Ala Asp Ser Glu His Ser Ala Ile Phe Gln Cys Ile
225                 230                 235                 240

Gln Gly Leu Pro Glu Gly Ala Leu Arg Arg Ile Ile Leu Thr Ala Ser
                245                 250                 255

Gly Gly Ala Phe Arg Asp Leu Pro Val Asp Lys Leu Lys Asp Val Lys
            260                 265                 270

Val Ala Asp Ala Leu Lys His Pro Asn Trp Asn Met Gly Lys Lys Ile
        275                 280                 285

Thr Val Asp Ser Ala Thr Leu Phe Asn Lys Gly Leu Glu Val Ile Glu
    290                 295                 300

Ala His Tyr Leu Phe Gly Ala Glu Tyr Asp Asp Ile Glu Ile Val Ile
305                 310                 315                 320

His Pro Gln Ser Ile Ile His Ser Met Ile Glu Thr Gln Asp Ser Ser
                325                 330                 335
```

Val Leu Ala Gln Leu Gly Trp Pro Asp Met Arg Leu Pro Ile Leu Tyr
            340                 345                 350

Thr Met Ser Trp Pro Asp Arg Ile Phe Cys Ser Glu Ile Thr Trp Pro
            355                 360                 365

Arg Leu Asp Leu Cys Lys Leu Gly Ser Leu Thr Phe Lys Met Pro Asp
        370                 375                 380

Asn Val Lys Tyr Pro Ser Met Asp Leu Ala Tyr Ala Ala Gly Arg Ala
385                 390                 395                 400

Gly Gly Thr Met Thr Gly Val Leu Ser Ala Ala Asn Glu Lys Ala Val
                405                 410                 415

Glu Met Phe Ile Asp Glu Lys Ile Gly Tyr Leu Asp Ile Phe Lys Val
            420                 425                 430

Val Glu Leu Thr Cys Asp Lys His Arg Ala Glu Leu Val Ser Ser Pro
        435                 440                 445

Ser Leu Asp Glu Ile Val His Tyr Asp Leu Trp Ala Arg Lys Tyr Ala
    450                 455                 460

Ala Ser Leu Gln Pro Ser Ser Gly Leu Ser Pro Ala Leu Val
465                 470                 475

<210> SEQ ID NO 114
<211> LENGTH: 472
<212> TYPE: PRT
<213> ORGANISM: Zea mays

<400> SEQUENCE: 114

Met Ala Ala Leu Lys Ala Ser Phe Arg Gly Glu Leu Ser Ala Ala Ser
1               5                   10                  15

Phe Leu Asp Ser Ser Arg Gly Pro Leu Val Gln His Lys Val Asp Phe
            20                  25                  30

Thr Phe Gln Arg Lys Gly Lys Arg Ala Ile Ser Leu Arg Arg Thr Cys
        35                  40                  45

Cys Ser Met Gln Gln Ala Pro Pro Ala Trp Pro Gly Arg Ala Val
    50                  55                  60

Ala Glu Pro Gly Arg Arg Ser Trp Asp Gly Lys Pro Ile Ser Ile
65              70                  75                  80

Val Gly Ser Thr Gly Ser Ile Gly Thr Gln Thr Leu Asp Ile Val Ala
                85                  90                  95

Glu Asn Pro Asp Lys Phe Arg Val Val Ala Leu Ala Ala Gly Ser Asn
            100                 105                 110

Val Thr Leu Leu Ala Asp Gln Val Lys Thr Phe Lys Pro Lys Leu Val
        115                 120                 125

Ala Val Arg Asn Glu Ser Leu Val Asp Glu Leu Lys Glu Ala Leu Ala
    130                 135                 140

Asp Cys Glu Glu Lys Pro Glu Ile Ile Pro Gly Glu Gln Gly Val Ile
145                 150                 155                 160

Glu Val Ala Arg His Pro Asp Ala Val Thr Val Thr Gly Ile Val
                165                 170                 175

Gly Cys Ala Gly Leu Lys Pro Thr Val Ala Ala Ile Glu Ala Gly Lys
            180                 185                 190

Asp Ile Ala Leu Ala Asn Lys Glu Thr Leu Ile Ala Gly Gly Pro Phe
        195                 200                 205

Val Leu Pro Leu Ala His Lys His Lys Val Lys Ile Leu Pro Ala Asp
    210                 215                 220

Ser Glu His Ser Ala Ile Phe Gln Cys Ile Gln Gly Leu Ser Glu Gly
225                 230                 235                 240

Ala Leu Arg Arg Ile Ile Leu Thr Ala Ser Gly Ala Phe Arg Asp
            245                 250                 255

Trp Pro Val Asp Arg Leu Lys Asp Val Lys Val Ala Asp Ala Leu Lys
        260                 265                 270

His Pro Asn Trp Asn Met Gly Arg Lys Ile Thr Val Asp Ser Ala Thr
        275                 280                 285

Leu Phe Asn Lys Gly Leu Glu Val Ile Glu Ala His Tyr Leu Phe Gly
        290                 295                 300

Ala Glu Tyr Asp Asp Ile Glu Ile Val Ile His Pro Gln Ser Ile Ile
305                 310                 315                 320

His Ser Met Val Glu Thr Gln Asp Ser Ser Val Leu Ala Gln Leu Gly
                325                 330                 335

Trp Pro Asp Met Arg Leu Pro Ile Leu Tyr Thr Leu Ser Trp Pro Asp
                340                 345                 350

Arg Ile Tyr Cys Ser Glu Val Thr Trp Pro Arg Leu Asp Leu Cys Lys
            355                 360                 365

Leu Gly Ser Leu Thr Phe Arg Ala Pro Asp Asn Val Lys Tyr Pro Ser
        370                 375                 380

Met Asp Leu Ala Tyr Ala Ala Gly Arg Ala Gly Gly Thr Met Thr Gly
385                 390                 395                 400

Val Leu Ser Ala Ala Asn Glu Lys Ala Val Glu Leu Phe Ile Asp Glu
                405                 410                 415

Lys Ile Ser Tyr Leu Asp Ile Phe Lys Val Val Glu Leu Thr Cys Asn
            420                 425                 430

Ala His Arg Asn Glu Leu Val Thr Ser Pro Ser Leu Glu Glu Ile Val
        435                 440                 445

His Tyr Asp Leu Trp Ala Arg Arg Tyr Ala Ala Ser Leu Gln Pro Ser
    450                 455                 460

Ser Gly Leu Ser Pro Val Pro Ala
465                 470

<210> SEQ ID NO 115
<211> LENGTH: 408
<212> TYPE: PRT
<213> ORGANISM: Cananga odorata

<400> SEQUENCE: 115

Met Ala Ser Thr His Phe Val Cys Gln His Phe Leu Leu Ser Ser Phe
1               5                   10                  15

Gly Asn Lys Gly Asn Thr Pro Gly Ser Ser Leu Ser Tyr Lys Asn Ser
            20                  25                  30

Ser Leu Phe Thr Pro Leu Arg His Arg Arg Ala Ser Leu Gly Lys Ser
        35                  40                  45

Thr Gln Lys Gln Arg Tyr Pro His Val Arg Ala Thr Ala Ser Asp Ser
    50                  55                  60

Lys Ala Ser Arg Lys Gln Val Glu Ile Val Tyr Asp Pro Asp Glu Arg
65                  70                  75                  80

Leu Asn Arg Leu Ala Asp Glu Val Asp Lys Asn Ala Gly Leu Gln Arg
                85                  90                  95

Leu Ser Leu Phe Ser Pro Cys Lys Ile Asn Val Phe Leu Arg Ile Thr
            100                 105                 110

Arg Lys Arg Glu Asp Gly Phe His Asp Leu Ala Ser Leu Phe His Val
        115                 120                 125

Ile Ser Leu Gly Asp Thr Ile Lys Phe Ser Leu Ser Pro Thr Arg Lys

```
        130                 135                 140
Lys Asp Gln Leu Ser Thr Asn Val Pro Gly Val Pro Leu Asp Asp Arg
145                 150                 155                 160

Asn Leu Ile Ile Lys Ala Leu Asn Leu Tyr Arg Glu Lys Thr Gly Thr
                165                 170                 175

Asp Asn Tyr Phe Trp Ile His Leu Asp Lys Lys Val Pro Thr Gly Ala
            180                 185                 190

Gly Leu Gly Gly Gly Ser Ser Asn Ala Ala Thr Ala Leu Trp Ala Ala
        195                 200                 205

Asn Gln Phe Ser Gly Gly Leu Ala Thr Glu Lys Glu Leu Gln Glu Trp
    210                 215                 220

Ser Gly Glu Ile Gly Ser Asp Cys Pro Phe Phe Ser His Gly Ala
225                 230                 235                 240

Ala Tyr Cys Thr Gly Arg Gly Glu Val Val Glu Asp Leu Pro Pro Pro
                245                 250                 255

Ile Pro Leu Asp Ile Pro Met Val Leu Ile Lys Pro Pro Gln Ala Cys
            260                 265                 270

Pro Thr Gly Glu Val Tyr Lys Arg Leu Arg Leu Asp Gln Thr Asn Ser
        275                 280                 285

Val Asp Pro Leu Thr Leu Leu Glu Asn Ile Thr Arg Thr Gly Ile Ser
    290                 295                 300

Gln Asp Val Cys Val Asn Asp Leu Glu Pro Pro Ala Phe Glu Val Leu
305                 310                 315                 320

Pro Ser Leu Lys Leu Leu Lys Lys Arg Ile Leu Ala Ala Gly Arg Gly
                325                 330                 335

Glu Tyr Asp Ala Val Phe Met Ser Gly Ser Gly Ser Thr Ile Val Gly
            340                 345                 350

Ile Gly Ser Pro Glu Pro Pro Gln Phe Val Tyr Asp Glu Asp Glu His
        355                 360                 365

Arg Asp Thr Phe Val Ser Glu Ala Arg Phe Leu Thr Arg Gly Glu Asn
    370                 375                 380

Gln Trp Tyr Thr Glu Met Ser Ser Thr Ala Ser Ser Phe Glu Ser Arg
385                 390                 395                 400

Glu Asp Leu Ala Ser Thr Val Gln
                405

<210> SEQ ID NO 116
<211> LENGTH: 408
<212> TYPE: PRT
<213> ORGANISM: Catharanthus roseus

<400> SEQUENCE: 116

Met Ala Ser Ser Gln Ser Leu Cys Gly Tyr Gln Leu Tyr Thr Cys Ser
1               5                   10                  15

Ser Gly Lys Thr Gln Leu Asn Ser Phe Lys Lys Gly Ser Ile Ser Val
                20                  25                  30

Ser Ser Thr Ala Thr Pro His Gly Phe Leu Ser Phe Gly Gln Asn Pro
            35                  40                  45

Gln Phe Gln Arg Ala Leu Phe Val Arg Ala Thr Ala Ser Ser Asp Ser
        50                  55                  60

Lys Thr Gly Arg Lys Gln Val Glu Ile Ile Tyr Asp Pro Glu Glu Glu
65                  70                  75                  80

Leu Asn Lys Leu Ala Asp Glu Val Asp Lys Asn Ala Gly Leu Ser Arg
                85                  90                  95
```

```
Leu Asn Leu Phe Ser Pro Cys Lys Ile Asn Val Phe Leu Arg Ile Thr
                100                 105                 110

Gly Lys Arg Glu Asp Gly Tyr His Asp Leu Ala Ser Leu Phe His Val
            115                 120                 125

Ile Ser Leu Gly Asp Lys Ile Lys Phe Ser Leu Ala Pro Ser Lys Ser
        130                 135                 140

Lys Asp Arg Leu Ser Thr Asn Val Ser Gly Val Pro Leu Asp Asp Lys
145                 150                 155                 160

Asn Leu Ile Ile Lys Ala Leu Asn Leu Tyr Arg Lys Lys Thr Gly Thr
                165                 170                 175

Asp Asn Phe Phe Trp Val His Leu Asp Lys Lys Val Pro Thr Gly Ala
            180                 185                 190

Gly Leu Gly Gly Gly Ser Ser Asn Ala Ala Thr Ala Leu Trp Ala Ala
        195                 200                 205

Asn Gln Phe Ala Gly Gly Ile Ala Ser Glu Asn Asp Leu Gln Glu Trp
210                 215                 220

Ser Ser Glu Ile Gly Ser Asp Ile Pro Phe Phe Ser His Gly Ala
225                 230                 235                 240

Ala Tyr Cys Thr Gly Arg Gly Glu Val Val Gln Asp Ile Pro Ser Pro
                245                 250                 255

Ile Pro Ser Asp Ile Pro Met Val Leu Ile Lys Pro Gln Ala Cys
            260                 265                 270

Ser Thr Ala Glu Val Tyr Lys Arg Leu Arg Leu Glu Thr Ser Lys
        275                 280                 285

Ile Asp Pro Leu Ile Leu Leu Glu Lys Ile Ser Lys Ala Gly Ile Ser
290                 295                 300

Gln Asp Val Cys Val Asn Asp Leu Glu Pro Val Phe Asp Val Leu
305                 310                 315                 320

Pro Ser Leu Lys Arg Leu Lys Gln Arg Val Leu Ala Ala Gly Arg Gly
                325                 330                 335

Gln Tyr Gly Ala Val Phe Met Ser Gly Ser Gly Ser Thr Ile Val Gly
            340                 345                 350

Val Gly Ser Pro Asp Pro Pro Gln Phe Ile Tyr Asp Asp Glu Glu Tyr
        355                 360                 365

Lys Asp Val Ser Leu Ser Glu Ala Ser Phe Leu Thr Arg Pro Pro Asn
370                 375                 380

Gln Trp Tyr Ser Glu Pro Gly Leu Ser Thr Ala Cys Ser Ser Ser Gly
385                 390                 395                 400

Thr Asp Phe Ser Gln Ser Ser Glu
                405

<210> SEQ ID NO 117
<211> LENGTH: 396
<212> TYPE: PRT
<213> ORGANISM: Salvia miltiorrhiz

<400> SEQUENCE: 117

Met Ala Ser Ser Ser Ser Gln Phe Leu Cys Ala His Asn Pro Lys Pro
1               5                   10                  15

His Phe Asn Ser Tyr Thr Asn Ala Thr Leu Pro Gln Phe Ser Ser Phe
            20                  25                  30

Lys Pro Asn Gly Ser Ser Leu Arg Lys Lys Ile Gln Ser Ser Arg
        35                  40                  45

Ile His Leu Ile Arg Ala Thr Ala Ser Asp Ser Thr Thr Gly Arg Lys
    50                  55                  60
```

Gln Leu Glu Val Val Tyr Asp Leu Glu Asn Lys Leu Asn Lys Leu Ala
 65                  70                  75                  80

Asp Glu Val Asp Arg Asp Ala Gly Ile Ser Arg Leu Thr Leu Phe Ser
             85                  90                  95

Pro Cys Lys Ile Asn Val Phe Leu Arg Ile Thr Gly Lys Arg Ala Asp
            100                 105                 110

Gly Phe His Asp Leu Ala Ser Leu Phe His Val Ile Ser Leu Gly Asp
            115                 120                 125

Lys Ile Lys Phe Ser Leu Ser Pro Ser Lys Ser Thr Asp Arg Leu Ser
130                 135                 140

Thr Asn Val Pro Gly Val Pro Leu Asp Glu Arg Asn Leu Ile Ile Lys
145                 150                 155                 160

Ala Leu Asn Leu Phe Arg Lys Lys Thr Gly Val Asp Asn Tyr Phe Trp
                165                 170                 175

Ile His Leu Asp Lys Lys Val Pro Thr Gly Ala Gly Leu Gly Gly Gly
            180                 185                 190

Ser Ser Asn Ala Ala Thr Ala Leu Trp Ala Ala Asn Gln Phe Ser Gly
            195                 200                 205

Cys Val Ala Ser Glu Lys Asp Leu Gln Glu Trp Ser Gly Glu Ile Gly
210                 215                 220

Ser Asp Ile Pro Phe Phe Ser His Gly Ala Ala Tyr Cys Thr Gly
225                 230                 235                 240

Arg Gly Glu Val Val Glu Asp Ile Pro Pro Val Pro Leu Asp Leu
                245                 250                 255

Pro Met Val Leu Ile Lys Pro Gln Glu Ala Cys Pro Thr Gly Glu Val
            260                 265                 270

Tyr Lys Arg Leu Arg Met Asn Gln Thr Ser Gln Ile Asp Pro Leu Val
            275                 280                 285

Leu Leu Glu Lys Ile Ser Lys Gly Gly Ile Ser Gln Asp Val Cys Val
290                 295                 300

Asn Asp Leu Glu Pro Pro Ala Phe Glu Val Val Pro Ser Leu Lys Arg
305                 310                 315                 320

Leu Lys Gln Arg Ile Ala Ala Ala Gly Arg Gly Gln Tyr Asp Ala Val
            325                 330                 335

Phe Met Ser Gly Ser Gly Ser Thr Ile Val Gly Val Gly Ser Pro Asp
            340                 345                 350

Pro Pro Gln Phe Val Tyr Asp Asp Glu Tyr Lys Asn Val Phe Leu
            355                 360                 365

Ser Asp Ala Lys Phe Ile Thr Arg Ser Ala His Gln Trp Tyr Ser Glu
370                 375                 380

Pro Leu Ser Thr Asp Glu Ser Thr Cys Asp Val Glu
385                 390                 395

<210> SEQ ID NO 118
<211> LENGTH: 406
<212> TYPE: PRT
<213> ORGANISM: Lonicera japonica

<400> SEQUENCE: 118

Met Ala Ser Ser His Phe Leu Cys Gly Gln His Leu Tyr Ser Ser Ser
1               5                   10                  15

His Gly Arg Thr Lys Ile Ser Ser Phe Lys Lys Gly Gly Leu Phe Gln
            20                  25                  30

Ser Ser Ser Cys Arg Pro Asn Gly Ser Phe Ser Phe Asp Lys Lys Thr

```
            35                  40                  45
Gln Tyr Gln Arg Thr Gln Leu Val Lys Ser Met Ala Ala Asp Ser Lys
 50                  55                  60

Thr Gly Lys Lys Gln Val Glu Ile Val Tyr Asp Pro Asp Glu Lys Met
 65                  70                  75                  80

Asn Ser Leu Ala Asp Glu Val Asp Lys Asn Ala Gly Leu Ser Arg Leu
                 85                  90                  95

Ser Leu Phe Ser Pro Cys Lys Ile Asn Val Phe Leu Arg Ile Thr Ser
                100                 105                 110

Lys Arg Glu Asp Gly Phe His Asp Leu Ala Ser Leu Phe His Val Ile
            115                 120                 125

Ser Leu Gly Asp Lys Ile Lys Phe Ser Leu Ala Pro Ser Lys Ser Lys
        130                 135                 140

Asp Arg Leu Ser Thr Asn Val Pro Gly Val Pro Leu Asp Ser Asn
145                 150                 155                 160

Leu Ile Ile Lys Ala Leu Asn Leu Tyr Arg Lys Lys Thr Gly Ser Asp
                165                 170                 175

Lys Phe Phe Trp Ile His Leu Asp Lys Lys Val Pro Thr Gly Ala Gly
            180                 185                 190

Leu Gly Gly Gly Ser Ser Asn Ala Ala Thr Ala Leu Trp Ala Ala Asn
        195                 200                 205

Gln Phe Ser Gly Gly Leu Ala Ser Glu Lys Glu Leu Gln Glu Trp Ser
    210                 215                 220

Gly Glu Ile Gly Ser Asp Val Pro Phe Phe Ser His Gly Ala Ala
225                 230                 235                 240

Tyr Cys Thr Gly Arg Gly Glu Val Val Glu Asp Val Thr Leu Pro Ile
                245                 250                 255

Gly Phe Asp Val Pro Met Val Leu Ile Lys Pro Pro Glu Ala Cys Ser
            260                 265                 270

Thr Ala Glu Val Tyr Arg Arg Phe Arg Leu Asp Gln Thr Ser Asn Ile
        275                 280                 285

Asp Pro Gln Thr Leu Leu Glu Lys Ile Ser Leu Asn Gly Ile Ser Pro
290                 295                 300

Asp Val Cys Val Asn Asp Leu Glu Pro Pro Ala Phe Glu Val Leu Pro
305                 310                 315                 320

Ser Leu Lys Arg Leu Lys Gln Arg Ile Ile Ala Ala Gly Arg Gly Glu
                325                 330                 335

Tyr Asp Ala Val Phe Met Ser Gly Ser Gly Ser Thr Ile Val Gly Ile
            340                 345                 350

Gly Ser Pro Asp Pro Pro Gln Phe Val Tyr Asp Glu Asp Tyr Lys
        355                 360                 365

Asp Val Phe Leu Ser Glu Ala Ser Phe Ile Thr Arg Ala Glu Asn Glu
    370                 375                 380

Trp Tyr Thr Glu Pro Phe Ser Thr Asn Asn Ala Ser Ala Pro Ser Gly
385                 390                 395                 400

Leu Ser Tyr Ala Thr Glu
                405

<210> SEQ ID NO 119
<211> LENGTH: 471
<212> TYPE: PRT
<213> ORGANISM: Cananga odorata

<400> SEQUENCE: 119
```

```
Met Asp Ser Gln Lys Asp Val Gly Ile Leu Ala Met Asp Ile Tyr Phe
1               5                   10                  15
Pro Pro Thr Cys Val Leu Gln Asp Ala Leu Glu Asp His Asp Gly Ala
            20                  25                  30
Ser Lys Gly Lys Tyr Thr Ile Gly Leu Gly Gln Asp Cys Met Ala Phe
        35                  40                  45
Cys Thr Glu Val Glu Asp Val Ile Ser Met Ser Leu Thr Val Val Thr
    50                  55                  60
Ser Leu Leu Glu Lys Tyr Gly Val Asp Pro Lys Gln Ile Gly Arg Leu
65              70                  75                  80
Glu Val Gly Ser Glu Thr Val Ile Asp Lys Ser Lys Ser Ile Lys Thr
                85                  90                  95
Trp Leu Met Gln Ile Phe Glu Lys His Gly Asn Thr Asp Ile Glu Gly
            100                 105                 110
Val Asp Ser Thr Asn Ala Cys Tyr Gly Gly Thr Ala Ala Leu Phe Asn
            115                 120                 125
Cys Val Asn Trp Val Glu Ser Ser Trp Asp Gly Arg Phe Gly Leu
    130                 135                 140
Val Val Cys Ala Asp Ser Ala Val Tyr Ala Glu Gly Pro Ala Arg Pro
145             150                 155                 160
Thr Gly Gly Ala Ala Ala Val Ala Met Leu Ile Gly Pro His Ala Pro
                165                 170                 175
Ile Val Phe Glu Asn Lys Tyr Arg Gly Thr His Met Ala His Val Tyr
            180                 185                 190
Asp Phe Tyr Lys Pro Asn Leu Ala Ser Glu Tyr Pro Val Val Asp Gly
        195                 200                 205
Lys Leu Ser Gln Thr Cys Tyr Leu Met Ala Leu Asp Ser Cys Tyr Lys
    210                 215                 220
Arg Phe Ser Ser Lys Tyr Glu Lys Leu Glu Lys Lys Pro Phe Ser Ile
225             230                 235                 240
Ser Asp Ala Asp Tyr Phe Val Phe His Ser Pro Tyr Asn Lys Leu Val
                245                 250                 255
Gln Lys Ser Phe Ala Arg Leu Tyr Tyr Asn Asp Phe Leu Arg Asn Pro
            260                 265                 270
Ser Phe Val Glu Asn Asp Ala Arg Ile Lys Leu Glu Ser Phe Ser Ser
        275                 280                 285
Leu Ser Gly Asp Glu Ser Tyr Gln Asn Arg Asp Leu Glu Lys Val Ser
    290                 295                 300
Gln Gln Val Ala Lys Gln Leu Tyr Asp Ala Lys Val Gln Pro Ser Thr
305             310                 315                 320
Leu Leu Pro Lys Gln Val Gly Asn Met Tyr Thr Ala Ser Leu Tyr Ala
                325                 330                 335
Ala Phe Ala Thr Val Leu His Asn Lys His Ser Thr Leu Glu Gly Lys
            340                 345                 350
Arg Val Val Met Phe Ser Tyr Gly Ser Gly Leu Ser Ser Thr Met Phe
        355                 360                 365
Ser Phe Gly Leu Gln Glu Gly Gln His Pro Phe Ser Leu Ser Asn Ile
    370                 375                 380
Val Ser Leu Leu Asp Val Tyr Arg Lys Leu Glu Ser Arg His Thr Phe
385             390                 395                 400
Pro Pro Glu Lys Phe Val Glu Thr Met Lys Leu Met Glu His Arg Tyr
                405                 410                 415
Gly Gly Lys Asp Phe Val Ile Asp Ile Lys Gly Thr Ser Leu Leu Ser
```

```
                    420              425              430
Pro Gly Thr Phe Tyr Leu Thr Lys Val Asp Ser Met Tyr Arg Arg Tyr
            435              440              445

Tyr Ala Lys Lys Ala Gly Glu Lys Pro Ser Thr Ile Ser Tyr Glu Asn
            450              455              460

Gly Ser Leu Pro Asn Gly His
465             470

<210> SEQ ID NO 120
<211> LENGTH: 470
<212> TYPE: PRT
<213> ORGANISM: Narcissus tazetta

<400> SEQUENCE: 120

Met Glu Thr Lys Ala Lys Asp Val Gly Ile Leu Ala Val Asp Ile Tyr
1               5                   10                  15

Phe Pro Pro Thr Cys Val Gln Gln Ala Glu Leu Glu Ala Tyr Asp Gly
            20                  25                  30

Ala Ser Lys Gly Lys Tyr Thr Ile Gly Leu Gly Gln Asp Cys Leu Ala
        35                  40                  45

Phe Cys Thr Glu Leu Glu Asp Val Ile Ser Met Ser Leu Thr Val Val
    50                  55                  60

Thr Ser Leu Leu Glu Lys Tyr Gln Ile Asp Pro Lys Met Ile Gly Arg
65                  70                  75                  80

Leu Glu Val Gly Thr Glu Thr Val Ile Asp Lys Ser Lys Ser Ile Lys
                85                  90                  95

Thr Trp Leu Met Gln Ile Phe Glu Glu His Gly Asn Thr Asp Ile Glu
            100                 105                 110

Gly Val Asp Ser Thr Asn Ala Cys Tyr Gly Gly Thr Ala Ala Leu Phe
        115                 120                 125

Asn Cys Val Asn Trp Val Glu Ser Asn Ser Trp Asp Gly Arg Tyr Gly
145 130                 135                 140

Leu Val Val Cys Thr Asp Ser Ala Val Tyr Ala Glu Gly Pro Ala Arg
145                 150                 155                 160

Pro Thr Gly Gly Ala Ala Ala Ile Ala Met Leu Ile Gly Pro His Ala
                165                 170                 175

Pro Ile Ala Phe Glu Ser Lys Tyr Arg Gly Thr His Met Ser His Val
            180                 185                 190

Tyr Asp Phe Tyr Lys Pro Asn Leu Ala Ser Glu Tyr Pro Val Val Asp
        195                 200                 205

Gly Lys Leu Ser Gln Thr Cys Tyr Leu Met Ala Leu Asp Ser Cys Tyr
    210                 215                 220

Lys Arg Phe Cys Ala Lys Tyr Glu Lys Phe Glu Gly Lys Gln Phe Ser
225                 230                 235                 240

Ile Ser Asp Ala Asp Tyr Phe Val Phe His Ser Pro Tyr Asn Lys Leu
                245                 250                 255

Val Gln Lys Ser Phe Ala Arg Leu Tyr Phe Asn Asp Phe Met Arg Asn
            260                 265                 270

Ser Ser Ser Val Asp Lys Glu Ala Arg Glu Lys Leu Glu Pro Phe Ser
        275                 280                 285

Ser Leu Ser Gly Asn Glu Ser Tyr Gln Ser Arg Asp Leu Glu Lys Val
    290                 295                 300

Ser Gln Gln Val Ala Lys Asn Leu Tyr Asp Glu Lys Val Gln Pro Ala
305                 310                 315                 320
```

```
Thr Leu Val Pro Lys Gln Val Gly Asn Met Tyr Thr Ala Ser Leu Tyr
            325                 330                 335

Ala Ala Phe Ala Ser Val Leu His Asp Lys His Ser Thr Leu Ala Gly
        340                 345                 350

Gln Arg Ile Val Met Phe Ser Tyr Gly Ser Gly Leu Ser Ser Ser Met
    355                 360                 365

Phe Ser Leu Arg Ile Gln Asp Gly Gln His Pro Phe Ser Leu Ser Asn
370                 375                 380

Ile Asp Asn Val Met Asn Val Ser Gly Lys Leu Glu Ala Arg His Val
385                 390                 395                 400

Phe Pro Pro Glu Lys Phe Val Glu Thr Met Lys Val Met Glu His Arg
                405                 410                 415

Tyr Gly Ala Lys Asp Phe Val Thr Ala Lys Asp Thr Ser Leu Leu Ser
            420                 425                 430

Pro Gly Thr Phe Tyr Leu Thr Gln Val Asp Ser Met Tyr Arg Arg Phe
        435                 440                 445

Tyr Ser Arg Lys Gly Leu Asn Glu Lys Ser Ser Ala Val Ala Asn Gly
    450                 455                 460

Thr Leu Ala Asn Gly His
465                 470

<210> SEQ ID NO 121
<211> LENGTH: 460
<212> TYPE: PRT
<213> ORGANISM: Glycine soja

<400> SEQUENCE: 121

Met Ala Lys Asn Val Gly Ile Leu Ala Ile Asp Ile Tyr Phe Pro Pro
1               5                   10                  15

Thr Cys Ile Gln Gln Glu Leu Leu Glu Ala His Asp Gly Ala Ser Lys
            20                  25                  30

Gly Lys Tyr Thr Ile Gly Leu Gly Gln Asp Cys Met Ala Phe Cys Thr
        35                  40                  45

Glu Val Glu Asp Val Ile Ser Met Ser Leu Thr Val Val Ser Ser Leu
    50                  55                  60

Leu Glu Lys Tyr Ala Ile Asp Pro Lys Gln Ile Gly Arg Leu Glu Val
65                  70                  75                  80

Gly Ser Glu Thr Val Ile Asp Lys Ser Lys Ser Ile Lys Thr Phe Ile
                85                  90                  95

Met Gln Ile Phe Glu Lys Tyr Gly Asn Thr Asp Ile Glu Gly Val Asp
            100                 105                 110

Ser Thr Asn Ala Cys Tyr Gly Gly Thr Ala Ala Leu Phe Asn Cys Val
        115                 120                 125

Asn Trp Val Glu Ser Ser Trp Asp Gly Arg Tyr Gly Leu Val Val
130                 135                 140

Cys Thr Asp Ser Ala Val Tyr Ala Glu Gly Pro Ala Arg Pro Thr Gly
145                 150                 155                 160

Gly Ala Ala Ala Val Ala Met Leu Ile Gly Pro Asp Ala Pro Ile Ser
                165                 170                 175

Phe Glu Ser Lys Leu Arg Gly Ser His Met Ala His Ala Tyr Asp Phe
            180                 185                 190

Tyr Lys Pro Asn Leu Ala Ser Glu Tyr Pro Val Gly Asp Gly Gln Leu
        195                 200                 205

Ser Gln Thr Cys Tyr Leu Met Ala Leu Asp Ser Cys Tyr Asn His Leu
    210                 215                 220
```

```
Ser His Lys Tyr Glu Lys Gln Glu Gly Lys Gln Phe Ser Ile Ser Asp
225                 230                 235                 240

Ala Glu Tyr Phe Val Phe His Ser Pro Tyr Asn Lys Leu Val Gln Lys
            245                 250                 255

Ser Phe Ala Arg Leu Val Phe Asn Asp Phe Leu Lys Asn Ala Ser Phe
        260                 265                 270

Val Asp Glu Ala Ala Lys Glu Lys Leu Glu Pro Phe Ala Thr Leu Ser
    275                 280                 285

Gly Asp Glu Ser Tyr Gln Ser Arg Asp Leu Glu Lys Ala Ser Gln Gln
    290                 295                 300

Val Ala Lys Pro Gln Tyr Asp Ala Lys Val Gln Pro Thr Thr Leu Ile
305                 310                 315                 320

Pro Lys Gln Val Gly Asn Met Tyr Thr Ala Ser Leu Tyr Ala Ala Phe
                325                 330                 335

Ile Ser Leu Ile His Asn Lys His Ser Thr Leu Asp Gly Lys Arg Val
            340                 345                 350

Ile Leu Phe Ser Tyr Gly Ser Gly Leu Thr Ser Thr Met Phe Ser Leu
        355                 360                 365

Leu Leu Arg Glu Gly Gln His Pro Phe Ser Leu Ser Asn Ile Asp Lys
    370                 375                 380

Met Met Asp Val Ala Gly Lys Leu Lys Ser Arg His Glu Phe Pro Pro
385                 390                 395                 400

Glu Lys Phe Val Glu Thr Met Lys Leu Met Glu His Arg Tyr Gly Gly
                405                 410                 415

Lys Glu Phe Val Thr Ser Lys Asp Thr Ser Leu Leu Ser Pro Gly Thr
            420                 425                 430

Phe Tyr Leu Thr Glu Val Asp Ser Met Tyr Arg Arg Phe Tyr Ala Lys
        435                 440                 445

Lys Thr Ser Glu Asn Gly Leu Val Thr Asn Gly His
    450                 455                 460

<210> SEQ ID NO 122
<211> LENGTH: 469
<212> TYPE: PRT
<213> ORGANISM: Panax notoginseng

<400> SEQUENCE: 122

Met Ala Ser Gln Lys Asn Val Gly Ile Leu Ala Met Glu Ile Tyr Phe
1               5                   10                  15

Pro Pro Thr Cys Ile Gln Gln Val Leu Glu Ala His Asp Gly Ala
            20                  25                  30

Ser Lys Gly Lys Tyr Thr Ile Gly Leu Gly Gln Asp Cys Met Gly Phe
        35                  40                  45

Cys Thr Glu Val Glu Asp Val Ile Ser Met Ser Leu Thr Thr Val Thr
    50                  55                  60

Ser Leu Leu Glu Lys Tyr Lys Ile Asp Pro Lys Gln Ile Gly Arg Leu
65                  70                  75                  80

Glu Val Gly Ser Glu Thr Val Ile Asp Lys Ser Lys Ser Ile Lys Thr
                85                  90                  95

Phe Leu Met Gln Ile Phe Glu Lys Cys Gly Asn Thr Asp Ile Glu Gly
            100                 105                 110

Val Asp Ser Thr Asn Ala Cys Tyr Gly Gly Thr Ala Ala Leu Phe Asn
        115                 120                 125

Cys Val Asn Trp Val Glu Ser Ser Ser Trp Asp Gly Arg Tyr Gly Leu
```

```
            130                 135                 140
Val Val Cys Thr Asp Ser Ala Val Tyr Ala Glu Gly Pro Ala Arg Pro
145                 150                 155                 160

Thr Gly Gly Ala Ala Thr Ile Ala Met Leu Ile Gly Thr Asp Ala Pro
                165                 170                 175

Ile Thr Phe Glu Ser Lys Phe Arg Gly Ser His Met Ser His Ala Tyr
            180                 185                 190

Asp Phe Tyr Lys Pro Asn Leu Ala Ser Glu Tyr Pro Val Val Asp Gly
        195                 200                 205

Lys Leu Ser Gln Thr Cys Tyr Leu Met Ala Leu Asp Ser Cys Tyr Lys
    210                 215                 220

Arg Tyr Cys Lys Lys Tyr Glu Lys Leu Glu Gly Lys Gln Phe Ser Met
225                 230                 235                 240

Asp Asp Ala Asp Tyr Phe Val Phe His Ser Pro Tyr Asn Lys Leu Val
                245                 250                 255

Gln Lys Ser Phe Ala Arg Leu Met Phe Asn Asp Phe Leu Arg Asn Ala
            260                 265                 270

Ser Ser Val Asp Glu Ser Ala Lys Glu Lys Leu Ala Pro Phe Ser Thr
        275                 280                 285

Leu Thr Gly Asp Glu Ser Tyr Ala Ser Arg Asp Leu Glu Lys Ala Thr
    290                 295                 300

Gln Gln Val Ala Lys Ser Gln Tyr Asp Val Lys Val Gln Pro Thr Thr
305                 310                 315                 320

Leu Ile Pro Lys Gln Val Gly Asn Met Tyr Thr Ala Ser Leu Tyr Ala
                325                 330                 335

Ala Phe Ala Ser Leu Ile His Asn Lys His Ser Thr Leu Ala Gly Lys
            340                 345                 350

Arg Val Met Met Phe Ser Tyr Gly Ser Gly Leu Ser Ala Thr Met Phe
        355                 360                 365

Ser Leu Arg Leu Arg Glu Gly Gln His Pro Phe Ser Leu Ser Asn Ile
    370                 375                 380

Ala Asn Val Met Asn Val Ala Glu Lys Leu Lys Ser Arg Asn Glu Phe
385                 390                 395                 400

Pro Pro Glu Lys Phe Val Glu Ile Met Lys Leu Met Glu His Arg Tyr
                405                 410                 415

Gly Ala Lys Asp Phe Val Thr Ser Lys Asp Cys Ser Leu Leu Ser Pro
            420                 425                 430

Gly Thr Tyr Tyr Leu Thr Glu Val Asp Ser Met Tyr Arg Arg Phe Tyr
        435                 440                 445

Ala Lys Lys Ala Val Asp Lys Thr Thr Ile Gly Thr Glu Asn Gly Thr
    450                 455                 460

Leu Ala Asn Gly His
465

<210> SEQ ID NO 123
<211> LENGTH: 513
<212> TYPE: PRT
<213> ORGANISM: Cananga odorata

<400> SEQUENCE: 123

Met Ala Glu Val Val Ile Ser Ala Pro Gly Lys Val Leu Val Thr Gly
1               5                   10                  15

Gly Tyr Leu Val Leu Glu Arg Ser Asn Pro Gly Ile Val Leu Ser Thr
            20                  25                  30
```

```
Thr Ala Arg Phe Tyr Ala Ile Val Lys Pro Leu Tyr Glu Ala Val Asp
            35                  40                  45

Pro Asn Ser Trp Ala Trp Ala Trp Thr Asp Val Lys Leu Ser Ser Pro
 50                  55                  60

Gln Leu Phe Arg Glu Thr Ser Tyr Lys Leu Ser Leu Arg Asn Leu Thr
 65                  70                  75                  80

Leu Gln Cys Ile Ser Pro Arg Asp Pro Arg Asn Pro Phe Ile Glu Gln
                 85                  90                  95

Ala Val Gln Tyr Ser Val Ala Ala His Ser Met Cys Ser Asp Lys
            100                 105                 110

Gly Met Lys Asp Gly Leu His Lys Leu Leu Gln Gly Leu Asp Ile
            115                 120                 125

Thr Ala Ile Gly Cys Asn Asp Phe Tyr Ser Tyr Arg Asn Gln Ile Glu
            130                 135                 140

Ala Asn Gly Ile Pro Leu Ala Pro Asp Val Leu Ala Ser Ile Pro Pro
145                 150                 155                 160

Phe Ser Pro Ile Asn Phe Asn Lys Glu Asn Ser Ser Gly Thr Ile Val
                165                 170                 175

Arg Glu Gln Ser Lys Pro Glu Val Ala Lys Thr Gly Leu Gly Ser Ser
            180                 185                 190

Ala Ala Met Thr Thr Ala Val Val Ala Ala Val Leu Gln Tyr Leu Gly
            195                 200                 205

Val Val Asp Leu Ser Ser Thr Ala Gly Asn Pro His Gly Thr Ile Cys
            210                 215                 220

Asn Pro Asp Leu Asp Leu Val His Ala Val Ala Gln Thr Ala His Cys
225                 230                 235                 240

Ile Ala Gln Gly Lys Val Gly Ser Gly Phe Asp Val Ser Ala Ala Val
                245                 250                 255

Tyr Gly Ser Gln Arg Tyr Ile Arg Phe Ser Pro Ser Val Leu Ser Pro
            260                 265                 270

Ala Gln Val Ala Val Thr Gly Gln Pro Leu Glu Glu Val Ile Ser His
            275                 280                 285

Ile Leu Lys Glu Lys Trp Asp His Glu Lys Ile Gln Phe Ser Leu Pro
            290                 295                 300

Pro Leu Met Thr Leu Leu Leu Gly Glu Pro Gly Thr Gly Gly Ser Ser
305                 310                 315                 320

Thr Pro Ser Met Val Gly Ala Val Lys Gln Trp Gln Arg Ser Glu Pro
                325                 330                 335

Gln Lys Ser Ala Glu Thr Trp Thr Arg Leu Ala Lys Ala Asn Ser Met
            340                 345                 350

Phe Glu Ile Gln Leu Ala Ala Leu Lys Lys Tyr Ala Gln Glu Lys Met
            355                 360                 365

Glu Thr Tyr Lys Ile Val Ile Gly Ser Cys Ser Ala His Ser His Glu
            370                 375                 380

Lys Trp Leu Glu Gln Ala Thr Asp Pro Cys Gln Glu Gly Ile Ile Arg
385                 390                 395                 400

Ser Leu Leu Ala Val Arg Asp Ala Met Leu Asp Ile Arg Phe His Met
                405                 410                 415

Arg Gln Met Gly Gln Ala Ala Gly Ala Pro Ile Glu Pro Glu Ser Gln
            420                 425                 430

Thr Leu Leu Leu Asp Ala Thr Met Asn Leu Glu Gly Val Leu Phe Ala
            435                 440                 445

Gly Val Pro Gly Ala Gly Gly Phe Asp Ala Ile Phe Val Val Val Leu
```

```
              450                 455                 460
Gly Asp Thr Arg Asn Asn Val Ala Asn Val Trp Cys Ser Gln Gly Val
465                 470                 475                 480

Leu Pro Met Leu Val Arg Glu Asp Pro Arg Gly Leu Cys Leu Glu Ser
                485                 490                 495

Gly Asp Pro Arg Thr Lys Glu Ile Ser Ser Ala Phe Ser Ala Ile Gln
                500                 505                 510

Val

<210> SEQ ID NO 124
<211> LENGTH: 509
<212> TYPE: PRT
<213> ORGANISM: Panax notoginseng
<220> FEATURE:
<221> NAME/KEY: misc_feature
<222> LOCATION: (158)..(158)
<223> OTHER INFORMATION: Xaa can be any naturally occurring amino acid
<220> FEATURE:
<221> NAME/KEY: misc_feature
<222> LOCATION: (234)..(234)
<223> OTHER INFORMATION: Xaa can be any naturally occurring amino acid

<400> SEQUENCE: 124

Met Ala Ile Val Ala Ser Ala Pro Gly Lys Val Leu Met Thr Gly Gly
1               5                   10                  15

Tyr Leu Ile Leu Glu Arg Pro Asn Glu Gly Leu Val Leu Ser Thr Asn
                20                  25                  30

Ala Arg Phe Tyr Ala Ile Val Lys Pro Leu Cys Asp Glu Leu Lys Pro
            35                  40                  45

Asp Ser Trp Ala Trp Ala Trp Thr Asp Val Lys Leu Thr Ser Pro Gln
50                  55                  60

Met Ala Arg Glu Thr Thr Tyr Lys Met Ser Leu Lys His Leu Leu Leu
65                  70                  75                  80

Gln Cys Ala Ser Ser Asn Ser Arg Asn Pro Phe Val Glu Tyr Ala
                85                  90                  95

Val Gln Tyr Ser Val Ala Ala Tyr Ala Thr Leu Asp Asn Asp Lys
            100                 105                 110

Lys Asn Ala Leu His Lys Leu Leu Leu Gln Gly Leu Asp Ile Thr Ile
            115                 120                 125

Leu Gly Cys Asn Gln Phe Tyr Ser Tyr Arg Asn Gln Ile Glu Ala Leu
            130                 135                 140

Gly Leu Pro Leu Ser Pro Glu Ser Phe Ala Thr Leu Lys Xaa Phe Thr
145                 150                 155                 160

Ser Ile Thr Phe Asn Ala Gly Glu Ser Asn Gly Glu Asn Ser Lys Pro
                165                 170                 175

Glu Val Ala Lys Thr Gly Leu Gly Ser Ser Ala Ala Met Thr Thr Val
                180                 185                 190

Val Val Ala Ala Leu Leu Ser Tyr Leu Gly Val Val Asn Leu Ser Ser
            195                 200                 205

Leu Ser Glu Asp Gln Asn Gln Glu Met Asp Thr Ala Asp Leu Asp Val
            210                 215                 220

Val His Val Ile Ala Gln Thr Ala His Xaa Ile Ala Gln Gly Lys Val
225                 230                 235                 240

Gly Ser Gly Phe Asp Val Ser Ser Ala Val Tyr Gly Ser Gln Arg Tyr
                245                 250                 255

Val Arg Phe Ser Pro Glu Val Leu Ser Ser Ala Gln Gly Ala Val Gly
                260                 265                 270
```

```
Gly Gln Pro Leu Asp Glu Val Ile Thr Asp Val Leu Lys Gly Lys Trp
            275                 280                 285

Asp His Glu Arg Thr Lys Phe Ser Leu Pro Pro Leu Met Met Leu Leu
    290                 295                 300

Leu Gly Glu Pro Gly Thr Arg Gly Ser Ser Thr Pro Ser Met Val Gly
305                 310                 315                 320

Ala Val Lys Lys Trp Gln Lys Ser Asp Pro Gln Lys Ser Arg Asp Thr
                325                 330                 335

Trp Thr Lys Leu Ser Asn Ala Asn Ser Ala Leu Glu Thr Gln Leu Asn
                340                 345                 350

Leu Leu Arg Lys Leu Ala Glu His Trp Asp Ala Tyr Lys Cys Val
            355                 360                 365

Ile Ser Ser Cys Asn Met Cys Lys Ser Glu Glu Trp Met Gly Gln Ala
    370                 375                 380

Ser Glu Pro Ser Gln Val Gln Ile Val Lys Ala Leu Leu Gly Ser Arg
385                 390                 395                 400

Asp Ala Thr Leu Glu Ile Arg Cys Gln Met Arg Gln Met Gly Asp Ala
                405                 410                 415

Ala Gly Ile Pro Ile Glu Pro Ser Gln Thr Arg Leu Leu Asp Ala
            420                 425                 430

Thr Met Lys Met Glu Gly Val Leu Ala Gly Val Pro Gly Ala Gly
    435                 440                 445

Gly Phe Asp Ala Ile Phe Ala Val Thr Leu Gly Asp Ala Ser Ser Thr
    450                 455                 460

Asn Leu Thr Lys Ala Trp Ser Ser His Asn Val Leu Ala Met Leu Val
465                 470                 475                 480

Arg Glu Asp Pro Arg Gly Val Ser Leu Gln Ser Ser Asp Pro Arg Ala
                485                 490                 495

Thr Glu Ile Thr Ser Gly Ile Ser Ala Val His Ile Glu
                500                 505

<210> SEQ ID NO 125
<211> LENGTH: 512
<212> TYPE: PRT
<213> ORGANISM: Zea mays

<400> SEQUENCE: 125

Met Glu Val Val Ala Ser Ala Pro Gly Lys Val Leu Ile Ala Gly Gly
1               5                   10                  15

Tyr Leu Val Leu Glu Arg Pro Asn Ala Gly Leu Val Leu Ser Thr Thr
            20                  25                  30

Ala Arg Phe Tyr Ala Val Val Arg Pro Leu Arg Asp Ser Leu Pro Ala
        35                  40                  45

Asp Ser Trp Thr Trp Ala Trp Thr Asp Val Lys Val Thr Ser Pro Gln
    50                  55                  60

Leu Ser Arg Val Ala Thr Tyr Lys Leu Ser Leu Asn Lys Thr Thr Leu
65                  70                  75                  80

Gln Leu Thr Ser Ser Arg Glu Ser Thr Asn Pro Phe Val Glu Gln Ala
                85                  90                  95

Ile Gln Phe Ser Val Ala Ala Lys Ala Thr Ile Ile Asp Lys Glu
            100                 105                 110

Arg Lys Asp Val Val Asp Lys Leu Leu Leu Gln Gly Leu Asn Ile Thr
        115                 120                 125

Ile Ile Gly His Asn Asp Phe Tyr Ser Tyr Arg Lys Gln Ile Glu Ala
```

```
            130                 135                 140
Arg Gly Leu Pro Leu Thr Pro Glu Val Leu Leu Ser Leu Pro Pro Phe
145                 150                 155                 160

Ser Ser Ile Thr Phe Asn Ser Glu Val Ala Asn Gly Thr Met Thr Gly
                165                 170                 175

Glu Lys Cys Lys Pro Glu Val Ala Lys Thr Gly Leu Gly Ser Ser Ala
                180                 185                 190

Ala Met Thr Thr Ser Val Val Ala Ala Leu Leu His Tyr Leu Gly Ala
                195                 200                 205

Val Asn Leu Ser Cys Pro Gly Gln Ser Ser Gly Asp Asn Ala Ser Gly
210                 215                 220

Arg Glu Leu Asp Leu Val His Thr Ile Ala Gln Ser Ala His Cys Leu
225                 230                 235                 240

Ala Gln Gly Lys Ile Gly Ser Gly Phe Asp Val Ser Ala Ala Val Tyr
                245                 250                 255

Gly Ser Gln Arg Tyr Val Arg Phe Ser Pro Glu Ile Leu Ser Ser Ala
                260                 265                 270

Gln Ala Ile Gly Gly Thr Val Leu Pro Asp Val Val Ser Asp Val Leu
                275                 280                 285

Thr Gln Arg Trp Asp His Glu Asn Lys Gln Phe Ser Leu Pro Pro Leu
290                 295                 300

Met Thr Leu Leu Leu Gly Glu Pro Gly Thr Gly Gly Ser Ser Thr Pro
305                 310                 315                 320

Ser Met Val Gly Ser Val Lys Arg Trp Leu Lys Ser Asp Pro Glu Lys
                325                 330                 335

Ser Arg Asp Thr Trp Ser Lys Leu Ala Ile Ala Asn Ser Thr Leu Glu
                340                 345                 350

Asn Gln Leu Arg Ile Leu Asn Gly Leu Ser Glu Asn His His Glu Ala
                355                 360                 365

Tyr Glu Ser Met Val Arg Ser Cys Ser His Leu Thr Tyr Gly Lys Trp
                370                 375                 380

Ala Glu Val Ala Thr Asn Gln His Gln Glu Leu Ile Ile Arg Ser Leu
385                 390                 395                 400

Leu Ala Ala Arg Asp Ala Cys Leu Glu Ile Arg Leu His Met Arg Glu
                405                 410                 415

Met Gly Ile Ala Ala Gly Val Pro Ile Glu Pro Asp Ser Gln Thr Arg
                420                 425                 430

Leu Leu Asp Ala Thr Met Asn Met Glu Gly Val Leu Leu Ala Gly Val
                435                 440                 445

Pro Gly Ala Gly Gly Phe Asp Ala Val Phe Ser Val Leu Gly Asp
450                 455                 460

Ala Ser Asn Ala Val Ala His Ala Trp Ser Ser Val Gly Val Leu Pro
465                 470                 475                 480

Leu Pro Val Arg Glu Asp Cys Arg Gly Val Ser Leu Glu Asp Ala Asp
                485                 490                 495

Pro Arg Thr Arg Glu Val Ser Ala Ala Val Trp Ser Ile Gln Ile Asn
                500                 505                 510
```

<210> SEQ ID NO 126
<211> LENGTH: 500
<212> TYPE: PRT
<213> ORGANISM: Arnebia euchroma

<400> SEQUENCE: 126

```
Met Ala Val Val Ala Ser Ala Pro Gly Lys Val Leu Met Thr Gly Gly
 1               5                  10                  15

Tyr Leu Val Leu Glu Arg Pro Asn Ala Gly Ile Val Leu Ser Thr Asn
                20                  25                  30

Ala Arg Phe Tyr Ser Val Val Lys Pro Ile Tyr Asp Glu Val Lys Pro
            35                  40                  45

Asp Ser Trp Ala Trp Ala Trp Ala Asp Val Lys Leu Thr Ser Pro Gln
        50                  55                  60

Met Ser Arg Glu Met Thr Tyr Lys Leu Ser Lys Tyr Leu Thr Leu
 65                  70                  75                  80

Gln Ser Val Ser Leu Ser Asp Ser Arg Asn Pro Phe Val Glu Tyr Ala
                85                  90                  95

Val Gln Tyr Val Val Ala Ala Tyr Ser Arg Leu Asp Ser Ser Gly
                100                 105                 110

Lys Asp Ala Leu Thr Lys Leu Leu Leu Arg Gly Leu Asp Ile Thr Ile
            115                 120                 125

Leu Gly Cys Asn Glu Phe Tyr Ser Tyr Arg Asn Gln Ile Glu Ala Arg
    130                 135                 140

Gly Leu Pro Leu Thr Pro Glu Ser Leu Ser Ser Leu Pro Pro Phe Thr
145                 150                 155                 160

Ser Ile Thr Phe Asn Lys Glu Glu Ser Gly Gly Gln Asn Ser Lys Pro
                165                 170                 175

Glu Val Ala Lys Thr Gly Leu Gly Ser Ser Ala Ala Met Thr Thr Ala
                180                 185                 190

Val Val Ala Ser Leu Leu His Tyr Leu Gly Val Val Asn Leu Ser Ser
            195                 200                 205

Val Lys Asp Asn Ser Glu Asp Leu Asp Thr Val His Met Ile Ala Gln
    210                 215                 220

Thr Ala His Cys Ile Ala Gln Gly Glu Val Gly Ser Gly Phe Asp Val
225                 230                 235                 240

Ser Ser Ala Val Tyr Gly Ser Gln Arg Tyr Val Arg Phe Ser Pro Gly
                245                 250                 255

Val Ile Ser Ser Ala Gln Asp Ala Val Lys Ala Ala Pro Leu Glu Glu
                260                 265                 270

Val Ile Asn Asp Val Leu Lys Ala Glu Trp Asp His Glu Lys Asp Met
            275                 280                 285

Ser His Ala Pro Leu Met Thr Ser Ile Arg Glu Pro Gly Thr Gly Gly
    290                 295                 300

Ser Ser Thr Pro Ser Met Val Gly Ala Val Lys Lys Trp Gln Lys Ala
305                 310                 315                 320

Asp Pro Gln Thr Ser Val Glu Thr Trp Arg Lys Leu Ser Glu Gly Asn
                325                 330                 335

Ala Ala Leu Glu Met Gln Leu Asn Thr Leu Ser Asn Leu Ala Arg Met
            340                 345                 350

Ser Phe Asp Val Tyr Lys Asp Val Ile Asn Asn Cys Ser Thr Leu Pro
    355                 360                 365

Ser Glu Lys Trp Leu Glu Val Ala Thr Glu Pro Ser Arg Thr Asp Ile
370                 375                 380

Val Lys Ala Leu Leu Gly Ala Lys Asp Val Met Leu Glu Ile Arg Tyr
385                 390                 395                 400

Gln Met Arg Lys Met Gly Glu Ala Ala Gly Ile Pro Ile Glu Pro Glu
                405                 410                 415

Ser Gln Thr Leu Leu Leu Asp Ser Thr Met Asn Met Glu Gly Val Leu
```

```
              420                 425                 430
Leu Ala Gly Val Pro Ala Gly Gly Phe Asp Ala Val Phe Ala Val
            435                 440                 445

Thr Leu Gly Asp Ala Ser Asp Lys Val Ile Lys Ser Trp Ser Arg Gln
450                 455                 460

Asn Val Leu Ala Leu Leu Val Arg Glu Asp Pro Asn Gly Val Leu Leu
465                 470                 475                 480

Glu Asn Asn Asp Ser Arg Ala Lys Glu Val Thr Ser Gly Val Ser Ala
                485                 490                 495

Ile Gln Ile Gln
            500

<210> SEQ ID NO 127
<211> LENGTH: 626
<212> TYPE: PRT
<213> ORGANISM: Cananga odorata

<400> SEQUENCE: 127

Met Arg Leu Arg Arg Ile Arg Val Cys Thr Ile Arg Leu Tyr Ala Ala
1               5                   10                  15

Gly Phe Asp Phe Phe Pro Lys Pro Asn Phe Tyr Phe Ala Thr Leu Ser
            20                  25                  30

Phe His Ser Tyr Pro Gln Leu Pro Arg Leu His Gln Thr His Phe Leu
        35                  40                  45

Gln Ile Leu Thr Asn Thr Thr His Ile Leu Leu Ile Cys Phe Gln Gly
    50                  55                  60

Ile Leu Ser Asp Ser Phe Pro Ser Leu Phe Phe Tyr Ile Thr Ser His
65                  70                  75                  80

Gln Glu Arg Arg Lys Gln Arg Ala Glu Asp Arg Glu Lys Met Ala Leu
                85                  90                  95

Ser Thr Thr Ser Ser Ser Leu Ser Ile Lys Thr Pro Leu Gln Ser Ser
            100                 105                 110

Ile Phe Pro Ala Ser Lys Ala His Gln His Ser Leu Pro Leu Leu Pro
        115                 120                 125

Thr Lys Pro Pro Lys Pro Ile Ser Ala Val His Ala Ala Glu Pro Ser
    130                 135                 140

Lys Asn Pro Val Val Ala Asp Lys Pro Val Lys Thr Ser Pro Pro Pro
145                 150                 155                 160

Ala Ala Thr Ala Pro Ala Phe Gly Lys Trp Thr Leu Asp Gly Trp Lys
                165                 170                 175

Ser Lys Lys Ala Leu Gln Leu Pro Glu Tyr Pro Lys Arg Glu Glu Leu
            180                 185                 190

Asp Ala Val Leu Lys Thr Leu Glu Ser Phe Pro Pro Ile Val Phe Ala
        195                 200                 205

Gly Glu Ala Arg His Leu Glu Asp Arg Leu Ala Asp Ala Ala Met Gly
    210                 215                 220

Lys Ala Phe Leu Leu Gln Gly Gly Asp Cys Ala Glu Ser Phe Lys Glu
225                 230                 235                 240

Phe Asn Ala Asn Asn Ile Arg Asp Thr Phe Arg Ile Leu Leu Gln Met
                245                 250                 255

Gly Val Val Leu Met Phe Gly Gly Gln Met Pro Val Val Lys Val Gly
            260                 265                 270

Arg Met Ala Gly Gln Phe Ala Lys Pro Arg Ser Asp Ala Phe Glu Glu
        275                 280                 285
```

```
Lys Asn Gly Val Lys Leu Pro Ser Tyr Arg Gly Asp Asn Ile Asn Gly
    290                 295                 300

Asp Ala Phe Asn Glu Lys Ser Arg Ile Pro Asp Pro Glu Arg Met Ile
305                 310                 315                 320

Arg Ala Tyr Cys Gln Ser Ala Ala Thr Leu Asn Leu Leu Arg Ala Phe
                325                 330                 335

Ala Thr Gly Gly Tyr Ala Ala Met Gln Arg Val Asn Gln Trp Asn Leu
            340                 345                 350

Asp Phe Thr Glu His Ser Glu Gln Gly Asp Arg Tyr Arg Glu Leu Ala
        355                 360                 365

His Arg Val Asp Glu Ala Leu Gly Phe Met Ala Ala Gly Leu Thr
370                 375                 380

Glu Asp His Pro Ile Thr Asn Thr Thr Asp Phe Trp Thr Ser His Glu
385                 390                 395                 400

Cys Leu Leu Leu Pro Tyr Gln Ala Leu Thr Arg Glu Asp Ser Thr
                405                 410                 415

Ser Gly Arg Tyr Tyr Asp Cys Ser Ala His Met Leu Trp Val Gly Glu
            420                 425                 430

Arg Thr Arg Gln Leu Asp Gly Ala His Val Glu Phe Leu Arg Gly Val
        435                 440                 445

Ala Asn Pro Leu Gly Ile Lys Val Ser Asp Lys Met Asp Pro Asn Glu
450                 455                 460

Leu Val Asn Leu Ile Glu Ile Leu Asn Pro Thr Asn Lys Pro Gly Arg
465                 470                 475                 480

Ile Thr Ile Ile Thr Arg Met Gly Ala Glu Asn Met Arg Val Lys Leu
                485                 490                 495

Pro His Leu Ile Arg Ala Val Arg Arg Ala Gly Gln Ile Val Thr Trp
            500                 505                 510

Val Ser Asp Pro Met His Gly Asn Thr Ile Lys Ala Pro Cys Gly Leu
        515                 520                 525

Lys Thr Arg Pro Phe Asp Ser Ile Arg Ala Glu Val Arg Ala Phe Phe
530                 535                 540

Asp Val His Glu Gln Glu Gly Ser His Pro Gly Gly Val His Leu Glu
545                 550                 555                 560

Met Thr Gly Gln Asn Val Thr Glu Cys Ile Gly Gly Ser Arg Thr Val
                565                 570                 575

Thr Phe Asp Asp Leu Ser Ser Arg Tyr His Thr His Cys Asp Pro Arg
            580                 585                 590

Leu Asn Ala Ser Gln Ser Leu Glu Leu Ala Phe Ile Ile Ala Glu Arg
        595                 600                 605

Leu Arg Lys Arg Arg Ile Gly Phe Gln Thr Ala Ser Val Ala Ser Leu
610                 615                 620

Gly Leu
625

<210> SEQ ID NO 128
<211> LENGTH: 532
<212> TYPE: PRT
<213> ORGANISM: Vitis vinifera

<400> SEQUENCE: 128

Met Ala Leu Ser Asn Ala Ser Thr Leu Ser Ser Lys Ser Val Tyr Gln
1               5                   10                  15

Thr His Ser Leu Phe Ser Ser Leu Ser His Gln Pro Ser Ser Ser Leu
            20                  25                  30
```

```
Val Pro Ser Lys Thr His Leu Arg Ser Leu His Pro Ile Ser Ala Val
        35                  40                  45

His Ala Glu Pro Ala Lys Asn Pro Val Val Asp Lys Pro Pro
 50                  55                  60

Lys Thr Ser Ser Pro Ser Val Pro Ala Gly Ser Gly Lys Trp Thr Val
 65                  70                  75                  80

Asp Ser Trp Lys Thr Lys Lys Ala Leu Gln Leu Pro Glu Tyr Pro Asn
                 85                  90                  95

Glu Ser Asp Leu Glu Ser Val Leu Gln Thr Leu Glu Ala Phe Pro Pro
                100                 105                 110

Ile Val Phe Ala Gly Glu Ala Arg Ser Leu Glu Arg Leu Gly Asp
            115                 120                 125

Ala Ala Met Gly Asn Ala Phe Leu Leu Gln Gly Gly Asp Cys Ala Glu
        130                 135                 140

Ser Phe Lys Glu Phe Ser Ala Asn Asn Ile Arg Asp Thr Phe Arg Ile
145                 150                 155                 160

Ile Leu Gln Met Gly Ala Val Leu Met Phe Gly Gly Gln Val Pro Val
                165                 170                 175

Ile Lys Val Gly Arg Met Ala Gly Gln Phe Ala Lys Pro Arg Ser Asp
            180                 185                 190

Pro Phe Glu Glu Lys Asn Gly Val Lys Leu Pro Ser Tyr Lys Gly Asp
                195                 200                 205

Asn Ile Asn Gly Asp Ala Phe Asn Glu Lys Ser Arg Ile Pro Asp Pro
            210                 215                 220

Gln Arg Met Ile Arg Ala Tyr Cys Gln Ala Ala Thr Leu Asn Leu
225                 230                 235                 240

Leu Arg Ala Phe Ala Thr Gly Gly Tyr Ala Ala Met Gln Arg Val Thr
                245                 250                 255

Gln Trp Asn Leu Asp Phe Ala Glu His Ser Glu Gln Gly Asp Arg Tyr
                260                 265                 270

Gln Glu Leu Ala His Arg Val Asp Glu Ala Leu Gly Phe Met Ser Ala
            275                 280                 285

Ala Gly Leu Thr Val Asp His Pro Ile Met Thr Thr Thr Glu Phe Trp
        290                 295                 300

Thr Ser His Glu Cys Leu Leu Leu Pro Tyr Glu Gln Ser Leu Thr Arg
305                 310                 315                 320

Lys Asp Ser Thr Ser Gly Leu Tyr Tyr Asp Cys Ser Ala His Met Leu
                325                 330                 335

Trp Val Gly Glu Arg Thr Arg Gln Leu Asp Gly Ala His Val Glu Phe
            340                 345                 350

Leu Arg Gly Val Ala Asn Pro Leu Gly Ile Lys Val Ser Asn Lys Met
        355                 360                 365

Asp Pro Asn Glu Leu Val Lys Leu Val Glu Ile Leu Asn Pro His Asn
        370                 375                 380

Lys Pro Gly Arg Ile Thr Val Ile Cys Arg Met Gly Ala Glu Asn Met
385                 390                 395                 400

Arg Val Lys Leu Pro His Leu Ile Arg Ala Val Arg Gln Ala Gly Gln
                405                 410                 415

Ile Val Thr Trp Val Cys Asp Pro Met His Gly Asn Thr Ile Lys Ala
            420                 425                 430

Pro Cys Gly Leu Lys Thr Arg Pro Phe Asp Ala Ile Leu Ala Glu Val
        435                 440                 445
```

```
Arg Ala Phe Phe Asp Val His Glu Gln Glu Gly Ser His Pro Gly Gly
    450                 455                 460

Val His Leu Glu Met Thr Gly Gln Asn Val Thr Glu Cys Ile Gly Gly
465                 470                 475                 480

Ser Arg Thr Val Thr Phe Asp Asp Leu Ser Ser Arg Tyr His Thr His
                    485                 490                 495

Cys Asp Pro Arg Leu Asn Ala Ser Gln Ser Leu Glu Leu Ala Phe Ile
                500                 505                 510

Ile Ala Glu Arg Leu Arg Lys Arg Met Gly Thr Gln Arg Leu Leu
            515                 520                 525

Ala Leu Gly Leu
    530

<210> SEQ ID NO 129
<211> LENGTH: 532
<212> TYPE: PRT
<213> ORGANISM: Medicago truncatula

<400> SEQUENCE: 129

Met Ser Leu Ser Ser Thr Ser Thr Ser Leu Ile Pro Thr Lys Ser
1               5                   10                  15

Leu Leu Gln Pro Thr Lys Pro Asn Pro Ser Phe Pro Ile Gly Leu
                20                  25                  30

Lys Pro Met Pro Lys Pro Lys Pro Gly Ser Ile Leu Ala Val His Ala
            35                  40                  45

Ala Glu Pro Ala Lys Asn Pro Val Leu Thr Glu Lys Pro Ser Lys Pro
    50                  55                  60

Gln Pro Thr Thr Ile Pro Arg Asn Ala Ser Thr Lys Trp Thr Ile Asp
65                  70                  75                  80

Ser Trp Lys Ser Lys Lys Ala Leu Gln Leu Pro Glu Tyr Pro Ser Gln
                85                  90                  95

Glu Asp Leu Glu Ala Val Leu Lys Thr Leu Asp Ala Phe Pro Pro Ile
            100                 105                 110

Val Phe Ala Gly Glu Ala Arg Thr Leu Glu Glu His Leu Gly Glu Ala
        115                 120                 125

Ala Met Gly Asn Ala Phe Leu Leu Gln Gly Gly Asp Cys Ala Glu Ser
    130                 135                 140

Phe Lys Glu Phe Asn Ala Asn Ile Arg Asp Thr Phe Arg Ile Ile
145                 150                 155                 160

Leu Gln Met Ser Val Val Met Met Phe Gly Gly Gln Met Pro Val Ile
                165                 170                 175

Lys Val Gly Arg Met Ala Gly Gln Phe Ala Lys Pro Arg Ser Asp Asn
            180                 185                 190

Phe Glu Glu Lys Asn Gly Val Lys Leu Pro Ser Tyr Arg Gly Asp Asn
        195                 200                 205

Ile Asn Gly Asp Ala Phe Asp Glu Lys Ser Arg Thr Pro Asp Pro Gln
    210                 215                 220

Arg Met Ile Arg Ala Tyr Cys Gln Ala Ala Thr Leu Asn Leu Leu
225                 230                 235                 240

Arg Ala Phe Ala Thr Gly Gly Tyr Ala Ala Met Gln Arg Val Thr Gln
                245                 250                 255

Trp Asn Leu Asp Phe Thr Glu Gln Ser Glu Gln Gly Asp Arg Tyr Arg
            260                 265                 270

Glu Leu Ala Asn Arg Val Asp Glu Ala Leu Gly Phe Met Ala Ala Ala
        275                 280                 285
```

```
Gly Leu Thr Val Asp His Pro Ile Met Arg Thr Thr Asp Phe Trp Thr
        290                 295                 300
Ser His Glu Cys Leu Leu Pro Tyr Glu Gln Ser Leu Thr Arg Leu
305                 310                 315                 320
Asp Ser Thr Ser Gly Leu Tyr Tyr Asp Cys Ser Ala His Met Ile Trp
                325                 330                 335
Val Gly Glu Arg Thr Arg Gln Leu Asp Gly Ala His Val Glu Phe Leu
            340                 345                 350
Arg Gly Val Ala Asn Pro Leu Gly Ile Lys Val Ser Asp Lys Met Asp
        355                 360                 365
Pro Asn Glu Leu Val Lys Leu Ile Glu Ile Leu Asn Pro Gln Asn Lys
    370                 375                 380
Pro Gly Arg Ile Thr Ile Ile Thr Arg Met Gly Ala Glu Asn Met Arg
385                 390                 395                 400
Val Lys Leu Pro His Leu Ile Arg Ala Val Arg Arg Ala Gly Gln Ile
                405                 410                 415
Val Thr Trp Val Ser Asp Pro Met His Gly Asn Thr Ile Lys Ala Pro
            420                 425                 430
Cys Gly Leu Lys Thr Arg Pro Phe Asp Ala Ile Arg Ala Glu Val Arg
        435                 440                 445
Ala Phe Phe Asp Val His Glu Gln Glu Gly Ser His Pro Gly Gly Val
    450                 455                 460
His Leu Glu Met Thr Gly Gln Asn Val Thr Glu Cys Ile Gly Gly Ser
465                 470                 475                 480
Lys Ile Val Thr Phe Asp Asp Leu Ser Ser Arg Tyr His Thr His Cys
                485                 490                 495
Asp Pro Arg Leu Asn Ala Ser Gln Ser Leu Glu Leu Ala Phe Ile Ile
            500                 505                 510
Ala Glu Arg Leu Arg Lys Ser Arg Ile Arg Ser Gln Pro Pro Leu Glu
        515                 520                 525
Ser Thr Gly Phe
    530

<210> SEQ ID NO 130
<211> LENGTH: 544
<212> TYPE: PRT
<213> ORGANISM: Hevea brasiliensis

<400> SEQUENCE: 130

Met Ser Phe Thr Ser Thr Ser Leu Ile Pro Thr Lys Ala Leu Ile Thr
1               5                   10                  15
Ser Asn Lys Pro His Gln Pro Ser Phe Val Ala Asn Lys Ala Pro Ser
            20                  25                  30
Arg Ser Val Leu Gln Ile Ser Ala Val Tyr Ser Ser Glu Pro Ser Lys
        35                  40                  45
Asn Pro Ile Val Ser Asp Lys Ser Gly Lys Gln Thr Thr Lys Thr
    50                  55                  60
Ser Thr Ser Ala Ala Ala Thr Ser Ala Pro Ala Ala Ala Ala Pro
65                  70                  75                  80
Thr Thr Asn Val Val Pro Gly Lys Trp Ser Val Asp Ser Trp Lys Ser
                85                  90                  95
Lys Lys Ala Leu Gln Leu Pro Glu Tyr Pro Asn Lys Glu Glu Leu Glu
            100                 105                 110
Ser Val Leu Arg Thr Leu Asp Ala Phe Pro Pro Ile Val Phe Ala Gly
```

-continued

```
            115                 120                 125
Glu Ala Arg Ser Leu Glu Arg Leu Ser Glu Ala Ala Met Gly Asn
        130                 135                 140
Ala Phe Leu Leu Gln Gly Gly Asp Cys Ala Glu Ser Phe Lys Glu Phe
145                 150                 155                 160
Asn Ala Asn Asn Ile Arg Asp Thr Phe Arg Ile Leu Leu Gln Met Gly
                165                 170                 175
Ala Val Leu Met Phe Gly Gly Gln Met Pro Val Val Lys Val Gly Arg
            180                 185                 190
Met Ala Gly Gln Phe Ala Lys Pro Arg Ser Glu Pro Phe Glu Glu Lys
            195                 200                 205
Asn Gly Val Lys Leu Pro Ser Tyr Arg Gly Asp Asn Val Asn Gly Asp
        210                 215                 220
Thr Phe Asp Glu Lys Ser Arg Val Pro Asp Pro Gln Arg Met Ile Arg
225                 230                 235                 240
Ala Tyr Cys Gln Ser Ala Ala Thr Leu Asn Leu Leu Arg Ala Phe Ala
                245                 250                 255
Thr Gly Gly Tyr Ala Ala Met Gln Arg Val Asn Gln Trp Asn Leu Asp
            260                 265                 270
Phe Thr Glu His Ser Glu Gln Gly Asp Arg Tyr Arg Glu Leu Ala His
            275                 280                 285
Arg Val Asp Glu Ala Leu Gly Phe Met Ser Ala Ala Gly Leu Thr Val
        290                 295                 300
Asp His Pro Ile Met Thr Thr Thr Glu Phe Trp Thr Ser His Glu Cys
305                 310                 315                 320
Leu Leu Leu Pro Tyr Glu Gln Ser Leu Ala Arg Leu Asp Ser Thr Ser
                325                 330                 335
Gly Leu Tyr Tyr Asp Cys Ser Ala His Phe Leu Trp Val Gly Glu Arg
            340                 345                 350
Thr Arg Gln Leu Asp Gly Ala His Val Glu Phe Leu Arg Gly Val Ala
        355                 360                 365
Asn Pro Leu Gly Ile Lys Val Ser Asp Lys Met Asp Pro Asn Glu Leu
        370                 375                 380
Val Lys Leu Ile Glu Ile Leu Asn Pro Gln Asn Lys Pro Gly Arg Ile
385                 390                 395                 400
Thr Ile Ile Thr Arg Met Gly Ala Glu Asn Met Arg Val Lys Leu Pro
                405                 410                 415
His Leu Ile Arg Ala Val Arg Arg Ala Gly Gln Ile Val Thr Trp Val
            420                 425                 430
Ser Asp Pro Met His Gly Asn Thr Ile Lys Ala Pro Cys Gly Leu Lys
        435                 440                 445
Thr Arg Pro Phe Asp Ser Ile Arg Ala Glu Val Arg Ala Phe Phe Asp
        450                 455                 460
Val His Glu Gln Glu Gly Ser His Pro Gly Gly Val His Leu Glu Met
465                 470                 475                 480
Thr Asp Gln Asn Val Thr Glu Cys Ile Gly Gly Ser Arg Thr Val Thr
                485                 490                 495
Phe Asp Asp Leu Ser Ser Arg Tyr His Thr His Cys Asp Pro Arg Leu
            500                 505                 510
Asn Ala Ser Gln Ser Leu Glu Leu Ala Phe Ile Ile Ala Glu Arg Leu
        515                 520                 525
Arg Lys Arg Arg Ile Asn Ser Gln Pro Lys Ile Ala Ser Thr Ser Leu
        530                 535                 540
```

<210> SEQ ID NO 131
<211> LENGTH: 442
<212> TYPE: PRT
<213> ORGANISM: Cananga odorata

<400> SEQUENCE: 131

```
Met Ala Ser Ser Ile Ser Ser Pro Phe Leu Lys Gly Thr Lys
1               5                   10                  15

Thr Glu Gly Phe Trp Gly Ile Gly Phe His Ala Ser Asp Leu Arg Gly
                20                  25                  30

Leu Thr Tyr Pro Ser Val Gln Ile Ser Ile Arg Arg Ala Pro Pro Arg
            35                  40                  45

Arg Lys Leu Glu Val His Ala Ala Gly Ser Ser Phe Gly Asn Phe Phe
        50                  55                  60

Arg Ile Thr Thr Tyr Gly Glu Ser His Gly Gly Val Gly Cys Val
65                  70                  75                  80

Ile Asp Gly Cys Pro Pro Gln Ile Pro Leu Ser Glu Ala Asp Leu Gln
                85                  90                  95

Val Asp Leu Asp Arg Arg Pro Gly Gln Ser Arg Ile Thr Thr Pro
                100                 105                 110

Arg Lys Glu Thr Asp Thr Cys Lys Ile Tyr Ser Gly Val Ser Glu Gly
        115                 120                 125

Leu Thr Thr Gly Thr Pro Ile His Val Ser Val Pro Asn Thr Asp Gln
    130                 135                 140

Arg Gly His Asp Tyr Ser Glu Met Ser Ile Ala Tyr Arg Pro Ser His
145                 150                 155                 160

Ala Asp Ala Thr Tyr Asp Phe Lys Tyr Gly Val Arg Ser Val Gln Gly
                165                 170                 175

Gly Gly Arg Ser Ser Ala Arg Glu Thr Ile Gly Arg Val Ile Pro Gly
            180                 185                 190

Ala Val Ala Lys Lys Ile Leu Lys Met Val Ser Glu Thr Glu Val Leu
        195                 200                 205

Ala Tyr Val Ser Gln Val His Lys Val Ile Leu Pro Glu Gly Val Val
    210                 215                 220

Asp His Asp Asn Val Thr Leu Glu Gln Ile Glu Ser Asn Ile Val Arg
225                 230                 235                 240

Cys Pro Asp Pro Glu Tyr Ala Glu Lys Met Ile Ser Ala Ile Asp Ala
                245                 250                 255

Val Arg Val Arg Gly Asp Ser Val Gly Gly Val Val Thr Cys Ile Val
            260                 265                 270

Arg Asn Val Pro Arg Gly Leu Gly Ser Pro Val Phe Asp Lys Leu Glu
        275                 280                 285

Ala Glu Leu Ala Lys Ala Val Leu Ser Leu Pro Ala Thr Lys Gly Phe
    290                 295                 300

Glu Ile Gly Ser Gly Phe Gly Gly Thr Phe Leu Thr Gly Ser Glu His
305                 310                 315                 320

Asn Asp Glu Phe Tyr Thr Asp Glu Gln Gly Arg Ile Arg Thr Lys Thr
                325                 330                 335

Asn Arg Ser Gly Gly Ile Gln Gly Gly Ile Ser Asn Gly Glu Thr Ile
            340                 345                 350

Thr Met Arg Val Ala Phe Lys Pro Thr Ser Thr Ile Ser Arg Lys Gln
        355                 360                 365

His Thr Val Thr Arg Asp Lys Gln Glu Ile Glu Leu Leu Ala Arg Gly
```

```
            370                 375                 380
Arg His Asp Pro Cys Val Val Pro Arg Ala Val Pro Met Val Glu Ala
385                 390                 395                 400

Met Val Ala Leu Val Leu Val Asp Gln Leu Met Ala His Tyr Ala Gln
                405                 410                 415

Cys Gln Leu Leu Pro Ile Asn Pro Ser Leu Gln Glu Pro Leu Glu Ala
            420                 425                 430

Pro Lys Leu Glu Ala Ala His Val Pro Leu
        435                 440

<210> SEQ ID NO 132
<211> LENGTH: 435
<212> TYPE: PRT
<213> ORGANISM: Ricinus communis

<400> SEQUENCE: 132

Met Ala Ser Cys Ser Ser Leu Val Ser Lys Pro Phe Leu Gly Ala
1               5                   10                  15

Ser Arg Leu Asn Gly Ser Asp Asn Arg Lys Leu Ser Ile Ser Thr Val
                20                  25                  30

Arg Ile Ser Phe Ser Pro Arg Ala Pro Lys Lys Leu Gln Ile His Ala
            35                  40                  45

Ala Gly Ser Thr Phe Gly Thr His Phe Arg Val Thr Thr Phe Gly Glu
        50                  55                  60

Ser His Gly Gly Gly Val Gly Cys Thr Ile Asp Gly Cys Pro Pro Arg
65                  70                  75                  80

Val Pro Leu Ser Glu Ala Asp Met Gln Val Asp Leu Asp Arg Arg Arg
                85                  90                  95

Pro Gly Gln Ser Arg Ile Thr Thr Pro Arg Lys Glu Thr Asp Thr Cys
            100                 105                 110

Lys Ile Tyr Ser Gly Val Ser Glu Gly Met Thr Thr Gly Thr Pro Ile
        115                 120                 125

His Val Phe Val Pro Asn Thr Asp Gln Arg Gly His Asp Tyr Ser Glu
130                 135                 140

Met Ser Val Ala Tyr Arg Pro Ser His Ala Asp Ala Thr Tyr Asp Met
145                 150                 155                 160

Lys Tyr Gly Val Arg Ser Val Gln Gly Gly Gly Arg Ser Ser Ala Arg
                165                 170                 175

Glu Thr Ile Gly Arg Val Ala Ser Gly Ala Ile Ala Lys Lys Ile Leu
            180                 185                 190

Lys Gln Phe Ser Gly Thr Glu Val Leu Ala Tyr Val Ser Gln Val His
        195                 200                 205

Lys Val Val Leu Pro Glu Asp Met Val Asp His Glu Thr Leu Thr Leu
210                 215                 220

Asp Gln Ile Glu Ser Asn Ile Val Arg Cys Pro Asp Pro Glu Tyr Ala
225                 230                 235                 240

Glu Lys Met Ile Ala Ala Ile Asp Lys Ile Arg Val Arg Gly Asp Ser
                245                 250                 255

Val Gly Gly Val Val Thr Cys Ile Val Arg Asn Val Pro Arg Gly Leu
            260                 265                 270

Gly Ser Pro Val Phe Asp Lys Leu Glu Ala Glu Leu Ala Lys Ala Val
        275                 280                 285

Met Ser Leu Pro Ala Thr Lys Gly Phe Glu Phe Gly Ser Gly Phe Ala
        290                 295                 300
```

```
Gly Thr Phe Leu Thr Gly Ser Glu His Asn Asp Glu Phe Tyr Met Glu
305                 310                 315                 320

Glu His Gly Lys Ile Arg Thr Arg Thr Asn Arg Ser Gly Gly Ile Gln
            325                 330                 335

Gly Gly Ile Ser Asn Gly Glu Thr Ile Tyr Met Arg Ile Ala Phe Lys
        340                 345                 350

Pro Thr Ser Thr Ile Gly Lys Lys Gln His Thr Val Thr Arg Asp Lys
            355                 360                 365

Val Glu Thr Glu Leu Ile Ala Arg Gly Arg His Asp Pro Cys Val Val
370                 375                 380

Pro Arg Ala Val Pro Met Val Glu Ala Met Val Ala Leu Val Leu Val
385                 390                 395                 400

Asp Gln Leu Met Ala Gln Tyr Ala Gln Cys Tyr Met Phe Pro Ile Asn
                405                 410                 415

Pro Glu Leu Gln Glu Pro Leu Lys Leu Pro Arg Ala Glu Ser Val Asn
            420                 425                 430

Met Thr Ile
        435

<210> SEQ ID NO 133
<211> LENGTH: 438
<212> TYPE: PRT
<213> ORGANISM: Hevea brasiliensis

<400> SEQUENCE: 133

Met Ala Ser Ser Leu Ser Ser Lys Pro Phe Leu Gly Ala Tyr Arg
1               5                   10                  15

Leu Asp Gly Ser Ser Leu Ser Asn Leu Arg Asp Leu Ser Ile Ala
                20                  25                  30

Thr Val Gln Ile Ser Phe Arg Pro Arg Thr Pro Lys Lys Leu Gln Ile
            35                  40                  45

His Ala Ala Gly Ser Thr Tyr Gly Thr Tyr Phe Arg Val Thr Thr Phe
        50                  55                  60

Gly Glu Ser His Gly Gly Val Gly Cys Ile Val Asp Gly Cys Pro
65                  70                  75                  80

Pro Arg Ile Pro Leu Ser Glu Ala Asp Leu Gln Val Asp Leu Asp Arg
                85                  90                  95

Arg Arg Pro Gly Gln Ser Arg Ile Thr Thr Pro Arg Lys Glu Thr Asp
            100                 105                 110

Thr Cys Lys Ile Tyr Ser Gly Val Ser Glu Gly Val Thr Thr Gly Thr
        115                 120                 125

Pro Ile His Val Phe Val Pro Asn Thr Asp Gln Arg Gly His Asp Tyr
130                 135                 140

Ser Glu Met Ser Val Ala Tyr Arg Pro Ser His Ala Asp Ala Thr Tyr
145                 150                 155                 160

Asp Met Lys Tyr Gly Val Arg Ser Val Gln Gly Gly Gly Arg Ser Ser
                165                 170                 175

Ala Arg Glu Thr Ile Gly Arg Val Ala Ser Gly Ala Ile Ala Lys Lys
            180                 185                 190

Ile Leu Arg Gln Phe Ser Gly Thr Glu Ile Leu Ala Tyr Val Ser Gln
        195                 200                 205

Val His Gln Val Val Leu Pro Glu Asp Gln Ile Asp His Gln Ser Leu
210                 215                 220

Thr Ile Asp Gln Ile Glu Ser Asn Ile Val Arg Cys Pro Asp Pro Glu
225                 230                 235                 240
```

```
Tyr Ala Glu Lys Met Ile Ala Ala Ile Asp Thr Val Arg Val Arg Gly
                245                 250                 255

Asp Ser Val Gly Val Val Thr Cys Ile Val Arg Asn Ala Pro Arg
            260                 265                 270

Gly Leu Gly Ser Pro Val Phe Asp Lys Leu Glu Ala Glu Leu Ala Lys
            275                 280                 285

Ala Ala Leu Ser Leu Pro Ala Thr Lys Gly Phe Glu Phe Gly Ser Gly
        290                 295                 300

Phe Ala Gly Thr Phe Leu Thr Gly Ser Glu His Asn Asp Glu Phe Tyr
305                 310                 315                 320

Val Asp Glu His Gly Lys Ile Arg Thr Arg Thr Asn Arg Ser Gly Gly
                325                 330                 335

Ile Gln Gly Gly Ile Ser Asn Gly Glu Thr Ile Asn Ile Arg Ile Ala
            340                 345                 350

Phe Lys Pro Thr Ser Thr Ile Gly Arg Lys Gln His Thr Val Thr Arg
        355                 360                 365

Asp Lys Lys Glu Thr Glu Leu Ile Ala Arg Gly Arg His Asp Pro Cys
    370                 375                 380

Val Val Pro Arg Ala Val Pro Met Val Glu Ala Met Val Ala Leu Val
385                 390                 395                 400

Leu Met Asp Gln Leu Met Ala Gln Tyr Ala Gln Cys Tyr Met Phe Pro
                405                 410                 415

Val Asn Pro Glu Leu Gln Glu Pro Ile Lys Leu Pro Pro Ser Ile Glu
            420                 425                 430

Ala Thr Asn Met Ser Ile
            435

<210> SEQ ID NO 134
<211> LENGTH: 437
<212> TYPE: PRT
<213> ORGANISM: populus trichocarpa

<400> SEQUENCE: 134

Met Ala Ser Ser Thr Leu Thr Ser Lys Ser Phe Leu Gly Ser Ser Arg
1               5                   10                  15

Ile Asp Gly Ala Ser Ile Ser Ser Asp Leu Arg Gln Leu Ser Ile Ser
            20                  25                  30

Ser Val Gln Ile Ser Phe Arg Ser Arg Ile Pro Lys Lys Leu Gln Ile
        35                  40                  45

Asn Ala Ala Gly Ser Thr Phe Gly Thr Asn Phe Arg Val Thr Thr Phe
    50                  55                  60

Gly Glu Ser His Gly Gly Gly Val Gly Cys Ile Ile Asp Gly Cys Pro
65                  70                  75                  80

Pro Arg Ile Pro Leu Ser Glu Ala Asp Met Gln Phe Asp Leu Asp Arg
                85                  90                  95

Arg Arg Pro Gly Gln Ser Arg Ile Thr Thr Pro Arg Lys Glu Thr Asp
            100                 105                 110

Thr Cys Lys Ile Ser Ser Gly Val Ser Glu Gly Leu Thr Thr Gly Thr
        115                 120                 125

Pro Ile His Val Phe Val Pro Asn Thr Asp Gln Arg Gly Leu Asp Tyr
    130                 135                 140

Ser Glu Met Ser Val Ala Tyr Arg Pro Ser His Ala Asp Ala Thr Tyr
145                 150                 155                 160

Asp Met Lys Tyr Gly Val Arg Ser Val Gln Gly Gly Gly Arg Ser Ser
```

```
                       165                 170                 175
Ala Arg Glu Thr Ile Gly Arg Val Ala Ala Gly Gly Val Ala Lys Lys
                180                 185                 190

Ile Leu Lys Leu Tyr Ala Gly Thr Glu Ile Leu Ala Tyr Val Ser Gln
            195                 200                 205

Val His Lys Val Val Leu Pro Glu Gly Val Val Asp His Asp Ser Leu
        210                 215                 220

Thr Leu Asp Gln Met Glu Ser Asn Ile Val Arg Cys Pro Asp Pro Glu
225                 230                 235                 240

Tyr Ala Glu Lys Met Ile Ala Ala Ile Asp Ala Val Arg Val Lys Gly
                245                 250                 255

Asp Ser Val Gly Gly Val Val Thr Cys Ile Val Arg Asn Ala Pro Arg
            260                 265                 270

Gly Leu Gly Ser Pro Val Phe Asp Lys Leu Glu Ala Glu Leu Ala Lys
        275                 280                 285

Ala Ala Met Ser Leu Pro Ala Thr Lys Gly Phe Glu Phe Gly Ser Gly
    290                 295                 300

Phe Ala Gly Thr Leu Leu Thr Gly Ser Glu His Asn Asp Glu Phe Tyr
305                 310                 315                 320

Thr Asp Lys His Gly Arg Ile Arg Thr Arg Thr Asn Arg Ser Gly Gly
                325                 330                 335

Ile Gln Gly Gly Ile Ser Asn Gly Glu Ile Ile Asn Met Arg Ile Ala
            340                 345                 350

Phe Lys Pro Thr Ser Thr Ile Gly Lys Lys Gln His Thr Val Thr Arg
        355                 360                 365

Asp Lys Lys Glu Thr Asp Leu Ile Ala Arg Gly Arg His Asp Pro Cys
370                 375                 380

Val Val Pro Arg Ala Val Pro Met Val Glu Ala Met Val Ala Leu Val
385                 390                 395                 400

Leu Met Asp Gln Leu Met Ala Gln Tyr Ser Gln Cys Tyr Leu Leu Pro
                405                 410                 415

Ile Asn Ser Glu Leu Gln Glu Pro Leu Ile Met Pro Arg Leu Glu Ala
            420                 425                 430

Ala Asn Ala Ser Val
            435

<210> SEQ ID NO 135
<211> LENGTH: 708
<212> TYPE: PRT
<213> ORGANISM: Cananga odorata

<400> SEQUENCE: 135

Met Glu Phe Cys Gln Glu Ala Gln Asn Asn Gly Asn Gly Leu Cys Ile
1               5                   10                  15

Ala Asp Pro Leu Asn Trp Gly Val Val Ala Glu Ala Leu Lys Gly Ser
            20                  25                  30

His Leu Asp Glu Val Lys Lys Met Val Glu Glu Phe Arg Lys Pro Ser
        35                  40                  45

Ile Lys Leu Gly Gly Ala Thr Leu Thr Ile Ala Gln Val Ala Ala Val
    50                  55                  60

Ala His Glu Ala Gly Val Lys Val Glu Leu Ser Glu Ser Ala Arg Ala
65                  70                  75                  80

Gly Val Lys Ala Ser Ser Asp Trp Val Met Glu Ser Met Asn Lys Gly
                85                  90                  95
```

```
Thr Asp Ser Tyr Gly Val Thr Thr Gly Phe Ala Thr Ser His Arg
            100                 105                 110

Arg Thr Lys Gln Gly Gly Ala Leu Gln Lys Glu Leu Ile Arg Phe Leu
        115                 120                 125

Asn Ala Gly Ile Phe Thr Pro Gly Arg Glu Ser Gly Asn Thr Leu Pro
        130                 135                 140

Pro Thr Ala Thr Arg Ala Ala Met Leu Val Arg Ile Asn Thr Leu Leu
145                 150                 155                 160

Gln Gly Tyr Ser Gly Ile Arg Phe Glu Ile Leu Glu Ala Ile Thr Ser
                165                 170                 175

Phe Leu Asn His His Ile Thr Pro Cys Leu Pro Leu Arg Gly Thr Ile
            180                 185                 190

Thr Ala Ser Gly Asp Leu Val Pro Leu Ser Tyr Ile Ala Gly Leu Leu
        195                 200                 205

Thr Gly Arg Pro Asn Ser Lys Ala His Thr Ala Glu Gly Lys Glu Met
    210                 215                 220

Asp Ala Ala Glu Ala Phe Arg Ala Ala Gly Ile Glu Ser Ser Phe Phe
225                 230                 235                 240

Glu Leu Gln Pro Lys Glu Gly Leu Ala Leu Val Asn Gly Thr Ala Val
                245                 250                 255

Gly Ser Gly Phe Ala Ser Leu Val Leu Phe Glu Ala Asn Val Leu Ala
            260                 265                 270

Val Leu Ser Glu Val Met Ser Ala Ile Phe Cys Glu Val Met Gln Gly
        275                 280                 285

Lys Pro Glu Phe Thr Asp His Leu Thr His Lys Leu Lys His His Pro
290                 295                 300

Gly Gln Ile Glu Ala Ala Ile Met Glu His Ile Leu Asp Gly Ser
305                 310                 315                 320

Ser Tyr Met Lys Met Ala Lys Lys Leu His Glu Leu Asp Pro Leu Gln
                325                 330                 335

Lys Pro Lys Gln Asp Arg Tyr Ala Leu Arg Thr Ser Pro Gln Trp Leu
            340                 345                 350

Gly Pro Leu Ile Glu Val Ile Arg Thr Ser Thr Leu Ser Ile Glu Arg
        355                 360                 365

Glu Ile Asn Ser Val Asn Asp Asn Pro Leu Ile Asp Val Ser Arg Asn
370                 375                 380

Lys Ala Leu His Gly Gly Asn Phe Gln Gly Thr Pro Ile Gly Val Ser
385                 390                 395                 400

Met Asp Asn Thr Arg Leu Ala Val Ala Ser Ile Gly Lys Leu Leu Phe
                405                 410                 415

Ala Gln Phe Ser Glu Leu Val Asn Asp Phe Tyr Asn Asn Gly Leu Pro
            420                 425                 430

Ser Asn Leu Ser Gly Gly Arg Asn Pro Ser Leu Asp Tyr Gly Phe Lys
        435                 440                 445

Gly Ala Glu Ile Ala Met Ala Ala Tyr Cys Ser Glu Leu Gln Phe Leu
    450                 455                 460

Ala Asn Pro Val Thr Asn His Val Gln Ser Ala Glu Gln His Asn Gln
465                 470                 475                 480

Asp Val Asn Ser Leu Gly Leu Ile Ser Ala Arg Lys Thr Ala Glu Ala
                485                 490                 495

Val Glu Ile Leu Lys Leu Met Ser Ala Thr Tyr Leu Val Ala Leu Cys
            500                 505                 510

Gln Ala Val Asp Leu Arg His Leu Glu Glu Asn Leu Lys Ser Thr Val
```

```
                  515                 520                 525
Lys Asn Thr Val Ser Gln Val Ala Lys Arg Val Leu Thr Met Gly Thr
530                 535                 540

Asn Gly Glu Leu His Pro Ser Arg Phe Cys Glu Lys Asp Leu Ile Lys
545                 550                 555                 560

Val Val Asp Arg Glu His Val Phe Ala Tyr Val Asp Asp Pro Cys Ser
                565                 570                 575

Ser Thr Tyr Pro Leu Met Gln Lys Leu Arg Gln Val Leu Val Asp His
                580                 585                 590

Ala Leu Ser Asn Gly Glu Lys Glu Lys Asp Ala Ser Thr Ser Ile Phe
                595                 600                 605

Gln Lys Ile Gly Ala Phe Glu Glu Asp Leu Lys Thr Gln Leu Pro Lys
                610                 615                 620

Glu Val Glu Asn Ala Arg Ala Asp Phe Glu Ser Gly Asn Leu Ala Ile
625                 630                 635                 640

Pro Asn Arg Ile Lys Glu Cys Arg Ser Tyr Pro Leu Tyr Lys Leu Val
                645                 650                 655

Arg Asp Val Leu Asp Thr Gly Leu Leu Thr Gly Glu Lys Val Arg Ser
                660                 665                 670

Pro Gly Glu Asp Phe Asp Lys Val Phe Ala Ala Ile Cys Asp Gly Lys
                675                 680                 685

Leu Ile Asp Pro Leu Leu Glu Cys Leu Arg Gly Trp Asn Gly Ala Pro
                690                 695                 700

Leu Pro Ile Cys
705

<210> SEQ ID NO 136
<211> LENGTH: 711
<212> TYPE: PRT
<213> ORGANISM: Populus trichocarpa

<400> SEQUENCE: 136

Met Glu Phe Cys Gln Asp Ser Arg Asn Gly Asn Gly Ser Leu Gly Phe
1               5                   10                  15

Asn Thr Asn Asp Pro Leu Asn Trp Gly Met Ala Ala Glu Ser Leu Lys
                20                  25                  30

Gly Ser His Leu Asp Glu Val Lys Arg Met Ile Glu Glu Tyr Arg Lys
                35                  40                  45

Pro Val Val Lys Leu Gly Gly Glu Thr Leu Thr Ile Gly Gln Val Thr
                50                  55                  60

Ala Ile Ala Ser Arg Asp Val Gly Val Met Val Glu Leu Ser Glu Glu
65                  70                  75                  80

Ala Arg Ala Gly Val Lys Ala Ser Ser Asp Trp Val Met Asp Ser Met
                85                  90                  95

Ser Lys Gly Thr Asp Ser Tyr Gly Val Thr Thr Gly Phe Gly Ala Thr
                100                 105                 110

Ser His Arg Arg Thr Lys Gln Gly Gly Glu Leu Gln Lys Glu Leu Ile
                115                 120                 125

Arg Phe Leu Asn Ala Gly Ile Phe Gly Asn Gly Thr Glu Ser Ser His
                130                 135                 140

Thr Leu Pro Arg Ser Ala Thr Arg Ala Ala Met Leu Val Arg Ile Asn
145                 150                 155                 160

Thr Leu Leu Gln Gly Tyr Ser Gly Ile Arg Phe Glu Met Leu Glu Ala
                165                 170                 175
```

```
Ile Thr Lys Leu Leu Asn His Asn Ile Thr Pro Cys Leu Pro Leu Arg
            180                 185                 190

Gly Thr Ile Thr Ala Ser Gly Asp Leu Val Pro Leu Ser Tyr Ile Ala
            195                 200                 205

Gly Leu Leu Thr Gly Arg Pro Asn Ser Lys Ala Val Gly Pro Asn Gly
        210                 215                 220

Glu Pro Leu Ser Pro Ala Glu Ala Phe Thr Gln Ala Gly Ile Asp Gly
225                 230                 235                 240

Gly Phe Phe Glu Leu Gln Pro Lys Glu Gly Leu Ala Leu Val Asn Gly
                245                 250                 255

Thr Ala Val Gly Ser Gly Leu Ala Ser Met Val Leu Phe Glu Thr Asn
        260                 265                 270

Val Leu Ala Ile Leu Ser Glu Val Leu Ser Ala Ile Phe Ala Glu Val
            275                 280                 285

Met Gln Gly Lys Pro Glu Phe Thr Asp His Leu Thr His Lys Leu Lys
        290                 295                 300

His His Pro Gly Gln Ile Glu Ala Ala Ala Ile Met Glu His Ile Leu
305                 310                 315                 320

Asp Gly Ser Ser Tyr Val Lys Glu Ala Gln Lys Leu His Glu Ile Asp
                325                 330                 335

Pro Leu Gln Lys Pro Lys Gln Asp Arg Tyr Ala Leu Arg Thr Ser Pro
            340                 345                 350

Gln Trp Leu Gly Pro Leu Ile Glu Val Ile Arg Thr Ser Thr Lys Met
            355                 360                 365

Ile Glu Arg Glu Ile Asn Ser Val Asn Asp Asn Pro Leu Ile Asp Val
370                 375                 380

Ser Arg Asn Lys Ala Leu His Gly Gly Asn Phe Gln Gly Thr Pro Ile
385                 390                 395                 400

Gly Val Ser Met Asp Asn Thr Arg Leu Ala Ile Ala Ser Ile Gly Lys
            405                 410                 415

Leu Met Phe Ala Gln Phe Ser Glu Leu Val Asn Asp Phe Tyr Asn Asn
            420                 425                 430

Gly Leu Pro Ser Asn Leu Thr Gly Gly Arg Asn Pro Ser Leu Asp Tyr
        435                 440                 445

Gly Phe Lys Gly Ala Glu Ile Ala Met Ala Ser Tyr Cys Ser Glu Leu
450                 455                 460

Gln Phe Leu Ala Asn Pro Val Thr Asn His Val Gln Ser Ala Glu Gln
465                 470                 475                 480

His Asn Gln Asp Val Asn Ser Leu Gly Leu Ile Ser Ser Arg Lys Thr
                485                 490                 495

Ala Glu Ala Val Asp Ile Leu Lys Leu Met Ser Thr Thr Phe Leu Val
            500                 505                 510

Gly Leu Cys Gln Ala Val Asp Leu Arg His Ile Glu Glu Asn Leu Lys
        515                 520                 525

Ser Thr Val Lys Asn Thr Val Ser Gln Val Ala Lys Arg Val Leu Thr
530                 535                 540

Met Gly Phe Asn Gly Glu Leu His Pro Ser Arg Phe Cys Glu Lys Asp
545                 550                 555                 560

Leu Leu Lys Val Val Asp Arg Glu His Val Phe Ser Tyr Ile Asp Asp
                565                 570                 575

Pro Cys Ser Ala Thr Tyr Pro Leu Met Gln Lys Leu Arg Gln Val Leu
            580                 585                 590

Val Glu His Ala Leu Val Asn Gly Glu Arg Glu Arg Asn Ser Thr Thr
```

```
                595                 600                 605
Ser Ile Phe Gln Lys Ile Gly Ser Phe Glu Glu Leu Lys Thr Leu
        610                 615                 620
Leu Pro Lys Glu Val Glu Ser Ala Arg Leu Glu Val Glu Asn Gly Asn
625                 630                 635                 640
Pro Ala Ile Pro Asn Arg Ile Lys Glu Cys Arg Ser Tyr Pro Leu Tyr
                645                 650                 655
Lys Phe Val Arg Glu Glu Leu Gly Thr Ser Leu Leu Thr Gly Glu Lys
                660                 665                 670
Val Lys Ser Pro Gly Glu Glu Phe Asp Lys Val Phe Thr Ala Ile Cys
            675                 680                 685
Ala Gly Lys Leu Ile Asp Pro Leu Leu Glu Cys Leu Lys Glu Trp Asp
        690                 695                 700
Gly Ala Pro Leu Pro Ile Cys
705                 710

<210> SEQ ID NO 137
<211> LENGTH: 712
<212> TYPE: PRT
<213> ORGANISM: Musa balbisiana

<400> SEQUENCE: 137

Met Glu Phe Ala Pro Lys Ala Gln Val Val Glu Asn Gly Glu Ala Phe
1               5                   10                  15

Cys Leu Lys Ala Asp Pro Leu Asn Trp Ile Lys Ala Ala Glu Ser Leu
            20                  25                  30

Thr Gly Ser His Leu Asp Glu Val Lys Arg Met Val Glu Phe Arg
        35                  40                  45

Lys Pro Leu Val Arg Leu Glu Gly Ala Thr Leu Thr Ile Ser Gln Val
    50                  55                  60

Ala Ala Val Ala Ala Arg Ser Pro Val Arg Val Glu Leu Ser Glu
65                  70                  75                  80

Glu Ala Arg Asp Gly Val Arg Ala Ser Ser Glu Trp Val Met Glu Ser
                85                  90                  95

Met Asn Lys Gly Thr Asp Ser Tyr Gly Val Thr Thr Gly Phe Gly Ala
            100                 105                 110

Thr Ser His Arg Arg Thr Lys Gln Gly Gly Ala Leu Gln Lys Glu Leu
        115                 120                 125

Ile Arg Phe Leu Asn Ala Gly Ile Phe Gly Ser Gly Pro Glu Ser Gly
    130                 135                 140

Asn Thr Leu Pro Ser Ser Ala Ala Lys Ala Ala Met Leu Val Arg Val
145                 150                 155                 160

Asn Thr Leu Leu Gln Gly Tyr Ser Gly Ile Arg Phe Glu Ile Leu Glu
                165                 170                 175

Ala Ile Ala Ser Leu Leu Asn Asn Gly Ile Thr Pro Cys Leu Pro Leu
            180                 185                 190

Arg Gly Thr Ile Thr Ala Ser Gly Asp Leu Val Pro Leu Ser Tyr Ile
        195                 200                 205

Ala Gly Ile Leu Thr Gly Arg Pro Asn Ala Lys Ala Val Gly Pro Asp
    210                 215                 220

Gly Lys Val Ile Gly Ala Ala Glu Ala Phe Arg Leu Ala Ser Ile Ala
225                 230                 235                 240

Asp Gly Phe Phe Glu Leu Gln Pro Lys Glu Gly Leu Ala Leu Val Asn
                245                 250                 255
```

```
Gly Thr Ala Val Gly Ser Gly Leu Ala Ser Met Val Leu Phe Glu Ala
            260                 265                 270

Asn Val Leu Ala Val Leu Ser Glu Val Leu Ser Ala Val Phe Cys Glu
        275                 280                 285

Val Met Gln Gly Lys Pro Glu Phe Thr Asp His Leu Thr His Lys Leu
    290                 295                 300

Lys His His Pro Gly Gln Ile Glu Ala Ala Ile Met Glu His Ile
305                 310                 315                 320

Leu Glu Gly Ser Ser Tyr Met Lys Met Ala Lys Lys Leu His Glu Gln
                325                 330                 335

Asp Pro Leu Gln Lys Pro Lys Gln Asp Arg Tyr Ala Leu Arg Thr Ser
            340                 345                 350

Pro Gln Trp Leu Gly Pro Gln Ile Glu Val Ile Arg Ala Ser Thr Lys
        355                 360                 365

Ser Ile Glu Arg Glu Ile Asn Ser Val Asn Asp Asn Pro Leu Ile Asp
    370                 375                 380

Val Ser Arg Ser Lys Ala Leu His Gly Gly Asn Phe Gln Gly Thr Pro
385                 390                 395                 400

Ile Gly Val Ser Met Asp Asn Thr Arg Leu Ala Val Ala Ala Ile Gly
                405                 410                 415

Lys Leu Met Phe Ala Gln Phe Ser Glu Leu Val Asn Asp Phe Tyr Asn
            420                 425                 430

Asn Gly Leu Pro Ser Asn Leu Ser Gly Gly Arg Asn Pro Ser Leu Asp
        435                 440                 445

Tyr Gly Phe Lys Gly Ala Glu Ile Ala Met Ala Ala Tyr Cys Ser Glu
    450                 455                 460

Leu Gln Phe Leu Ala Asn Pro Val Thr Asn His Val Gln Ser Ala Glu
465                 470                 475                 480

Gln His Asn Gln Asp Val Asn Ser Leu Gly Leu Ile Ser Ala Arg Lys
                485                 490                 495

Thr Ala Glu Ala Val Asp Ile Leu Lys Leu Met Ser Thr Thr Tyr Leu
            500                 505                 510

Val Ala Leu Cys Gln Ala Val Asp Leu Arg His Leu Glu Glu Asn Leu
        515                 520                 525

Lys Ser Ala Val Lys Ser Thr Val Ser Gln Val Ala Lys Arg Val Leu
    530                 535                 540

Thr Met Gly Ala Asn Gly Glu Leu His Pro Ala Arg Phe Cys Glu Lys
545                 550                 555                 560

Glu Leu Ile Lys Val Val Asp Arg Glu His Val Phe Thr Tyr Val Asp
                565                 570                 575

Asp Pro Cys Ser Ala Thr Tyr Pro Leu Met Gln Lys Leu Arg Gln Val
            580                 585                 590

Leu Val Ala His Ala Leu Glu Asn Gly Asp Lys Glu Lys Asp Ala Gly
        595                 600                 605

Ser Ser Ile Phe Gln Lys Ile Ala Thr Phe Glu Glu Leu Thr Ala
    610                 615                 620

Gln Leu Pro Lys Glu Val Glu Ala Ala Arg Ala Ala Val Glu Gly Gly
625                 630                 635                 640

Lys Ala Ala Ile Pro Asn Arg Ile Glu Glu Cys Arg Ser Tyr Pro Leu
                645                 650                 655

Tyr Arg Leu Val Arg Glu Glu Leu Lys Thr Gly Phe Leu Thr Gly Glu
            660                 665                 670

Lys Val Arg Ser Pro Gly Glu Glu Phe Asp Lys Val Phe Asp Ala Ile
```

```
                    675                 680                 685
    Cys Gln Gly Lys Val Ile Asp Pro Leu Leu Glu Cys Leu Lys Glu Trp
        690                 695                 700

Asn Gly Ala Pro Leu Pro Ile Cys
    705                 710

<210> SEQ ID NO 138
<211> LENGTH: 719
<212> TYPE: PRT
<213> ORGANISM: Ricinus communis

<400> SEQUENCE: 138

Met Glu Phe Ser His Asp Asp Asn Asn Asn His Gly Ser Ser Leu
    1               5                   10                  15

Glu Ser Phe Cys Thr Ala Thr Ala Gly His His Asp Pro Leu Asn Trp
                    20                  25                  30

Gly Met Leu Ala Asp Ser Leu Lys Gly Ser His Leu Asp Glu Val Lys
                35                  40                  45

Arg Met Val Asp Glu Tyr Arg Arg Pro Val Val Arg Leu Gly Gly Glu
        50                  55                  60

Thr Leu Thr Ile Ala Gln Val Thr Ala Ile Ala Asn Arg Asp Ala Gly
    65                  70                  75                  80

Ile Lys Val Glu Leu Ser Glu Asp Ala Arg Ala Gly Val Lys Ala Ser
                    85                  90                  95

Ser Asp Trp Val Met Asp Ser Met Asn Lys Gly Thr Asp Ser Tyr Gly
                    100                 105                 110

Val Thr Thr Gly Phe Gly Ala Thr Ser His Arg Arg Thr Lys Gln Gly
                    115                 120                 125

Gly Ala Leu Gln Arg Glu Leu Ile Arg Phe Leu Asn Ala Gly Ile Phe
            130                 135                 140

Gly Asn Gly Thr Glu Ser Cys His Thr Leu Pro His Ser Ala Thr Arg
    145                 150                 155                 160

Ala Ala Met Leu Val Arg Ile Asn Thr Leu Leu Gln Gly Tyr Ser Gly
                    165                 170                 175

Ile Arg Phe Glu Ile Leu Glu Ala Ile Thr Lys Phe Ile Asn His Asn
                    180                 185                 190

Val Thr Pro Ser Leu Pro Leu Arg Gly Thr Ile Thr Ala Ser Gly Asp
                    195                 200                 205

Leu Val Pro Leu Ser Tyr Ile Ala Gly Leu Leu Ile Gly Arg Pro Asn
            210                 215                 220

Ser Lys Cys Val Gly Pro Asn Gly Glu Ser Leu Asp Pro Thr Glu Ala
    225                 230                 235                 240

Phe Thr Leu Ala Gly Ile Asn Ser Gly Phe Phe Asp Leu Gln Pro Lys
                    245                 250                 255

Glu Gly Leu Ala Leu Val Asn Gly Thr Ala Val Gly Ser Gly Leu Ala
                    260                 265                 270

Ser Met Val Leu Phe Glu Ala Asn Val Leu Gly Ile Leu Ser Glu Val
                    275                 280                 285

Leu Ser Ala Val Phe Ala Glu Val Met Gln Gly Lys Pro Glu Phe Thr
            290                 295                 300

Asp His Leu Thr His Lys Leu Lys His His Pro Gly Gln Ile Glu Ala
    305                 310                 315                 320

Ala Ala Ile Met Glu His Ile Leu Asp Gly Ser Ser Tyr Ile Lys Ala
                    325                 330                 335
```

Ala Gln Lys Leu His Glu Val Asp Pro Leu Gln Lys Pro Lys Gln Asp
            340                 345                 350

Arg Tyr Ala Leu Arg Thr Ser Pro Gln Trp Leu Gly Pro Gln Ile Glu
        355                 360                 365

Val Ile Arg Ser Ala Thr Lys Met Ile Glu Arg Glu Ile Asn Ser Val
370                 375                 380

Asn Asp Asn Pro Leu Ile Asp Val Ser Arg Asn Lys Ala Leu His Gly
385                 390                 395                 400

Gly Asn Phe Gln Gly Thr Pro Ile Gly Val Ser Met Asp Asn Thr Arg
                405                 410                 415

Leu Ala Ile Ala Ala Ile Gly Lys Leu Met Phe Ala Gln Phe Ser Glu
            420                 425                 430

Leu Val Asn Asp Phe Tyr Asn Asn Gly Leu Pro Ser Asn Leu Thr Gly
        435                 440                 445

Gly Arg Asn Pro Ser Leu Asp Tyr Gly Phe Lys Gly Ala Glu Ile Ala
    450                 455                 460

Met Ala Ser Tyr Cys Ser Glu Leu Gln Phe Leu Ala Asn Pro Val Thr
465                 470                 475                 480

Asn His Val Gln Ser Ala Glu Gln His Asn Gln Asp Val Asn Ser Leu
                485                 490                 495

Gly Leu Ile Ser Ala Arg Lys Thr Ala Glu Ala Val Asp Ile Leu Lys
            500                 505                 510

Leu Met Ser Ser Thr Phe Leu Val Ala Leu Cys Gln Ala Ile Asp Leu
        515                 520                 525

Arg His Leu Glu Glu Asn Leu Lys Ser Thr Val Lys Asn Thr Val Ser
    530                 535                 540

Gln Val Ala Lys Arg Val Leu Thr Met Gly Phe Asn Gly Glu Leu His
545                 550                 555                 560

Pro Ser Arg Phe Cys Glu Lys Asp Leu Leu Lys Val Val Asp Arg Glu
                565                 570                 575

Tyr Ile Phe Ala Tyr Ile Asp Asp Pro Cys Ser Ala Thr Tyr Pro Leu
            580                 585                 590

Met Gln Lys Leu Arg Gln Val Leu Val Asp His Ala Leu Leu Asn Gly
        595                 600                 605

Glu Lys Glu Lys Asn Ser Ser Thr Ser Ile Phe Gln Lys Ile Gly Ala
    610                 615                 620

Phe Glu Glu Glu Leu Lys Ala Leu Leu Pro Lys Glu Val Glu Asn Ala
625                 630                 635                 640

Arg Thr Glu Tyr Asp Asn Gly Asn Pro Ala Ile Pro Asn Lys Ile Lys
                645                 650                 655

Glu Cys Arg Ser Tyr Pro Leu Tyr Lys Phe Val Arg Glu Glu Leu Gly
            660                 665                 670

Thr Gly Leu Leu Thr Gly Glu Lys Ile Arg Ser Pro Gly Glu Glu Phe
        675                 680                 685

Asp Lys Val Phe Ser Ala Met Cys Ala Gly Lys Leu Ile Asp Pro Met
    690                 695                 700

Leu Glu Cys Leu Lys Glu Trp Asn Gly Ala Pro Leu Pro Ile Cys
705                 710                 715

<210> SEQ ID NO 139
<211> LENGTH: 506
<212> TYPE: PRT
<213> ORGANISM: Cananga odorata

<400> SEQUENCE: 139

```
Met Asp Leu Leu Leu Leu Gln Lys Thr Leu Phe Ala Leu Phe Phe Ser
1               5                   10                  15
Ile Val Val Ala Thr Val Val Ser Lys Leu Arg Gly Lys Arg Phe Lys
                20                  25                  30
Leu Pro Pro Gly Pro Leu Pro Ile Pro Val Phe Gly Asn Trp Leu Gln
            35                  40                  45
Val Gly Asp Asp Leu Asn His Arg Asn Leu Thr Asp Leu Ala Arg Lys
50                  55                  60
Phe Gly Asp Ile Phe Leu Leu Arg Met Gly Gln Arg Asn Leu Val Val
65                  70                  75                  80
Val Ser Ser Pro Asp Tyr Ala Lys Glu Val Leu His Thr Gln Gly Val
                85                  90                  95
Glu Phe Gly Ser Arg Thr Arg Asn Val Val Phe Asp Ile Phe Thr Gly
                100                 105                 110
Lys Gly Gln Asp Met Val Phe Thr Val Tyr Gly Asp His Trp Arg Lys
            115                 120                 125
Met Arg Arg Ile Met Thr Val Pro Phe Phe Thr Asn Lys Val Val Gln
        130                 135                 140
Gln Tyr Arg Tyr Gly Trp Glu Asp Glu Ile Ser Arg Val Val Glu Asp
145                 150                 155                 160
Val Lys Ala Asn Pro Asp Ala Ala Thr Lys Gly Ile Val Leu Arg Arg
                165                 170                 175
Arg Leu Gln Leu Met Met Tyr Asn Asn Met Tyr Arg Ile Met Phe Asp
            180                 185                 190
Arg Arg Phe Glu Ser Glu Asp Pro Leu Phe Val Lys Leu Lys Ala
            195                 200                 205
Leu Asn Gly Glu Arg Ser Arg Leu Ala Gln Ser Phe Glu Tyr Asn Tyr
210                 215                 220
Gly Asp Phe Ile Pro Ile Leu Arg Pro Leu Leu Arg Gly Tyr Leu Lys
225                 230                 235                 240
Ile Cys Lys Glu Val Lys Glu Arg Arg Leu Gln Leu Phe Lys Asp Tyr
                245                 250                 255
Phe Leu Glu Glu Arg Lys Lys Leu Ala Ser Thr Lys Ser Ser Thr Ser
            260                 265                 270
Ala Ser Gly Leu Ala Cys Ala Ile Asp His Ile Leu Asp Ala Gln Lys
        275                 280                 285
Lys Gly Glu Ile Asn Glu Asp Asn Val Leu Tyr Ile Val Glu Asn Ile
        290                 295                 300
Asn Val Ala Ala Ile Glu Thr Thr Leu Trp Ser Ile Glu Trp Gly Ile
305                 310                 315                 320
Ala Glu Leu Val Asn His Gln Asp Val Gln Gln Lys Leu Arg Asn Glu
                325                 330                 335
Leu Asp Thr Val Leu Gly Val Gly His Gln Ile Thr Glu Pro Asp Thr
            340                 345                 350
His Lys Leu Pro Tyr Leu Gln Ala Val Ile Lys Glu Thr Leu Arg Leu
        355                 360                 365
Arg Met Ala Ile Pro Leu Leu Val Pro His Met Asn Leu His Asp Ala
        370                 375                 380
Lys Leu Gly Gly Tyr Asp Ile Pro Ala Glu Ser Lys Ile Leu Val Asn
385                 390                 395                 400
Ala Trp Tyr Leu Ala Asn Asn Pro Ala His Trp Lys Lys Pro Glu Glu
                405                 410                 415
```

```
Phe Arg Pro Glu Arg Phe Glu Glu Ala His Val Glu Ala Asn
                420             425             430

Gly Asn Asp Phe Arg Tyr Leu Pro Phe Gly Val Gly Arg Arg Ser Cys
            435                 440                 445

Pro Gly Ile Ile Leu Ala Leu Pro Ile Leu Gly Ile Thr Leu Gly Arg
450                 455                 460

Leu Val Gln Asn Phe Glu Leu Leu Pro Pro Gly Gln Ser Lys Ile
465             470                 475                 480

Asp Thr Ser Glu Lys Gly Gly Gln Phe Ser Leu His Ile Leu Arg His
                485                 490                 495

Ser Thr Ile Val Val Arg Pro Arg Ala Phe
                500                 505

<210> SEQ ID NO 140
<211> LENGTH: 506
<212> TYPE: PRT
<213> ORGANISM: glycine max

<400> SEQUENCE: 140

Met Asp Leu Leu Leu Glu Lys Thr Leu Ile Gly Leu Phe Leu Ala
1               5                   10                  15

Ala Val Val Ala Ile Ala Val Ser Thr Leu Arg Gly Arg Lys Phe Lys
                20                  25                  30

Leu Pro Pro Gly Pro Leu Pro Val Pro Ile Phe Gly Asn Trp Leu Gln
            35                  40                  45

Val Gly Asp Asp Leu Asn His Arg Asn Leu Thr Asp Leu Ala Lys Lys
50                  55                  60

Phe Gly Asp Ile Phe Leu Leu Arg Met Gly Gln Arg Asn Leu Val Val
65                  70                  75                  80

Val Ser Ser Pro Glu Leu Ala Lys Glu Val Leu His Thr Gln Gly Val
                85                  90                  95

Glu Phe Gly Ser Arg Thr Arg Asn Val Val Phe Asp Ile Phe Thr Gly
            100                 105                 110

Lys Gly Gln Asp Met Val Phe Thr Val Tyr Gly Glu His Trp Arg Lys
        115                 120                 125

Met Arg Arg Ile Met Thr Val Pro Phe Phe Thr Asn Lys Val Val Gln
130                 135                 140

Gln Tyr Arg His Gly Trp Glu Ser Glu Ala Ala Val Val Glu Asp
145                 150                 155                 160

Val Lys Lys Asn Pro Asp Ala Ala Val Ser Gly Thr Val Ile Arg Arg
                165                 170                 175

Arg Leu Gln Leu Met Met Tyr Asn Asn Met Tyr Arg Ile Met Phe Asp
            180                 185                 190

Arg Arg Phe Glu Ser Glu Asp Pro Ile Phe Gln Arg Leu Arg Ala
        195                 200                 205

Leu Asn Gly Glu Arg Ser Arg Leu Ala Gln Ser Phe Glu Tyr Asn Tyr
            210                 215                 220

Gly Asp Phe Ile Pro Ile Leu Arg Pro Phe Leu Lys Gly Tyr Leu Lys
225                 230                 235                 240

Ile Cys Lys Glu Val Lys Glu Thr Arg Leu Lys Leu Phe Lys Asp Tyr
                245                 250                 255

Phe Val Asp Glu Arg Lys Lys Leu Gly Ser Thr Lys Ser Thr Asn Asn
            260                 265                 270

Asn Asn Glu Leu Lys Cys Ala Ile Asp His Ile Leu Asp Ala Gln Arg
        275                 280                 285
```

```
Lys Gly Glu Ile Asn Glu Asp Asn Val Leu Tyr Ile Val Glu Asn Ile
        290                 295                 300

Asn Val Ala Ala Ile Glu Thr Thr Leu Trp Ser Ile Glu Trp Gly Ile
305                 310                 315                 320

Ala Glu Leu Val Asn His Pro Glu Ile Gln Gln Lys Leu Arg Asp Glu
                325                 330                 335

Ile Asp Arg Val Leu Gly Ala Gly His Gln Val Thr Glu Pro Asp Ile
                340                 345                 350

Gln Lys Leu Pro Tyr Leu Gln Ala Val Val Lys Glu Thr Leu Arg Leu
                355                 360                 365

Arg Met Ala Ile Pro Leu Val Pro His Met Asn Leu His Asp Ala
370                 375                 380

Lys Leu Gly Gly Tyr Asp Ile Pro Ala Glu Ser Arg Ile Leu Val Asn
385                 390                 395                 400

Ala Trp Trp Leu Ala Asn Asn Pro Ala His Trp Lys Lys Pro Glu Glu
                405                 410                 415

Phe Arg Pro Glu Arg Phe Glu Glu Ser Leu Val Glu Ala Asn
                420                 425                 430

Gly Asn Asp Phe Arg Tyr Leu Pro Phe Gly Val Gly Arg Arg Ser Cys
                435                 440                 445

Pro Gly Ile Ile Leu Ala Leu Pro Ile Leu Gly Ile Thr Leu Gly Arg
450                 455                 460

Leu Val Gln Asn Phe Glu Leu Leu Pro Pro Gly Gln Ser Gln Ile
465                 470                 475                 480

Asp Thr Ser Glu Lys Gly Gly Gln Phe Ser Leu His Ile Leu Lys His
                485                 490                 495

Ser Thr Ile Val Ala Lys Pro Arg Ser Phe
                500                 505

<210> SEQ ID NO 141
<211> LENGTH: 505
<212> TYPE: PRT
<213> ORGANISM: Theobroma cacao

<400> SEQUENCE: 141

Met Asp Leu Leu Leu Glu Lys Ala Leu Ser Leu Phe Ile Thr
1               5                   10                  15

Val Ile Leu Ala Ile Leu Ile Ser Lys Leu Arg Ser Lys Arg Phe Arg
                20                  25                  30

Leu Pro Pro Gly Pro Ile Pro Val Pro Val Phe Gly Asn Trp Leu Gln
                35                  40                  45

Val Gly Asp Asp Leu Asn His Arg Asn Leu Thr Asp Leu Ala Lys Lys
50                  55                  60

Phe Gly Asp Ile Phe Leu Leu Arg Met Gly Gln Arg Asn Leu Val Val
65                  70                  75                  80

Val Ser Ser Pro Glu Leu Ala Lys Glu Val Leu His Thr Gln Gly Val
                85                  90                  95

Glu Phe Gly Ser Arg Thr Arg Asn Val Val Phe Asp Ile Phe Thr Gly
                100                 105                 110

Lys Gly Gln Asp Met Val Phe Thr Val Tyr Gly Glu His Trp Arg Lys
                115                 120                 125

Met Arg Arg Ile Met Thr Val Pro Phe Phe Thr Asn Lys Val Val Gln
130                 135                 140

Gln Tyr Arg His Gly Trp Glu Asp Glu Val Ala Arg Val Val Glu Asp
```

```
            145                 150                 155                 160
Val Arg Lys Asn Pro Glu Ala Ala Thr Asn Gly Ile Val Leu Arg Arg
                165                 170                 175

Arg Leu Gln Leu Met Met Tyr Asn Asn Met Tyr Arg Ile Met Phe Asp
                180                 185                 190

Arg Arg Phe Glu Ser Glu Asp Asp Pro Leu Phe Val Lys Leu Lys Ala
                195                 200                 205

Leu Asn Gly Glu Arg Ser Arg Leu Ala Gln Ser Phe Glu Tyr Asn Tyr
                210                 215                 220

Gly Asp Phe Ile Pro Ile Leu Arg Pro Phe Leu Arg Gly Tyr Leu Lys
225                 230                 235                 240

Leu Cys Lys Glu Val Lys Glu Met Arg Leu Gln Leu Phe Lys Asp Tyr
                245                 250                 255

Phe Leu Glu Glu Arg Lys Asn Leu Ala Ser Thr Thr Ile Ser Asp Asn
                260                 265                 270

Asn Ala Leu Lys Cys Ala Ile Asp His Ile Leu Asp Ala Gln Gln Lys
                275                 280                 285

Gly Glu Ile Asn Glu Asp Asn Val Leu Tyr Ile Val Glu Asn Ile Asn
                290                 295                 300

Val Ala Ala Ile Glu Thr Thr Leu Trp Ser Ile Glu Trp Gly Ile Ala
305                 310                 315                 320

Glu Leu Val Asn His Pro Glu Ile Gln Gln Lys Leu Arg Asn Glu Ile
                325                 330                 335

Asp Thr Val Leu Gly Pro Gly Val Pro Val Thr Glu Pro Asp Thr His
                340                 345                 350

Lys Leu Pro Tyr Leu Gln Ala Val Ile Lys Glu Thr Leu Arg Leu Arg
                355                 360                 365

Met Ala Ile Pro Leu Leu Val Pro His Met Asn Leu His Asp Ala Lys
                370                 375                 380

Leu Gly Gly Tyr Asp Ile Pro Ala Glu Ser Lys Val Leu Val Asn Ala
385                 390                 395                 400

Trp Trp Leu Ala Asn Asn Pro Ala Lys Trp Lys Asn Pro Glu Glu Phe
                405                 410                 415

Arg Pro Glu Arg Phe Phe Glu Glu Ala Lys Val Glu Ala Asn Gly
                420                 425                 430

Asn Asp Phe Arg Tyr Leu Pro Phe Gly Val Gly Arg Arg Ser Cys Pro
                435                 440                 445

Gly Ile Ile Leu Ala Leu Pro Ile Leu Gly Ile Thr Leu Gly Arg Leu
                450                 455                 460

Val Gln Asn Phe Glu Leu Leu Pro Pro Gly Gln Ala Lys Leu Asp
465                 470                 475                 480

Thr Ser Glu Lys Gly Gly Gln Phe Ser Leu His Ile Leu Lys His Ser
                485                 490                 495

Thr Ile Val Ala Lys Pro Arg Val Phe
                500                 505

<210> SEQ ID NO 142
<211> LENGTH: 505
<212> TYPE: PRT
<213> ORGANISM: Gossypium arboreum

<400> SEQUENCE: 142

Met Asp Leu Leu Phe Leu Glu Lys Val Leu Ile Ser Leu Phe Phe Thr
1               5                   10                  15
```

-continued

```
Ile Ile Phe Ala Ile Leu Val Ser Lys Leu Arg Gly Lys Arg Phe Lys
            20                  25                  30

Leu Pro Pro Gly Pro Leu Pro Ile Pro Val Phe Gly Asn Trp Leu Gln
        35                  40                  45

Val Gly Asp Asp Leu Asn His Arg Asn Leu Thr Asp Leu Ala Lys Lys
    50                  55                  60

Phe Gly Asp Ile Phe Leu Leu Arg Met Gly Gln Arg Asn Leu Val Val
65                  70                  75                  80

Ile Ser Ser Pro Glu Leu Ala Lys Glu Val Leu His Thr Gln Gly Val
                85                  90                  95

Glu Phe Gly Ser Arg Thr Arg Asn Val Val Phe Asp Ile Phe Thr Gly
            100                 105                 110

Lys Gly Gln Asp Met Val Phe Thr Val Tyr Gly Glu His Trp Arg Lys
        115                 120                 125

Met Arg Arg Ile Met Thr Val Pro Phe Phe Thr Asn Lys Val Val Gln
    130                 135                 140

Gln Tyr Arg His Gly Trp Glu Asp Glu Ala Ala Ser Val Val Glu Asp
145                 150                 155                 160

Val Lys Lys Asn Pro Glu Ala Ala Thr Asn Gly Ile Val Leu Arg Arg
                165                 170                 175

Lys Leu Gln Leu Met Met Tyr Asn Asn Met Tyr Arg Ile Met Phe Asp
            180                 185                 190

Arg Arg Phe Glu Ser Glu Asp Asp Pro Leu Phe Val Lys Leu Lys Ala
        195                 200                 205

Leu Asn Gly Glu Arg Ser Arg Leu Ala Gln Ser Phe Glu Tyr Asn Tyr
    210                 215                 220

Gly Asp Phe Ile Pro Ile Leu Arg Pro Phe Leu Arg Gly Tyr Leu Lys
225                 230                 235                 240

Leu Cys Lys Glu Val Lys Glu Ile Arg Leu Gln Leu Phe Arg Asp Gln
                245                 250                 255

Phe Leu Glu Glu Arg Lys Lys Leu Ala Thr Thr Lys Arg Ile Asp Asn
            260                 265                 270

Asn Ala Leu Lys Cys Ala Ile Asp His Ile Leu Asp Ala Gln Arg Lys
        275                 280                 285

Gly Glu Ile Asn Glu Asp Asn Val Leu Tyr Ile Val Glu Asn Ile Asn
    290                 295                 300

Val Ala Ala Ile Glu Thr Thr Leu Trp Ser Ile Glu Trp Gly Ile Ala
305                 310                 315                 320

Glu Leu Val Asn His Pro Glu Ile Gln Gln Lys Leu Arg Asn Glu Ile
                325                 330                 335

Asp Thr Val Leu Gly Pro Gly Val Gln Val Thr Glu Pro Asp Thr His
            340                 345                 350

Lys Leu Pro Tyr Leu Gln Ala Val Ile Lys Glu Thr Leu Arg Leu Arg
        355                 360                 365

Met Ala Ile Pro Leu Leu Val Pro His Met Asn Leu His Asp Ala Lys
    370                 375                 380

Leu Gly Gly Tyr Asp Ile Pro Ala Glu Ser Lys Ile Leu Val Asn Ala
385                 390                 395                 400

Trp Trp Leu Ala Asn Asn Pro Ala His Trp Lys Asn Pro Glu Glu Phe
                405                 410                 415

Arg Pro Glu Arg Phe Phe Glu Glu Ser Lys Val Glu Ala Asn Gly
            420                 425                 430

Asn Asp Phe Arg Tyr Leu Pro Phe Gly Val Gly Arg Arg Ser Cys Pro
```

```
                435                 440                 445
Gly Ile Ile Leu Ala Leu Pro Ile Leu Gly Ile Thr Leu Gly Arg Leu
450                 455                 460

Val Gln Asn Phe Glu Leu Leu Pro Pro Lys Gly Gln Ser Lys Leu Asp
465                 470                 475                 480

Thr Ser Glu Lys Gly Gly Gln Phe Ser Leu His Ile Leu Lys His Ser
                485                 490                 495

Thr Ile Val Ala Lys Pro Arg Val Phe
                500                 505

<210> SEQ ID NO 143
<211> LENGTH: 718
<212> TYPE: PRT
<213> ORGANISM: Cananga odorata

<400> SEQUENCE: 143

Met Leu Met Ala Leu Ala Ala Phe Pro His Pro Cys His Phe Ile Gly
1               5                   10                  15

Ser Ala Ala Ser Ile Leu Gln Lys Ser Thr Pro His Cys Ser Tyr Leu
                20                  25                  30

Leu Gly Glu Ala Asp Leu Gln Leu Ser Tyr His His Lys Leu Pro Lys
            35                  40                  45

Gly Lys Lys Val Pro Trp Ile Cys Ala Ser Leu Ser Glu Thr Gly Glu
50                  55                  60

Tyr Tyr Ser Gln Arg Pro Glu Thr Pro Leu Leu Asp Thr Ile Asn Tyr
65                  70                  75                  80

Pro Ile His Met Lys Asn Leu Ser Thr Lys Glu Leu Lys Gln Leu Ala
                85                  90                  95

Asp Glu Leu Arg Ser Asp Val Ile Phe Asn Val Ser Lys Thr Gly Gly
            100                 105                 110

His Leu Gly Ser Ser Leu Gly Val Val Glu Leu Thr Val Ala Leu His
        115                 120                 125

Tyr Val Phe Asn Ala Pro Gln Asp Lys Ile Leu Trp Asp Val Gly His
    130                 135                 140

Gln Ala Tyr Pro His Lys Ile Leu Thr Gly Arg Arg Asp Lys Met Pro
145                 150                 155                 160

Thr Ile Arg Gln Thr Asn Gly Leu Ser Gly Phe Thr Lys Arg Ala Glu
                165                 170                 175

Ser Glu Tyr Asp Cys Phe Gly Ala Gly His Ser Ser Thr Ser Ile Ser
            180                 185                 190

Ala Ala Leu Gly Met Ala Val Gly Arg Asp Leu Lys Gly Arg Lys Asn
        195                 200                 205

His Val Val Ala Val Ile Gly Asp Gly Ala Met Thr Ala Gly Gln Ala
    210                 215                 220

Tyr Glu Ala Met Asn Asn Ala Gly Tyr Leu Asp Ser Asn Met Ile Val
225                 230                 235                 240

Ile Leu Asn Asp Asn Lys Gln Val Ser Leu Pro Thr Ala Thr Leu Asp
                245                 250                 255

Gly Pro Val Pro Pro Val Gly Ala Leu Ser Ser Ala Leu Ser Arg Leu
            260                 265                 270

Gln Ser Ser Arg Pro Leu Arg Glu Leu Arg Glu Val Ala Lys Gly Val
        275                 280                 285

Thr Lys Gln Ile Gly Gly Pro Met His Glu Leu Ala Ala Lys Val Asp
    290                 295                 300
```

```
Glu Tyr Ala Arg Gly Met Ile Ser Gly Ser Gly Ser Thr Leu Phe Glu
305                 310                 315                 320

Glu Leu Gly Leu Tyr Tyr Ile Gly Pro Val Asp Gly His Asn Ile Asp
            325                 330                 335

Asp Leu Val Ser Ile Leu Lys Glu Val Lys Asn Thr Lys Ile Thr Gly
        340                 345                 350

Pro Val Leu Ile His Val Val Thr Glu Lys Gly Arg Gly Tyr Pro Tyr
    355                 360                 365

Ala Glu Arg Ala Ser Asp Lys Tyr His Gly Val Thr Lys Phe Asp Pro
370                 375                 380

Ala Thr Gly Lys Gln Phe Lys Gly Ser Ser Pro Thr Gln Ser Tyr Thr
385                 390                 395                 400

Met Tyr Phe Ala Glu Ala Leu Ile Ala Glu Ala Glu Ala Asp Lys Asp
                405                 410                 415

Ile Val Gly Ile His Ala Ala Met Gly Gly Thr Gly Met Asn Leu
                420                 425                 430

Phe Leu Arg Arg Phe Pro Thr Arg Cys Phe Asp Val Gly Ile Ala Glu
        435                 440                 445

Gln His Ala Val Thr Phe Ala Ala Gly Leu Ala Cys Glu Gly Leu Lys
    450                 455                 460

Pro Phe Cys Ala Ile Tyr Ser Ser Phe Leu Gln Arg Ala Tyr Asp Gln
465                 470                 475                 480

Val Ile His Asp Val Asp Leu Gln Lys Leu Pro Val Arg Phe Ala Met
                485                 490                 495

Asp Arg Ala Gly Leu Val Gly Ala Asp Gly Pro Thr His Ser Gly Ser
            500                 505                 510

Phe Asp Val Thr Tyr Met Ala Cys Leu Pro Asn Met Val Val Met Ala
        515                 520                 525

Pro Ser Asp Glu Ala Glu Leu Phe His Met Val Ala Thr Ala Ala Ala
530                 535                 540

Ile Asn Asp Arg Pro Ser Cys Phe Arg Tyr Pro Arg Gly Asn Gly Ile
545                 550                 555                 560

Gly Val Pro Leu Pro Pro Gly Asn Lys Gly Val Pro Leu Glu Ile Gly
                565                 570                 575

Lys Gly Arg Val Leu Ile Gly Gly Glu Arg Val Ala Leu Leu Gly Tyr
            580                 585                 590

Gly Thr Ala Val Gln Ser Cys Leu Ala Ala Ala Ser Leu Val Gly Gln
        595                 600                 605

Gln Gly Leu Gln Ile Thr Val Ala Asp Ala Arg Phe Cys Lys Pro Leu
    610                 615                 620

Asp Gln Asp Leu Ile Arg Ser Leu Ala Lys Ser His Glu Val Leu Ile
625                 630                 635                 640

Thr Val Glu Glu Gly Ser Ile Gly Gly Phe Gly Ser His Val Ala Gln
                645                 650                 655

Phe Met Ser Leu Asp Gly Leu Leu Asp Gly Thr Thr Lys Trp Arg Pro
            660                 665                 670

Leu Ile Leu Pro Asp Arg Tyr Ile Glu His Gly Ser Pro Val Asp Gln
        675                 680                 685

Met Val Glu Ala Gly Leu Met Pro Ser His Val Ala Thr Val Phe
    690                 695                 700

Asn Val Leu Gly Lys Thr Arg Glu Ala Leu Asn Ile Met Ser
705                 710                 715
```

<210> SEQ ID NO 144
<211> LENGTH: 730
<212> TYPE: PRT
<213> ORGANISM: Cananga odorata

<400> SEQUENCE: 144

```
Met Ala Ala Ser Ala Val Phe Met His Ser Ser Leu Pro Leu Ser
 1               5                  10                  15

Asp Phe Thr Gln Glu His Ser Ile Arg Lys Leu Arg Ser Ile Ser Arg
            20                  25                  30

Pro Ala Ala Arg Lys Asn Thr Phe Lys Phe Tyr Ile Ala Ala Cys Ser
        35                  40                  45

Lys Asp Ser Asp Ser Tyr Ser Thr Ser Ala Ile Ser Val Asn Lys Asp
    50                  55                  60

Val Pro Glu Ser Gln Glu Asn Ser Leu Ser Leu Asn Phe Thr Gly Glu
65                  70                  75                  80

Lys Pro Glu Thr Pro Ile Leu Asn Thr Val Asn Tyr Pro Ile His Met
                85                  90                  95

Lys Asn Leu Thr Ile Lys Glu Leu Ala Arg Leu Ala Asp Glu Leu Arg
            100                 105                 110

Glu Glu Ile Val Tyr Thr Val Ser Lys Thr Gly Gly His Leu Ser Ser
        115                 120                 125

Ser Leu Gly Val Ala Glu Leu Thr Val Ala Leu His His Val Phe Asn
    130                 135                 140

Thr Pro Glu Asp Lys Ile Val Trp Asp Val Gly His Gln Ala Tyr Ala
145                 150                 155                 160

His Lys Ile Leu Thr Gly Arg Arg Ser Arg Met His Thr Ile Arg Gln
                165                 170                 175

Thr Ser Gly Leu Ala Gly Phe Pro Lys Arg Asp Glu Ser Lys His Asp
            180                 185                 190

Ala Phe Gly Val Gly His Ser Ser Thr Ser Ile Ser Ala Gly Leu Gly
        195                 200                 205

Met Ala Ile Gly Arg Asp Leu Leu Arg Lys Asn Asn His Val Val Ala
    210                 215                 220

Val Ile Gly Asp Gly Ala Met Thr Ala Gly Gln Ala Tyr Glu Ala Met
225                 230                 235                 240

Asn Asn Ala Gly Tyr Leu Asp Ser Asn Leu Ile Ile Val Leu Asn Asp
                245                 250                 255

Asn Lys Gln Val Ser Leu Pro Thr Ala Thr Ile Asp Gly Pro Ala Pro
            260                 265                 270

Pro Val Gly Ala Leu Ser Lys Ala Leu Thr Arg Leu Gln Ser Ser Arg
        275                 280                 285

Lys Leu Arg Gln Leu Arg Glu Val Ala Lys Gly Ile Thr Lys Ser Ile
    290                 295                 300

Gly Gly Gln Thr His Glu Ile Ala Ala Lys Val Asp Glu Tyr Ala Arg
305                 310                 315                 320

Gly Leu Met Gly Ala Pro Gly Ala Thr Leu Phe Glu Glu Leu Gly Leu
                325                 330                 335

Tyr Tyr Ile Gly Pro Val Asp Gly His Asn Val Glu Glu Leu Val His
            340                 345                 350

Ile Phe Glu Lys Val Lys Ala Thr Pro Ala Thr Gly Pro Val Leu Ile
        355                 360                 365

His Ile Ile Thr Glu Lys Gly Lys Gly Tyr Pro Pro Ala Glu Ala Ala
    370                 375                 380
```

Ala Asp Lys Met His Gly Val Val Lys Phe Asp Pro Lys Thr Gly Lys
385                 390                 395                 400

Gln Thr Lys Val Lys Ala Pro Thr Leu Ser Tyr Thr Gln Tyr Phe Ala
            405                 410                 415

Glu Gly Leu Ile Ala Glu Ala Lys Gln Asp Glu Lys Ile Val Ala Ile
            420                 425                 430

His Ala Ala Met Gly Gly Thr Gly Leu Asn Val Phe Gln Lys Gln
            435                 440                 445

Phe Pro Glu Arg Cys Phe Asp Val Gly Ile Ala Glu Gln His Ala Val
        450                 455                 460

Thr Phe Ala Ala Gly Leu Ala Ala Glu Gly Leu Lys Pro Phe Cys Ala
465                 470                 475                 480

Ile Tyr Ser Ser Phe Leu Gln Arg Gly Tyr Asp Gln Val Val His Asp
                485                 490                 495

Val Asp Leu Gln Lys Leu Pro Val Arg Phe Ala Met Asp Arg Ala Gly
            500                 505                 510

Leu Val Gly Ala Asp Gly Pro Thr His Cys Gly Ala Phe Asp Thr Ala
            515                 520                 525

Tyr Met Ala Cys Leu Pro Asn Met Val Val Met Gly Pro Ser Asp Glu
530                 535                 540

Thr Glu Leu Ile His Met Ile Ala Thr Ala Ala Ala Ile Asp Asp Arg
545                 550                 555                 560

Pro Ser Cys Phe Arg Tyr Pro Arg Gly Asn Gly Val Gly Ser Val Leu
                565                 570                 575

Pro Pro Asp Tyr Lys Gly Thr Pro Leu Glu Ile Gly Lys Gly Lys Val
            580                 585                 590

Leu Val Glu Gly Ser Arg Val Ala Ile Leu Gly Phe Gly Thr Ile Val
            595                 600                 605

Gln Asn Cys Met Leu Ala Gln Gln Met Leu Arg Glu Met Gly Val Ser
            610                 615                 620

Ala Thr Val Ala Asp Ala Arg Phe Cys Lys Pro Leu Asp Gly Glu Leu
625                 630                 635                 640

Ile Arg Arg Leu Ala Asn Glu His Glu Leu Ile Ile Thr Val Glu Glu
                645                 650                 655

Ala Ser Ile Gly Gly Phe Gly Ser His Val Ser His Phe Leu Ala Leu
            660                 665                 670

Asn Gly Leu Leu Asp Gly Lys Val Lys Trp Arg Pro Met Thr Leu Pro
            675                 680                 685

Asp Arg Tyr Ile Asp His Gly Ser Pro Lys Asp Gln Ile Glu Glu Ala
            690                 695                 700

Gly Leu Thr Ala Lys His Ile Ala Ala Thr Val Leu Ser Leu Leu Gly
705                 710                 715                 720

Glu Asn Lys Glu Ala Phe Asn Leu Leu Thr
                725                 730

<210> SEQ ID NO 145
<211> LENGTH: 571
<212> TYPE: PRT
<213> ORGANISM: Cananga odorata

<400> SEQUENCE: 145

Met Leu Ala Lys Leu Pro Ala Leu Cys Pro Phe Ser Pro Leu Pro Arg
1               5                   10                  15

Pro Ala Ala Thr Cys Lys Arg Gln Trp Cys Val Lys Ala Ser Ala Ser
            20                  25                  30

```
Asp Asp Glu Gly Arg Leu Ala Ile Arg Lys Glu Lys Gly Gly Trp Lys
         35                  40                  45

Ile Asp Phe Thr Glu Glu Lys Pro Ala Thr Pro Leu Leu Asp Thr Ile
 50                  55                  60

Asn Tyr Pro Val His Met Lys Asn Leu Arg Val His Asp Leu Glu Gln
 65                  70                  75                  80

Leu Ala Ala Glu Ile Arg Ala Asp Ile Val His Thr Val Ser Lys Thr
                 85                  90                  95

Gly Gly His Leu Ser Ala Ser Leu Gly Val Val Glu Leu Ser Ile Ala
                100                 105                 110

Leu His His Val Phe Asn Ala Pro Asp Asp Lys Ile Ile Trp Asp Val
         115                 120                 125

Gly His Gln Ala Tyr Pro His Lys Ile Leu Thr Gly Arg Arg Ser Lys
         130                 135                 140

Met His Thr Ile Arg Lys Thr Ser Gly Leu Ala Gly Phe Pro Lys Arg
145                 150                 155                 160

Asp Glu Ser Ile Tyr Asp Ala Phe Gly Ala Gly His Ser Ser Thr Ser
                165                 170                 175

Ile Ser Ala Gly Leu Gly Met Ala Val Ala Arg Asp Leu Leu Gly Lys
                180                 185                 190

Lys Asn His Val Ile Ser Val Ile Gly Asp Gly Ala Met Thr Ala Gly
         195                 200                 205

Gln Ala Tyr Glu Ala Met Asn Asn Ser Gly Tyr Leu Asp Ser Asn Leu
         210                 215                 220

Ile Val Ile Leu Asn Asp Asn Lys Gln Val Ser Leu Pro Thr Ala Thr
225                 230                 235                 240

Leu Asp Gly Pro Ala Thr Pro Val Gly Ala Leu Ser Ser Ala Leu Ser
                245                 250                 255

Asn Leu Gln Ala Ser Thr Glu Phe Arg Lys Leu Arg Glu Ala Ala Lys
                260                 265                 270

Ser Ile Thr Lys Gln Ile Gly Gly Glu Ala His Glu Ala Ala Ala Lys
         275                 280                 285

Met Asp Glu Tyr Ala Arg Gly Met Ile Ser Pro Ser Lys Ser Cys Leu
         290                 295                 300

Phe Glu Glu Leu Gly Leu Tyr Tyr Ile Gly Pro Val Asp Gly His Asn
305                 310                 315                 320

Met Glu Gly Leu Ile Thr Ile Leu Gln Lys Val Lys Ala Met Pro Ala
                325                 330                 335

Pro Gly Pro Val Leu Ile His Val Val Thr Glu Lys Gly Lys Gly Tyr
                340                 345                 350

Pro Pro Ala Glu Ala Ala Asp Lys Met His Gly Val Val Lys Phe
         355                 360                 365

Asp Pro Ala Thr Gly Lys Gln Phe Lys Pro Gln Ser Ser Thr Leu Ser
         370                 375                 380

Tyr Thr Gln Tyr Phe Ala Glu Ser Leu Ile Lys Glu Ala Glu Val Asp
385                 390                 395                 400

Asp Lys Ile Val Ala Ile His Ala Ala Met Gly Gly Gly Thr Gly Leu
                405                 410                 415

Asn Tyr Phe Gln Lys Lys Phe Pro Glu Arg Cys Phe Asp Val Gly Ile
                420                 425                 430

Ala Glu Gln His Ala Val Thr Phe Ala Ala Gly Leu Ala Thr Glu Gly
         435                 440                 445
```

```
Leu Lys Pro Phe Cys Ala Ile Tyr Ser Ser Phe Leu Gln Arg Gly Tyr
    450                 455                 460

Asp Gln Val Val His Asp Val Asp Leu Gln Lys Leu Pro Val Arg Phe
465                 470                 475                 480

Ala Leu Asp Arg Ala Gly Leu Val Gly Ala Asp Gly Pro Thr His Cys
                485                 490                 495

Gly Ala Phe Asp Ile Thr Tyr Met Ala Cys Leu Pro Asn Met Ile Val
                500                 505                 510

Met Ala Pro Ser Asp Glu Ala Glu Leu Met His Met Val Ala Thr Ala
            515                 520                 525

Ala Thr Ile Asp Asp Gln Pro Cys Cys Phe Arg Phe Pro Arg Gly Asn
        530                 535                 540

Gly Val Gly Val Ala Leu Pro Leu Ile Ala Arg Ala Lys Asn Arg Pro
545                 550                 555                 560

Lys Pro Ala Phe Leu Val Ala Asn Ser Ser His
                565                 570

<210> SEQ ID NO 146
<211> LENGTH: 660
<212> TYPE: PRT
<213> ORGANISM: Cananga odorata

<400> SEQUENCE: 146

Met Gln Val Ser Ala Leu Pro Asp Leu Asp Asp Phe Phe Trp Glu Lys
1               5                   10                  15

Ala Pro Thr Pro Val Leu Asp Met Val Lys Asn Pro Met His Leu Lys
                20                  25                  30

Asn Leu Ser Ser Lys Glu Leu Lys Gln Leu Ala Glu Glu Ile Arg Ser
            35                  40                  45

Glu Ile Ser Phe Ser Met Ser Arg Thr Arg Arg Pro Phe Lys Ala Ser
        50                  55                  60

Leu Gly Val Val Glu Leu Ser Ile Ala Ile His Tyr Val Phe His Ala
65                  70                  75                  80

Pro Met Asp Lys Ile Leu Trp Asp Val Gly Glu Gln Thr Tyr Ala His
                85                  90                  95

Lys Ile Leu Thr Gly Arg Arg Ser Leu Met His Thr Leu Arg Gln Lys
                100                 105                 110

Asn Gly Leu Ser Gly Phe Thr Ser Arg Phe Glu Ser Glu Tyr Asp Ala
            115                 120                 125

Phe Gly Ala Gly His Gly Cys Asn Ser Ile Ser Ala Gly Leu Gly Met
        130                 135                 140

Ala Val Ala Arg Asp Leu Lys Gly Glu Lys Glu Arg Ile Val Thr Val
145                 150                 155                 160

Ile Ser Asn Gly Thr Thr Met Ala Gly Gln Ala Tyr Glu Ala Met Ser
                165                 170                 175

Asn Ala Gly Phe Leu Asp Ser Asn Met Val Val Ile Leu Asn Asp Ser
                180                 185                 190

Arg His Cys Leu His Pro Lys Leu Asp Glu Gly Ser Lys Met Ser Ile
            195                 200                 205

Ser Ala Leu Ser Ser Thr Leu Ser Lys Ile Gln Ser Ser Lys Ser Phe
        210                 215                 220

Arg Gln Leu Arg Glu Ala Ala Lys Val Val Thr Lys Arg Ile Gly Arg
225                 230                 235                 240

Gly Met His Glu Leu Ala Ala Lys Val Asp Glu Phe Ala Arg Gly Met
                245                 250                 255
```

-continued

```
Met Gly Pro Leu Gly Ser Thr Leu Phe Glu Leu Gly Leu Tyr Tyr
            260                 265                 270

Ile Gly Pro Val Asn Gly His Asn Ile Asp Asp Leu Ile Cys Val Leu
        275                 280                 285

Gln Glu Val Ala Ser Leu Asp Ser Ser Gly Pro Val Leu Ile His Val
    290                 295                 300

Ile Thr Glu Asp Glu Gly Ser Glu Glu Asp Gln Lys Ser Arg Leu Val
305                 310                 315                 320

Gly Lys His Gln Gly Leu Thr Ala Ser Tyr Ser Arg Val Met Ser Ser
                325                 330                 335

Ser Leu Pro Arg Thr Tyr Asn Asp Cys Phe Val Glu Ala Leu Val Ala
            340                 345                 350

Gly Ala Glu Arg Asp Lys Asp Ile Val Val His Ala Gly Met Gly
        355                 360                 365

Met Asp Pro Ser Leu Glu Leu Phe Gln Glu Thr Phe Pro Asp Asn Phe
    370                 375                 380

Phe Gly Ile Gly Met Ala Glu Gln His Ala Val Thr Phe Ala Ala Gly
385                 390                 395                 400

Leu Ser Cys Gly Gly Leu Lys Pro Phe Cys Val Ile Pro Ser Thr Phe
                405                 410                 415

Leu Gln Arg Ala Tyr Asp Gln Ile Val Gln Asp Val Asp Leu Gln Lys
            420                 425                 430

Ile Pro Val Arg Phe Ala Ile Thr Ser Ala Gly Leu Val Gly Ser Asp
        435                 440                 445

Gly Pro Thr His Cys Gly Ala Phe Asp Ile Thr Phe Met Ser Cys Leu
    450                 455                 460

Pro Asn Lys Ile Cys Met Ala Pro Ala Asp Glu Asp Leu Val His
465                 470                 475                 480

Met Val Ala Thr Ala Ala Cys Ile Asn Asp Arg Pro Val Cys Phe Arg
                485                 490                 495

Phe Pro Arg Gly Ala Ile Val Gly Met Asn Ile Pro Leu His Ser Gly
            500                 505                 510

Leu Pro Leu Glu Ile Gly Lys Gly Arg Ile Leu Ala Val Gly Lys Asp
        515                 520                 525

Ala Ala Leu Leu Gly Tyr Gly Ile Met Val Gln Asn Cys Leu Lys Ala
    530                 535                 540

Arg Ser Leu Leu Ala Asn Pro Gly Ile His Val Thr Val Ala Asp Ala
545                 550                 555                 560

Arg Phe Cys Lys Pro Leu Asp Ile Glu Leu Val Arg Lys Leu Cys Gln
                565                 570                 575

Glu His Glu Phe Leu Ile Thr Val Glu Glu Gly Thr Ile Gly Gly Phe
            580                 585                 590

Gly Ser His Val Ser His Phe Ile Ser Leu Asp Gly Gln Leu Asp Glu
        595                 600                 605

Asn Val Lys Trp Arg Pro Ile Val Leu Pro Asp Asn Tyr Ile Glu Gln
    610                 615                 620

Ala Ser Pro Lys Glu Gln Leu Gly Leu Ala Gly Leu Thr Gly His His
625                 630                 635                 640

Ile Ala Ala Thr Ala Leu Asn Leu Leu Gly Arg Thr Arg Asp Ala Leu
                645                 650                 655

Leu Leu Met Arg
            660
```

<210> SEQ ID NO 147
<211> LENGTH: 592
<212> TYPE: PRT
<213> ORGANISM: Magnolia grandiflora

<400> SEQUENCE: 147

```
Met Ala Leu Lys Leu Leu Phe Gln Cys Ser Pro Cys Ser Pro Ser Ser
1               5                   10                  15

Leu Ala Pro Leu Gln Pro Val Leu Val Leu Val Arg Pro Pro Ser Gly
                20                  25                  30

Ala Lys Ala Arg Arg Asn Leu Arg Cys Cys Ala Ser Thr Gln Val Thr
            35                  40                  45

Glu Leu Met Thr Ala Arg Arg Ser Ala Asn Tyr His Pro Asn Ile Trp
50                  55                  60

Asp Tyr Asp Ser Val Gln Ser Leu Thr Ser Asp Tyr Lys Ala Tyr Thr
65                  70                  75                  80

Tyr Leu Glu Arg Val Glu Lys Leu Lys Glu Asp Val Arg Arg Thr Leu
                85                  90                  95

Gln Glu Ala Val Gly Leu Leu Asp Gln Leu Glu Leu Val Asp Cys Ile
                100                 105                 110

His Arg Leu Gly Val Gly Tyr His Phe Asp Lys Glu Ile Lys Glu Ile
            115                 120                 125

Leu Lys Thr Ile Ser Thr Glu Pro Asn Asn Met Gly Leu Ile Asp Gly
130                 135                 140

Asp Leu Tyr Ala Met Ala Leu Tyr Phe Arg Leu Leu Arg Gln His Gly
145                 150                 155                 160

Tyr Glu Val Pro Gln Gly Val Phe Asn Arg Phe Met Asp Asp Ser Ser
                165                 170                 175

Ser Phe Lys Ala Ser Leu Cys Asn Asp Val Lys Gly Met Leu Ser Leu
                180                 185                 190

Tyr Glu Ala Ser Tyr Leu Ala Leu Glu Gly Glu Thr Thr Leu Asp Glu
            195                 200                 205

Ala Lys Ala Phe Thr Tyr Arg His Leu Arg Gly Leu Lys Gly Asn Ile
210                 215                 220

Asp Ser Asn Leu Lys Gly Leu Val Glu His Ala Leu Glu Leu Pro Leu
225                 230                 235                 240

His Trp Arg Val Leu Arg Leu Glu Ala Arg Trp Tyr Ile Asp Thr Tyr
                245                 250                 255

Glu Arg Met Glu Asp Met Asn Pro Leu Leu Leu Glu Leu Ala Lys Leu
                260                 265                 270

Asp Phe Asn Ile Val Gln Asn Val Tyr Gln Gly Gln Val Arg Lys Met
            275                 280                 285

Ser Gly Trp Trp Lys Asp Leu Gly Leu Gly Gln Lys Leu Gly Phe Ala
290                 295                 300

Arg Asp Arg Leu Met Glu Gly Phe Leu Trp Thr Ile Gly Val Lys Phe
305                 310                 315                 320

Glu Pro Gln Phe Ala Gln Cys Arg Glu Val Leu Thr Lys Ile Asn Gln
                325                 330                 335

Leu Ile Thr Thr Ile Asp Asp Val Tyr Asp Val Tyr Gly Ser Leu Glu
                340                 345                 350

Glu Leu Glu Leu Phe Thr Lys Ala Val Asp Arg Trp Asp Thr Asn Ala
            355                 360                 365

Met Glu Glu Leu Pro Glu Tyr Met Lys Ile Cys Phe Leu Ala Leu Tyr
370                 375                 380
```

-continued

```
Asn Thr Val Asn Glu Ile Ala Tyr Asp Thr Leu Lys Glu Gln Gly Val
385                 390                 395                 400

Asp Val Ile Pro Tyr Leu Gln Lys Ser Trp Ala Asp Leu Cys Lys Ala
            405                 410                 415

Tyr Leu Val Glu Ala Arg Trp Tyr Tyr Ser Gly Tyr Thr Pro Thr Leu
        420                 425                 430

Asp Glu Tyr Leu Asn Asn Ala Trp Ile Ser Ile Ala Gly Pro Val Ile
            435                 440                 445

Leu Val His Ala Tyr Val Ser Met Ile Gln Met Ile Thr Lys Glu Ala
    450                 455                 460

Leu Leu Asp Cys Val Gly Ser Tyr Glu Ser Ile Met Gln Trp Ser Ser
465                 470                 475                 480

Met Ile Leu Arg Leu Ala Asp Asp Leu Ala Thr Ser Thr Asp Glu Leu
                485                 490                 495

Glu Arg Gly Asp Val Pro Lys Ser Ile Gln Cys Tyr Met His Glu Asn
            500                 505                 510

Thr Ala Ser Glu Val Val Ala Arg Glu Gln Met Arg Ala Arg Ile Ser
        515                 520                 525

Asp Ile Trp Lys Lys Met Asn Lys Asp Val Ala Leu Ser Pro Leu Pro
            530                 535                 540

Gln Pro Phe Lys Ala Ala Val Asn Leu Ala Arg Met Ala Gln Cys
545                 550                 555                 560

Met Tyr Gln His Gly Asp Gly His Gly Asn Pro His Arg Glu Ser Lys
                565                 570                 575

Asp His Ile Leu Ser Leu Val Val Glu Pro Ile Gln Leu Met Glu Ser
            580                 585                 590
```

<210> SEQ ID NO 148
<211> LENGTH: 590
<212> TYPE: PRT
<213> ORGANISM: Salvia officinalis

<400> SEQUENCE: 148

```
Met Ser Ser Ile Ser Ile Asn Ile Ala Met Pro Leu Asn Ser Leu His
1               5                   10                  15

Asn Phe Glu Arg Lys Pro Ser Lys Ala Trp Ser Thr Ser Cys Thr Ala
                20                  25                  30

Pro Ala Ala Arg Leu Arg Ala Ser Ser Ser Leu Gln Gln Glu Lys Pro
            35                  40                  45

His Gln Ile Arg Arg Ser Gly Asp Tyr Gln Pro Ser Leu Trp Asp Phe
    50                  55                  60

Asn Tyr Ile Gln Ser Leu Asn Thr Pro Tyr Lys Glu Gln Arg His Phe
65                  70                  75                  80

Asn Arg Gln Ala Glu Leu Ile Met Gln Val Arg Met Leu Leu Lys Val
                85                  90                  95

Lys Met Glu Ala Ile Gln Gln Leu Glu Leu Ile Asp Asp Leu Gln Tyr
                100                 105                 110

Leu Gly Leu Ser Tyr Phe Phe Gln Asp Glu Ile Lys Gln Ile Leu Ser
            115                 120                 125

Ser Ile His Asn Glu Pro Arg Tyr Phe His Asn Asn Asp Leu Tyr Phe
    130                 135                 140

Thr Ala Leu Gly Phe Arg Ile Leu Arg Gln His Gly Phe Asn Val Ser
145                 150                 155                 160

Glu Asp Val Phe Asp Cys Phe Lys Ile Glu Lys Cys Ser Asp Phe Asn
```

```
                165                 170                 175
Ala Asn Leu Ala Gln Asp Thr Lys Gly Met Leu Gln Leu Tyr Glu Ala
            180                 185                 190

Ser Phe Leu Leu Arg Glu Gly Glu Asp Thr Leu Glu Leu Ala Arg Arg
            195                 200                 205

Phe Ser Thr Arg Ser Leu Arg Glu Lys Phe Asp Glu Gly Gly Asp Glu
            210                 215                 220

Ile Asp Glu Asp Leu Ser Ser Trp Ile Arg His Ser Leu Asp Leu Pro
225                 230                 235                 240

Leu His Trp Arg Val Gln Gly Leu Glu Ala Arg Trp Phe Leu Asp Ala
                245                 250                 255

Tyr Ala Arg Arg Pro Asp Met Asn Pro Leu Ile Phe Lys Leu Ala Lys
                260                 265                 270

Leu Asn Phe Asn Ile Val Gln Ala Thr Tyr Gln Glu Glu Leu Lys Asp
            275                 280                 285

Ile Ser Arg Trp Trp Asn Ser Ser Cys Leu Ala Glu Lys Leu Pro Phe
            290                 295                 300

Val Arg Asp Arg Ile Val Glu Cys Phe Phe Trp Ala Ile Ala Ala Phe
305                 310                 315                 320

Glu Pro His Gln Tyr Ser Tyr Gln Arg Lys Met Ala Ala Val Ile Ile
                325                 330                 335

Thr Phe Ile Thr Ile Ile Asp Asp Val Tyr Asp Val Tyr Gly Thr Ile
            340                 345                 350

Glu Glu Leu Glu Leu Leu Thr Asp Met Ile Arg Arg Trp Asp Asn Lys
            355                 360                 365

Ser Ile Ser Gln Leu Pro Tyr Tyr Met Gln Val Cys Tyr Leu Ala Leu
370                 375                 380

Tyr Asn Phe Val Ser Glu Arg Ala Tyr Asp Ile Leu Lys Asp Gln His
385                 390                 395                 400

Phe Asn Ser Ile Pro Tyr Leu Gln Arg Ser Trp Val Ser Leu Val Glu
            405                 410                 415

Gly Tyr Leu Lys Glu Ala Tyr Trp Tyr Asn Gly Tyr Lys Pro Ser
            420                 425                 430

Leu Glu Glu Tyr Leu Asn Asn Ala Lys Ile Ser Ile Ser Ala Pro Thr
            435                 440                 445

Ile Ile Ser Gln Leu Tyr Phe Thr Leu Ala Asn Ser Ile Asp Glu Thr
450                 455                 460

Ala Ile Glu Ser Leu Tyr Gln Tyr His Asn Ile Leu Tyr Leu Ser Gly
465                 470                 475                 480

Thr Ile Leu Arg Leu Ala Asp Asp Leu Gly Thr Ser Gln His Glu Leu
            485                 490                 495

Glu Arg Gly Asp Val Pro Lys Ala Ile Gln Cys Tyr Met Asn Asp Thr
            500                 505                 510

Asn Ala Ser Glu Arg Glu Ala Val Glu His Val Lys Phe Leu Ile Arg
            515                 520                 525

Glu Ala Trp Lys Glu Met Asn Thr Val Thr Thr Ala Ser Asp Cys Pro
            530                 535                 540

Phe Thr Asp Asp Leu Val Ala Ala Ala Asn Leu Ala Arg Ala Ala
545                 550                 555                 560

Gln Phe Ile Tyr Leu Asp Gly Asp Gly His Gly Val Gln His Ser Glu
            565                 570                 575

Ile His Gln Gln Met Gly Gly Leu Leu Phe Gln Pro Tyr Val
            580                 585                 590
```

<210> SEQ ID NO 149
<211> LENGTH: 627
<212> TYPE: PRT
<213> ORGANISM: Picea sitchensis

<400> SEQUENCE: 149

```
Met Ser Val Ile Ser Ile Val Pro Leu Ala Ser Asn Ser Cys Leu Tyr
1               5                   10                  15

Lys Ser Leu Met Ser Ser Thr His Glu Leu Lys Ala Leu Cys Arg Pro
            20                  25                  30

Ile Ala Thr Leu Gly Met Cys Arg Arg Gly Lys Ser Val Met Ala Ser
        35                  40                  45

Met Ser Thr Ser Leu Thr Thr Ala Val Ser Asp Asp Gly Val Gln Arg
    50                  55                  60

Arg Ile Gly His His His Ser Asn Leu Trp Asp Asn Phe Ile Gln
65                  70                  75                  80

Ser Leu Ser Ser Pro Tyr Gly Ala Ser Ser Tyr Ala Glu Ser Ala Lys
                85                  90                  95

Lys Leu Ile Gly Glu Val Lys Glu Ile Phe Asn Ser Leu Ser Met Ala
            100                 105                 110

Ala Gly Gly Leu Met Ser Pro Val Asp Asp Leu Leu Gln His Leu Ser
        115                 120                 125

Met Val Asp Asn Val Glu Arg Leu Gly Ile Asp Arg His Phe Gln Thr
    130                 135                 140

Glu Ile Lys Val Ser Leu Asp Tyr Val Tyr Ser Tyr Trp Ser Glu Lys
145                 150                 155                 160

Gly Ile Gly Ser Gly Arg Asp Ile Val Cys Thr Asp Leu Asn Thr Thr
                165                 170                 175

Ala Leu Gly Phe Arg Ile Leu Arg Leu His Gly Tyr Thr Val Phe Pro
            180                 185                 190

Asp Val Phe Glu His Phe Lys Asp Gln Met Gly Arg Ile Ala Cys Ser
        195                 200                 205

Ala Asn His Thr Glu Arg Gln Ile Ser Ser Ile Leu Asn Leu Phe Arg
    210                 215                 220

Ala Ser Leu Ile Ala Phe Pro Gly Glu Lys Val Met Glu Glu Ala Glu
225                 230                 235                 240

Ile Phe Ser Ala Thr Tyr Leu Lys Glu Ala Leu Gln Thr Ile Pro Val
                245                 250                 255

Ser Ser Leu Ser Gln Glu Met Gln Tyr Val Leu Asp Tyr Arg Trp His
            260                 265                 270

Ser Asn Leu Pro Arg Leu Glu Thr Arg Thr Tyr Ile Asp Ile Leu Gly
        275                 280                 285

Glu Thr Thr Ile Asn Gln Met Gln Asp Val Asn Ile Gln Lys Leu Leu
    290                 295                 300

Glu Leu Ala Lys Leu Glu Phe Asn Ile Phe His Ser Ile Gln Gln Asn
305                 310                 315                 320

Glu Leu Lys Cys Ile Ser Arg Trp Trp Lys Glu Ser Gly Ser Pro Glu
                325                 330                 335

Leu Thr Phe Ile Arg His Arg Ile Glu Phe Tyr Thr Leu Ala Ser
            340                 345                 350

Gly Ile Asp Met Glu Pro Lys His Ser Ala Phe Arg Leu Ser Phe Val
        355                 360                 365

Lys Met Cys His Leu Ile Thr Val Leu Asp Asp Ile Tyr Asp Thr Phe
```

```
                    370                 375                 380
Gly Thr Met Asp Glu Leu Arg Leu Phe Thr Ser Ala Val Lys Arg Trp
385                 390                 395                 400

Asp Arg Ser Glu Ile Glu Cys Leu Pro Glu Tyr Met Lys Gly Val Tyr
                405                 410                 415

Ile Ile Leu Tyr Glu Thr Val Asn Glu Met Ala Arg Glu Ala Arg Lys
                420                 425                 430

Ser Gln Gly Arg Asp Thr Leu Asn Tyr Ala Arg Leu Ala Leu Glu Asp
            435                 440                 445

Tyr Ile Gly Ala Tyr Leu Lys Glu Ala Glu Trp Ile Ser Met Val Tyr
            450                 455                 460

Leu Pro Thr Phe Glu Glu Tyr Phe Lys Asn Gly Lys Val Ser Ser Gly
465                 470                 475                 480

His Arg Ile Ala Thr Leu Gln Pro Ile Leu Thr Leu Asp Ile Pro Phe
                485                 490                 495

Pro His His Ile Leu Gln Glu Ile Asp Phe Pro Ser Lys Phe Asn Glu
                500                 505                 510

Leu Ala Cys Ser Ile Leu Arg Leu Arg Gly Asp Thr Arg Cys Tyr Gln
            515                 520                 525

Ala Asp Arg Asp Arg Gly Glu Lys Ala Ser Cys Ile Ser Cys Tyr Met
            530                 535                 540

Lys Asp Asn Pro Gly Ser Thr Glu Glu Asp Ala Leu Asn His Ile Asn
545                 550                 555                 560

Gly Met Ile Glu Asp Thr Ile Lys Gln Leu Asn Trp Glu Leu Leu Arg
                565                 570                 575

Pro Asp Asn Asn Val Pro Ile Ser Ser Lys Lys His Ser Phe Asp Ile
                580                 585                 590

Ser Arg Ala Phe His His Leu Tyr Arg Tyr Arg Asp Gly Tyr Thr Val
            595                 600                 605

Ser Ser Asn Glu Thr Lys Asn Leu Val Val Arg Thr Val Leu Glu Pro
            610                 615                 620

Leu Pro Met
625

<210> SEQ ID NO 150
<211> LENGTH: 558
<212> TYPE: PRT
<213> ORGANISM: Ricinus communis

<400> SEQUENCE: 150

Met Ser Leu Gln Val Ser Ala Val Pro Ile Lys Thr Ser Thr Gln Asn
1               5                   10                  15

Ala Thr Ser Ala Val Lys Arg His Ser Ser Thr Tyr His Pro Thr Ile
                20                  25                  30

Trp Gly Asp His Phe Leu Ala Asn Leu Ser His Ser Lys Ile Ile Asp
            35                  40                  45

Gly Ser Ile Glu Gln Gln Phe Glu Gly Leu Lys Gln Lys Val Arg Lys
        50                  55                  60

Met Ile Ile Asp Leu Asn Asn Glu Pro Cys Lys Lys Leu Gly Leu Ile
65                  70                  75                  80

Asp Ala Val Gln Arg Leu Gly Val Gly Tyr His Phe Lys Ser Glu Ile
                85                  90                  95

Glu Asp Val Leu Gln Lys Val Tyr His Asp Tyr Ser Asp Asp Glu Asp
                100                 105                 110
```

```
Asp Leu Asn Thr Val Ala Leu Arg Phe Arg Leu Leu Arg Gln His Gly
            115                 120                 125
Ile Lys Val Ser Cys Ala Ile Phe Glu Lys Phe Lys Asp Ser Glu Gly
        130                 135                 140
Asn Phe Lys Thr Ser Leu Ile Asn Asp Ala Leu Gly Met Leu Ser Leu
145                 150                 155                 160
Tyr Glu Ala Thr His Leu Ser Ile Arg Gly Glu Asp Val Leu Asp Glu
                165                 170                 175
Ala Leu Ala Phe Thr Thr Thr Asn Leu Gln Ser Val Leu Pro Gln Leu
            180                 185                 190
Asn Thr His Leu Ala Ala Gln Ile Ser Arg Ala Leu Asn Arg Pro Ile
        195                 200                 205
Arg Lys Tyr Leu Pro Arg Leu Glu Ala Arg Asn Tyr Ile Asp Ile Tyr
    210                 215                 220
Ala Thr Glu Glu Ser Tyr Asn Thr Thr Leu Leu Asn Phe Ala Lys Leu
225                 230                 235                 240
Asp Phe Asn Met Leu Gln Glu Leu His Gln Lys Glu Leu Asn Val Val
                245                 250                 255
Thr Lys Trp Trp Lys Ser Leu Asp Val Ala Thr Lys Leu Pro Tyr Ala
            260                 265                 270
Arg Asp Arg Val Val Glu Cys Tyr Phe Trp Met Val Gly Val Tyr Phe
        275                 280                 285
Glu Pro Gln Tyr Ser Phe Ala Arg Ile Met Met Thr Lys Ile Ile Ala
    290                 295                 300
Ile Thr Ser Leu Leu Asp Asp Thr Tyr Asp Asn Tyr Ala Thr Gly Glu
305                 310                 315                 320
Glu Leu Glu Ile Leu Thr Glu Ala Ile Glu Arg Trp Asp Ile Lys Ala
                325                 330                 335
Lys Asp Ala Leu Pro Glu Tyr Met Lys Ile Ile Tyr Thr Thr Leu Leu
            340                 345                 350
Asp Ile Tyr Asn Glu Tyr Glu Glu Asn Ile Ala Lys Glu Glu Lys Ser
        355                 360                 365
Leu Leu Tyr Ser Val Tyr Tyr Ala Lys Glu Val Met Lys Arg Val Val
    370                 375                 380
Arg Ala Tyr Leu Ala Glu Val Arg Trp Arg Asp Asn Cys Tyr Thr Pro
385                 390                 395                 400
Thr Met Glu Glu Tyr Met Gln Ser Ala Leu Leu Thr Thr Cys Ser Pro
                405                 410                 415
Met Leu Ala Ile Ala Ser Phe Leu Gly Leu Lys Glu Ile Ala Thr Lys
            420                 425                 430
Glu Ala Tyr Glu Trp Ala Ser Glu Asp Pro Lys Ile Ile Arg Ala Ser
        435                 440                 445
Ser Ile Val Cys Arg Leu Met Asp Asp Ile Val Ser His Glu Phe Glu
    450                 455                 460
Gln Thr Arg Lys His Val Ala Ser Gly Val Glu Cys Tyr Ile Lys Gln
465                 470                 475                 480
Tyr Gly Ala Ser Glu Glu Val Ile Lys Leu Phe Arg Lys Glu Val
                485                 490                 495
Thr Asn Ala Trp Lys Asp Leu Asn Glu Glu Cys Leu Asn Pro Thr Pro
            500                 505                 510
Val Pro Met Pro Met Leu Glu Arg Val Val Asn Leu Thr Arg Ala Ile
        515                 520                 525
Asp Val Ile Tyr Lys Asp Asp Asp Gly Tyr Thr Asn Ser His Ile Met
```

```
                530                 535                 540
Lys Asp Tyr Val Ala Ser Val Leu Lys Asp Pro Val Pro Val
545                 550                 555

<210> SEQ ID NO 151
<211> LENGTH: 550
<212> TYPE: PRT
<213> ORGANISM: Magnolia grandiflora

<400> SEQUENCE: 151

Met Asp Ser Pro Thr Thr Gln Arg Pro Asn Met Glu Ile Gly Arg Ala
1               5                   10                  15

Phe Val Asn Tyr His Pro Ser Ile Trp Gly Glu His Phe Ile Ala Ala
            20                  25                  30

Ser Pro Asp Val Met Arg Leu Asp Ala His Lys Gly Arg Gly Glu Glu
        35                  40                  45

Leu Lys Glu Val Val Arg Asn Met Phe Ser Thr Val Asn Asp Pro Leu
    50                  55                  60

Leu Lys Met Asn Leu Ile Asp Ala Ile Gln Arg Leu Gly Val Ala Tyr
65                  70                  75                  80

His Phe Glu Met Glu Ile Asp Lys Ala Leu Gly Gln Met Tyr Asp Asp
                85                  90                  95

His Ile Asn Gly Lys Asp Asp Gly Phe Asp Leu Gln Thr Leu Ala Leu
            100                 105                 110

Gln Phe Arg Leu Leu Arg Gln Gln Gly Tyr Asn Val Ser Ser Gly Val
        115                 120                 125

Phe Ala Lys Phe Lys Asp Asp Glu Gly Asn Phe Ser Ser Ile Leu Ser
    130                 135                 140

Lys Asp Thr His Gly Leu Leu Ser Leu Tyr Glu Ala Ala Phe Leu Gly
145                 150                 155                 160

Thr His Gly Asp Asp Ile Leu Asp Glu Ala Ile Thr Phe Thr Thr Val
                165                 170                 175

His Leu Lys Ser Thr Leu Pro His Val Ser Ala Pro Leu Thr Lys Leu
            180                 185                 190

Val Glu Leu Ala Leu Glu Ile Pro Leu His Arg Arg Met Glu Arg Leu
        195                 200                 205

Gln Thr Arg Phe Tyr Ile Ser Ile Tyr Glu Glu Asp Arg Glu Arg Asn
    210                 215                 220

Asp Val Leu Leu Glu Phe Ser Lys Leu Glu Phe Leu Arg Leu Gln Ser
225                 230                 235                 240

Leu His Gln Arg Glu Leu Arg Asp Ile Ser Leu Trp Trp Lys Glu Met
                245                 250                 255

Asp Leu Leu Ala Lys Leu Pro Phe Thr Arg Asp Arg Val Leu Glu Gly
            260                 265                 270

Tyr Phe Trp Thr Val Gly Val Tyr Phe Glu Pro His Tyr Ser Arg Ala
        275                 280                 285

Arg Met Ile Met Thr Lys Met Ile Ala Phe Ala Thr Val Met Asp Asp
    290                 295                 300

Thr Tyr Asp Val Tyr Gly Thr Leu Glu Glu Leu Glu Leu Leu Thr Ala
305                 310                 315                 320

Thr Ile Glu Arg Trp Asn Arg Gly Asp Met Asp Gln Leu Pro Asp Tyr
                325                 330                 335

Met Lys Val Ile Phe Ile Ala Leu Leu Asp Gly Val Asp Ala Thr Glu
            340                 345                 350
```

Asp Asp Leu Thr Gly Glu Gly Lys Ser Tyr Arg Ile Tyr Tyr Leu Lys
            355                 360                 365

Glu Ala Val Lys Asp Leu Ala Lys Ala Tyr Leu Ala Glu Ala Arg Trp
370                 375                 380

Val Ser Ser Gly Tyr Val Pro Thr Ser Glu Glu Tyr Met Lys Val Ala
385                 390                 395                 400

Leu Ile Ser Ala Val Tyr Pro Met Leu Phe Val Ala Phe Leu Ile Gly
            405                 410                 415

Met Asp Glu Val Val Thr Lys Glu Val Leu Glu Trp Ala Ile His Met
            420                 425                 430

Pro Thr Met Leu Arg Thr Cys Ser Ile Val Ala Arg Leu Met Asp Asp
            435                 440                 445

Ile Pro Ser Asn Lys Leu Glu Gln Glu Arg Lys His Val Ser Ser Ser
450                 455                 460

Val Glu Cys Tyr Met Lys Glu His Gly Thr Ser Tyr His Glu Ser Ile
465                 470                 475                 480

Gln Lys Leu Arg Glu Met Val Ala Ser Gly Trp Lys Asp Ile Asn Lys
            485                 490                 495

Glu Cys Leu Lys Pro Thr Pro Val Pro Thr Ala Val Ile Asn Val Ile
            500                 505                 510

Leu Asn Phe Thr Arg Val Leu Glu Ile Ile Tyr Gln His Arg Asp Gly
            515                 520                 525

Tyr Thr Asp Ala Ser Val Glu Thr Lys Glu His Ile Ala Ser Leu Phe
            530                 535                 540

Val Asp Pro Ile Pro Leu
545                 550

<210> SEQ ID NO 152
<211> LENGTH: 555
<212> TYPE: PRT
<213> ORGANISM: Helianthus annuus

<400> SEQUENCE: 152

Met Ala Thr Thr Glu Ala Asn Thr Met Ala Gln Ala Asn Ser Gln Thr
1               5                   10                  15

Thr Ile Glu Pro Val Arg His Leu Ala Asn Phe Pro Ser Ile Trp
            20                  25                  30

Gly Asp Gln Phe Leu Ser Phe Ser Leu Asp Asn Ser Gln Leu Glu Ala
            35                  40                  45

Tyr Ser Lys Ala Met Glu Gln Pro Lys Glu Asn Val Arg Arg Met Ile
50                  55                  60

Leu Asn Pro Ala Ile Asp Thr Asn Glu Lys Leu Gly Leu Ile Tyr Cys
65                  70                  75                  80

Val Tyr Arg Leu Gly Leu Thr Tyr Asn Phe Ser Lys Asp Ile Asp Gly
            85                  90                  95

Gln Leu Asp Glu Leu Phe Lys Gln Leu Asn Leu Gln Ser Tyr Asn Glu
            100                 105                 110

Ala Asp Leu Tyr Thr Ile Ser Ile His Phe Gln Val Phe Arg His Phe
            115                 120                 125

Gly Tyr Arg Phe Ser Cys Asp Val Phe Asn Lys Phe Lys Asp Ser Ser
            130                 135                 140

Ser Gly Lys Phe Lys Glu Asp Met Thr Arg Asp Val Arg Gly Met Ile
145                 150                 155                 160

Ser Leu Tyr Glu Ser Ala Gln Leu Arg Ile Arg Gly Glu Ser Ile Leu
            165                 170                 175

```
Asp Glu Ala Gly Ala Phe Ala Glu Ser Lys Leu Lys Thr Ile Glu Lys
            180                 185                 190

Thr Leu Asp Gly Thr Leu Ala Gln Gln Val Lys His Val Leu Glu Arg
        195                 200                 205

Pro Phe Asn Arg Gly His Gln Met Val Glu Ala Arg Lys Tyr Leu Phe
    210                 215                 220

Leu Phe Glu Glu Glu Ile Ser Arg Tyr Asp Ser Leu Leu Met Leu Ala
225                 230                 235                 240

Lys Val His Phe Asn Tyr Leu Gln Leu Leu Gln Lys Glu Glu Leu Arg
                245                 250                 255

Ser Val Ser Lys Trp Trp Lys Asp Leu Asp Leu Pro Ala Lys Thr Leu
            260                 265                 270

Tyr Val Arg Asp Arg Val Pro Glu Leu Tyr Val Trp Ile Leu Ala Phe
        275                 280                 285

Phe Leu Glu Pro Tyr Tyr Ser Glu Val Arg Ile Ile Thr Thr Lys Ile
    290                 295                 300

Val Leu Leu Val Leu Val Leu Asp Asp Thr Tyr Asp Ala Tyr Ala Thr
305                 310                 315                 320

Ile Glu Glu Ser Arg Leu Leu Thr His Ala Ile Asn Arg Trp Glu Val
                325                 330                 335

Ser Ala Met Leu Gln Leu Pro Glu Tyr Met Lys Pro Leu Tyr Glu Ile
            340                 345                 350

Leu Leu Asn Glu Tyr Asp Gly Phe Tyr Lys His Gly Arg Thr Asn Val
        355                 360                 365

Ile Glu Thr Ser Lys Lys Ala Phe Gln Asp Leu Ala Arg Ser Tyr His
    370                 375                 380

Gln Glu Ser Glu Trp Arg His Ala Lys Glu Val Pro Ser Phe Glu Glu
385                 390                 395                 400

Tyr Met Lys Ile Gly Thr Thr Ser Ala His Asn Val Leu Ser Lys
                405                 410                 415

Thr Ala Leu Ile Gly Met Gly Asn Ile Val Thr Arg Glu Ala Leu Ala
            420                 425                 430

Trp Tyr Glu Ser Tyr Pro Lys Ile Val Gln Leu Ser Glu Leu Ile Gly
        435                 440                 445

Arg Leu Glu Asp Asp Val Val Ser Val Glu Phe Glu Arg Glu Arg Ala
450                 455                 460

Pro Thr Ala Thr Ser Val Asp Ala Tyr Met Lys Thr Tyr Gly Val Ser
465                 470                 475                 480

Glu Asn Val Ala Val Lys Ile Leu Lys Lys Leu Val Glu Asn Gly Trp
                485                 490                 495

Lys Asp Leu Asn Glu Ala Cys Leu Lys Pro Thr Glu Val Ser Leu Asp
            500                 505                 510

Leu Leu Ala Pro Ile Ile Gly Leu Thr Asn Met Thr Asp Val Ala Tyr
        515                 520                 525

Arg His Asn Asp Gly Leu Thr Phe Pro Glu Lys Thr Leu Lys Glu Tyr
    530                 535                 540

Ile Thr Leu Leu Phe Cys Val Pro Val Pro Met
545                 550                 555

<210> SEQ ID NO 153
<211> LENGTH: 582
<212> TYPE: PRT
<213> ORGANISM: Litsea cubeba
```

<400> SEQUENCE: 153

Met Ser Leu Ile Ile Gln Ser Leu Pro His Trp Ser Arg Ile Pro Pro
1               5                   10                  15

Arg Pro Pro Gln Leu Ser Gln Phe Gln Asn Ser Ser Arg Pro Lys Pro
            20                  25                  30

Leu Ile Gln Ala Gly Gln Val Gln His Asn Ala Leu Gln Ile Ala Arg
        35                  40                  45

Arg Ser Ala Asn Tyr His Pro Ser Ile Trp Asp Pro Gln Tyr Ile Glu
    50                  55                  60

Ser Leu Lys Ser Pro Tyr Gly Asp Glu Cys Phe Gly Thr Arg Leu Glu
65                  70                  75                  80

Lys Leu Lys Phe Glu Ala Lys Arg Leu Leu Glu Ala Thr Ile Glu Pro
                85                  90                  95

Leu Ser Trp Leu Glu Leu Val Asp Ser Ile Gln Arg Leu Gly Val Ala
            100                 105                 110

Tyr His Phe Glu Asp Glu Ile Lys Glu Gly Leu Asp Gly Val Tyr Gly
        115                 120                 125

Val Gly Ala His Ala Gly Asp Asp Leu Tyr Thr Ala Ala Leu Gln Phe
    130                 135                 140

Arg Leu Leu Arg Gln His Gly Tyr Gly Val Thr Pro Asp Ile Phe Asn
145                 150                 155                 160

Lys Phe Leu Glu Lys Glu Arg Thr Phe Lys Ala Cys Thr Ser Leu Asp
                165                 170                 175

Ala Lys Gly Leu Leu Ser Leu Tyr Glu Ala Ser His Thr Met Ile His
            180                 185                 190

Gly Glu Glu Val Leu Glu Asp Ala Lys Glu Phe Ser Val Lys His Leu
        195                 200                 205

Asn Tyr Leu Met Gly Asn Leu Gln Asn Asn Leu Arg Glu Gln Val Gln
    210                 215                 220

His Ala Leu Glu Met Pro Leu His Trp Arg Met Pro Arg Leu Glu Ala
225                 230                 235                 240

Lys His Tyr Ile Asp Val Asn Gly Arg Ser Asp Glu Arg Asn Met Val
                245                 250                 255

Leu Leu Glu Leu Ala Arg Leu Asp Phe Asn Phe Val Gln Ser Lys His
            260                 265                 270

Gln Glu Glu Leu Lys Glu Val Ser Arg Trp Arg Asp Leu Gly Leu
        275                 280                 285

Ala Lys Lys Leu Gly Phe Ser Arg Asp Arg Leu Val Glu Asn Tyr Leu
    290                 295                 300

Trp Ala Val Gly Ile Ala Pro Glu Pro Lys Phe Ser Asn Cys Arg Lys
305                 310                 315                 320

Gly Leu Thr Lys Leu Ile Ser Ile Leu Thr Val Ile Asp Asp Ile Tyr
                325                 330                 335

Asp Val Tyr Gly Ser Leu Asp Glu Leu Glu Leu Phe Thr Glu Ala Val
            340                 345                 350

Lys Arg Trp Asp Ile Glu Ala Leu Glu Thr Leu Pro Glu Tyr Met Lys
        355                 360                 365

Ile Cys Tyr Leu Ala Leu Phe Asn Phe Val His Glu Val Ser Tyr Asp
    370                 375                 380

Thr Leu Lys Asp Tyr Gly Trp Asn Ile Leu Pro Phe Ile Arg Glu Glu
385                 390                 395                 400

Trp Glu Arg Leu Cys Met Ser Tyr Leu Val Glu Ala Glu Trp Phe Gly
                405                 410                 415

```
Asn Gly Asn Lys Pro Ala Leu Asp Glu Tyr Leu Arg Asn Gly Trp Ile
            420                 425                 430

Ser Val Gly Gly Pro Val Ala Met Val His Ala Tyr Phe Leu Gln Gly
        435                 440                 445

Arg Pro Ile Arg Lys Asp Ser Ile Asn Phe Leu Asp His Gly Ser Glu
    450                 455                 460

Leu Ile Tyr Trp Ser Ser Val Ala Thr Arg Leu Asn Asp Asp Leu Gly
465                 470                 475                 480

Thr Ser Lys Ala Glu Met Lys Arg Gly Asp Val Pro Lys Ala Val Glu
            485                 490                 495

Cys Tyr Met Ile Gln Thr Gly Glu Ser Tyr Asp Ala Arg Glu His
            500                 505                 510

Ile Gln Gly Leu Val Arg Asp Cys Trp Lys Lys Met Asn Glu Glu Cys
        515                 520                 525

Leu Lys Cys Cys Leu Pro Lys Ser Tyr Val Glu Thr Val Leu Asn Met
    530                 535                 540

Val Arg Thr Ala Gln Cys Ile Tyr Gln His Gly Asp Gly Ile Gly Thr
545                 550                 555                 560

Ser Thr Gly Val Thr Gln Asp Arg Val Ile Ser Leu Ile Cys Glu Pro
            565                 570                 575

Val Pro Ser Gln Trp Pro
            580

<210> SEQ ID NO 154
<211> LENGTH: 538
<212> TYPE: PRT
<213> ORGANISM: Lavandula angustifolia

<400> SEQUENCE: 154

Met Glu Ala Arg Arg Ser Gly Asn Phe Glu Ser Ser Ile Trp Asp Asp
1               5                   10                  15

Asp Tyr Ile Gln Ser Leu Thr Ser Ser Tyr Thr Gly Lys Met Tyr Val
            20                  25                  30

Asp Lys Ser Glu Lys Leu Lys Ile Glu Val Lys Met Met Met Asp Glu
        35                  40                  45

Ala Thr Asp Glu Leu Glu Gln Leu Glu Leu Ile Asn Asp Leu Gln Arg
    50                  55                  60

Leu Gly Ile Ser Tyr His Phe Lys Asp Gly Ile Ala Lys Met Leu Asn
65                  70                  75                  80

Asn Ile Tyr Lys Ser Asp Ser Lys Tyr Met Glu Lys Asp Leu His Leu
            85                  90                  95

Thr Ala Leu Lys Phe Arg Leu Leu Arg Gln His Gly Tyr Arg Val Pro
            100                 105                 110

Gln Asp Val Phe Ser Ser Phe Met Asp Asp Glu Gly Asn Phe Glu Ala
        115                 120                 125

Trp Val Val Glu Asp Val Ser Val Leu Val Ser Leu Tyr Glu Ala Ser
    130                 135                 140

His Ile Ser Val Glu Gly Glu Ser Ile Leu Asp Met Ala Lys Asp Phe
145                 150                 155                 160

Ser Ser His His Leu Thr Glu Met Val Glu Gln Ile Gly Glu Ala Cys
            165                 170                 175

Leu Ala Glu Gln Val Lys Arg Thr Leu Glu Leu Pro Leu His Trp Arg
            180                 185                 190

Val Gly Arg Leu Glu Ala Arg Trp Phe Val Gln Ala Tyr Glu Thr Arg
```

```
            195                 200                 205
Pro Asn Ser Asn Pro Thr Leu Val Glu Leu Ala Lys Leu Asp Phe Asn
210                 215                 220

Met Val Gln Ala Lys Tyr Gln Asp Glu Leu Lys Arg Cys Ser Arg Trp
225                 230                 235                 240

Tyr Glu Glu Thr Gly Leu Pro Glu Lys Met Ser Phe Ala Arg His Arg
                245                 250                 255

Leu Ala Glu Cys Phe Leu Trp Ser Leu Gly Phe Ile Pro Asp Pro His
            260                 265                 270

His Gly Tyr Ser Arg Glu Ile Met Thr Lys Ile Ala Val Leu Ile Thr
        275                 280                 285

Ile Thr Asp Asp Ile Tyr Asp Ile Tyr Gly Ala Leu Glu Glu Leu Gln
290                 295                 300

Glu Phe Thr Glu Ala Phe Glu Arg Trp Asp Ile Asn Ser Leu Asp Leu
305                 310                 315                 320

Leu Pro Glu Tyr Met Gln Ile Cys Phe Leu Ala Ile Phe Asn Ser Ala
                325                 330                 335

Asn Glu Leu Gly Tyr Gln Ile Leu Arg Asp Gln Gly Leu Asn Ile Ile
            340                 345                 350

Pro Asn Leu Lys Arg Ser Trp Ala Glu Leu Ser Arg Ala Tyr Tyr Leu
        355                 360                 365

Glu Ala Arg Trp Phe His Asn Gly Phe Val Pro Thr Thr Asp Gln Tyr
370                 375                 380

Leu Asn Thr Ala Trp Ile Ser Ile Ser Gly Pro Leu Leu Ser Tyr
385                 390                 395                 400

Gly Tyr Leu Thr Thr Thr Asn Pro Ile Asn Asn Lys Glu Leu Lys Ser
                405                 410                 415

Leu Glu Lys His Pro Ser Ile Ile Arg Trp Pro Ser Met Val Leu Arg
            420                 425                 430

Leu Ala Asp Asp Leu Gly Thr Ser Ser Glu Glu Ile Lys Arg Gly Asp
        435                 440                 445

Val Ser Lys Ser Ile Gln Cys Tyr Met Asn Glu Thr Gly Cys Cys Glu
450                 455                 460

Gly Asp Ala Arg His His Val Lys Ser Leu Ile Glu Val Ala Leu Lys
465                 470                 475                 480

Arg Met Asn Asp Glu Ile Leu Met Glu Lys Pro Phe Lys Ser Phe Asp
                485                 490                 495

Thr Asn Ala Met Asn Leu Ala Arg Ile Ser Leu Cys Phe Tyr Gln Tyr
            500                 505                 510

Gly Asp Gly Phe Gly Lys Pro His Ser Asp Thr Ile Lys Asn Leu Val
        515                 520                 525

Ser Leu Ile Val Leu Pro Phe His Met Pro
530                 535

<210> SEQ ID NO 155
<211> LENGTH: 542
<212> TYPE: PRT
<213> ORGANISM: Lippia dulcis

<400> SEQUENCE: 155

Met Glu Ala Arg Arg Ser Gly Asn Phe Lys Ala Ser Ile Trp Asp Asp
1               5                   10                  15

Asp Phe Leu Gln Ser Leu Thr Ser Pro Tyr Thr Ala Lys Glu Tyr Leu
                20                  25                  30
```

Lys Gln Ala Asp Lys Leu Lys Trp Gln Val Lys Val Ile Lys Glu
         35                  40                  45

Thr Lys Gln Arg Leu Asp Gln Leu Asp Leu Ile Asp Asn Ile Gln Arg
 50                  55                  60

Leu Gly Ile Ser His His Phe Arg Asp Glu Ile Gln Arg Val Leu Gln
 65                  70                  75                  80

Asn Ile Tyr Glu Lys Met Arg Val Glu Cys Pro Asp Arg Met Leu Met
                 85                  90                  95

Glu Lys Asp Leu Tyr Ser Thr Ser Leu Gln Phe Arg Leu Leu Arg Gln
            100                 105                 110

His Gly Tyr His Val Ser Gln Asp Val Phe Cys Ser Phe Met Asp Gly
        115                 120                 125

Ala Gly Asn Phe Gln Ala Val Asp Asp Leu Lys Gly Ile Leu Ala Leu
    130                 135                 140

Tyr Glu Ala Ser Phe Leu Ser Arg Glu Gly Glu Asn Ile Leu Gly Ser
145                 150                 155                 160

Ala Arg Asp Phe Ser Thr Arg His Leu Lys Gln Lys Leu Glu Glu Ile
                165                 170                 175

Thr Asp Pro Ile Leu Ala Glu Lys Ile Arg Arg Ala Leu Glu Leu Pro
            180                 185                 190

Leu His Trp Arg Leu Gln Lys Leu Glu Ala Ile Trp Phe Ile Asn Ile
        195                 200                 205

Tyr Glu Ser Arg Phe Asp Ala Asn Leu Ile Leu Gln Leu Ala Lys
    210                 215                 220

Leu Glu Phe Asn Met Val Gln Ala Gln Tyr Gln Glu Asp Leu Lys Trp
225                 230                 235                 240

Leu Ser Arg Trp Tyr Lys Glu Thr Gly Leu Pro Glu Lys Met Asn Phe
                245                 250                 255

Ala Arg Asp Arg Leu Ala Glu Cys Phe Leu Trp Ala Leu Gly Phe Ile
            260                 265                 270

Pro Glu Ala His Leu Gly Gln Ala Arg Lys Ile Leu Thr Lys Ile Ala
        275                 280                 285

Val Leu Ile Val Ile Met Asp Asp Phe Tyr Asp Ile Tyr Gly Thr Leu
    290                 295                 300

Asp Glu Ile Lys Val Phe Thr Glu Glu Leu Gln Arg Trp Asp Ile Asn
305                 310                 315                 320

Ala Leu Asp Asn Leu Pro Glu Tyr Met Arg Ile Cys Phe Leu Ala Ile
                325                 330                 335

Phe Asn Thr Ala Asn Glu Ile Ala Tyr Asp Ile Leu Arg Asp Gln Gly
            340                 345                 350

Ile Asn Ile Ile Ser Asn Leu Arg Arg Leu Trp Ala Glu Leu Gly Arg
        355                 360                 365

Val Tyr Tyr Thr Glu Ala Lys Trp Tyr His Ser Gly Tyr Phe Pro Ser
    370                 375                 380

Thr Glu Glu Tyr Leu Asn Val Ala Trp Ile Ser Ile Thr Gly Pro Val
385                 390                 395                 400

Leu Leu Phe His Ala Tyr Phe Ser Ile Met Asn Pro Ile Asp Met Lys
                405                 410                 415

Glu Leu Gln Tyr Leu Glu Gln Tyr Pro Gly Ile Ile Arg Trp Pro Ser
            420                 425                 430

Thr Val Leu Arg Leu Ala Asp Asp Leu Gly Thr Ala Ser Asp Glu Ile
        435                 440                 445

Lys Arg Gly Asp Val Pro Lys Ser Ile Gln Cys Tyr Met His Glu Thr

```
                    450                 455                 460
Gly Cys Ser Glu Glu Ala Arg Glu Tyr Val Lys Gln Leu Ile Asp
465                 470                 475                 480

Thr Thr Leu Lys Lys Met Asn Lys Glu Ile Leu Met Glu Lys Pro Thr
                485                 490                 495

Asn Asp Phe Gly Ala Thr Ala Met Asn Leu Ala Arg Ile Ser Leu Phe
            500                 505                 510

Phe Tyr Gln Tyr Gly Asp Gly Phe Gly Val Pro His Asn Gln Thr Lys
            515                 520                 525

Glu Asn Leu Val Ser Leu Ile Val Lys Pro Ile Cys Leu Thr
            530                 535                 540

<210> SEQ ID NO 156
<211> LENGTH: 583
<212> TYPE: PRT
<213> ORGANISM: Olea europaea

<400> SEQUENCE: 156

Met Asp Cys Thr Met Thr Ser Ile Ser Leu Phe Ser Gln Ser Ser Asn
1               5                   10                  15

Gly Ile Ser Gly Thr Ala Arg Ser Pro Phe Gln Trp Pro Ile Asn His
            20                  25                  30

Arg Phe Ser Ser Gly Gln Arg Asp Phe Ile Cys Lys Ser Leu Pro Val
        35                  40                  45

Ser Ser Pro Ser Ala Thr Pro Leu Ile Pro Ala Glu Asn Gly Ala Met
    50                  55                  60

Tyr Asn Tyr Ile Arg Gln Pro Val Ile Val Thr Pro Glu Val Asp Asp
65                  70                  75                  80

Gly Thr Lys His Ser Glu Leu Val Glu Arg Thr Arg Arg Glu Leu Gln
                85                  90                  95

Arg Ser Thr Lys Pro Val Glu Thr Leu Lys Leu Ile Asp Asn Leu Gln
            100                 105                 110

Arg Leu Gly Ile Ala Tyr Tyr Phe Glu Asp Asp Ile Asn Ala Ile Leu
        115                 120                 125

Asp Gln Phe Ser Asp Gly Leu Pro Asp Glu Asp Leu Phe Thr Thr Ala
    130                 135                 140

Leu Cys Phe Arg Leu Leu Arg Asp Gln Arg Leu Gln Thr Gly Ser Asp
145                 150                 155                 160

Val Phe Leu Lys Phe Met Glu Lys Asn Met Lys Phe Lys Glu His Leu
                165                 170                 175

Ala Gln Asp Thr Ile Gly Leu Val Ser Leu Tyr Glu Ala Ser Ser Met
            180                 185                 190

Gly Ala Asn Gly Glu Glu Ile Leu Ser Glu Ala Lys Glu Phe Thr Glu
        195                 200                 205

Met His Leu Arg Gln Ser Met Pro Gln Leu Ala Pro Gln Leu Arg Arg
    210                 215                 220

Gln Val Ser Ser Ala Leu Glu Leu Pro Arg His Leu Arg Met Ala Arg
225                 230                 235                 240

Leu Glu Ala Arg Arg Tyr Ile Glu Glu Tyr Gly Asn Glu Ser Asp His
                245                 250                 255

Asp Pro Ala Leu Leu Glu Leu Ala Arg Leu Asp Tyr Asn Lys Val Gln
            260                 265                 270

Leu Gln His Gln Met Glu Leu Ala Glu Ile Thr Arg Trp Trp Lys Gln
        275                 280                 285
```

```
Leu Gly Leu Val Glu Lys Leu Ser Phe Ala Arg Asp Arg Pro Leu Glu
290                 295                 300

Cys Phe Leu Trp Thr Val Gly Leu Leu Pro Glu Pro Lys Tyr Ser Ser
305                 310                 315                 320

Cys Arg Ile Glu Leu Ala Lys Thr Ile Ala Ile Leu Leu Val Ile Asp
                325                 330                 335

Asp Ile Phe Asp Thr Tyr Gly Lys Met Glu Glu Leu Val Leu Phe Thr
            340                 345                 350

Glu Ala Ile Gln Arg Trp Asp Leu Asp Glu Leu Glu Thr Leu Pro Pro
                355                 360                 365

Tyr Met Arg Ile Cys Tyr Met Ala Leu Tyr Asn Thr Thr Asn Glu Ile
370                 375                 380

Cys Tyr Lys Ile Leu Lys Glu Tyr Gly Phe Cys Val Leu Pro Tyr Leu
385                 390                 395                 400

Lys Ser Thr Trp Ile Asp Met Ile Glu Gly Phe Met Val Glu Ala Asn
                405                 410                 415

Trp Phe Asn Gly Gly His Gly Pro Asn Leu Glu Glu Tyr Ile Glu Asn
            420                 425                 430

Gly Val Ser Thr Ala Gly Ala Tyr Met Ala Leu Val His Leu Phe Phe
                435                 440                 445

Leu Ile Gly Glu Gly Val Thr Asn Glu Asn Ile Ala Lys Leu Leu Arg
450                 455                 460

Lys Pro Tyr Pro Lys Leu Phe Ser Ala Ala Gly Arg Ile Leu Arg Leu
465                 470                 475                 480

Trp Asp Asp Leu Gly Thr Ala Lys Glu Glu Glu Arg Gly Asp Leu
                485                 490                 495

Ala Ser Cys Met Gln Ile Leu Met Arg Glu Lys Asn Ile Asp Cys Glu
                500                 505                 510

Asn Glu Gly Arg Asn Tyr Ile Leu Lys Ala Ile Asn Gly Leu Trp Lys
            515                 520                 525

Asp Leu Asn Asp Glu Leu Ile Ser Pro Asn Ala Met Pro Leu Ala Ile
                530                 535                 540

Thr Lys Val Ala Leu Asn Met Ala Arg Ala Phe Glu Val Val Tyr Lys
545                 550                 555                 560

His Glu Glu Asp Ser Tyr Phe Ser Ser Val Asp Asn Tyr Val Gln Ala
                565                 570                 575

Leu Phe Phe Thr Pro Ile Asn
            580

<210> SEQ ID NO 157
<211> LENGTH: 567
<212> TYPE: PRT
<213> ORGANISM: Ocimum basilicum

<400> SEQUENCE: 157

Met Ser Cys Ala Arg Ile Thr Val Thr Leu Pro Tyr Arg Ser Ala Lys
1               5                   10                  15

Thr Ser Ile Gln Arg Gly Ile Thr His Tyr Pro Ala Leu Ile Arg Pro
                20                  25                  30

Arg Phe Ser Ala Cys Thr Pro Leu Ala Ser Ala Met Pro Leu Ser Ser
            35                  40                  45

Thr Pro Leu Ile Asn Gly Asp Asn Ser Gln Arg Lys Asn Thr Arg Gln
        50                  55                  60

His Met Glu Glu Ser Ser Ser Lys Arg Arg Glu Tyr Leu Leu Glu Glu
65                  70                  75                  80
```

```
Thr Thr Arg Lys Leu Gln Arg Asn Asp Thr Glu Ser Val Glu Lys Leu
                85                  90                  95
Lys Leu Ile Asp Asn Ile Gln Gln Leu Gly Ile Gly Tyr Tyr Phe Glu
            100                 105                 110
Asp Ala Ile Asn Ala Val Leu Arg Ser Pro Phe Ser Thr Gly Glu Glu
            115                 120                 125
Asp Leu Phe Thr Ala Ala Leu Arg Phe Arg Leu Leu Arg His Asn Gly
            130                 135                 140
Ile Glu Ile Ser Pro Glu Ile Phe Leu Lys Phe Lys Asp Glu Arg Gly
145                 150                 155                 160
Lys Phe Asp Glu Ser Asp Thr Leu Gly Leu Leu Ser Leu Tyr Glu Ala
                165                 170                 175
Ser Asn Leu Gly Val Ala Gly Glu Glu Ile Leu Glu Glu Ala Met Glu
                180                 185                 190
Phe Ala Glu Ala Arg Leu Arg Arg Ser Leu Ser Glu Pro Ala Ala Pro
                195                 200                 205
Leu His Gly Glu Val Ala Gln Ala Leu Asp Val Pro Arg His Leu Arg
            210                 215                 220
Met Ala Arg Leu Glu Ala Arg Arg Phe Ile Glu Gln Tyr Gly Lys Gln
225                 230                 235                 240
Ser Asp His Asp Gly Asp Leu Leu Glu Leu Ala Ile Leu Asp Tyr Asn
                245                 250                 255
Gln Val Gln Ala Gln His Gln Ser Glu Leu Thr Glu Ile Ile Arg Trp
                260                 265                 270
Trp Lys Glu Leu Gly Leu Val Asp Lys Leu Ser Phe Gly Arg Asp Arg
            275                 280                 285
Pro Leu Glu Cys Phe Leu Trp Thr Val Gly Leu Leu Pro Glu Pro Lys
            290                 295                 300
Tyr Ser Ser Val Arg Ile Glu Leu Ala Lys Ala Ile Ser Ile Leu Leu
305                 310                 315                 320
Val Ile Asp Asp Ile Phe Asp Thr Tyr Gly Glu Met Asp Asp Leu Ile
                325                 330                 335
Leu Phe Thr Asp Ala Ile Arg Arg Trp Asp Leu Glu Ala Met Glu Gly
            340                 345                 350
Leu Pro Glu Tyr Met Lys Ile Cys Tyr Met Ala Leu Tyr Asn Thr Thr
            355                 360                 365
Asn Glu Val Cys Tyr Lys Val Leu Arg Asp Thr Gly Arg Ile Val Leu
            370                 375                 380
Leu Asn Leu Lys Ser Thr Trp Ile Asp Met Ile Glu Gly Phe Met Glu
385                 390                 395                 400
Glu Ala Lys Trp Phe Asn Gly Ser Ala Pro Lys Leu Glu Glu Tyr
                405                 410                 415
Ile Glu Asn Gly Val Ser Thr Ala Gly Ala Tyr Met Ala Phe Ala His
            420                 425                 430
Ile Phe Phe Leu Ile Gly Glu Gly Val Thr His Gln Asn Ser Gln Leu
            435                 440                 445
Phe Thr Gln Lys Pro Tyr Pro Lys Val Phe Ser Ala Ala Gly Arg Ile
            450                 455                 460
Leu Arg Leu Trp Asp Asp Leu Gly Thr Ala Lys Glu Glu Gln Glu Arg
465                 470                 475                 480
Gly Asp Leu Ala Ser Cys Val Gln Leu Phe Met Lys Glu Lys Ser Leu
                485                 490                 495
```

-continued

```
Thr Glu Glu Glu Ala Arg Ser Arg Ile Leu Glu Ile Lys Gly Leu
                500                 505                 510
Trp Arg Asp Leu Asn Gly Glu Leu Val Tyr Asn Lys Asn Leu Pro Leu
            515                 520                 525
Ser Ile Ile Lys Val Ala Leu Asn Met Ala Arg Ala Ser Gln Val Val
530                 535                 540
Tyr Lys His Asp Gln Asp Thr Tyr Phe Ser Ser Val Asp Asn Tyr Val
545                 550                 555                 560
Asp Ala Leu Phe Phe Thr Gln
                565

<210> SEQ ID NO 158
<211> LENGTH: 589
<212> TYPE: PRT
<213> ORGANISM: Catharanthus roseus

<400> SEQUENCE: 158

Met Ala Ala Thr Ile Ser Asn Leu Ser Phe Leu Ala Lys Ser Arg Ala
1               5                   10                  15
Leu Ser Arg Pro Ser Ser Ser Leu Ser Trp Leu Glu Arg Pro Lys
            20                  25                  30
Thr Ser Thr Ile Cys Met Ser Met Pro Ser Ser Ser Ser Ser
        35                  40                  45
Ser Ser Ser Met Ser Leu Pro Leu Ala Thr Pro Leu Ile Lys Asp
    50                  55                  60
Asn Glu Ser Leu Ile Lys Phe Leu Arg Gln Pro Leu Val Leu Pro His
65                  70                  75                  80
Glu Val Asp Asp Ser Thr Lys Arg Arg Glu Leu Leu Glu Arg Thr Arg
                85                  90                  95
Lys Glu Leu Glu Leu Asn Ala Glu Lys Pro Leu Glu Ala Leu Lys Met
            100                 105                 110
Ile Asp Ile Ile Gln Arg Leu Gly Leu Ser Tyr His Phe Glu Asp Asp
        115                 120                 125
Ile Asn Ser Ile Leu Thr Gly Phe Ser Asn Ile Ser Ser Gln Thr His
    130                 135                 140
Glu Asp Leu Leu Thr Ala Ser Leu Cys Phe Arg Leu Leu Arg His Asn
145                 150                 155                 160
Gly His Lys Ile Asn Pro Asp Ile Phe Gln Lys Phe Met Asp Asn Asn
                165                 170                 175
Gly Lys Phe Lys Asp Ser Leu Lys Asp Asp Thr Leu Gly Met Leu Ser
            180                 185                 190
Leu Tyr Glu Ala Ser Tyr Leu Gly Ala Asn Gly Glu Glu Ile Leu Met
        195                 200                 205
Glu Ala Gln Glu Phe Thr Lys Thr His Leu Lys Asn Ser Leu Pro Ala
    210                 215                 220
Met Ala Pro Ser Leu Ser Lys Lys Val Ser Gln Ala Leu Glu Gln Pro
225                 230                 235                 240
Arg His Arg Arg Met Leu Arg Leu Glu Ala Arg Arg Phe Ile Glu Glu
                245                 250                 255
Tyr Gly Ala Glu Asn Asp His Asn Pro Asp Leu Leu Glu Leu Ala Lys
            260                 265                 270
Leu Asp Tyr Asn Lys Val Gln Ser Leu His Gln Met Glu Leu Ser Glu
        275                 280                 285
Ile Thr Arg Trp Trp Lys Gln Leu Gly Leu Val Asp Lys Leu Thr Phe
    290                 295                 300
```

```
Ala Arg Asp Arg Pro Leu Glu Cys Phe Leu Trp Thr Val Gly Leu Leu
305                 310                 315                 320

Pro Glu Pro Lys Tyr Ser Gly Cys Arg Ile Glu Leu Ala Lys Thr Ile
            325                 330                 335

Ala Ile Leu Leu Val Ile Asp Asp Ile Phe Asp Thr His Gly Thr Leu
            340                 345                 350

Asp Glu Leu Leu Leu Phe Thr Asn Ala Ile Lys Arg Trp Asp Leu Glu
        355                 360                 365

Ala Met Glu Asp Leu Pro Glu Tyr Met Arg Ile Cys Tyr Met Ala Leu
    370                 375                 380

Tyr Asn Thr Thr Asn Glu Ile Cys Tyr Lys Val Leu Lys Glu Asn Gly
385                 390                 395                 400

Trp Ser Val Leu Pro Tyr Leu Lys Ala Thr Trp Ile Asp Met Ile Glu
            405                 410                 415

Gly Phe Met Val Glu Ala Glu Trp Phe Asn Ser Asp Tyr Val Pro Asn
            420                 425                 430

Met Glu Glu Tyr Val Glu Asn Gly Val Arg Thr Ala Gly Ser Tyr Met
        435                 440                 445

Ala Leu Val His Leu Phe Phe Leu Ile Gly Gln Gly Val Thr Glu Asp
    450                 455                 460

Asn Val Lys Leu Leu Ile Lys Pro Tyr Pro Lys Leu Phe Ser Ser Ser
465                 470                 475                 480

Gly Arg Ile Leu Arg Leu Trp Asp Asp Leu Gly Thr Ala Lys Glu Glu
            485                 490                 495

Gln Glu Arg Gly Asp Leu Ala Ser Ser Ile Gln Leu Phe Met Arg Glu
            500                 505                 510

Lys Glu Ile Lys Ser Glu Glu Glu Gly Arg Lys Gly Ile Leu Glu Ile
        515                 520                 525

Ile Glu Asn Leu Trp Lys Glu Leu Asn Gly Glu Leu Val Tyr Arg Glu
        530                 535                 540

Glu Met Pro Leu Ala Ile Ile Lys Thr Ala Phe Asn Met Ala Arg Ala
545                 550                 555                 560

Ser Gln Val Val Tyr Gln His Glu Glu Asp Thr Tyr Phe Ser Ser Val
            565                 570                 575

Asp Asn Tyr Val Lys Ala Leu Phe Phe Thr Pro Cys Phe
            580                 585
```

US 10,266,837 B2

TERPENE SYNTHASES FROM YLANG YLANG (*CANANGA ODORATA* VAR. *FRUTICOSA*)

CROSS-REFERENCE TO RELATED APPLICATIONS

The present application is a national stage filing under 35 U.S.C. § 371 of PCT/SG2015/050400, filed on 19 Oct. 2015, and claims the benefit of priority to U.S. Provisional Application No. 62/067,191, filed 22 Oct. 2014. Each application is incorporated herein by reference in its entirety.

SEQUENCE SUBMISSION

The present application is being filed along with a Sequence Listing in electronic format. The Sequence Listing is entitled 2577241SequencListing.txt, was created on 9 Oct. 2015 and is 287 kb in size. The information in the electronic format of the Sequence Listing is part of the present application and is incorporated herein by reference in its entirety.

BACKGROUND OF THE INVENTION

The present invention relates to the field of plant molecular biology. More particularly, the present invention relates to the isolation of nucleic acids encoding terpene synthases (TPSs), including a novel, multifunctional TPS identified herein as CoTPS2.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

Plants emit a large group of phytogenic volatile organic compounds (VOCs) for their defense against pathogens, parasites and herbivores and for attracting pollinators (Kessler and Baldwin, 2001; Dudareva et al., 2013). VOCs are synthesized in all plant organs such as flowers, stems, leaves, roots, fruits and seeds, but the quantity and diversity of VOCs change in response to environmental stimuli (Dudareva et al., 2013). VOCs are major components of floral scent in a wide range of flowers (Knudsen et al., 1993). Over 1,700 floral VOCs have been identified from 90 different plants, and they are assumed to have functions in both attraction of pollinators and defence against pathogens (Knudsen et al., 2006; Muhlemann et al., 2014). Given the role of VOCs, the production and emission of VOCs are highly regulated spatially and developmentally. Floral VOCs are mainly composed of terpenoids, phenylpropanoids/benzenoids and volatile fatty acid derivatives which are derived from different biosynthetic routes in plants (Muhlemann et al., 2014). Terpenoids, also referred to as isoprenoids, are the largest and most diverse class of VOCs in plants (Dudareva et al., 2013). Terpenes are synthesized from two distinct and compartmentally separated pathways, the mevalonate (MVA) and 2-C-methyl-D-erythritol 4-phosphate (MEP) pathways (McGarvey and Croteau, 1995). Phenylpropanoids and benzenoids class of metabolites are primarily derived from the carbon skeleton of phenylalanine which is produced by the shikimate pathway (Vogt, 2010; Orlova et al., 2006).

Terpene synthases (TPSs) are responsible for generating the immense diversity in terpenes produced by plants (McGarvey and Croteau, 1995). Many TPSs have the ability to synthesize multiple products from a single prenyl diphosphate substrate (Degenhardt et al., 2009). Based on the sequence relatedness and functional assessment, the TPS gene family has been divided into seven subfamilies designated TPS-a through TPS-g (Bohlmann et al., 1998; Lee and Chappell, 2008; Martin et al., 2010). TPS-a subfamily typically contains angiosperm-specific sesqui-TPSs, whereas angiosperm mono-TPSs form the TPS-b subfamily. The TPS-b subfamily contains the arginine-tryptophan motif, $R(R)X_8W$ (SEQ ID NO:1) which plays a role in the RR-dependent isomerization of GPP (Martin et al., 2010). Another angiosperm mono-TPS subfamily, the TPS-g contains members of mono-TPSs that lack the $R(R)X_8W$ (SEQ ID NO:1) motif characteristic. These TPSs produce acyclic monoterpenes that contribute to the floral VOCs (Dudareva et al., 2013). TPS-c and TPS-e subfamilies consist of angiosperm di-TPSs responsible for gibberellic acid (GA) biosynthesis namely copalyl diphosphate synthases (CPS) and kaurene synthases (KS). The different mono-, sesqui-, and di-TPS genes for synthesis of conifer-specialized terpenes belong to the gymnosperm-specific TPS-d subfamily (Martin et al., 2004). TPS-f includes the monoterpene linalool synthase of the genus *Clarkia* (Dudareva et al., 1996).

*Cananga odorata*, commonly called ylang ylang is a tropical evergreen tree of the Annonaceae family that produces fragrant flowers and is widely cultivated throughout Southeast Asia. Essential oils obtained by steam distillation from mature fresh ylang ylang flowers are used in the cosmetic industry as major components of perfumes and fragrances, in the food industry as ingredients of aromas and flavours, and in the pharmaceutical industry as active components of antibacterials and in aromatherapy (Benini et al., 2010; Burdock and Carabin, 2008; Gaydou et al., 1986). The chemical composition of floral VOCs produced by ylang ylang varieties has been previously reported (Gaydou et al., 1986; Benini et al., 2010, 2012; Brokl et al., 2013). These papers show the presence of volatile terpenes, benzenoid and phenylpropanoids in floral VOCs. Gaydou et al., described the composition of essential oils of ylang ylang flowers originating from Madagascar (*Cananga odorata* Hook Fil. et Thomson forma genuina). These authors found that the primary component was the monoterpene linalool (19%), and the other major compounds were two sesquiterpenes, β-caryophyllene (10.7%) and germacrene D (10.3%) (Gaydou et al., 1986). Additionally, this variety of ylang ylang from Madagascar contained more than 20% of other aromatic compounds such as p-methylanisole, benzyl benzoate, methyl benzoate and benzyl salicylate (Gaydou et al., 1986). *Cananga odorata* var. *fruticosa* or dwarf ylang ylang is another variety which is popularly grown in Southeast Asia as a small and compact shrub with highly scented flowers. Its essential oil is also used in the perfume industry. Despite the economic and social importance of this species, the biosynthetic pathways leading to the production of the floral scent of ylang ylang have not been fully understood.

SUMMARY OF THE INVENTION

The present invention relates to the field of plant molecular biology. More particularly, the present invention relates to the isolation of nucleic acids encoding terpene synthases (TPSs), including a novel, multifunctional TPS identified herein as CoTPS2.

As described herein, the chemical composition of floral VOC was determined at 4 different stages of flower formation and performed RNA-seq on mature yellow flowers of *C. odorata* var. *fruticosa* where the production of floral VOCs is at the maximum. Terpenes formed the bulk of floral VOCs. The transcriptome data revealed 16 TPS transcripts from dwarf ylang ylang flowers out of which 4 were functionally characterized. Two TPSs were identified as mono-TPSs, CoTPS1 and CoTPS4, which catalyze the formation of multiproduct β-thujene/sabinene/β-pinene/α-terpinene and geraniol, respectively. The other two CoTPS2 and CoTPS3 were ascertained as sesqui-TPSs. CoTPS3 was shown to catalyze the formation of α-bergamotene. CoTPS2 was found to be a multifunctional and novel TPS which could synthesize three sesquiterpene compounds, β-ylangene/β-copaene/β-cubebene from the farnesyl pyrophosphate (FPP) substrate.

Thus, in one aspect, the present invention provides an isolated nucleic acid encoding a CoTPS protein. In one embodiment, the nucleic acid further comprises a plant operable promoter operably linked to the coding sequence. In some embodiments, the CoTPS protein is CoTPS2 protein comprising the amino acid sequence set forth in SEQ ID NO:10. In one embodiment, the nucleic acid comprises the nucleotide sequence set forth in SEQ ID NO:9. In a further embodiment, the nucleic acid encodes a variant CoTPS2 protein. In one embodiment, the variant CoTPS2 protein has at least 90% sequence identity with the CoTPS2 protein while having the activity of the CoTPS2 protein. In another embodiment, the variant CoTPS2 protein has one or more amino acid changes in the amino acid sequence of the CoTPS2 protein while having the activity of the CoTPS2 protein.

In other embodiments, the CoTPS protein is CoTPS3 protein comprising the amino acid sequence set forth in SEQ ID NO:6. In one embodiment, the nucleic acid comprises the nucleotide sequence set forth in SEQ ID NO:5. In a further embodiment, the nucleic acid encodes a variant CoTPS3 protein. In one embodiment, the variant CoTPS3 protein has at least 90% sequence identity with the CoTPS3 protein while having the activity of the CoTPS3 protein. In another embodiment, the variant CoTPS3 protein has one or more amino acid changes in the amino acid sequence of the CoTPS3 protein while having the activity of the CoTPS3 protein.

In some embodiments, the CoTPS protein is CoTPS1 protein comprising the amino acid sequence set forth in SEQ ID NO:8. In one embodiment, the nucleic acid comprises the nucleotide sequence set forth in SEQ ID NO:7. In a further embodiment, the nucleic acid encodes a variant CoTPS1 protein. In one embodiment, the variant CoTPS1 protein has at least 90% sequence identity with the CoTPS1 protein while having the activity of the CoTPS1 protein. In another embodiment, the variant CoTPS1 protein has one or more amino acid changes in the amino acid sequence of the CoTPS1 protein while having the activity of the CoTPS1 protein.

In other embodiments, the CoTPS protein is CoTPS4 protein comprising the amino acid sequence set forth in SEQ ID NO:12. In one embodiment, the nucleic acid comprises the nucleotide sequence set forth in SEQ ID NO:11. In a further embodiment, the nucleic acid encodes a variant CoTPS4 protein. In one embodiment, the variant CoTPS4 protein has at least 90% sequence identity with the CoTPS4 protein while having the activity of the CoTPS4 protein. In another embodiment, the variant CoTPS4 protein has one or more amino acid changes in the amino acid sequence of the CoTPS4 protein while having the activity of the CoTPS4 protein.

In a second aspect, the present invention provides a construct or vector comprising an isolated nucleic acid as described herein. In one embodiment, the construct or vector is an expression construct or vector. In another embodiment, the construct or vector further comprises a selectable marker. In a further embodiment, the construct or vector comprises a recombination marker free system. In some embodiments, the recombination marker free system is a Cre-lox recombination marker free system, a Zinc finger marker free system, a TALE nucleases marker free system or a CRISPR-Cas marker free system.

In a third aspect, the present invention provides a transgenic plant comprising a nucleic acid, construct or vector described herein. In one embodiment, the transgenic plant may be any plant species. In another embodiment, the transgenic plant may be a member of the *Cananga* genus. In an additional embodiment, the transgenic plant is a *Cananga odorata* plant. In a further embodiment, the transgenic plant may be *Cananga odorata* var. *fruticosa* (dwarf ylang ylang). In one embodiment, the transgenic *Cananga* plant or *Cananga odorata* plant or *Cananga odorata* var. *fruticosa* plant overexpresses a CoTPS protein compared to non-transgenic plants. In other embodiments, the transgenic plant expresses a lower amount of a CoTPS protein compared to a non-transgenic plant.

In a fourth aspect, the present invention provides a method for manipulating synthesis of a terpene or sesquiterpene in a transgenic plant to alter fragrance/flavor characteristics and/or plant pathogen interactions and/or insect interactions. In one embodiment, the transgenic plant may be any plant species. In another embodiment, the transgenic plant may be a *Cananga odorata* plant. In a further embodiment, the transgenic plant may be *Cananga odorata* var. *fruticosa* (dwarf ylang ylang). In one embodiment, the synthesis of the sesquiterpenes ylangene, β-copaene and β-cubebene is manipulated by overexpressing the CoTPS2 protein in the transgenic plant compared to a non-transgenic plant. In another embodiment, the synthesis of the sesquiterpene α-bergamotene is manipulated by overexpressing the CoTPS3 protein in the transgenic plant compared to a non-transgenic plant. In an additional embodiment, the synthesis of the terpene β-thujene/sabinene/β-pinene/α-terpinene is manipulated by overexpressing the CoTPS1 protein in the transgenic plant compared to a non-transgenic plant. In a further embodiment, the synthesis of the terpene geraniol is manipulated by overexpressing the CoTPS4 protein in the transgenic plant compared to a non-transgenic plant. In some embodiments, the synthesis of the described terpenes or sesquiterpenes is manipulated by reducing expression of the corresponding CoTPS protein in the transgenic plant compared to a non-transgenic plant.

In a fifth aspect, the present invention provides a method of preparing at least one terpene or sesquiterpene comprising the steps of (a) culturing a cell which has been genetically modified with a polynucleotide of the invention to provide CoTPS activity and (b) separating the at least one terpene or sesquiterpene produced. In one embodiment, the cells may be any cell type that can be grown in culture. In another embodiment, the cells may be bacteria or yeast cells for producing the terpene or sesquiterpene. In one embodiment, the at least one sesquiterpene is β-ylangene, β-copaene and/or β-cubebene and the CoTPS activity is CoTPS2 activity. In another embodiment, the at least one sesquiterpene is α-bergamotene and the CoTPS activity is CoTPS3 activity. In an additional embodiment, the at least one terpene is β-thujene/sabinene/β-pinene/α-terpinene and the CoTPS activity is CoTPS1 activity. In a further embodiment, the at least one terpene is geraniol and the CoTPS activity is CoTPS4 activity. In one embodiment, the cell contains a metabolic pathway for producing farnesyl pyrophosphate which provides the farnesyl pyrophosphate that is the substrate for CoTPS2 or CoTPS3. In another embodiment, the cell has been transformed with a nucleic acid encoding farnesyl pyrophosphate synthase to produce farnesyl pyrophosphate which provides the farnesyl pyrophosphate that is the substrate for CoTPS2 or CoTPS3. In one embodiment, the cell contains a metabolic pathway for producing geranyl diphosphate which provides the geranyl diphosphate that is the substrate for CoTPS1 or CoTPS4. In another embodiment, the cell has been transformed with a nucleic acid encoding geranyl diphosphate synthase to produce geranyl diphosphate which provides the geranyl diphosphate that is the substrate for CoTPS1 or CoTPS4.

BRIEF DESCRIPTION OF THE FIGURES

FIG. 1A: The photograph of ylang ylang flowers showing the development of newly emerged flower bud to fully open yellow flower. I, undeveloped small flower; II, mature green flower; III, fully mature yellow flower. Scale bar, 1 cm. FIG. 1B: GC trace of essential oils from floral buds, undeveloped small flowers (I), mature green flowers (II), and fully mature yellow flowers (III). The arrows indicate the retention time of camphor (10 µg/µl) as an internal standard. The peaks numbered in GC traces were identical to those listed in Table 2. These are magnified images of the corresponding zones indicated by a dotted line in FIG. 9.

FIG. 4A: The maximum likelihood tree was drawn by MEGA 6 program from an alignment of full-length CoTPSs with other plant TPSs. AaADS, *Artemisia annua* (Aa) amorpha-411-diene synthase (AFA34434); AaFS, β-farnesene synthase (Q9FXY7); AaQHS1, (3-caryophyllene synthase (AAL79181); AaQH5, linalool synthase (AAF13356); Ag10, *Abies grandis* (Ag) 4S-limonene synthase (AAB70907); Ag2, myrcene synthase (AAB71084); Ag4, δ-selinene synthase (AAC05727); Ag3, pinene synthase (AAB71085); Ag9, terpinolene synthase (AAF61454); AmNES/LIS-1, *Antirrhium majus* (Am) nerolidol/linalool synthase1 (ABR24417); AmMS, myrcene synthase (AAO41727); AtCPS1, *Arabidopsis thaliana* (At) copalyl diphosphate synthase (NP_192187); AtGA2, kaurene synthase; AtTPS10 (AAC39443), myrcene/ocimene synthase (AAG09310); AtTPS14, linalool synthase (NP176361); CbLIS, *Clarkia breweri* S-linalool synthase (AAC49395); ClLS1, *Citrus limon* limonene synthase 1 (AAM53944); CmCPS, Cucurbits maxima copalyl diphosphate synthase (AAD04292); CrGES, *Catharanthus roseus* geraniol synthase (AFD64744); FaNES2, *Fragaria×ananassa* nerolidol synthase (CAD57081); LsLTC1, *Lactuca sativus* germacrene A synthase (AAM11626); MpFS, *Mentha piperita* β-farnesene synthase (AAB95209); MsLS, *Mentha spicata* 4S-limonene synthase (AAC37366); ObGES, *Ocimum basilicum* geraniol synthase (AAR11765); OeGES1, *Olea europaea* geraniol synthase 1 (AFI47926); PaTPS-Bis, *Picea abies* α-bisabolene synthase (AAS47689); PcLS, *Perilla citriodora* limonene synthase (AAG31435); PfLS, *Perilla frutescens* linalool synthase (AAL38029); SaSSy, *Santalum album* santalene/bergamotene synthase (AD087000); ScGAS, *Solidago canadensis* (Sc) germacrene A synthase (CAC36896); ScGDS, gennacrene D synthase (AAR31145); ShSBS, *Solanum habrochaites* santalene/bergamotene synthase (B8XA41); SlSBS, *Solanum lycopersicum* (Sl) santalene and bergamotene synthase (XP004244438); SlCPS, copalyl diphosphate synthase (BAA84918); SlGCS, germacrene C synthase (AAC39432); santalene/bergamotene synthase (BAA84918); Sl TPS38, Sl terpene synthase 38 (AEP82768); SoBPS, *Salvia officinalis* (So) bornyl diphosphate synthase (AAC26017); SoCS, 1,8-cineole synthase (AAC26016); SoSS, sabinene synthase (AAC26018); SrCPS, *Stevia rebaudiana* (Sr) copalyl pyrophosphate synthase (AAB87091); SrKS, kaurene synthase (AAD34294); VvPNGer, *Vitis vinifera* geraniol synthase (ADR74218); ZmTPS1, *Zea mays* terpene synthase 1 (AA018435). Seven TPS subfamilies, a to g are delimited by dashed lines as based on the taxonomic distribution of the TPS families (Chen et al., 2011). FIG. 4B: Comparison of deduced amino acid sequences of dwarf ylang ylang TPSs. The deduced amino acid sequences of CoTPSs were aligned using CLUSTAL W method. The Asp-rich domain, DDXXD (SEQ ID NO:2), the R(R)X$_8$W (SEQ ID NO:1) motif, and NSE/DTE (SEQ ID NO:3/SEQ ID NO:4) motif, which are highly conserved in plant TPSs and required for TPS activity, are indicated on the sequences. The arrowheads denote the predicted cleavage sites of plastidial transit peptides. Completely conserved residues are shaded in dark gray, and identical residues are shaded in gray, and similar residues are shaded in light gray. Dashes indicate gaps introduced to maximize sequence alignment. The deduced amino acid sequences for the CoTPSs are: CoTPS3—SEQ ID NO:6; CoTPS1—SEQ ID NO:8; CoTPS2—SEQ ID NO:10; and CoTPS4—SEQ ID NO:12. Nucleic acid sequences encoding these amino acid sequences are set forth in SEQ ID NOs:5, 7, 9 and 11, respectively.

FIG. 10A: GC traces showing no difference between fresh and dried flowers. FIG. 10B: GC traces of flowers and leaves from dwarf ylang ylang. 1, α-pinene; 2, Elixene; 3, β-elemene; 4, β-caryophyllene; 5, γ-muurolene; 6, Humulene; 7, Germacrene D; 8, γ-elemene; 9 and 10, phytol.

Figure 14A:
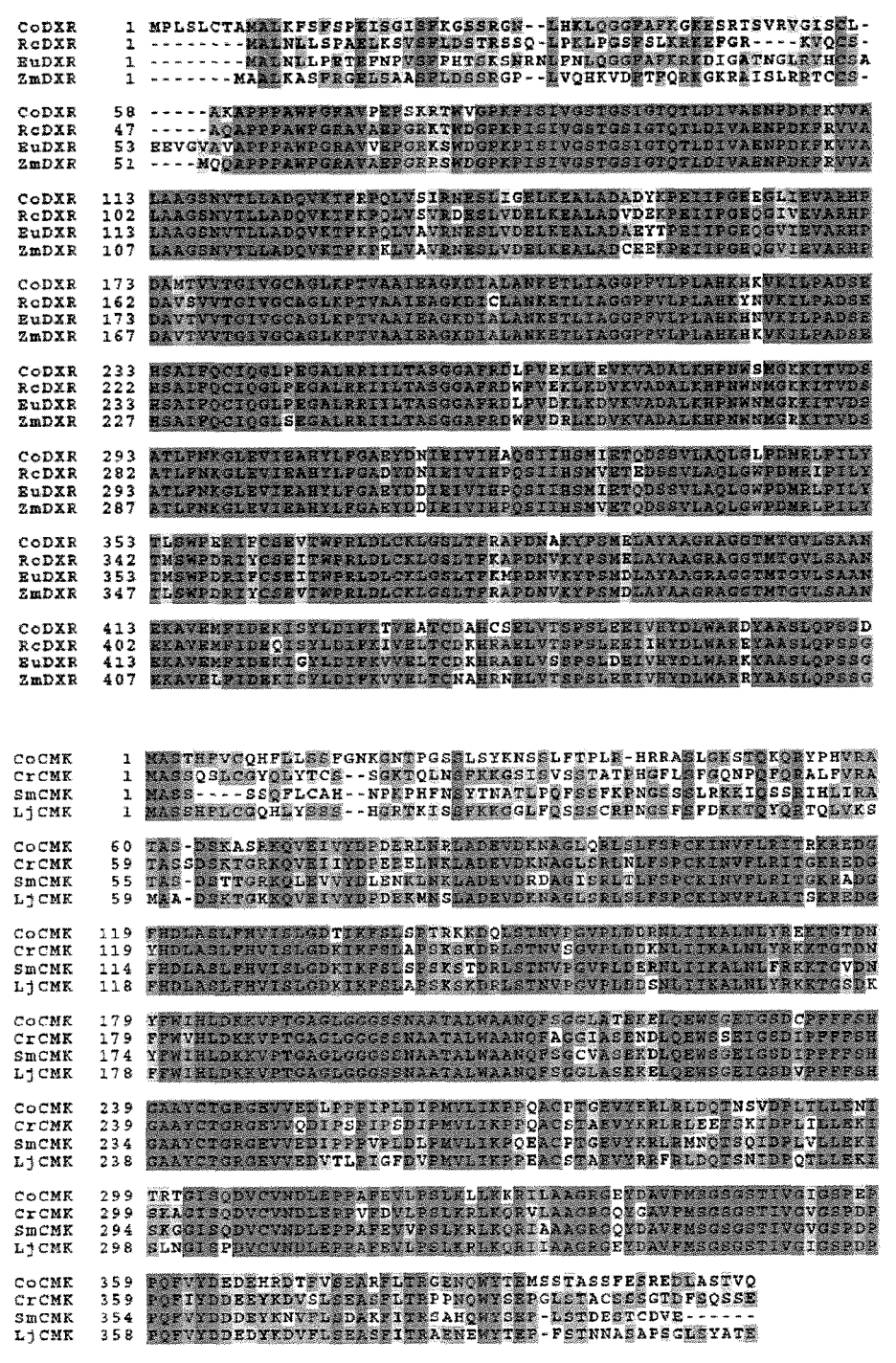
Figure 14C:
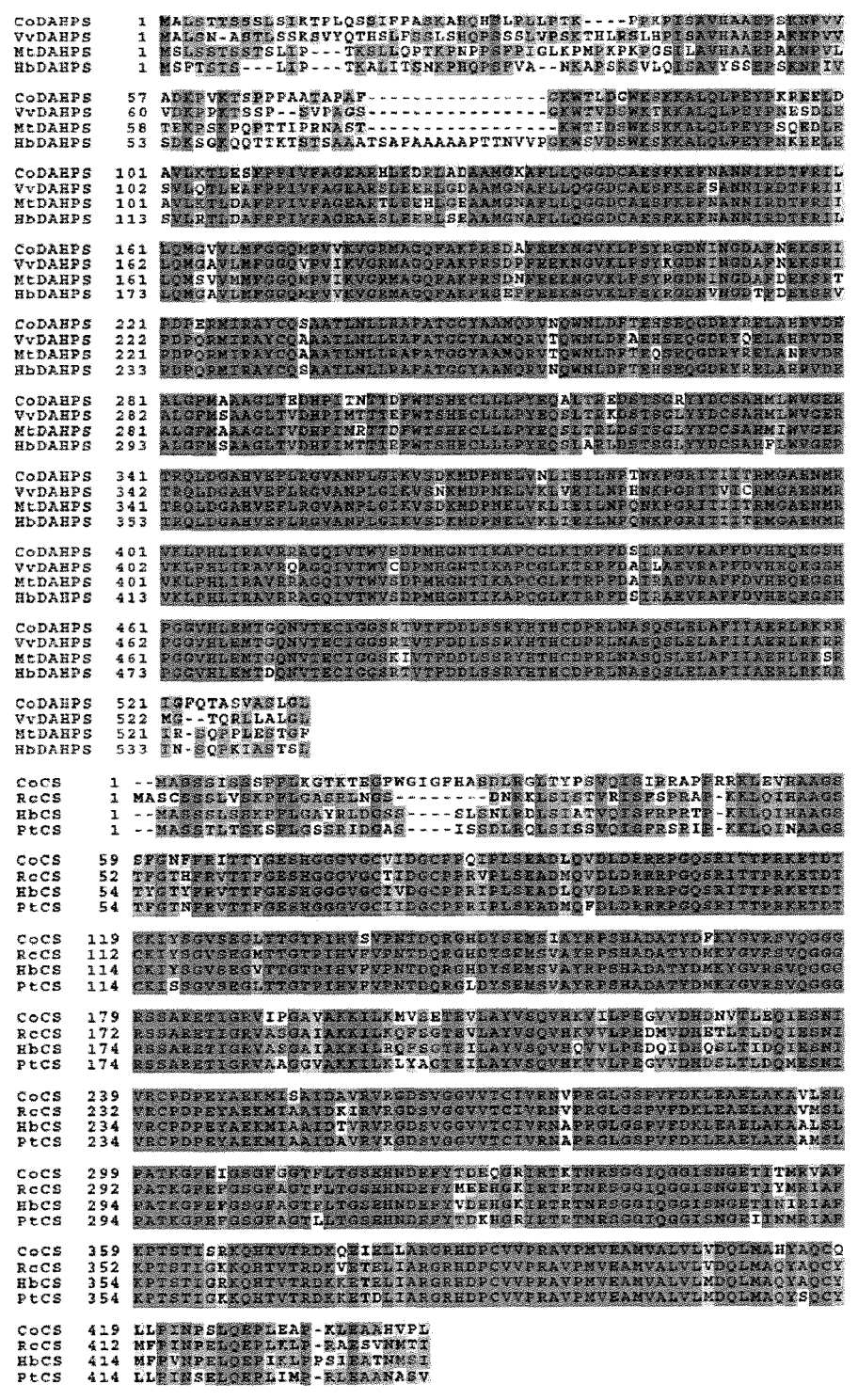
Figure 14D:
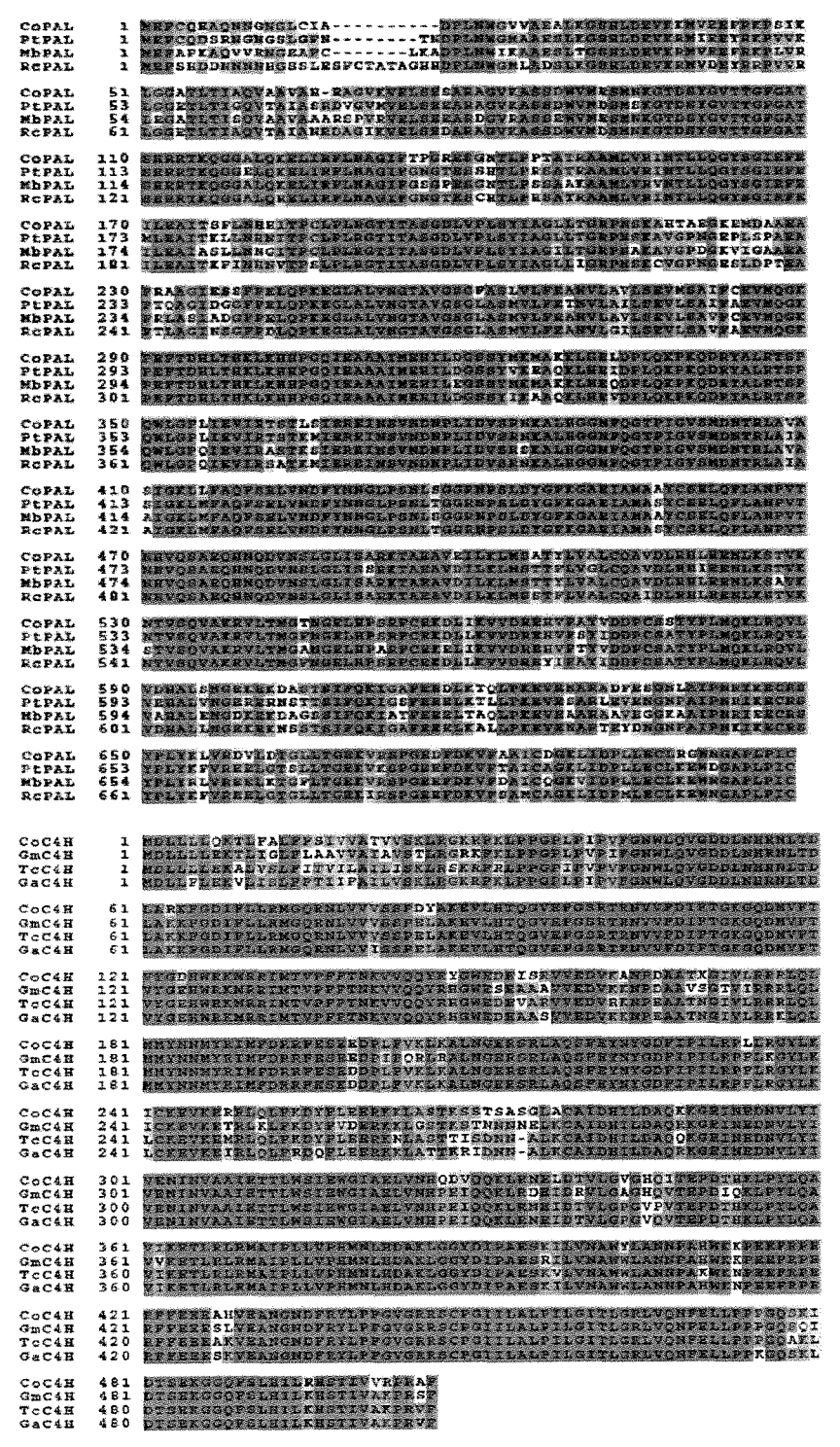

FIG. 14A-14D shows the alignment of deduced amino acid sequences of representative genes involved in biosynthetic pathways for VOCs. FIG. 14A: Alignment of deduced amino acid sequences of two representative genes, DXR and CMK, involved in MEP pathway. DXR, 1-deoxy-D-xylulose 5-phosphate reductoisomerase; CMK, 4-(cytidine 5'-diphospho)-2-C-methyl-D-erythritol kinase. Co, *Cananga odorata*; Cr, *Catharanthus roseus*; Eu, *Eucommia ulmoides*; Lj, *Lonicera japonica*; Rc, *Ricinus communis*; Sm, *Salvia miltiorrhiz*; Zm, *Zea mays*. The CoDXR sequence is SEQ ID NO:111, and the CoCK sequence is SEQ ID NO:115. Accession numbers: RcDXR (XP_002511399; SEQ ID NO:112), EuDXR (AFU93070; SEQ ID NO:113), ZmDXR (NP_001105139; SEQ ID NO:114), CrCMK (ABI35992; SEQ ID NO:116), SmCMK (ABP96842; SEQ ID NO:117), LjCMK (AGE10581; SEQ ID NO:118). FIG. 14B: Alignment of deduced amino acid sequences of two representative genes, HMGS and PMK, involved in MVA pathway. HMGS, hydroxymethylglutaryl-CoA synthase; PMK, phosphomevalonate kinase. Ae, *Arnebia euchroma*; Co, *Cananga odorata*; Gs, *Glycine soja*; Nt, *Narcissus tazetta*; Pn, *Panax notoginseng*; Zm, *Zea mays*. The CoHMGS sequence is SEQ ID NO:119, and the CoPMK sequence is SEQ ID NO:123. Accession number of the orthologous genes used in the alignment: NtHMGS (AHF81872; SEQ ID NO:120), GsHMGS (KHN14128; SEQ ID NO:121), PnHMGS (AIK21781; SEQ ID NO:122), PnPMK (AIK21784; SEQ ID NO:124), ZmPMK (NP_001149345; SEQ ID NO:125), AePMK (ABY27562; SEQ ID NO:126). FIG. 14C: Alignment of deduced amino acid sequences of two representative genes, DAHPS and CS, involved in shikimate pathway. DAHPS, 3-deoxy-D-arabino-heptulosonate-7-phosphate synthase; CS, chorismate synthase. Co, *Cananga odorata*; Hb, *Hevea brasiliensis*; Mt, *Medicago truncatula*; Pt, *Populus trichocarpa*; Re, *Ricinus communis*; Vv, *Vitis vinifera*. The CoDAHPS sequence is SEQ ID NO:127, and the CoCS sequence is SEQ ID NO:131. Accession number of the orthologous genes used in the alignment: VvDAHPS (NP_001268127; SEQ ID NO:128), MtDAHPS (XP_003615152; SEQ ID NO:129), HbDAHPS (AFY09700; SEQ ID NO:130), RcCS (XP_002529571; SEQ ID NO:132), HbCS (ADR70879; SEQ ID NO:133), PtCS (XP_002315301; SEQ ID NO:134). FIG. 14D: Alignment of deduced amino acid sequences of two representative genes, PAL and C4H, involved in phenyl propanoid pathway. PAL, phenylalanine ammonia lyase; C4H, cinnamate-4-hydroxylase. Co, *Cananga odorata*; Ga, *Gossypium arboreum*; Gm, *Glycine max*; Mb, *Musa balbisiana*; Pt, *Populus trichocarpa*; Rc, *Ricinus communis*; Tc, *Theobroma cacao*. The CoPAL sequence is SEQ ID NO:135, and the CoC4H sequence is SEQ ID NO:139. Accession number of the orthologous genes used in the alignment: PtPAL (ACC63889; SEQ ID NO:136), MbPAL (BAG70992; SEQ ID NO:137), RcPAL (XP_002531677; SEQ ID NO:138), GmC4H (ACR44227; SEQ ID NO:140), TcC4H (XP_007011365; SEQ ID NO:141), GaC4H (AAG10197; SEQ ID NO:142).

FIG. 16 shows the comparison of deduced amino acid sequences of four CoDXS small gene family. The thiamin diphosphate-binding site and the pyridine binding DRAG domain are indicated by the open box and the horizontal line, respectively. Completely conserved residues are shaded in dark gray, and identical residues are shaded in gray, and similar residues are shaded in light gray. Dashes indicate gaps introduced to maximize sequence alignment. The sequences are as follows: CoDXS1: SEQ ID NO:143; CoDXS2: SEQ ID NO:144; CoDXS3: SEQ ID NO:145; and CoDXS4: SEQ ID NO:146.

FIGS. 17A-17D shows the alignment of deduced amino acid sequences of CoTPSs and other plant TPSs. FIG. 17A: Alignment of deduced amino acid sequences of CoTPS1 (SEQ ID NO:8) and other plant TPSs. PsSS, *Picea sitchensis* sabinene synthase (ADU85930; SEQ ID NO:149); SoSS, *Salvia officinalis* sabinene synthase (AAC26018; SEQ ID NO:148); Mg17, *Magnolia grandiflora* α-terpineol synthase (B3TPQ7; SEQ ID NO:147). The conserved motifs DDXXD (SEQ ID NO:2) and NSE/DTE (SEQ ID NO:3/SEQ ID NO:4) are marked. Completely conserved residues are shaded in dark gray, and identical residues are shaded in gray, and similar residues are shaded in light gray. Dashes indicate gaps introduced to maximize sequence alignment. FIG. 17B: Alignment of deduced amino acid sequences of CoTPS2 (SEQ ID NO:10) and other plant TPSs. RcSeTPS1, *Ricinus communis* α-copaene synthase (B9S9Z3; SEQ ID NO:150); Mg25, *Magnolia grandiflora* β-cubebene synthase (B3TPQ6; SEQ ID NO:151); HaCS, *Helianthus annuus* α-copaene synthase (Q4U3F6; SEQ ID NO:152). The conserved motifs DDXXD (SEQ ID NO:2) and NSE/DTE (SEQ ID NO:3/SEQ ID NO:4) are marked. Completely conserved residues are shaded in dark gray, and identical residues are shaded in gray, and similar residues are shaded in light gray. Dashes indicate gaps introduced to maximize sequence alignment. FIG. 17C: Alignment of deduced amino acid sequences of CoTPS3 (SEQ ID NO:6) and other plant TPSs. LcTOS, *Litsea cubeba* trans-ocimene synthase (AEJ91554; SEQ ID NO:153); LaBERS, *Lavandula angustifolia* α-bergamotene synthase (Q2XSC4; SEQ ID NO:154); LdTPS7, *Lippia dulcis* α-bergamotene synthase (J7LQ09; SEQ ID NO:155). The conserved motifs DDXXD (SEQ ID NO:2) and NSE/DTE (SEQ ID NO:3/SEQ ID NO:4) are marked. Completely conserved residues are shaded in dark gray, and identical residues are shaded in gray, and similar residues are shaded in light gray. Dashes indicate gaps introduced to maximize sequence alignment. FIG. 17D: Alignment of deduced amino acid sequences of CoTPS4 (SEQ ID NO:12) and other plant TPSs. ObGES, *Ocimum basilicum* geraniol synthase (AAR11765; SEQ ID NO:157); OeGES1, *Olea europaea* geraniol synthase 1 (AFI47926; SEQ ID NO:156); CrGES, Catharanthus *roseus* geraniol synthase (AFD64744; SEQ ID NO:158). The conserved motifs DDXXD (SEQ ID NO:2) and NSE/DTE (SEQ ID NO:3/SEQ ID NO:4) are marked. Completely conserved residues are shaded in dark gray, and identical residues are shaded in gray, and similar residues are shaded in light gray. Dashes indicate gaps introduced to maximize sequence alignment.

DETAILED DESCRIPTION OF THE INVENTION

Figure 1A:
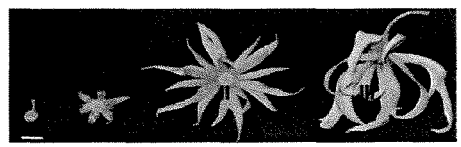
FIGS. 1A and 1B show the compositional variation of ylang ylang essential oils during flower development.

The present invention relates to the field of plant molecular biology. More particularly, the present invention relates to the isolation of nucleic acids encoding terpene synthases (TPSs), including a novel, multifunctional TPS identified herein as CoTPS2.

Unless defined otherwise, all technical and scientific terms used herein have the same meaning as is commonly understood by one of skill in the art to which the invention belongs.

As used herein, "allele" refers to any of one or more alternative forms of a gene locus, all of which alleles relate to a trait or characteristic. In a diploid cell or organism, the two alleles of a given gene occupy corresponding loci on a pair of homologous chromosomes.

As used herein, "gene" refers to a nucleic acid sequence that encompasses a 5' promoter region associated with the expression of the gene product, any intron and exon regions and 3' or 5' untranslated regions associated with the expression of the gene product.

As used herein, "genotype" refers to the genetic constitution of a cell or organism.

The term "heterologous" or "exogenous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous or exogenous protein indicates that the protein comprises two or more subsequences that are not found in the same relationship to each other in nature (e.g., a fusion protein).

"Operable linkage" or "operably linked" as used herein is understood as meaning, for example, the sequential arrangement of a promoter and the nucleic acid to be expressed and, if appropriate, further regulatory elements such as, for example, a terminator, in such a way that each of the regulatory elements can fulfill its function in the recombinant expression of the nucleic acid to make RNA. This does not necessarily require direct linkage in the chemical sense. Genetic control sequences such as, for example, enhancer sequences, can also exert their function on the target sequence from positions which are somewhat distant, or indeed from other DNA molecules (cis or trans localization). Preferred arrangements are those in which the nucleic acid sequence to be expressed recombinantly is positioned downstream of the sequence which acts as promoter, so that the two sequences are covalently bonded with one another.

As used herein, "phenotype" refers to the detectable characteristics of a cell or organism, which characteristics are the manifestation of gene expression.

The terms "polynucleotide," nucleic acid" and "nucleic acid molecule are used interchangeably herein to refer to a polymer of nucleotides which may be a natural or synthetic linear and sequential array of nucleotides and/or nucleosides, including deoxyribonucleic acid, ribonucleic acid, and derivatives thereof. It includes chromosomal DNA, self-replicating plasmids, infectious polymers of DNA or RNA and DNA or RNA that performs a primarily structural role. Unless otherwise indicated, nucleic acids or polynucleotide are written left to right in 5' to 3' orientation, Nucleotides are referred to by their commonly accepted single-letter codes. Numeric ranges are inclusive of the numbers defining the range. The "nucleic acid" may also optionally contain non-naturally occurring or altered nucleotide bases that permit correct read through by a polymerase and do not reduce expression of the nucleic acid.

The terms "polypeptide," "peptide," and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. Amino acids may be referred to by their commonly known three-letter or one-letter symbols. Amino acid sequences are written left to right in amino to carboxy orientation, respectively. Numeric ranges are inclusive of the numbers defining the range.

As used herein, the term "substantially homologous" or "substantial homology", with reference to a nucleic acid sequence, includes a nucleotide sequence that hybridizes under stringent conditions to a referenced SEQ ID NO, or a portion or complement thereof, are those that allow an antiparallel alignment to take place between the two sequences, and the two sequences are then able, under stringent conditions, to form hydrogen bonds with corresponding bases on the opposite strand to form a duplex molecule that is sufficiently stable under conditions of appropriate stringency, including high stringency, to be detectable using methods well known in the art. Substantially homologous sequences may have from about 70% to about 80% sequence identity, or more preferably from about 80% to about 85% sequence identity, or most preferable from about 90% to about 95% sequence identity, to about 99% sequence identity, to the referent nucleotide sequences as set forth the sequence listing, or the complements thereof. Alternatively, substantially homologous sequences include those which hybridize under stringent conditions to the target regions of introns of plant genes. As used herein, stringent conditions are those that (1) employ low ionic strength and high temperature for washing, for example, 0.015 M NaCl/0.0015 M sodium citrate/0.1% NaDodSO$_4$ at 50° C.; (2) employ during hybridization a denaturing agent such as formamide, for example, 50% (vol/vol) formamide with 0.1% bovine serum albumin, 0.1% Ficoll, 0.1% polyvinylpyrrolidone, 50 mM sodium phosphate buffer at pH 6.5 with 750 mM NaCl, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 g/ml), 0.1% SDS and 10% dextran sulfate at 42° C. in 0.2×SSC and 0.1% SDS. For stringency conditions, see also U.S. Pat. Nos. 8,455,716 and 8,536,403.

As used herein, the term "sequence identity", "sequence similarity" or "homology" is used to describe sequence relationships between two or more nucleotide sequences. The percentage of "sequence identity" between two sequences is determined by comparing two optimally aligned sequences over a comparison window such as the full length of a referenced SEQ ID NO, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. A sequence that is identical at every position in comparison to a reference sequence is said to be identical to the reference sequence and vice-versa. A first nucleotide sequence when observed in the 5' to 3' direction is said to be a "complement" of, or complementary to, a second or reference nucleotide sequence observed in the 3' to 5' direction if the first nucleotide sequence exhibits complete complementarity with the second or reference sequence. As used herein, nucleic acid sequence molecules are said to exhibit "complete complementarity" when every nucleotide of one of the sequences read 5' to 3' is complementary to every nucleotide of the other sequence when read 3' to 5'. A nucleotide sequence that is complementary to a reference nucleotide sequence will exhibit a sequence identical to the reverse complement sequence of the reference nucleotide sequence. These terms and descriptions are well defined in the art and are easily understood by those of ordinary skill in the art.

As used herein, a "comparison window" or "window of comparison" refers to a conceptual segment of at least 6 contiguous positions, usually about 50 to about 100, more usually about 100 to about 150, in which a sequence is compared to a reference sequence of the same number of contiguous positions after the two sequences are optimally aligned. The comparison window may comprise additions or deletions (i.e. gaps) of about 20% or less as compared to the reference sequence (which does not comprise additions or deletions) for optimal alignment of the two sequences. Those skilled in the art should refer to the detailed methods used for sequence alignment, such as in the Wisconsin Genetics Software Package Release 7.0 (Genetics Computer Group, 575 Science Drive Madison, Wis., USA).

As described herein, the chemical composition of floral VOC was determined at 4 different stages of flower formation and performed RNA-seq on mature yellow flowers of C. odorata var. fruticosa where the production of floral VOCs is at the maximum. Terpenes formed the bulk of floral VOCs. The transcriptome data revealed 16 TPS transcripts from dwarf ylang ylang flowers out of which 4 were functionally characterized. Two TPSs were identified as mono-TPSs, CoTPS1 and CoTPS4, which catalyze the formation of multiproduct β-thujene/sabinene/β-pinene/α-terpinene and geraniol, respectively. The other two CoTPS2 and CoTPS3 were ascertained as sesqui-TPSs. CoTPS3 was shown to catalyze the formation of α-bergamotene. CoTPS2 was found to be a multifunctional and novel TPS which could synthesize three sesquiterpene compounds, β-ylangene/β-copaene/β-cubebene from the farnesyl pyrophosphate (FPP) substrate.

In a first aspect, the present invention provides an isolated nucleic acid encoding a CoTPS protein. In one embodiment, the nucleic acid further comprises a plant operable promoter operably linked to the coding sequence. In some embodiments, the CoTPS protein is CoTPS2 protein comprising the amino acid sequence set forth in SEQ ID NO:10. In one embodiment, the nucleic acid comprises the nucleotide sequence set forth in SEQ ID NO:9. In a further embodiment, the nucleic acid encodes a variant CoTPS2 protein. In one embodiment, the variant CoTPS2 protein has at least 90% sequence identity with the CoTPS2 protein while having the activity of the CoTPS2 protein. In another embodiment, the variant CoTPS2 protein has one or more amino acid changes in the amino acid sequence of the CoTPS2 protein while having the activity of the CoTPS2 protein.

In other embodiments, the CoTPS protein is CoTPS3 protein comprising the amino acid sequence set forth in SEQ ID NO:6. In one embodiment, the nucleic acid comprises the nucleotide sequence set forth in SEQ ID NO:5. In a further embodiment, the nucleic acid encodes a variant CoTPS3 protein. In one embodiment, the variant CoTPS3 protein has at least 90% sequence identity with the CoTPS3 protein while having the activity of the CoTPS3 protein. In another embodiment, the variant CoTPS3 protein has one or more amino acid changes in the amino acid sequence of the CoTPS3 protein while having the activity of the CoTPS3 protein.

In some embodiments, the CoTPS protein is CoTPS1 protein comprising the amino acid sequence set forth in SEQ ID NO:8. In one embodiment, the nucleic acid comprises the nucleotide sequence set forth in SEQ ID NO:7. In a further embodiment, the nucleic acid encodes a variant CoTPS1 protein. In one embodiment, the variant CoTPS1 protein has at least 90% sequence identity with the CoTPS1 protein while having the activity of the CoTPS1 protein. In another embodiment, the variant CoTPS1 protein has one or more amino acid changes in the amino acid sequence of the CoTPS1 protein while having the activity of the CoTPS1 protein.

In other embodiments, the CoTPS protein is CoTPS4 protein comprising the amino acid sequence set forth in SEQ ID NO:12. In one embodiment, the nucleic acid comprises the nucleotide sequence set forth in SEQ ID NO:11. In a further embodiment, the nucleic acid encodes a variant CoTPS4 protein. In one embodiment, the variant CoTPS4 protein has at least 90% sequence identity with the CoTPS4 protein while having the activity of the CoTPS4 protein. In another embodiment, the variant CoTPS4 protein has one or more amino acid changes in the amino acid sequence of the CoTPS4 protein while having the activity of the CoTPS4 protein.

In some embodiments, the polynucleotide may be one encoding a polypeptide of a variant of the amino acid sequences disclosed herein, which variant is an amino acid sequence disclosed herein having one or several amino acid residues substituted, deleted, inserted and/or added. The site at which one or several amino acid residues are substituted, deleted, inserted and/or added may be any site in the amino acid sequence, as long as the polypeptide with one or several amino acid residues substituted, deleted, inserted and/or added has the function of regulating the flowering time of a plant. As used herein, the term "one or several amino acid residues" refers specifically to up to 10 amino acid residues in number, preferably to up to 6 amino acid residues, more preferably to up to 2 amino acid residues and even more preferably to one amino acid residue.

When the amino acids are altered, for example, by substitution, it is preferable to be conservatively substituted. This means that a particular amino acid residue is substituted with a different amino acid in which the properties of the amino acid side-chain are conserved. Non-limited examples of such the conservative substitution include substitution between hydrophobic amino acids such as alanine, isoleucine, leucine, methionine, phenylalanine, proline, tryptophan, tyrosine and valine, substitution between hydrophilic amino acids such as arginine, aspartic acid, asparagine, cysteine, glutamic acid, glutamine, glycine, histidine, lysine, serine and threonine, substitution between amino acids having an aliphatic side chain such as glycine, alanine, valine, leucine, isoleucine and proline, substitution between amino acids having a hydroxy-containing side chain such as serine, threonine and tyrosine, substitution between amino acids having a sulfur atom-containing side chain such as cysteine and methionine, substitution between amino acids having a carboxylic acid- and amide-containing side chain such as aspartic acid, asparagine, glutamic acid and glutamine, substitution between amino acids having a base-containing side chain such as arginine, lysine and histidine, and substitution between amino acids having an aromatic-containing side chain such as histidine, phenylalanine, tyrosine and tryptophan. The substitutions between amino acids having the same amino acid side-chain properties may retain the biological activity of the polypeptide.

In some embodiments, the polynucleotide may be a variant of a polynucleotide selected from the group consisting of the polynucleotides described herein, which variant has one to 30 nucleotides substituted, deleted, inserted and/or added. The site at which nucleotides are substituted, deleted, inserted and/or added may be any site, as long as the polynucleotide with substituted, deleted, inserted and/or added nucleotides has the function of synthesizing the terpene or sesquiterpene described herein for each of the CoTPS proteins described herein.

Examples of methods for preparing a nucleic acid encoding a protein comprising altered amino acids are well known to those skilled in the art, including site-directed mutagenesis (Kramer and Fritz, 1987). Examples of specific methods for altering nucleotides also include methods using a commercially available kit (e.g. Transformer Site-Directed Mutagenesis Kit: Clonetech; QuickChange Site Directed Mutagenesis Kit: Stratagene) and methods using polymerase chain reaction (PCR). These methods are well known to those skilled in the art. The amino acid sequence of a protein may also be mutated in nature due to the mutation of a nucleotide sequence. A nucleic acid encoding proteins having the amino acid sequence of a natural CoTPS protein (such as the CoTPS2, CoTPS3, CoTPS1 or CoTPS4 protein) wherein one or more amino acids are substituted, deleted, and/or added are also included in the polynucleotide of the present invention, so long as they encode a protein functionally equivalent to a natural CoTPS protein. Also natural CoTPS protein homologs in related ylang ylang plants which show high identities to the sequences of the CoTPS protein are also included in the polynucleotide of the present invention, so long as they encode a protein functionally equivalent to a natural CoTPS protein. Additionally, nucleotide sequence variants that do not give rise to amino acid sequence changes in the protein (degeneracy variants) are also included in the polynucleotide of the present invention.

In a second aspect, the present invention provides a construct or vector comprising an isolated nucleic acid as described herein. In one embodiment, the construct or vector is an expression construct or vector. In another embodiment, the construct or vector further comprises a selectable marker. In a further embodiment, the construct or vector comprises a recombination marker free system. In some embodiments, the recombination marker free system is a Cre-lox recombination marker free system, a Zinc finger marker free system, a TALE nucleases marker free system or a CRISPR-Cas marker free system.

The construct typically includes regulatory regions operatively linked to the 5' side of the nucleic acid described herein (such as a nucleic acid encoding a CoTPS2 protein, a nucleic acid encoding a CoTPS3 protein, a nucleic acid encoding a CoTPS1 protein or a nucleic acid encoding a CoTPS4 protein) and/or to the 3' side of the nucleic acid. A cassette containing all of these elements is also referred to herein as an expression cassette. The expression cassettes may additionally contain 5' leader sequences in the expression cassette construct. The regulatory regions (i.e., promoters, transcriptional regulatory regions, and translational termination regions) and/or the polynucleotide encoding a signal anchor may be native/analogous to the host cell or to each other. Alternatively, the regulatory regions and/or the polynucleotide encoding a signal anchor may be heterologous to the host cell or to each other. See, U.S. Pat. No. 7,205,453 and U.S. Patent Application Publication Nos. 2006/0218670, 2006/0248616 and 20090100536, and the references cited therein. The expression cassettes may additionally contain 5' leader sequences in the expression cassette construct. Such leader sequences can act to enhance translation. Translation leaders are known in the art and include those described in International Publication No. WO 2008/094127 and the references cited therein. In some embodiments, the nucleic acid construct further comprises a plant operable terminator. Plant operable terminators are well known in the art. In one embodiment, the terminator is the native CoTPS terminator.

A number of promoters can be used in the practice of the invention. The promoters can be selected based on the desired outcome. That is, the nucleic acids can be combined with constitutive, tissue-preferred, or other promoters for expression in the host cell of interest. Such constitutive promoters include, for example, the core promoter of the Rsyn7 (WO 99/48338 and U.S. Pat. No. 6,072,050); the core CaMV 35S promoter (Odell et al., 1985); rice actin (McElroy et al., 1990); ubiquitin (Christensen and Quail, 1989; Christensen et al., 1992); pEMU (Last et al., 1991); MAS (Velten et al., 1984); ALS promoter (U.S. Pat. No. 5,659,026), and the like. Other constitutive promoters include, for example, those disclosed in U.S. Pat. Nos. 5,608,149; 5,608,144; 5,604,121; 5,569,597; 5,466,785; 5,399,680; 5,268,463; and 5,608,142.

Other promoters include inducible promoters, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. Other promoters include those that are induced locally at or near the site of pathogen infection. In further embodiments, the promoter may be a wound-inducible promoter. In other embodiments, chemical-regulated promoters can be used to modulate the expression of a gene in a plant through the application of an exogenous chemical regulator. The promoter may be a chemical-inducible promoter, where application of the chemical induces gene expression, or a chemical-repressible promoter, where application of the chemical represses gene expression. In addition, tissue-preferred promoters can be utilized to target enhanced expression of a polynucleotide of interest within a particular plant tissue. Each of these promoters are described in U.S. Pat. Nos. 6,506,962, 6,575,814, 6,972,349 and 7,301,069 and in U.S. Patent Application Publication Nos. 2007/0061917 and 2007/0143880.

Generally, the expression cassette may additionally comprise a selectable marker gene for the selection of transformed cells. Selectable marker genes are utilized for the selection of transformed cells or tissues. Usually, the plant selectable marker gene will encode antibiotic resistance, with suitable genes including at least one set of genes coding for resistance to the antibiotic spectinomycin, the streptomycin phosphotransferase (spt) gene coding for streptomycin resistance, the neomycin phosphotransferase (nptII) gene encoding kanamycin or geneticin resistance, the hygromycin phosphotransferase (hpt or aphiv) gene encoding resistance to hygromycin, acetolactate synthase (als) genes. Alternatively, the plant selectable marker gene will encode herbicide resistance such as resistance to the sulfonylurea-type herbicides, glufosinate, glyphosate, ammonium, bromoxynil, imidazolinones, and 2,4-dichlorophenoxyacetate (2,4-D), including genes coding for resistance to herbicides which act to inhibit the action of glutamine synthase such as phosphinothricin or Basta (e.g., the bar gene). See generally, International Publication No. WO 02/36782, U.S. Pat. No. 7,205,453 and U.S. Patent Application Publication Nos. 2006/0218670, 2006/0248616, 2007/0143880 and 2009/0100536, and the references cited therein. See also, Jefferson et al. (1987); De Wet et al. (1987); Goff et al. (1990); Kain et al. (1995) and Chiu et al. (1996). This list of selectable marker genes is not meant to be limiting. Any selectable marker gene can be used. The selectable marker gene is also under control of a promoter operable in the plant species to be transformed. Such promoters include those described in International Publication No. WO 2008/094127 and the references cited therein.

Alternatively, the expression cassette may additionally comprise a recombination marker free system. In some embodiments, the recombination marker free system is a Cre-lox recombination marker free system, a Zinc finger marker free system, a TALE nucleases marker free system or a CRISPR-Cas marker free system. Such a system is useful for producing selection marker free transgenic oil palm plants or other plants.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g. transitions and transversions may be involved.

In a third aspect, the present invention provides a transgenic plant comprising a nucleic acid, construct or vector described herein. In one embodiment, the transgenic plant may be any plant species. In another embodiment, the transgenic plant may be a member of the *Cananga* genus. In an additional embodiment, the transgenic plant is a *Cananga odorata* plant. In a further embodiment, the transgenic plant may be *Cananga odorata* var. *fruticosa* (dwarf ylang ylang). In some embodiments, the transgenic *Cananga* plant or *Cananga odorata* plant or *Cananga odorata* var. *fruticosa* plant overexpresses a CoTPS protein compared to a non-transgenic plant. In these embodiments, a nucleic acid, nucleic acid construct or expression vector as described above is introduced into a plant cell by conventional techniques such as those described below or those well known to the skilled artisan to produce transgenic plants that overexpress a CoTPS protein.

In other embodiments, the transgenic plant expresses a lower amount of a CoTPS protein compared to a non-transgenic plant, i.e., the expression of a CoTPS gene is down regulated. A reduced expression level of a CoTPS protein be brought about by using well known techniques, including, but not limited to, RNAi techniques, such as dsRNA, miRNA, siRNA, smRNA, hpRNA or ihpRNA (collectively referred to as RNAi molecules), sense suppression (co-suppression), antisense, and the like. Such techniques are described in U.S. Pat. No. 7,312,323 and references cited therein. For example, reduction might be accomplished, for example, with transformation of a plant cell to comprise a promoter and other 5' and/or 3' regulatory regions described herein linked to an antisense nucleotide sequence, hairpin, RNA interfering molecule, double stranded RNA, microRNA or other nucleic acid molecule, such that tissue-preferred expression of the molecule interferes with translation of the mRNA of the native DNA sequence or otherwise inhibits expression of the native DNA sequence in plant cells. For further description of RNAi techniques or microRNA techniques, see, e.g., U.S. Pat. Nos. 5,034,323; 6,326,527; 6,452,067; 6,573,099; 6,753,139; and 6,777,588. See also International Publication Nos. WO 97/01952, WO 98/36083, WO 98/53083, WO 99/32619 and WO 01/75164; and U.S. Patent Application Publication Nos. 2003/0175965, 2003/0175783, 2003/0180945, 2004/0214330, 2005/0244858, 2005/0277610, 2006/0130176, 2007/0265220, 2008/0313773, 2009/0094711, 2009/0215860, 2009/0308041, 2010/0058498 and 2011/0091975. RNAi molecules or microRNA molecules (referred to collectively herein as RNAi molecules) can be prepared by the skilled artisan using techniques well known in the art, including techniques for the selection and testing of RNAi molecules and microRNA molecules that are useful for down regulating a CoTPS genes. See, for example, Wesley et al. (2001), Mysara et al. (2011) and Yan et al. (2012).

It has typically been found that dsRNA of 200-700 bp are particularly suited for inducing RNAi in plants. It has also been found that hairpin RNAs containing an intron, for example, a construct comprising an RNA encoding sequence in a sense direction operably linked to an intron operably linked to an RNA encoding sequence in an antisense direction or vice versa which is capable of forming an intron-hairpin RNA (ihpRNA), is suitable for inducing RNAi in plants. See, for example, Wang et al. (2000), Fuentes et al. (2006), Bonfim et al. (2007) Vanderschuren et al. (2007a, 2007b), Zrachya et al. (2007). For example, a nucleic acid construct can be prepared that includes a nucleic acid that is transcribed into an RNA that can anneal to itself, e.g., a double stranded RNA having a stem-loop structure. In addition, hairpin structures can be prepared as described by Guo et al. (2003).

For example, a nucleic acid construct can be prepared that includes a nucleic that is transcribed into an RNA that can anneal to itself, e.g., a double stranded RNA having a stem-loop structure. In some embodiments, one strand of the stem portion of a double stranded RNA comprises a sequence that is similar or identical to the sense coding sequence, or a fragment thereof, of a CoTPS as described herein, and that is from about 10 nucleotides to about 1,800 nucleotides in length. The length of the sequence that is similar or identical to the sense coding sequence can be from 10 nucleotides to 1000 nucleotides, from 15 nucleotides to 600 nucleotides, from 20 nucleotides to 500 nucleotides, or from 25 nucleotides to 100 nucleotides, or any length within the 10 nucleotides to 2,500 nucleotides. The other strand of the stem portion of a double stranded RNA comprises a sequence that is similar or identical to the antisense strand, or a fragment thereof, of the coding sequence of the polypeptide of interest, and can have a length that is shorter, the same as, or longer than the corresponding length of the sense sequence. In some cases, one strand of the stem portion of a double stranded RNA comprises a sequence that is similar or identical to the 3' or 5' untranslated region, or a fragment thereof, of the mRNA encoding the CoTPS, and the other strand of the stem portion of the double stranded RNA comprises a sequence that is similar or identical to the sequence that is complementary to the 3' or 5' untranslated region, respectively, or a fragment thereof, of the mRNA encoding the CoTPS. In other embodiments, one strand of the stem portion of a double stranded RNA comprises a sequence that is similar or identical to the sequence of an intron or a fragment thereof in the pre-mRNA encoding the CoTPS, and the other strand of the stem portion comprises a sequence that is similar or identical to the sequence that is complementary to the sequence of the intron or fragment thereof in the pre-mRNA.

The loop portion of a double stranded RNA can be from 3 nucleotides to 5,000 nucleotides, e.g., from 3 nucleotides to 2500 nucleotides, from 15 nucleotides to 1,000 nucleotides, from 20 nucleotides to 500 nucleotides, or from 25 nucleotides to 200 nucleotides, or any length within the 3 nucleotides to 5,000 nucleotides. The loop portion of the RNA can include an intron or a fragment thereof. A double stranded RNA can have zero, one, two, three, four, five, six, seven, eight, nine, ten, or more stem-loop structures.

Once a nucleic acid has been cloned into an expression vector, it may be introduced into a plant cell using conventional transformation procedures. Similarly, once a nucleic acid construct has been prepared that contains or encodes a molecule which suppresses or inhibits the expression of a CoTPS gene, the nucleic acid may be introduced into a plant cell using conventional transformation procedures. The term "plant cell" is intended to encompass any cell derived from a plant including undifferentiated tissues such as callus and suspension cultures, as well as plant seeds, pollen or plant embryos. Plant tissues suitable for transformation include leaf tissues, root tissues, meristems, protoplasts, hypocotyls, cotyledons, scutellum, shoot apex, root, immature embryo, pollen, and anther. "Transformation" means the directed modification of the genome of a cell by the external application of recombinant DNA from another cell of different genotype, leading to its uptake and integration into the subject cell's genome. In this manner, genetically modified plants, plant cells, plant tissue, seed, and the like can be obtained.

DNA constructs containing the nucleic acids of the present invention encoding the CoTPS proteins can be used to transform any monocot or dicot plant and particularly ylang ylang varieties. The constructs may be introduced into the genome of the desired plant host by a variety of conventional techniques. Techniques for transforming a wide variety of higher plant species are well known and described in the technical and scientific literature. Transformation protocols may vary depending on the type of plant or plant cell, i.e., monocot or dicot, targeted for transformation, as is well known to the skilled artisan. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. Thus, any method, which provides for effective transformation/transfection may be employed. See, for example, U.S. Pat. Nos. 7,241,937, 7,273,966 and 7,291,765 and U.S. Patent Application Publication Nos. 2007/0231905 and 2008/0010704 and references cited therein. See also, International Published Application Nos. WO 2005/103271 and WO 2008/094127 and references cited therein.

Transformed plant cells which are derived by any of the above transformation techniques can be cultured to regenerate a whole plant which possesses the transformed genotype and thus the desired phenotype, e.g., a transgenic plant. A "transgenic plant" is a plant into which foreign DNA has been introduced. A "transgenic plant" encompasses all descendants, hybrids, and crosses thereof, whether reproduced sexually or asexually, and which continue to harbor the foreign DNA. Regeneration techniques rely on manipulation of certain phytohormones in a tissue culture growth medium, typically relying on a biocide and/or herbicide marker which has been introduced together with the desired nucleotide sequences. See for example, International Published Application No. WO 2008/094127 and references cited therein.

The foregoing methods for transformation are typically used for producing a transgenic variety in which the expression cassette is stably incorporated. After the expression cassette is stably incorporated in transgenic plants, it can be transferred to other plants by sexual crossing. In one embodiment, the transgenic variety could then be crossed, with another (non-transformed or transformed) variety, in order to produce a new transgenic variety. Alternatively, a genetic trait which has been engineered into a particular ylang ylang line using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties which do not contain that gene. As used herein, "crossing" can refer to a simple X by Y cross, or the process of backcrossing, depending on the context. Any of a number of standard breeding techniques can be used, depending upon the species to be crossed.

Once transgenic plants of this type are produced, the plants themselves can be cultivated in accordance with conventional procedures. Transgenic seeds can, of course, be recovered from the transgenic plants. These seeds can then be planted in the soil and cultivated using conventional procedures to produce transgenic plants. The cultivated transgenic plants will express the DNA of interest in a tissue-preferred or tissue-specific manner as described herein.

In a fourth aspect, the present invention provides a method for manipulating synthesis of a terpene or sesquiterpene in a transgenic plant to alter fragrance/flavor characteristics and/or plant pathogen interactions and/or insect interactions. In one embodiment, the transgenic plant may be any plant species. In another embodiment, the transgenic plant may be a *Cananga odorata* plant. In a further embodiment, the transgenic plant may be *Cananga odorata* var. *fruticosa* (dwarf ylang ylang). In one embodiment, the synthesis of the sesquiterpenes β-ylangene, β-copaene and β-cubebene is manipulated by overexpressing the CoTPS2 protein in the transgenic plant compared to a non-transgenic plant. In another embodiment, the synthesis of the sesquiterpene α-bergamotene is manipulated by overexpressing the CoTPS3 protein in the transgenic plant compared to a non-transgenic plant. In an additional embodiment, the synthesis of multiproduct β-thujene/sabinene/β-pinene/α-terpinene is manipulated by overexpressing the CoTPS I protein in the transgenic plant compared to a non-transgenic plant. In a further embodiment, the synthesis of the terpene geraniol is manipulated by overexpressing the CoTPS4 protein in the transgenic plant compared to a non-transgenic plant. In some embodiments, the synthesis of the described terpenes or sesquiterpenes is manipulated by reducing expression of the corresponding CoTPS protein in the transgenic plant compared to a non-transgenic plant.

In one embodiment, an expression vector described herein is introduced into plant cells to obtain a transgenic plant, in which the synthesis of the terpene (β-thujene/sabinene/β-pinene/α-terpinene or geraniol) or sesquiterpene (α-bergamotene or β-ylangene/β-copaene/β-cubebene) is manipulated. Even a transgenic plant is not necessary to be obtained. Depending on the host plant, the nucleic acids of the present invention may be introduced into plant cells such that the nucleic acid encoding a flowering protein described herein can be expressed in the plant cells.

In another embodiment, a nucleotide sequence is integrated into the genomic DNA of a plant to enhance the expression of the endogenous CoTPS gene. Preferably, examples of such a nucleotide sequence include an expression control sequence. More specifically, examples of such an expression control sequence include promoter sequences and enhancer sequences. Such an expression control sequence is operably integrated into the genomic DNA of a plant to enhance the expression of the endogenous CoTPS gene in the plant. As described herein, enhanced expression of CoTPS2 gene in the plant will enhance synthesis of β-ylangene, β-copaene and β-cubebene in the plant. Similarly, enhanced expression of CoTPS3 gene in the plant will enhance synthesis of α-bergamotene in the plant. Similarly, enhanced expression of CoTPS1 gene in the plant will enhance synthesis of β-thujene/sabinene/β-pinene/α-terpinene in the plant. Similarly, enhanced expression of CoTPS4 gene in the plant will enhance synthesis of geraniol in the plant.

In a fifth aspect, the present invention provides a method of preparing at least one terpene or sesquiterpene comprising the steps of (a) culturing a cell which has been genetically modified with a polynucleotide of the invention to provide CoTPS activity and (b) separating the at least one terpene or sesquiterpene produced. In one embodiment, the cells may be any cell type that can be grown in culture. In another embodiment, the cells may be bacteria or yeast cells for producing the terpene or sesquiterpene. In one embodiment, the at least one sesquiterpene is β-ylangene, β-copaene and/or β-cubebene and the CoTPS activity is CoTPS2 activity. In another embodiment, the at least one sesquiterpene is α-bergamotene and the CoTPS activity is CoTPS3 activity. In an additional embodiment, the at least one terpene is β-thujene/sabinene/β-pinene/α-terpinene and the CoTPS activity is CoTPS1 activity. In a further embodiment, the at least one terpene is geraniol and the CoTPS activity is CoTPS4 activity. In one embodiment, the cell contains a metabolic pathway for producing farnesyl pyrophosphate which provides the farnesyl pyrophosphate that is the substrate for CoTPS2 or CoTPS3. In another embodiment, the cell has been transformed with a nucleic acid encoding farnesyl pyrophosphate synthase to produce farnesyl pyrophosphate which provides the farnesyl pyrophosphate that is the substrate for CoTPS2 or CoTPS3. In one embodiment, the cell contains a metabolic pathway for producing geranyl diphosphate which provides the geranyl diphosphate that is the substrate for CoTPS1 or CoTPS4. In another embodiment, the cell has been transformed with a nucleic acid encoding geranyl diphosphate synthase to produce geranyl diphosphate which provides the geranyl diphosphate that is the substrate for CoTPS1 or CoTPS4. Techniques for synthesizing terpenes and/or sesquiterpenes in cell culture are described in, for example U.S. Pat. Nos. 7,453,024 and 8,062,878, U.S. Patent Application Publication Nos. 2012/0107893 and 2013/0302861 and International Published Application No. WO 2011/074954.

In this aspect of the invention, the nucleic acid construct contains a promoter that is operably in the host cell and that is operatively linked to the CoTPS2 encoding nucleic acid described herein. Examples of suitable yeast promoters include, but not limited to, cupper inducible promoter CUP1 ($P_{CUP1}$) as well as promoters for pyruvate decarboxylase (PDC1), phosphoglycerate kinase (PGK), xylose reductase (XR), xylitol dehydrogenase (XDH), L-(+)-lactate-cytochrome c oxidoreductase (CYB2), translation elongation factor-1 (TEF1) and translation elongation factor-2 (TEF2) genes. Additional yeast promoters include the GAP promoter, GAL1 promoter, AOX1 promoter, FLD1 promoter, ADH1 promoter, GAL3 promoter, GAL4 promoter, GALT promoter, CTR1 promoter, CTR3 promoter, MET3 promoter and TDH1 promoter. The nucleic acid construct may also contain a terminator. Examples of yeast terminators include, but not limited to, terminators for ADH1, TDH1, pyruvate decarboxylase (PDC1), xylose reductase, (XR), xylitol dehydrogenase (XDH), L-lactate:ferricytochrome c oxidoreductase (CYB2) or iso-2-cytochrome c (CYC) genes (e.g., terminator of CYC1 ($T_{CYC1}$)), or a terminator from the galactose family of genes in yeast, particularly the GAL10 terminator and GAL80 terminator.

Various methods can be used to introduce the expression vector of some embodiments of the invention into bacterial or yeast cells. Such methods are generally described in Sambrook et al., Molecular Cloning: A Laboratory Manual, Cold Springs Harbor Laboratory, New York (1982, 1989, 2001, 2012), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et al. (Biotechniques 4 (6): 504-512, 1986) and include, for example, stable or transient transfection, lipofection, electroporation and infection with recombinant viral vectors. In addition, see U.S. Pat. Nos. 5,464,764 and 5,487,992 for positive-negative selection methods.

The method further comprises providing and/or maintaining conditions suitable for sesquiterpene production within the yeast cell, e.g. cultivating the yeast under conditions conducive to the production of the sesquiterpenes, prior to isolating the sesquiterpenes. These conditions are known to the skilled person. Generally, they may be adjusted by selection of an adequate medium, temperature, and pH.

The sesquiterpenes may be isolated from the culture medium or the yeast cells by any method used in the art including, but not limited to, chromatography, extraction, in-situ product removal and distillation.

It will also be appreciated that transformation of other non-plant hosts is feasible, including well known prokaryotic and eukaryotic cells, such as bacteria (e.g. *E. coli, Agrobacterium, Lactobacillus*), fungi, yeast, insect cells and animal cells. Such transformation enables production of recombinant polypeptides of the invention. Cell free systems (e.g. Roche Rapid Translation System) for production of recombinant proteins can also be used (Zubay Annu Rev Genet 7, 267-287 (1973)). The polypeptides of the invention produced in any such hosts may be isolated and purified from same using well known techniques. The polypeptides may be used in cell-free systems for synthesis of sesquiterpenes for flavoring or scent uses, or for use in pheromone or antimicrobial agents. Such compounds could be β-ylangene, β-copaene or β-cubebene.

The pleasant fragrance of ylang ylang varieties (*Cananga odorata*) are mainly due to volatile organic compounds (VOCs) produced by the flowers. Floral scents are a key factor in plant-insect interactions and are vital for successful pollination. *C. odorata* var. *fruticosa* or dwarf ylang ylang is a variety of ylang ylang which is popularly grown in Southeast Asia as a small and compact shrub with aromatic flowers. The following Examples describe the combined use of bioinformatics and chemical analysis to discover the VOC biosynthesis pathways and related genes. The scented flowers of *C. odorata* var. *fruticosa* were analysed by GC-MS and a total of 49 volatile organic compounds were identified at four different stages of flower development. The bulk of these VOCs were terpenes—mainly sesquiterpenes. The various terpene synthases (TPSs) involved in the production of these essential oils was identified using RNA-seq on mature flowers. From the RNA-seq data, 4 full-length TPSs were functionally characterized. In vitro assays showed that recombinant proteins from two TPSs, CoTPS1 and CoTPS4 synthesized β-thujene/sabinene/β-pinene/α-terpinene and geraniol from geranyl diphosphate, respectively. Accordingly, they were classified as mono-TPSs. The other two TPSs were identified as sesqui-TPSs. CoTPS3 catalysed the conversion of farnesyl diphosphate to α-bergamotene, whereas CoTPS2 was found to be a multifunctional and novel TPS which could catalyse the synthesis of three sesquiterpene compounds, β-ylangene/β-copaene/β-cubebene. Additionally, in vitro results of the two sesqui-TPSs were confirmed in planta by transient expression of these TPSs in *N. benthamiana* leaves by *Agrobacterium*-mediated infiltration.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, Molecular Cloning (Cold Spring Harbor Laboratory Press, Cold Spring Harbor, N.Y.); Sambrook et al., 1989, Molecular Cloning, 2nd Ed. (Cold Spring Harbor Laboratory Press, Cold Spring Harbor, N.Y.); Sambrook and Russell, 2001, Molecular Cloning, 3rd Ed. (Cold Spring Harbor Laboratory Press, Cold Spring Harbor, N.Y.); Green and Sambrook, 2012, Molecular Cloning, 4th Ed. (Cold Spring Harbor Laboratory Press, Cold Spring Harbor, N.Y.); Ausubel et al., 1992), *Current Protocols in Molecular Biology* (John Wiley & Sons, including periodic updates); Glover, 1985, DNA Cloning (IRL Press, Oxford); Russell, 1984, *Molecular biology of plants: a laboratory course manual* (Cold Spring Harbor Laboratory Press, Cold Spring Harbor, N.Y.); Anand, *Techniques for the Analysis of Complex Genomes*, (Academic Press, New York, 1992); Guthrie and Fink, *Guide to Yeast Genetics and Molecular Biology* (Academic Press, New York, 1991); Harlow and Lane, 1988, *Antibodies*, (Cold Spring Harbor Laboratory Press, Cold Spring Harbor, N.Y.); *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, Blackwell Scientific Publications, Oxford, 1988; Fire et al., *RNA Interference Technology: From Basic Science to Drug Development*, Cambridge University Press, Cambridge, 2005; Schepers, *RNA Interference in Practice*, Wiley-VCH, 2005; Engelke, *RNA Interference (RNAi): The Nuts & Bolts of siRNA*

*Technology*, DNA Press, 2003; Gott, *RNA Interference, Editing, and Modification: Methods and Protocols (Methods in Molecular Biology)*, Human Press, Totowa, N.J., 2004; Sohail, *Gene Silencing by RNA Interference: Technology and Application*, C R C, 2004.

EXAMPLES

The present invention is described by reference to the following Examples, which are offered by way of illustration and are not intended to limit the invention in any manner. Standard techniques well known in the art or the techniques specifically described below were utilized

Example 1

Materials and Methods

Plant Materials:

*Cananga odorata* var. *fruticosa* (known as dwarf ylang ylang) was grown in Singapore were collected in November for RNA-seq. Four different stages of flowers and leaves of of dwarf ylang ylang were obtained in April for further experiments. The four different stages of flowers are as follows: (B) bud stage; completely closed petal, green; (I) initial-flowering stage: semi-open small and short petals, green, 9 days after bud stage; (II) full-flowering stage: completely open large and long petals, yellowish green, 20 days after bud stage; (III) end-flowering stage: fully matured petals, yellow, 30 days after bud stage.

Four-week old *Nicotiana benthamiana* plants grown in a greenhouse were used for in vivo characterization and subcellular localization of CoTPSs.

Essential Oils Extraction from Ylang Ylang Flowers:

Flowers and leaves from ylang ylang were frozen in liquid nitrogen and ground to a powder by pre-chilled mortar and pestle. About 500 mg of powder was dissolved in 500 µl ethyl acetate (Fisher Scientific) including 1 µl (10 mg/ml) of camphor (Sigma-Aldrich) as internal standard. The slush was vortexed and incubated on a horizontal shaker at 50 rpm for 2 hr. After centrifugation of the mixture at 13,000 g for 10 min, the resulting ethyl acetate upper layer extract was transferred into a new Eppendorf tube and mixed with 300 mg anhydrous $Na_2SO_4$ (Sigma-Aldrich) to remove water. Following the second centrifugation, the extract was transferred into a 2 ml glass vial for gas chromatography-mass spectrometry (GC-MS) analysis (Agilent Technologies).

RNA Isolation for RNA Sequencing:

Frozen ylang ylang flowers were homogenized using pre-chilled mortar and pestle into a fine powder, and total RNA was isolated using the TRIzol method (Invitrogen). Purified RNA samples were first treated with RNase-free DNase1 (Roche) to remove genomic DNA and then extracted by chloroform. The RNA quantity was determined with Nanodrop spectrophotometer, ND-1000 (Thermo Fisher Scientific). The RNA integrity number (RIN) was evaluated using Agilent 2100 bioanalyzer and RNA 6000 Nano Labchip Kit (Agilent Technologies). RNA with a RN value of 7<x<10 was sent for RNA-seq to the Rockefeller University Genomics Resource Center (New York, USA). RNA-seq and assembly were described in Jin et al (2014).

Quantitative Real Time PCR (qRT-PCR):

Quantitative RT-PCR was performed to investigate gene expression pattern during ylang ylang flower development. One µg of total RNA was used for first-strand cDNA synthesis with M-MLV reverse transcriptase (RT) (Promega). The qRT-PCR reactions were performed using Applied Biosystems (AB) 7900HT fast real-time PCR system and AB power SYBR green PCR master mix (Life technologies). Oligonucleotide primers for qRT-PCR were designed for selected genes of MEP, MVA, shikimate, benzyl and phenyl propanoid pathways using the Primer3 (http colon slash slash bioinfo dot ut dot ee slash primer3-0.4.0 slash) and listed in Table 1. Each PCR product obtained from regular PCR was cloned into pGEM-T easy vector (Promega) and then verified by sequencing. Specificity of the amplified PCR product was assessed by a melting curve analysis. All experiments were carried out in technical triplicates and with biological duplicates. Non-template control was included for each gene to exclude random/reagent contamination and primer-dimer formation. A mock reaction containing all the RT-PCR reagents except the reverse transcriptase was used as a negative control. Actin gene was used as an internal normalization in each qRT-PCR.

TABLE 1

Oligonucleotide Primers

| Name | Forward (SEQ ID NO:) | Reverse (SEQ ID NO:) |
|---|---|---|
| For qRT-PCR | | |
| DXS1 | TTTGATTGGGGGTGAGAGAG (13) | GCCATCAAGGGACATGAACT (14) |
| DXS2 | GGGGATCACAAAATCCATTG (15) | TGGGTAGCCTTTTCCCTTTT (16) |
| DXS3 | CTTCTGCAAGCCCCTAGATG (17) | GTTGCAGCAATGTGCCTAGA (18) |
| DXS4 | AAGGGGAGAATCCTTGCAGT (19) | TGTTCTTGGCAAAGCTTCCT (20) |
| DXR | GTTCTGAGTGCAGCCAATGA (21) | CAAGAACAGGTCGCAGATCA (22) |
| CMS | AGGAGCGTGTCAGTGGTTCT (23) | TGGCAAATTTCAGGTCAACA (24) |
| CMK | TCGGTTCTGATTGTCCCTTC (25) | CGAAGGCGCTTGTAAACTTC (26) |
| MCS | ACGCAAGCAAAAACTCTCGT (27) | CGGTAGCGTTATCAGCATCA (28) |
| HDS | GTGGCTCCATTTGAGGAAAA (29) | AATCCACAGTGGCAAGATCC (30) |
| IDI1 | ACTGTACAAGGCCCCATCTG (31) | CCCACCATTTCAGAAGGAAA (32) |
| ID12 | CATGAGTTGCTCCTTCAGCA (33) | AAGCTTCCTTTGTGCAGCAT (34) |
| AACT | TGCAGTGAAGTCTGCTGGTC (35) | CAACAGAGTTGCCACACAGC (36) |
| HMGS | CAAGACTTGGCTGATGCAAA (37) | AACAACAAGCCCAAATCGTC (38) |
| HMGR | CAGGCTGATTTCCCTGACAT (39) | CTGGCATGTGCATTGTATCC (40) |
| MVK | GGTGTTTCGGAGAGAGCTTG (41) | ACCCCCATGCACTGAAGTAG (42) |
| PMK | TGCTCCTCGATGCTACAATG (43) | AGGGTCTTCTCTGACCAGCA (44) |
| MPDC | CCCATCAATGACAGCATCAG (45) | CGTATTCGGATCTCCCTCAA (46) |
| DAHPS | ATCCTCCATCTTCCCTGCTT (47) | TTCTTGGATTTCCAGCCATC (48) |
| DHQS | CCTTTCCTTCCGCTTTCTCT (49) | TTCCATGAACATGCCTTTGA (50) |
| SDH | TGATCAGCTAGAGCGCAGAA (51) | CCATCTGTTCGACGGATTTT (52) |

TABLE 1-continued

Oligonucleotide Primers

| Name | Forward (SEQ ID NO:) | Reverse (SEQ ID NO:) |
|---|---|---|
| SK | CACCGTTCCGAAGATTTGTT (53) | CCAGACCCCATCATACCAAC (54) |
| CS | GCTGCTGGAAGTTCTTTTGG (55) | TCTGTCCTGGCCTCCTTCTA (56) |
| PAL | AATCTCTCAGGGGGAAGGAA (57) | CAACCCCAGCGAGTTTACAT (58) |
| SAMT | TTAACGGCAGGAAGAGCCTA (59) | ATCACGGCCTTCATTTCTTG (60) |
| CHS | TTCTGTTCCTCAAGCGGAGT (61) | CGGAAGTAGCCCACATTCAT (62) |
| CHI | CATGAGCATGGTCAGGAAGA (63) | GCACAGCAACTCACTTTCCA (64) |
| F3H | TATCTCTGGTGGGGATCGAC (65) | CTGCTTCTCCCTGAAGATGG (66) |
| DFR | GCAATGGTGATTGGTCCTCT (67) | GAAGCGGAATTGATGGGTAA (68) |
| C4H | ACCCACAAGCTTCCCTACCT (69) | AGGTACCAGGCATTCACCAG (70) |
| 4CL | GTTGCACCTGCAGAACTTGA (71) | ACCTTCCGCAGTCTCTTGAA (72) |
| CCR | GGAGCGATCTGGACTACTGC (73) | GAACATCGACGTAGGCCTGT (74) |
| CVOMT | GCATGCTCACTCATTCTGGA (75) | CCCAAAGACTTTTTCCGTGA (76) |
| C3H | ACGCTCCAGGAGAAGTACGA (77) | CACACGGTCCAATTCCTCTT (78) |
| COMT | ACTCTCCAGTGCCTGTGCTT (79) | AGCTGCCCGTTGTCTAGTGT (80) |
| CCOMT | TTGGATACCAGCGTCTACCC (81) | CTCACGGTTGATGTCCATTG (82) |
| CAD | AAAGTGGGAACAACGAATGC (83) | ACCGACCTCTTTGACCACAC (84) |
| TPS1 | AGGGCCTTCCAGATTACATGAAGC (85) | AGCGTTGGAGTGTACTTGCTATTG (86) |
| TPS2 | CATCGATCATGGATGACACATATGATG (87) | CTCAACAGCAGTCAGAAGGGCAC (88) |
| TPS3 | AGGCTGTGGCTGAACCTCTA (89) | AGCAGATCCTTCTTGCTGGA (90) |
| TPS4 | TAGCCATCTTACTGGTGATTGACG (91) | GTAGTGTTGTACAATGCCATGTAAC (92) |
| actin | CTGGACGTGACCTCACAGATGCT (93) | TCTTCTCAACAGAGGAGCTGCTCT (94) |

For TOPO Cloning

| TPS1 | CACCATGGCCTTGAATACGTTCTTGCATTTTCC (95) | CTCAAGCACGATGGGTTCAACGGTAAGTGA (96) |
| TPS2 | CACCATGGCACTTATATTTGCAAATGGCCACTCTGA (97) | ATCAACAAAACGGTCCACTAGCACCATCGCA (98) |
| TPS3 | CACCATGAATCCTGTTTCTCTTTTGAGCTTATCAGGAG (99) | AACTTGTTGGGAAAATAGAGCCATGGCTTGA (100) |
| TPS4 | CACCATGGCTGCTACGAGAAACCTTTCTTTACTT (101) | ATTGAAAGGCGTGAAAAACAAAGCTTGCA (102) |

For E. coli expression vectors

| TPS1 | aaGGATCCgATGGCCITGAATACGTTCTTGCATTTTC (103) | aaGCGGCCGCTTACTCAAGCACGATGGGTTCAAC (104) |
| TPS2 | aacGTCGACATGGCACTTATATTTGCAAATGGCCACTCTGA (105) | aaaGCGGCCGCTTAATCAACAAAACGGTCCACTAGCA (106) |
| TPS3 | aacGGATCCgATGAATCCTGTTTCTCTTTTGAGCTTATCAGGAG (107) | aacGTCGACAACTTGTTGGGAAAATAGAGCCATGGCT (108) |
| TPS4 | aaaGGATCCtATGGCTGCTACGAGAAACCTTTCTTTACTT (109) | aaaGTCGACATTGAAAGGCGTGAAAAACAAAGCTTGCA (110) |

GGATCC, Bam HI; GCGGCCGC, Not I; GTCGAC, Sal I

Sequence Identification, Multiple Sequence Alignments and Phylogenetic Analysis:

DNA sequences were edited and assembled using DNAS-TAR Lasergene 8 (DNASTAR, Inc.). The phylogenetic analysis of CoTPSs was performed using the maximum likelihood method in MEGA version 6 program (Tamura et al., 2011).

Isolation of Full-Length cDNA of CoTPS and Vector Construction for Agrobacterium-Mediated Gene Expression:

Full-length open reading frames (ORFs) of CoTPSs were amplified by PCR from dwarf ylang ylang flowers-derived cDNA with the primer sets listed in Table 1. Purified PCR products were cloned into pENTR/D-TOPO (Invitrogen). For YFP-fusion construct, the pTOPO clone harbouring each CoTPS gene was integrated into the destination vector, pBA-DC-YFP expression vector (Zhang et al., 2005), which contains the CaMV 35S promoter and C-terminal in frame YFP, to create CoTPS-YFP by LR Clonase (Invitrogen). All constructs were verified by DNA sequencing. The final plasmid was then transformed into GV3101 Agrobacterium tumefaciens by electroporation system (Bio-Rad), plated on LB plate containing spectinomycin (100 µg/ml) and gentamycin (20 µg/ml), and incubated at 28° C. for 2 days.

Subcellular Localization of CoTPSs:

To determine the subcellular localization of CoTPSs, Agrobacterium-mediated transient gene expression was performed using leaves of 4 week old N. benthamiana plant as described (Jin et al., 2014). Infiltrated N. benthamiana leaves expressing YFP-fused protein were excised, mounted onto slides, and imaged by a confocal laser scanning microscopy (Carl Zeiss LSM5 Exciter) with a standard filter set. Images were processed with LSM Image Browser (Carl Zeiss).

Preparation of Recombinant Proteins:

To construct the vectors for the recombinant N-terminal poly-histidine (His)-tagged proteins, the full-length cDNAs of CoTPS was amplified by PCR with the primers designed restriction enzymes sites to the ends (Table 1). The PCR-amplified product and pET28b plasmid (Novagen) were separately digested with the corresponding restriction enzymes (New England Biolabs) and purified with Qiagen PCR purification kit (Qiagen). Then, the digested PCR product was cloned into pET28b expression vector using Rapid DNA ligation kit (Roche). The final construct was transformed into E. coli BL21(DE3)pLysS (invitrogen) and recombinant proteins purified from E. coli extracts after isopropyl β-D-1-thiogalactopyranoside induction as described (Jang et al., 2005).

In Vitro TPS Assay:

In vitro enzyme assay for TPS activity was performed in a final volume of 500 µl of reaction buffer (25 mM HEPES pH 7.4, 100 mM KCl, 7.5 mM MgCl2, 5% (v/v) glycerol, 5 mM DTT), with about 20 µg of recombinant protein, and 10 µg of either farnesyl pyrophosphate (FPP) or geranyl pyrophosphate (GPP) (Sigma-Aldrich). The reaction mixtures were gently mixed and carefully overlaid with 250 µl hexane (Sigma-Aldrich) to trap volatile products. The tube was then sealed with parafilm and incubated at 30° C. for 2 hr, followed by 1 min vortex. After centrifugation at 1,200 g, 4°

C. for 30 min, the hexane upper layer was transferred into a 2 ml glass vial for GC-MS analysis (see below GC-MS analysis). As a negative control, heat-inactivated recombinant protein was added to the enzyme assay.

In Vivo Characterization of CoTPSs:

For in vivo TPS activity assay, *Agrobacterium* strain harbouring CoTPS construct was infiltrated with or without the strain carrying *Arabidopsis* HMGR (3-hydroxy-3-methylglutaryl-CoA reductase; AtHMGR) under the control of the CaMV 35S promoter into the underside of *N. benthamiana* leaves (Jin et al., 2014). All experiments were carried out with the viral-encoded protein P19 to improve transgene expression by suppressing post-transcriptional gene silencing (Voinnet et al, 2003). After infiltration, tobacco plants were maintained in a growth chamber at 25° C., under long day condition (16 hr light/8 hr dark) for 3 days. Four to five infiltrated leaves were frozen immediately in liquid nitrogen and then homogenized with a pre-chilled mortar and pestle. Up to 400-600 mg of leaf powder were obtained from 4-5 leaves. Subsequent sample processing for GC-MS analysis was performed as described above (See *Essential oils extraction from ylang ylang flowers*). A CaMV 35S::AtHMGR construct served as a negative control.

GC-MS Analysis:

GC-MS analysis was performed on Agilent 7890A GC (Agilent Technologies) system and an Agilent-Technologies 5975C inert XL Mass selective detector, equipped with a HP-5MS UI column (30 m×0.25 mm×0.25 µm; Agilent Technologies). Conditions were as follows: 5 µl sample injection, splitless injection, oven program 50° C. (1 min hold) at 8° C. min-1 to 300° C. (5 min hold). For data processing, MSD ChemStation Data Analysis (Agilent Technologies) was used. The essential oil components were identified by comparison of their mass spectra with those in NIST 2011 library data of GC-MS system and comparison of their retention indices (RI). The retention indices (RI) were determined on the basis of n-alkanes (C8-C40) mix standard (Sigma-Aldrich) under the same operation conditions. Camphor was added to serve as an internal standard. The amount of each compound was calculated by measuring its peak area related to that of a known amount of camphor. The identified components along with their RI and relative % values are listed in Table 2.

Example 2

Figure 1B:
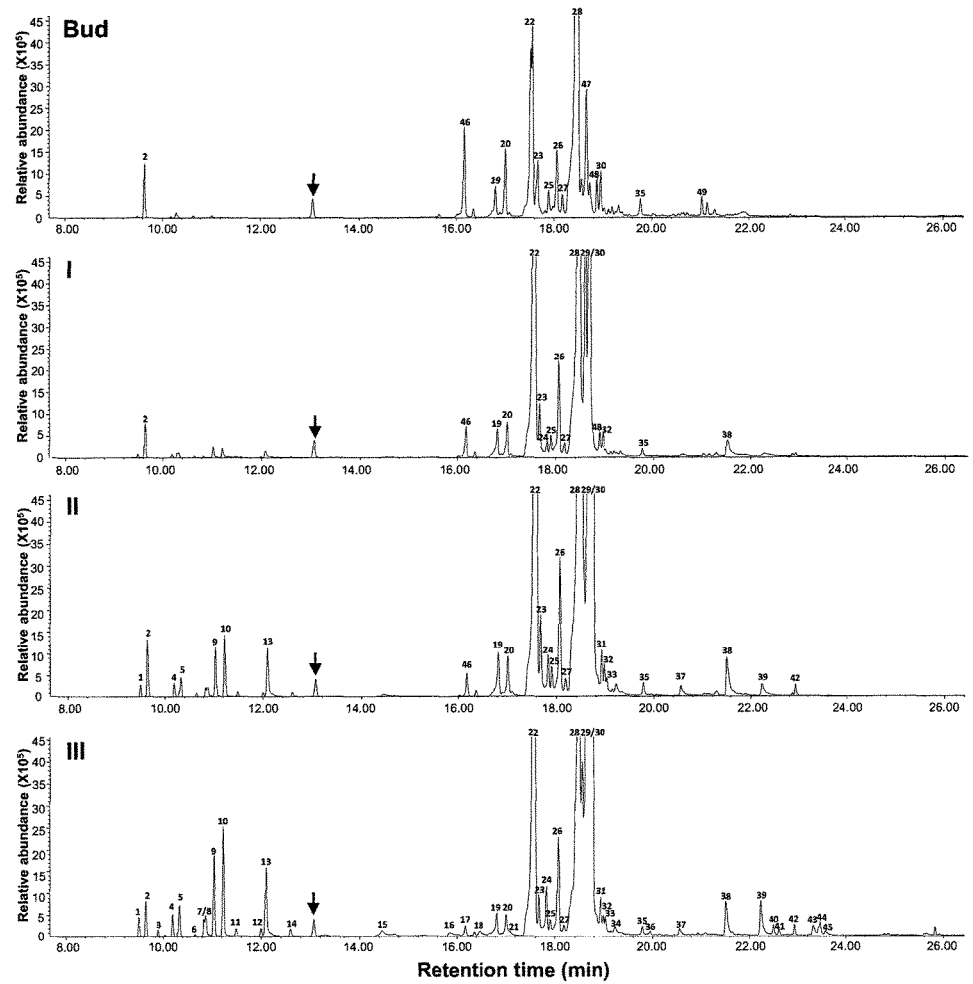
Figure 9:
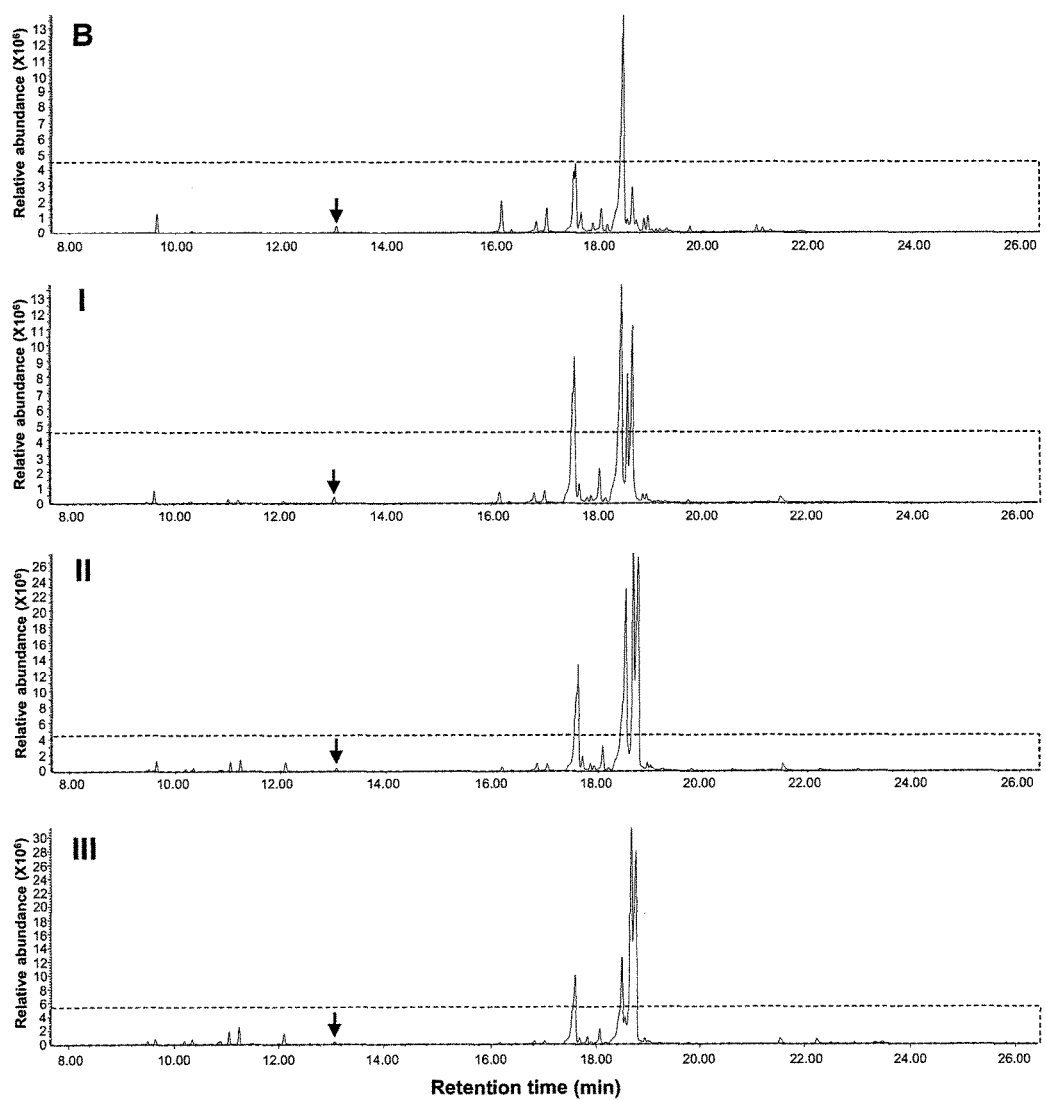
FIG. 9 shows the compositional variation of dwarf ylang ylang essential oils during flower development. B, floral buds; I, undeveloped small flowers; II, mature green flowers; III, fully mature yellow flowers.
Figure 10A:
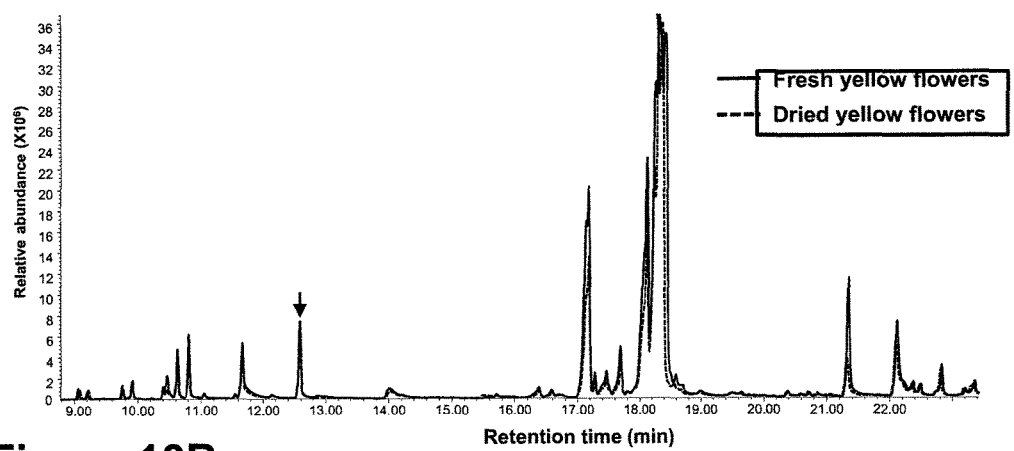
FIGS. 10A and 10B show total ion chromatograms of essential oils from dwarf ylang ylang flowers.
Figure 10B:
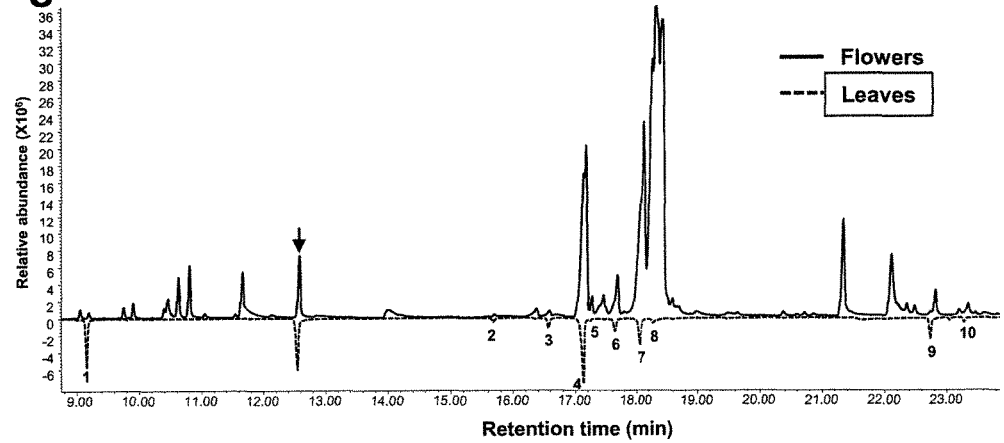

Stage Specific Variations of Volatile Organic Compounds in Dwarf Ylang Ylang Flowers Flowers can emit different volatile compounds at different stages of development (Dudareva et al., 2000). The dwarf ylang ylang flowers have little floral scent when the petals are green but their scent gradually becomes stronger as the flower matures. To examine the overall intensity and the diversity of the floral scent during flower development, total essential oils from flowers at four different stages of development were analysed by gas chromatography-mass spectrometry (GC-MS) (FIGS. 1A and 1B). FIG. 1B and FIG. 9 show that the chemical composition of the essential oils from the floral bud stage to the 3 different stages of open flower development was very diverse both quantitatively and qualitatively. Only 15 compounds that have meaningful levels>0.1% of total volatile compounds were detected from floral buds (FIG. 1B and Table 2). The number of peaks increased progressively during maturation of flower buds into fully open flowers. More than 20, 27, and 45 volatile compounds were obtained from the three different stages of flower development, undeveloped small flower (I), mature green flower (II) and fully-mature yellow flower (III). Hence, the fully-mature stage represents the stage where there was maximum production of VOCs by the flowers. At this stage majority of the volatiles were terpenes with a few benzenoids/phenolpropanoids compounds. Out of 45 compounds identified, 31 were identified as mono- and sesquiterpenes using the mass spectra reference library (FIG. 1B and Table 2). Interestingly, over 90% of the total identified terpenes were sesquiterpenes consisting of α-farnesene (31.50%), α-bergamotene (26.79%), germacrene D (13.26%), β-caryophyllene (11.57%), humulene (1.63%), farnesol (0.75%), trans-β-farnesene (0.77%) and β-ylangen (0.63%), whereas monoterpenes were quantitatively less than 10%, mainly cis-β-ocimene (1.99%), trans-β-ocimene (1.55%) and β-linalool (1.40%). Other aromatic compounds were less than 3%. The relative amounts of all identified volatiles are shown in Table 2 (see mature yellow flowers, III). Dried yellow flowers of ylang ylang also showed similar volatile composition (FIG. 10A). Compared to flowers, ylang ylang leaves contained very low levels of terpenes mainly comprising of α-pinene, β-caryophyllene, germacrene D, and phytol (FIG. 10B).

TABLE 2

Essential Oils Composition of the Flowers from *Cananga odorata* var. *fruticosa*

| | | | | | Relative contents (%)[d] | | | |
|---|---|---|---|---|---|---|---|---|
| No[a] | Compounds | RT (min)[b] | RI[c] | Formula | Bud | I | II | III |
| 1 | β-Thujene | 9.507 | 904 | $C_{10}H_{16}$ | — | — | 0.21 | 0.36 |
| 2 | α-Pinene | 9.652 | 919 | $C_{10}H_{16}$ | 3.08 | 1.30 | 0.99 | 0.65 |
| 3 | Camphene | 9.894 | 943 | $C_{10}H_{16}$ | — | — | — | 0.13 |
| 4 | Sabinene | 10.199 | 974 | $C_{10}H_{16}$ | — | — | 0.26 | 0.43 |
| 5 | β-Pinene | 10.342 | 988 | $C_{10}H_{16}$ | — | — | 0.45 | 0.66 |
| 6 | α-Phellandrene | 10.661 | 993 | $C_{10}H_{16}$ | — | — | — | 0.05 |
| 7 | α-Terpinene | 10.846 | 1012 | $C_{10}H_{16}$ | — | — | — | 0.27 |
| 8 | p-Cresol methyl ether | 10.884 | 1016 | $C_8H_{10}O$ | — | — | — | 0.49 |
| 9 | trans-β-Ocimene | 11.054 | 1023 | $C_{10}H_{16}$ | — | 0.46 | 0.88 | 1.55 |
| 10 | β-Ocimene | 11.170 | 1024 | $C_{10}H_{16}$ | — | 0.40 | 1.09 | 1.99 |
| 11 | γ-Terpinene | 11.397 | 1027 | $C_{10}H_{16}$ | — | — | — | 0.15 |
| 12 | Terpinolene | 12.011 | 1032 | $C_{10}H_{16}$ | — | — | — | 0.16 |
| 13 | β-Linalool | 12.102 | 1040 | $C_{10}H_{18}O$ | — | 0.38 | 0.99 | 1.40 |
| 14 | Neo-allo-ocimene | 12.594 | 1089 | $C_{10}H_{16}$ | — | — | — | 0.18 |
| 15 | 3,4-Dimethoxytoluene | 14.460 | 1197 | $C_9H_{12}O_2$ | — | — | — | 0.39 |
| 16 | 2-Methoxy-4-vinylphenol | 15.854 | 1276 | $C_9H_{10}O_2$ | — | — | — | 0.19 |
| 17 | γ-Elemene | 16.176 | 1306 | $C_{15}H_{24}$ | — | — | — | 0.16 |

TABLE 2-continued

Essential Oils Composition of the Flowers from *Cananga odorata* var. *fruticosa*

| | | | | | Relative contents (%)[d] | | | |
|---|---|---|---|---|---|---|---|---|
| No[a] | Compounds | RT (min)[b] | RI[c] | Formula | Bud | I | II | III |
| 18 | Eugenol | 16.481 | 1309 | $C_{10}H_{12}O_2$ | — | — | — | 0.17 |
| 19 | α-Copaene | 16.831 | 1321 | $C_{15}H_{24}$ | 1.81 | 1.24 | 0.83 | 0.44 |
| 20 | γ-Gurjunene | 17.025 | 1340 | $C_{15}H_{24}$ | 3.00 | 1.16 | 0.56 | 0.32 |
| 21 | Methyleugenol | 17.062 | 1344 | $C_{11}H_{14}O_2$ | — | — | — | 0.08 |
| 22 | β-Caryophyllene | 17.600 | 1398 | $C_{15}H_{24}$ | 16.47 | 23.50 | 15.90 | 11.57 |
| 23 | β-Ylangene | 17.683 | 1406 | $C_{15}H_{24}$ | 3.55 | 1.80 | 1.16 | 0.63 |
| 24 | (E)-β-Farnesene | 17.836 | 1421 | $C_{15}H_{24}$ | — | 0.51 | 0.61 | 0.77 |
| 25 | γ-Muurolene | 17.910 | 1429 | $C_{15}H_{24}$ | 1.21 | 0.60 | 0.38 | 0.20 |
| 26 | Humulene | 18.020 | 1440 | $C_{15}H_{24}$ | 3.44 | 3.44 | 2.24 | 1.63 |
| 27 | β-Cubebene | 18.110 | 1449 | $C_{15}H_{24}$ | 1.02 | 0.35 | 0.19 | 0.08 |
| 28 | GermacreneD | 18.580 | 1450 | $C_{15}H_{24}$ | 50.17 | 33.17 | 27.33 | 13.26 |
| 29 | α-Farnesene | 18.686 | 1461 | $C_{15}H_{24}$ | — | 10.03 | 19.89 | 31.50 |
| 30 | α-Bergamotene | 18.771 | 1469 | $C_{15}H_{24}$ | — | 18.67 | 23.63 | 26.79 |
| 31 | Cedrene | 18.932 | 1485 | $C_{15}H_{24}$ | — | — | 0.32 | 0.33 |
| 32 | δ-Cadinene | 18.989 | 1491 | $C_{15}H_{24}$ | 1.54 | 0.43 | 0.17 | 0.17 |
| 33 | α-Patchoulene | 19.035 | 1495 | $C_{15}H_{24}$ | — | — | 0.07 | 0.13 |
| 34 | Elemicin | 19.233 | 1515 | $C_{12}H_{16}O_3$ | — | — | — | 0.13 |
| 35 | Germacrene D-4-ol | 19.845 | 1537 | $C_{15}H_{26}O$ | 0.75 | 0.21 | 0.16 | 0.13 |
| 36 | β-Caryophyllene oxide | 19.950 | 1548 | $C_{15}H_{24}O$ | — | — | — | 0.07 |
| 37 | Isoelemicin | 20.561 | 1609 | $C_{12}H_{16}O_3$ | — | — | 0.15 | 0.13 |
| 38 | Farnesol | 21.527 | 1763 | $C_{15}H_{26}O$ | — | 0.88 | 0.85 | 0.75 |
| 39 | Benzyl benzoate | 22.236 | 1812 | $C_{14}H_{12}O_2$ | — | — | 0.27 | 0.69 |
| 40 | cis-11-Hexadecenal | 22.505 | 1830 | $C_{16}H_{30}O$ | — | — | — | 0.11 |
| 41 | Octadecanal | 22.623 | 1841 | $C_{18}H_{36}O$ | — | — | — | 0.07 |
| 42 | (E,E,) farnesol acetate | 22.941 | 1873 | $C_{17}H_{28}O_2$ | — | — | 0.10 | 0.10 |
| 43 | Z-9-Hexadecen-1-ol | 23.328 | 1912 | $C_{16}H_{32}O$ | — | — | — | 0.17 |
| 44 | 9-Nonadecene | 23.475 | 1918 | $C_{19}H_{38}$ | — | — | — | 0.18 |
| 45 | Benzyl salicylate | 23.600 | 1931 | $C_{14}H_{12}O_3$ | — | — | — | 0.21 |
| 46 | δ-Elemene | 16.173 | 1308 | $C_{15}H_{24}$ | 4.81 | 0.98 | 0.34 | — |
| 47 | α-Ylangene | 18.662 | 1458 | $C_{15}H_{24}$ | 7.16 | — | — | — |
| 48 | γ-Cadinene | 18.910 | 1483 | $C_{15}H_{24}$ | 1.31 | 0.52 | — | — |
| 49 | α-Copaene-11-ol | 21.094 | 1720 | $C_{15}H_{24}O$ | 0.67 | — | — | — |

[a]Compound listed in order of elution in a HP-5MS UI column;
[b]RT, retention time (min);
[c]RI, retention indices calculated against $C_8$-$C_{40}$ n-alkanes on the HP-5MS UI column;
[d]Relative contents were done by calculating percentage of moles using internal standard, camphor (10 ug/ul).

Figure 11:
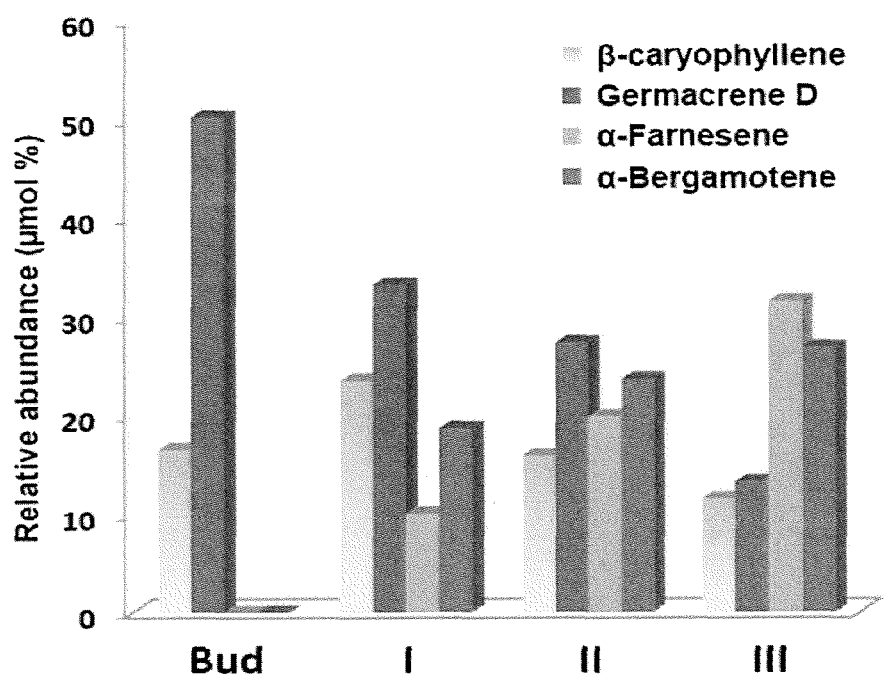
FIG. 11 shows variation of four major terpenes during flower development. Bud, floral buds; I, undeveloped small flowers; II, mature green flowers; III, fully mature yellow flowers.
Figure 12:
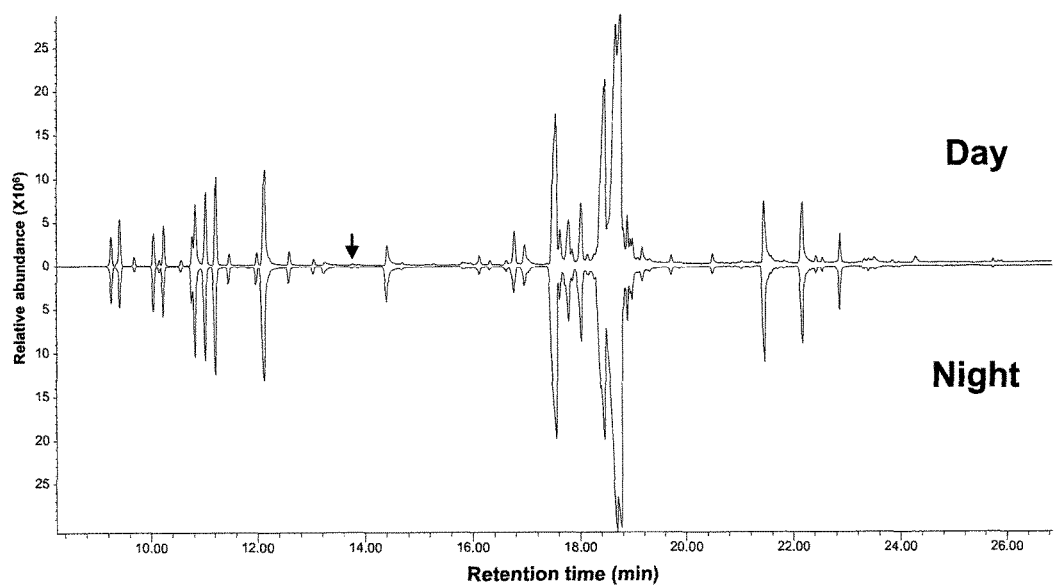
FIG. 12 shows the total ion chromatograms of essential oils from dwarf ylang ylang flowers sampled at day and night.

Two sesquiterpenes, β-caryophyllene and germacrene D could be found at all stages and their levels were retained or slightly decreased during open flower development (#22, 28, FIG. 1B and FIG. 11). However, the other two major sesquiterpenes, α-farnesene and α-bergamotene were undetectable at the floral bud stage, but they were found at early flower development (#29, 30 in I, FIG. 1B and FIG. 11) and subsequently became the most abundant components of essential oils at mature stages of flower development (II and III, FIG. 1B). Interestingly, most of the monoterpenes except α-pinene were undetectable at the floral bud stage, but they gradually increased during open flower development (FIG. 1B). This increase in VOCs as the flower matures suggests the VOCs play a role in pollinator attraction. Among the monoterpenes, trans-β-ocimene, β-ocimene, and β-linalool were highly inducible during flower maturation (#9, 10, and 13, FIG. 1B). Additionally, GC-MS analysis identified several sesquiterpenes or sesquiterpene alcohols that decreased during flower maturation such as such as δ-elemene (#46), α-ylangene (#47), γ-cadinene (#48) and α-copaene-11-ol (#49). Other aromatic compounds such as benzenoid/phenolpropanoid and volatile fatty acids were almost exclusively found in mature yellow flowers (FIG. 1B, FIG. 9, and Table 2). GC-MS analysis of flowers at night did not show any change in VOC profile suggesting that there is no diurnal changes in the emission pattern (FIG. 12).

Example 3

RNA Sequencing, De Novo Assembly and Annotation of Transcriptome

Figure 2:
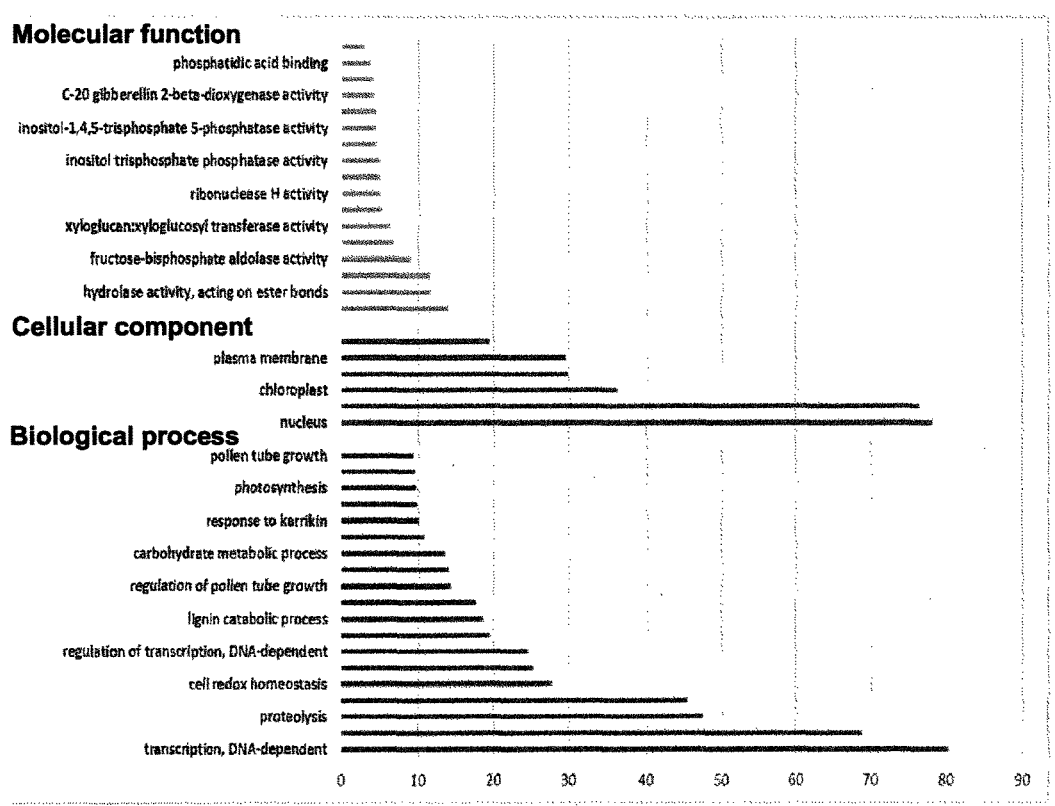
FIG. 2 shows the GO terms for the top 1,000 highly expressed transcripts in dwarf ylang ylang flowers.
Figure 13:
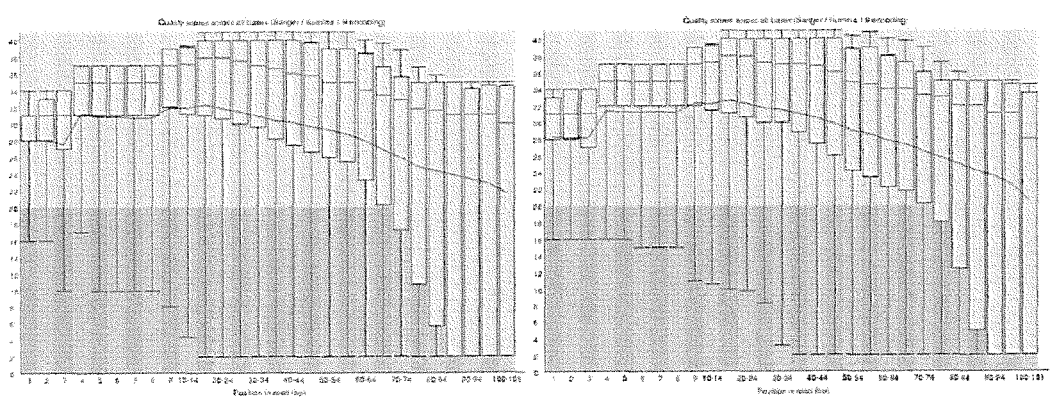
FIG. 13 shows the quality of deep sequencing. The sequence quality was evaluated by FastQC.

To profile ylang ylang floral transcriptome, RNA-seq libraries that were synthesized from the ylang ylang mature yellow flowers were sequenced. Illumina sequencing runs generated more than 110 million reads of 101 base pairs (bp) and the quality of reads were evaluated by FastQC (FIG. 13). Due to the absence of reference genomic sequences of ylang ylang, the Trinity method was used for de novo assembly of short sequence reads (Grabherr et al., 2011). These assemblies generated a total of 45,379 non-redundant (nr) unigenes with a N50 value of 2,016 bp (Table 3). The assembled unigenes were blasted against the National Centre for Biotechnology Information (NCBI) nr protein database and protein databases from *Arabidopsis thaliana*, *Vitis vinifera*, and *Oryza sativa*. Among 45,379 non-redundant unigenes, 30,539 (67.3%) unigenes were annotated through BLASTX search with E-value<=1e-3 (Table 3). Functional classifications of Gene Ontology (GO) term of all unigenes were performed using Trinotate (Quevillon et al., 2005). FIG. 2 shows enriched GO terms for the top 1,000 highly expressed transcripts. From the annotated unigenes, 16 of them were identified as TPSs, which were more than 500 bp in length.

TABLE 3

Overview of the Assembly Results of RNA-seq

| # isoforms | N50 (bp) | # unigenes | # annotation | % annotation |
|---|---|---|---|---|
| 86,512 | 2,016 | 45,379 | 30,539 | 67.3 |

Example 4

RNA-Seq Analysis of Different Biosynthetic Pathways Active in Flowers

Figure 3:
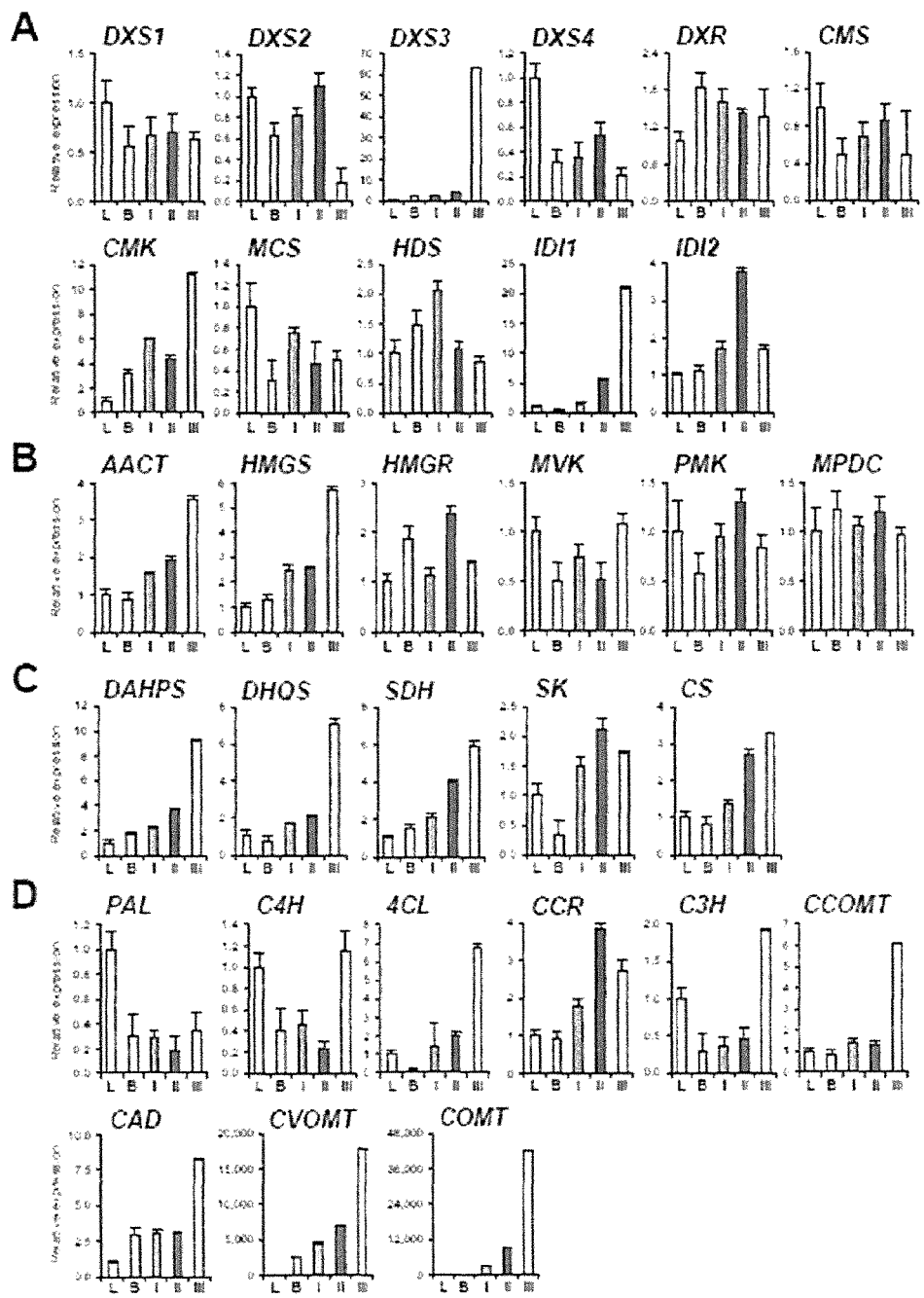
FIGS. 3A-3D show the qRT-PCR analyses of different biosynthetic pathway genes. Expression of genes involved in MEP (FIG. 3A), MVA (FIG. 3B), shikimate (FIG. 3C), and phenyl propanoid (FIG. 3D) were examined from leaves (L), buds (B) and three different stages of flower development, undeveloped small flower (I), mature green flower (II) and fully mature yellow flower (III) by qRT-PCR. MEP, 2-C-methyl-D-erythritol 4-phosphate; DXS, 1-deoxy-D-xylulose 5-phosphate synthase; DXR, 1-deoxy-D-xylulose 5-phosphate reductoisomerase; CMS, 2-C-methyl-D-erythritol 4-phosphate cytidylyltransferase; CMK, 4-(cytidine 5'-diphospho)-2-C-methyl-D-erythritol kinase; MCS, 2-C-methyl-D-erythritol 2,4-cyclodiphosphate synthase; IDS, 4-hydroxy-3-methylbut-2-en-1-yl diphosphate synthase; IDI, isopentenyl pyrophosphate isomerase; MVA, mavalonate; AACT, acetyl-CoA acetyltransferase; HMGS, hydroxymethylglutaryl-CoA synthase; HMGR, hydroxymethylglutaryl-CoA reductase; MVK, mevalonate kinase; PMK, phosphomevalonate kinase; MPDC, mevalonate diphosphate decarboxylase; DAHPS, 3-deoxy-D-arabino-heptulosonate-7-phosphate synthase; DHQS, 3-dehydroquinate synthase; SDH, shikimate dehydrogenase; SK, Shikimate kinase; CS, chorismate synthase; PAL, phenylalanine ammonia lyase; C4H, cinnamate-4-hydroxylase; 4CL, 4-coumaroyl-CoA ligase; CCR, cinnamoyl-CoA reductase; C3H, p-coumarate-3-hydroxylase; CCOMT, caffeoyl-CoA 3-O-methyltransferase; CAD, cinnamyl alcohol dehydrogenase; CVOMT, chavicol O-methyltransferase; COMT, caffeic acid/5-hydroxyferulic acid O-methyltransferase.
Figure 15:
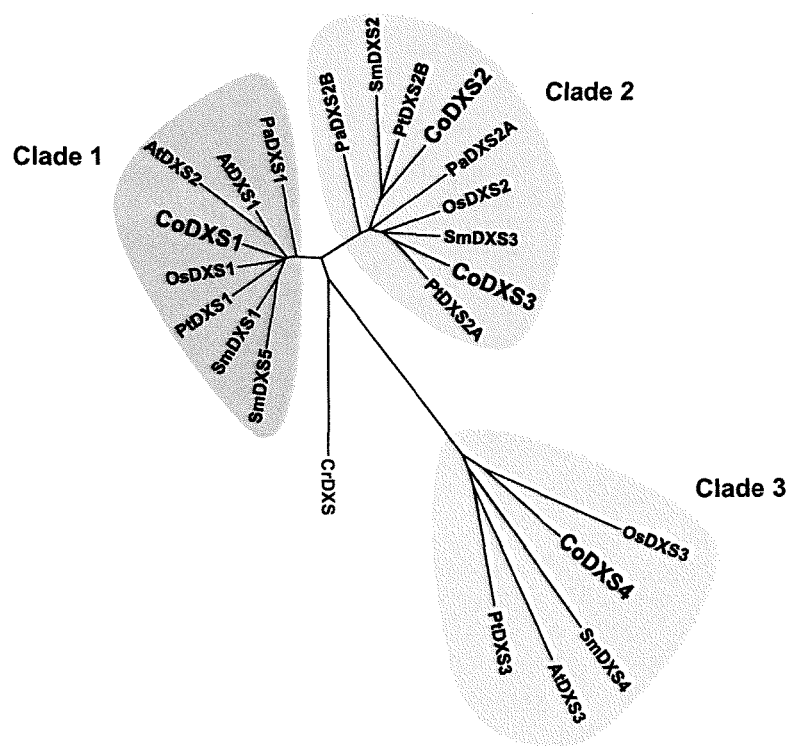
FIG. 15 shows a phylogenetic analysis of DXSs from dwarf ylang ylang. The maximum likelihood tree was drawn by MEGA 6 program from an alignment of full-length CoDXSs (1-deoxy-D-xylulose 5-phosphate synthase) with other plant DXSs. At, *Arabidopsis thaliana*; Os, *Oryza sativa*; Pa, *Picea abies*; Pt, *Populus trichocarpa*; Sm, *Salvia miltiorrhiza*.
Figure 16:
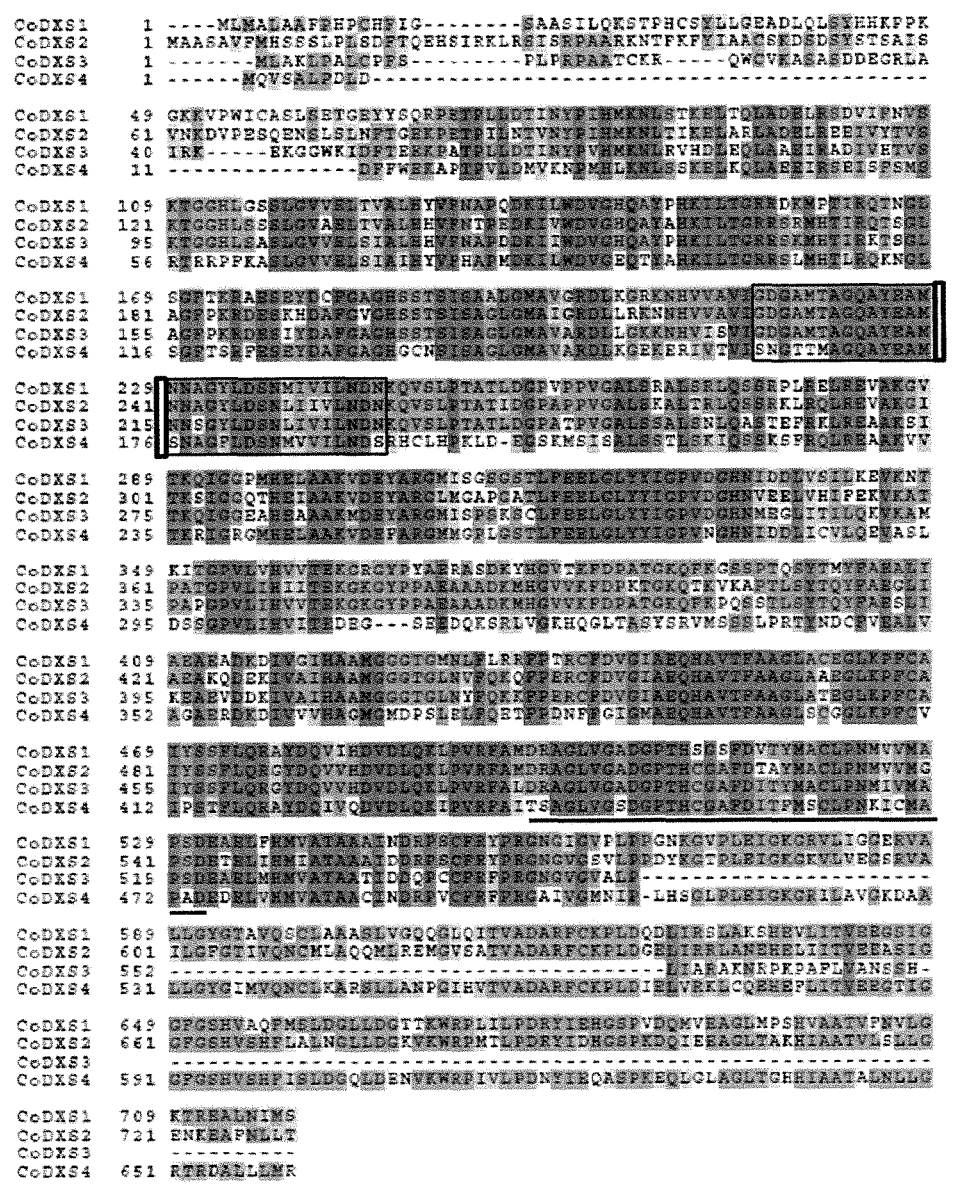

GC-MS analysis of the mature flowers showed a domination of VOCs by terpenes and minor benzenoids/phenolpropanoid compounds. The RNA-seq data was used to analyze the expression profile of the precursor pathways leading to the formation of VOCs in mature flowers. Majority of ylang ylang orthologue unigenes were full length and showed high sequence similarity with known enzymes of these pathways from other plants (FIGS. 14A-14D). The MEP and MVA pathways are the pathways leading to the formation of mono- and sesquiterpenes. Transcripts of all the enzyme genes involved in these 2 pathways were detected in our RNA-seq data and the expression was validated by qRT-PCR (FIGS. 3A-3D). Additionally, the expressions of these enzyme genes were examined at earlier stages of flower development and leaves by qRT-PCR. Genes encoding the MEP and MVA enzymes were active in all stages of flower development consistent with the high production of terpenes in the flowers (FIGS. 3A and 3B). It has been reported that 1-deoxy-D-xylulose-5-phosphate synthase (DXS), the first enzyme of the MEP pathway is important for the overall regulation of the pathway and is encoded by a small gene family (Cordoba et al., 2011). From the RNA-seq data four different 1-deoxy-D-xylulose-5-phosphate synthase (DXS) unigenes showing different levels of abundance in flowers and leaf were identified. One of them DXS3 belongs to clade 2, which may be related to secondary metabolism (Walter et al., 2002; Phillips et al., 2007) was highly induced in stage III flowers (FIG. 3A, FIG. 15, and FIG. 16). The majority of the genes except PAL for the shikimate pathway enzymes, which produce the aromatic precursor phenylalanine for the production of benzenoids and phenylproponids, appeared to be more expressed in mature flowers (FIGS. 3C and 3D). The significant benzenoids in VOCs were benzyl benzoate and benzyl salicylcate and the phenylproponoid was eugenol. These compounds were only detected in mature flowers (#18, 39, and 45, FIG. 1B and Table 2). Previous in vitro experiments have indicated that benzyl benzoate might play a role in pollinator attraction (Hoballah et al., 2005; Huber et al., 2005) or in plant defence (miticide) (Harju et al., 2004).

Example 5

Phylogenetic Analysis of TPS Genes from Dwarf Ylang Ylang Flowers

Figures 4A, 4B:
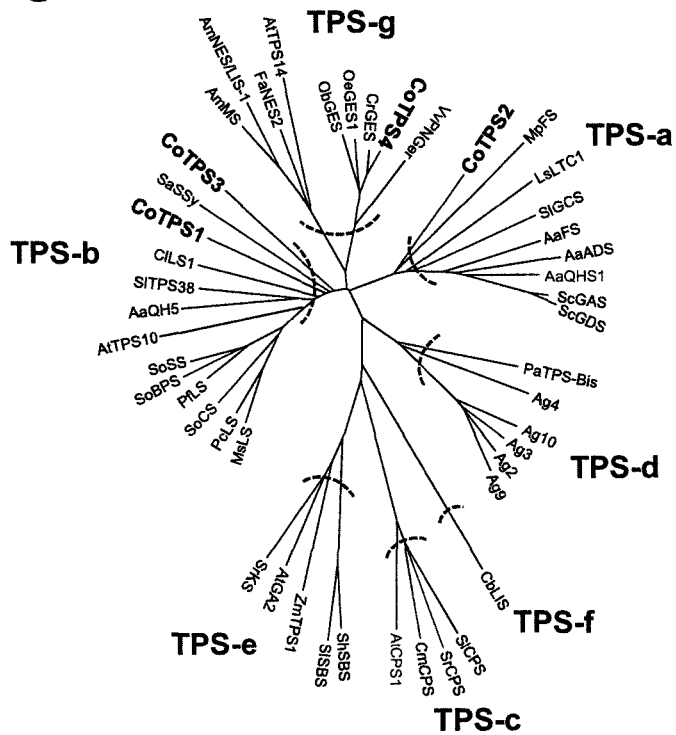
FIGS. 4A and 4B show the phylogenetic analysis and alignment of TPSs from dwarf ylang ylang.

Domination of terpenes is observed in the floral VOCs. From the dwarf ylang ylang RNA-seq data 4 full-length open reading frames (ORFs) of TPSs were PCR-amplified from cDNA pools of dwarf ylang ylang flowers. Phylogenetic analysis based on the deduced amino acid sequences of four CoTPS cDNAs showed that CoTPS2 (561 amino acids) belongs to the TPS-a subfamily representing the sesqui-TPSs, whereas CoTPS1 (590 amino acids) and CoTPS3 (547 amino acids) fall into the TPS-b subfamily, which consist mainly of mono-TPSs (Chen et al., 2011; FIG. 4A). CoTPS4 (586 amino acids) is a member of the TPS-g, subfamily that lacks the $R(R)X_8W$ (SEQ ID NO:1) motif in the N-terminal region of mono-TPSs and produces an acyclic monoterpenes (Dudareva et al., 2003; Chen et al., 2011; Yuan et al., 2008; FIG. 4A). All four CoTPSs had the conserved aspartate-rich motif (DDXXD; SEQ ID NO:2) and NSE/DTE (SEQ ID NO:3/SEQ ID NO:4) motifs that chelate the divalent metal ion, typically $Mg2+$, in C-terminal domain (FIG. 4B). Both motifs are required for cyclization of the universal acyclic terpene precursors, such as genanyl and farnesyl diphosphate to synthesize mono- and sesquiterpene, respectively (Chen et al., 2011). The arginine-tryptophan motif, $R(R)X_8W$ (SEQ ID NO:1) present at the N-terminal of most mono-TPS and in some sesqui-TPS and di-TPS were found in CoTPS1, CoTPS2, and CoTPS3 except CoTPS4 (FIG. 4B). One of the distinguishing structural features between mono- and sesqui-TPS is the presence of a N-terminal plastid transit peptide (Tp) sequence. Using the signal sequence analysis programs, ChloroP (http colon slash slash cbs dot dtu dot dk slash services slash ChloroP) and WoLF PSORT (http colon slash slash wolfpsort dot org), a putative N-terminal plastid Tp sequence of 41 and 35 amino acids for CoTPS1 and CoTPS4, respectively, was predicted indicating they are likely to be mono-TPSs. However, a putative plastid Tp sequence for CoTPS3, which was supposed to be mono-TPS belonging to TPS-b subfamily, could not be found. CoTPS2 did not contain a plastid Tp sequence which correlated well with the prediction of it being a sesqui-TPS.

Example 6

Subcellular Localization and Expression of Four CoTPSs

Figure 5:
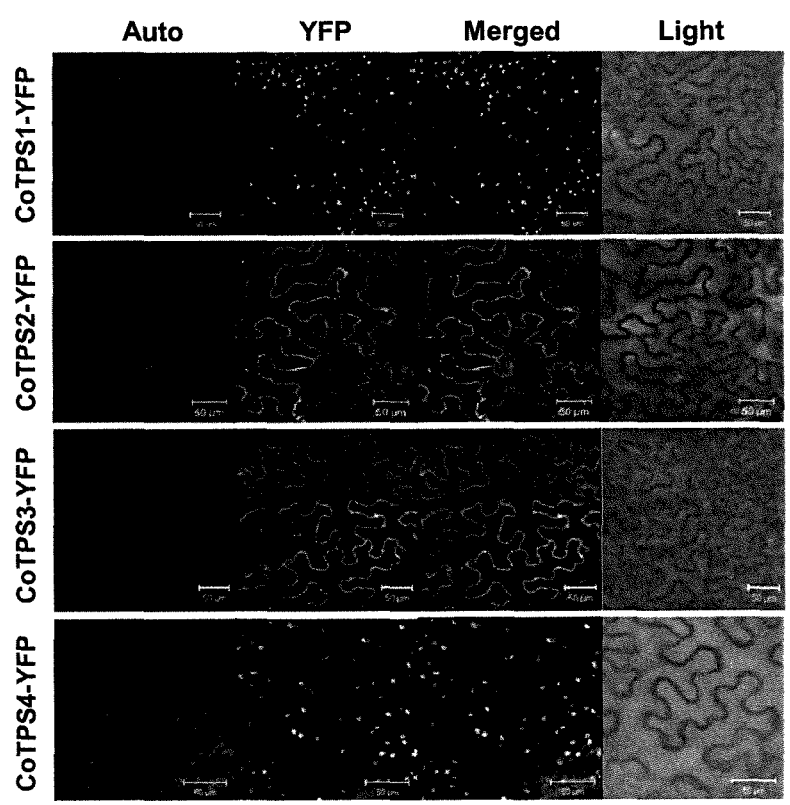
FIG. 5 shows the subcellular localization of CoTPSs. YFP-fused CoTPSs (CoTPS1-YFP, CoTPS2-YFP, CoTPS3-YFP, and CoTPS4-YFP) were transiently expressed in *N. benthamiana* leaves by *Agrobacterium*-mediated infiltration and visualized 3 dpi (days post-infiltration) using YFP channel of a confocal microscope. Auto, chlorophyll autofluorescence; YFP, YFP channel image; Light, light microscope image; Merged, merged image between Auto and YFP. Scale bars, 50 μm.

Apart from the phylogenetic analysis and bioinformatics-based attempts to classify TPSs, their subcellular localization is also important for function prediction. This is especially true for CoTPS3, since its function was unpredictable from the bioinformatics analyses based on amino acid sequences. To address this issue, full-length cDNA of each CoTPS fused to yellow fluorescent protein (YFP) reporter gene to produce a CoTPS-YFP fusion protein was transiently expressed in N. benthamiana leaves using Agrobacterium-mediated infiltration. FIG. 5 shows that CoTPS1-YFP and CoTPS4-YFP which had N-terminal plastid Tp sequence were localized in chloroplasts as expected, whereas CoTPS2-YFP and CoTPS3-YFP were distributed throughout the cytosol. Based on results of subcellular localization experiments, it is likely that CoTPS1 and CoTPS4 are involved in monoterpenes synthesis in plastids, whereas, CoTPS2 and CoTPS3 produce sesquiterpenes in the cytosol.

Figure 6:
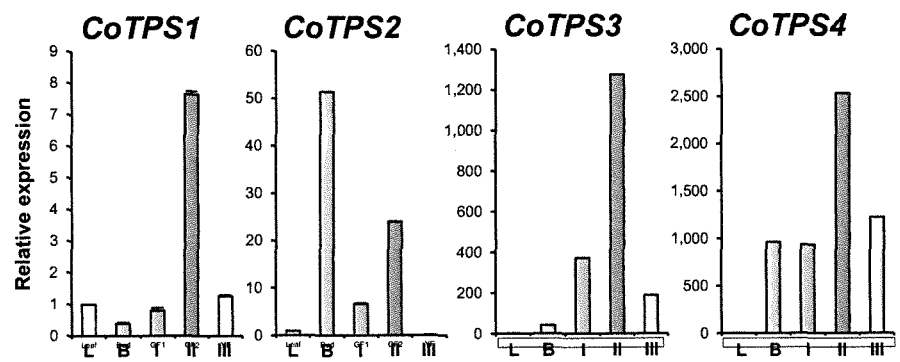
FIG. 6 shows transcript levels of dwarf ylang ylang TPS genes, CoTPS1, CoTPS2, CoTPS3, and CoTPS4 during flower development. Total RNAs were isolated from leaves (L), floral buds (B) and three different stages of flower development, undeveloped small flower (I), mature green flower (II) and fully mature yellow flower (III) and used as the templates for qRT-PCR. Amplification of Actin mRNA was use as internal control.

Transcript levels for the four CoTPS genes at different developmental stages of dwarf ylang ylang flowers were examined by qRT-PCR. The expression levels of all four transcripts were very low or below detection limits in leaf tissues and greatly elevated in flower tissues (FIG. 6). Transcripts for three TPS genes, CoTPS1, CoTPS3 and CoTPS4 were highest in mature green flowers (II), whereas CoTPS2 was highly expressed at the floral bud stage (FIG. 6).

Example 7

Functional Characterization of CoTPSs

Figure 7:
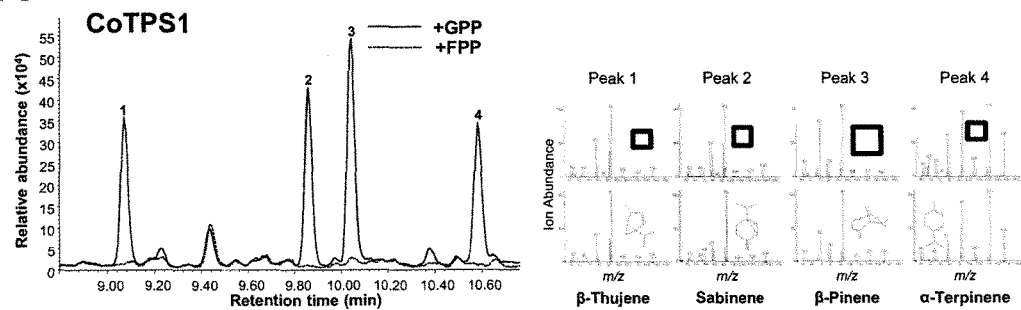
FIGS. 7A-7D show in vitro enzymatic assays of recombinant CoTPSs. In vitro enzyme assays using recombinant His-tagged CoTPS1 (FIG. 7A), CoTPS2 (FIG. 7B), CoTPS3 (FIG. 7C), or CoTPS4 (FIG. 7D) protein using GPP or FPP as substrate. The reaction products were analysed by GC-MS. The peaks marked with an arrow in the GC traces were identified by the mass spectra reference library. Mass spectra for the peaks formed with FPP or GPP are shown on the right side of the figure with the references. m/z, mass-to-charge ratio.
Figure 7:
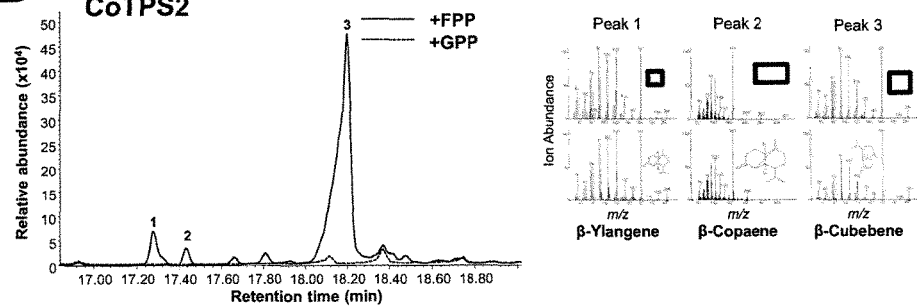
Figure 7:
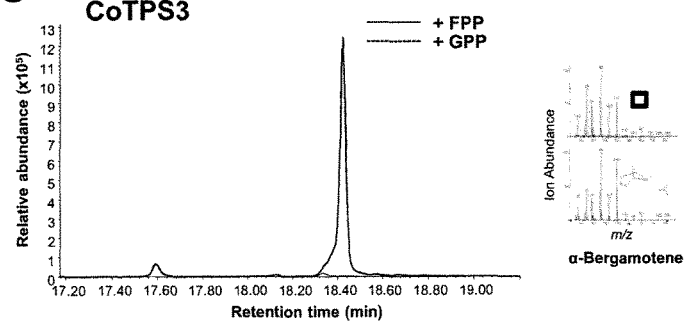
Figure 7:
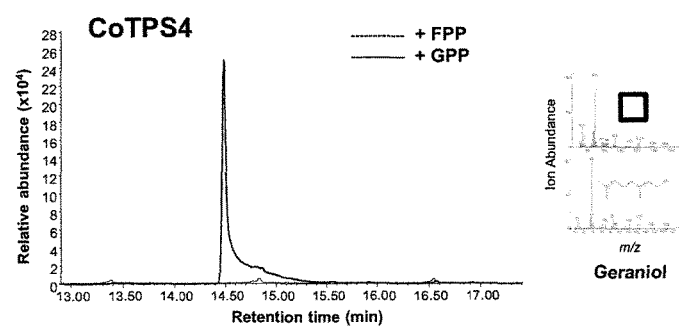
Figure 18:
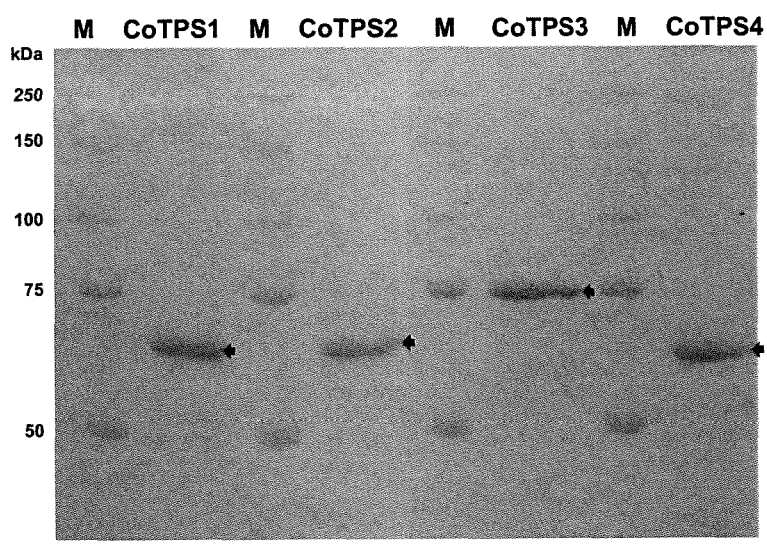
FIG. 18 shows a SDS-PAGE of recombinant His-tagged CoTPS1, CoTPS2, CoTPS3, or CoTPS4 protein. M; Precision Plus Protein all blue standards (Bio-rad), kDa; kilodalton, −; minus IPTG, +; plus IPTG, PP; Purified protein.
Figure 19:
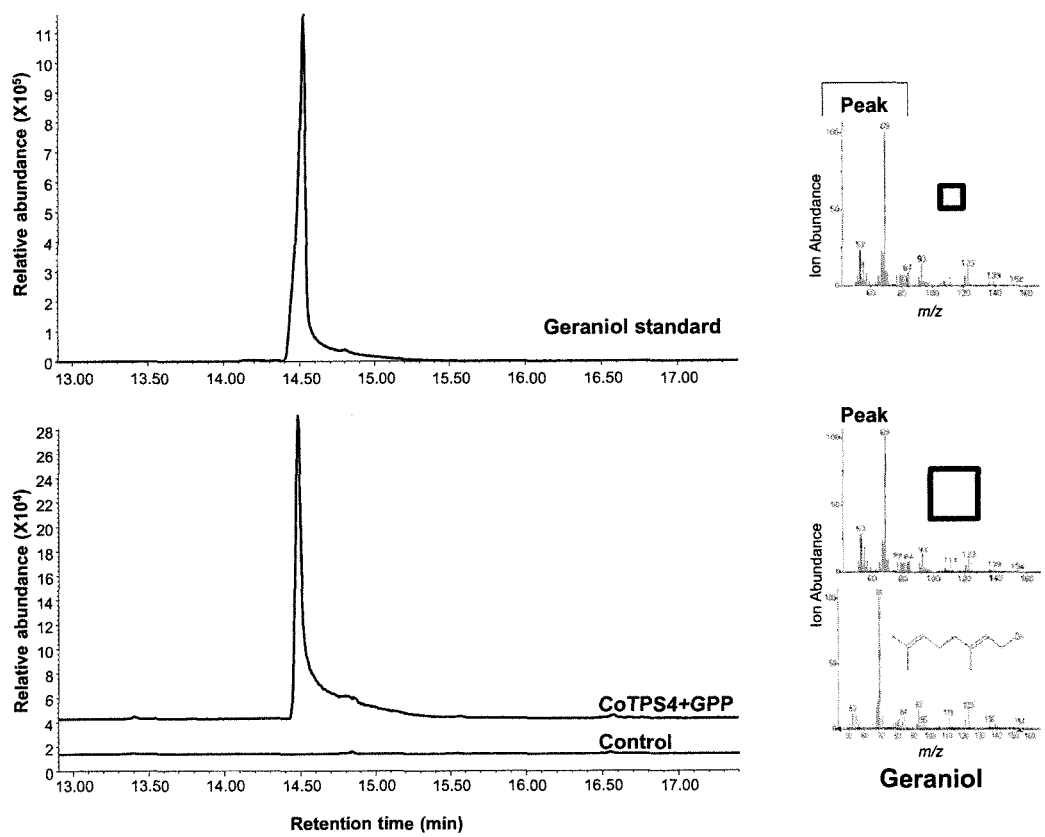
FIG. 19 shows in vitro enzymatic assay of recombinant 6His-tagged CoTPS4s using GPP. The reaction products were analysed by GC-MS. The peak was identified by the mass spectra reference library and comparison of retention time with those of authentic standard (geraniol standard). Mass spectra for the peak formed with GPP are shown on the right side of the figure with the references. m/z, mass-to-charge ratio. Control, control assay using a heat-activated recombinant protein.

The subcellular localization of each CoTPS-YFP provided preliminary evidence to elucidate the function of each TPS. The exact functional annotation of a new TPS requires activity characterization of the recombinant protein. To determine the enzymatic activity of CoTPSs in vitro, 6His-tagged CoTPSs recombinant proteins purified from *E. coli* BL21(DE3) (FIG. 18) were used for in vitro assays. GPP (C10) or FPP (C15) was used as the common substrate for mono- and sesqui-TPS, respectively. Control assays using heat-inactivated recombinant 6His-tagged CoTPSs did not form any terpenes from GPP or FPP (FIG. 19). FIG. 7A shows that CoTPS1, a member of the TPS-b family synthesized two products corresponding to β-thujene, sabinene, β-pinene and α-terpinene from GPP, but not from FPP, which were found in the essential oil profiles of dwarf ylang ylang flowers (#1, 4, 5 and 7, FIG. 1 and Table 2). These results suggest that CoTPS1 is a multifunctional β-thujene/sabinene/β-pinene/α-terpinene synthase that is able to catalyse the synthesis of a mixture of monoterpenes namely β-thujene, sabinene, β-pinene and α-terpinene. It is not surprising because several multiproduct mono-TPSs that produce similar compounds, such as α-thujene, sabinene, α/β-pinene, α/γ-terpinene have been widely reported in other plant species (Chen et al., 2003; Fähnrich et al., 2011; Fäldt et al., 2003; Shimada et al., 2004; Lücker et al., 2002).

Similarly, recombinant CoTPS2 catalyzed the synthesis of three compounds, β-ylangene, β-copaene, and β-cubebene from FPP. These results suggest that CoTPS2 is a multifunctional β-ylangene/β-copaene/β-cubebene synthase capable of producing three sesquiterpenes, β-ylangene, β-copaene, and β-cubebene (FIG. 7B). This finding is not unique to CoTPS2 since many TPSs are known to be multi-functional (Steele et al., 1998; Lee and Chappell, 2008). However, TPSs that produce β-ylangene/β-copaene/β-cubebene have not yet been reported. Of these three sesquiterpene compounds, we could detect β-ylangene and β-cubebene in the flowers of dwarf ylang ylang (#23 and 27, FIGS. 1 and 1B and Table 2).

Figure 17A:
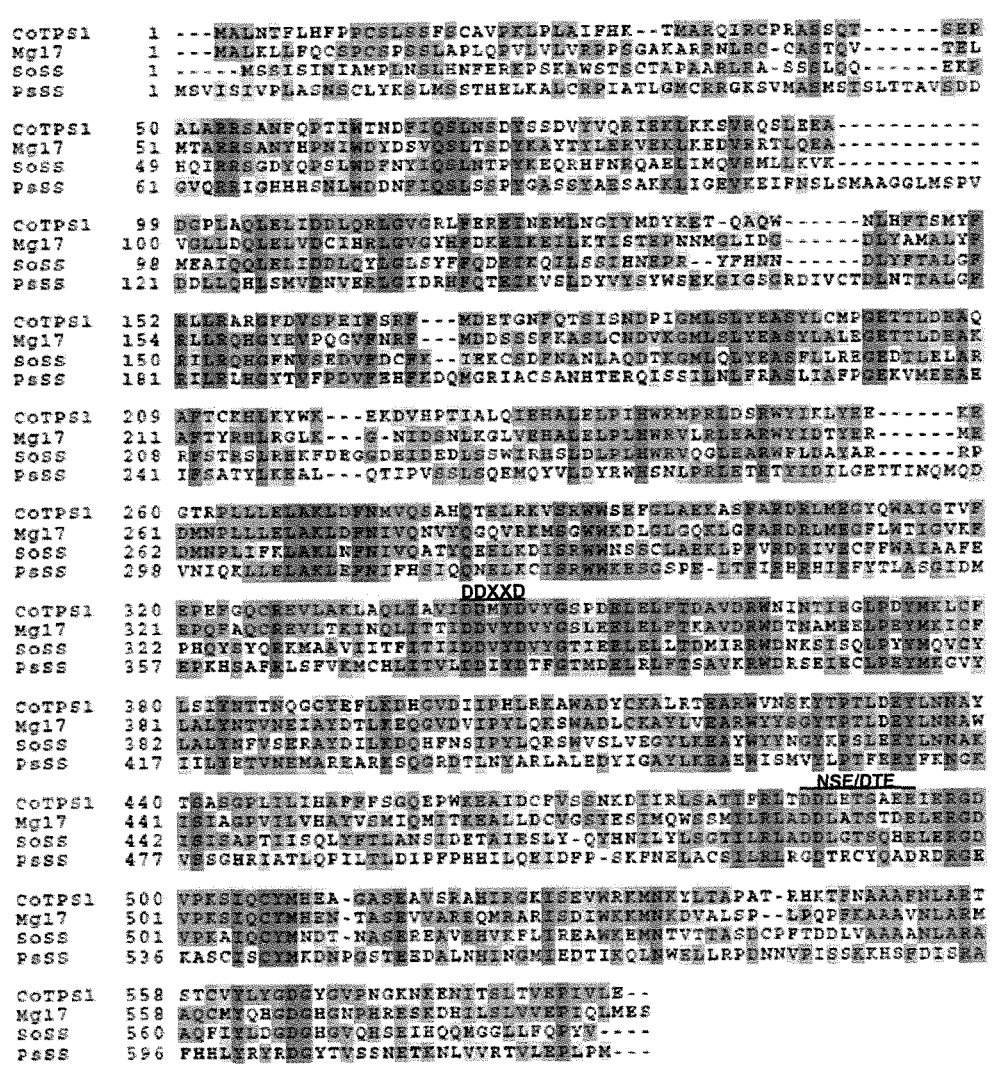
Figure 17B:
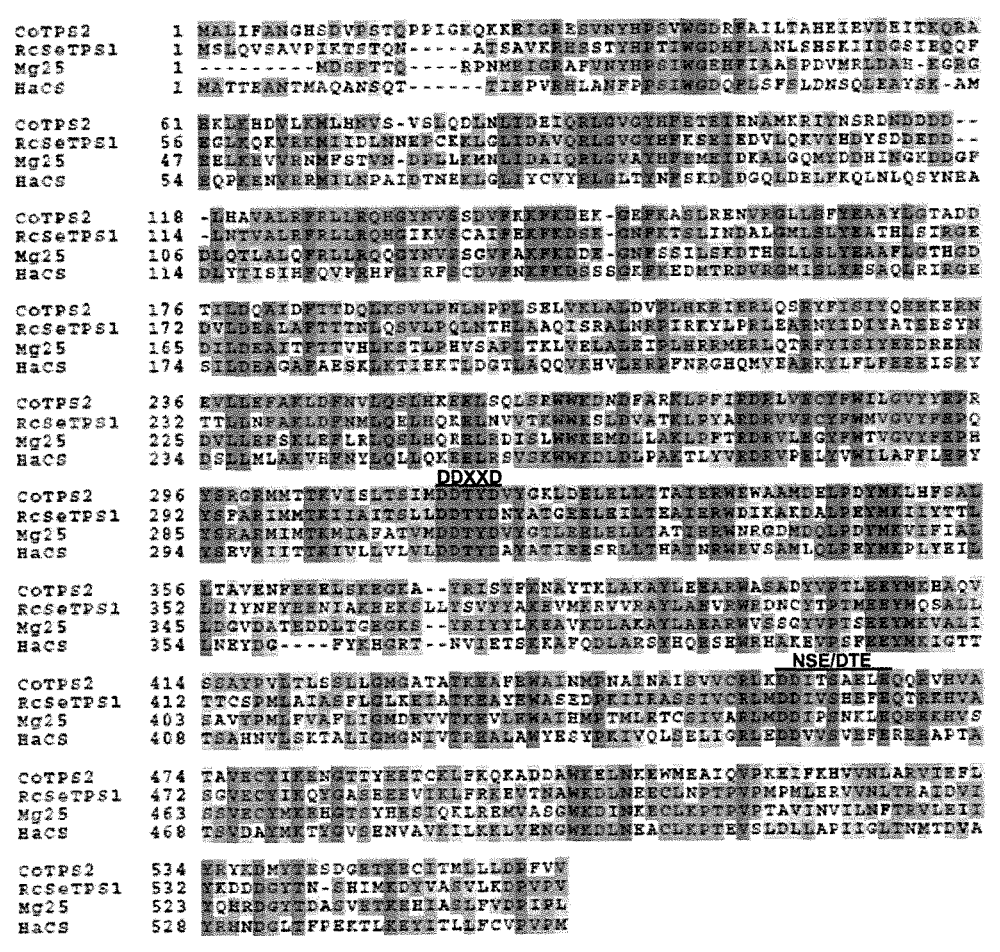

CoTPS3 is a member of TPS-b family with an unusual feature that it lacks a putative N-terminal Tp sequence. Enzyme assays showed that CoTPS3 catalysed the formation of α-bergamotene from FPP (FIG. 7C), which is a major sesquiterpene produced in the flowers of ylang ylang (#30, FIG. 1B and Table 2). As a member of the TPS-g family, CoTPS4 was capable of utilizing GPP to synthesize an acyclic monoterpene, geraniol (FIG. 7D). It was confirmed by comparison of retention time and mass spectra to those of authentic standard (FIG. 19). This result was expected since the protein showed the highest amino acid identity with geraniol synthases (84%) from Madagascar periwinkle (*Catharanthus roseus*) (FIG. 17D; Simkin et al., 2013). But geraniol was not detected in our GC-MS analysis of ylang ylang flowers.

Example 8

Functional Characterization of CoTPS In Vivo

Figure 8A:
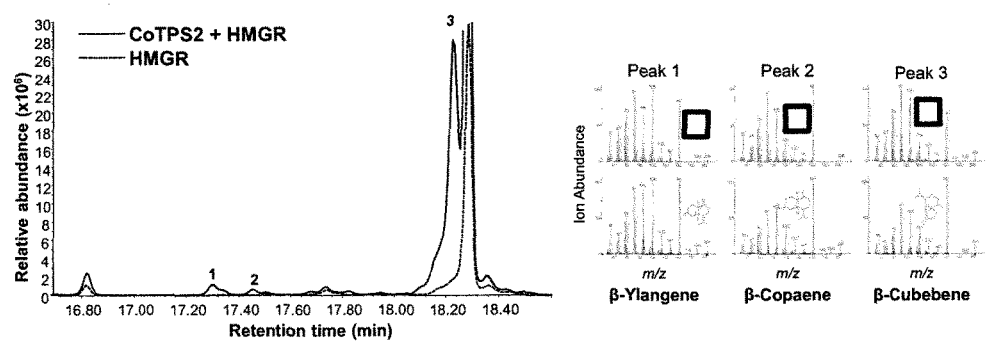
FIGS. 8A and 8B show in vivo characterization of CoTPS2 and CoTPS3. YFP-fused CoTPS2 (FIG. 8A) or CoTPS3 (FIG. 8B) with or without HMGR was transiently expressed in *N. benthamiana* leaves by *Agrobacterium*-mediated infiltration. The compounds were analysed 3 dpi by GC-MS. Numbered peaks were identified by the mass spectra reference library and the mass spectra of compounds were shown on the right side. The expression of HMGR alone in each figure was used as a control. The asterisk indicates a nonspecific peak derived from the expression of HMGR in *N. benthamiana* leaves
Figure 8B:
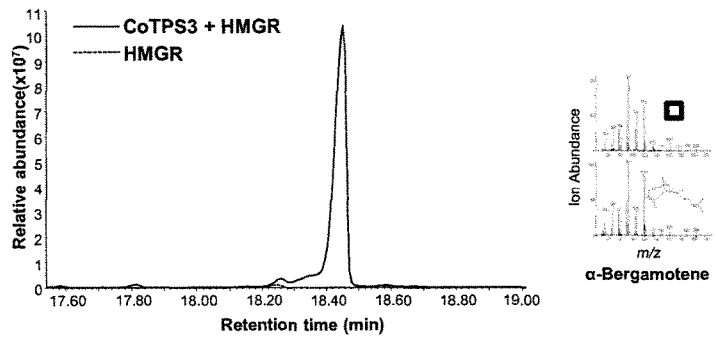
Figure 20:
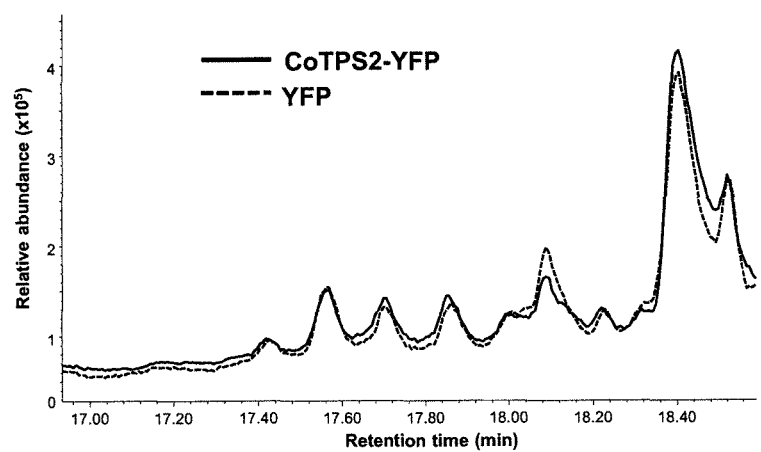
FIG. 20 shows transient expression of CoTPS2-YFP or YFP in *N. benthamiana*. CoTPS2-YFP or YFP was transiently expressed in *N. benthamiana* leaves by *Agrobacterium*-mediated infiltration. The compounds were analysed 3 dpi (days post-infiltration) by GC-MS.

Whether CoTPSs would produce the same terpene products in vivo was investigated using *Agrobacterium*-mediated transient gene expression in tobacco leaves. The YFP-fused CoTPS1, CoTPS2, CoTPS3, or CoTPS4 was expressed in *N. benthamiana* with or without co-expression of the *Arabidopsis* 3-Hydroxy-3-Methylglutaryl Coenzyme A Reductase (HMGR). HMGR catalyses a rate limiting step of the mevalonate pathway and its overexpression is known to increases heterologous sesquiterpene production (Song et al., 2012; Jin et al., 2014). Analysis by GC-MS showed that the in vivo results were consistent with those obtained in vitro. CoTPS2-YFP produced clearly three compounds, β-ylangene, β-copaene and β-cubebene when it was co-expressed with AtHMGR (FIG. 8A), whereas Co-TPS3 produced α-bergamotene when co-expressed with AtHMGR (FIG. 8B). The expression of CoTPS2 or CoTPS3 alone without AtHMGR in *N. benthamiana* did not produce any terpenes, which may be due to limiting amounts of the substrate, FPP (FIG. 20). CoTPS1 and CoTPS4 characterized as mono-TPS in vitro failed to produce any new peaks in planta suggesting that they might require the co-expression of additional genes, probably a rate-limiting step of the non-mevalonate pathway. Alternatively, compounds formed by these TPSs might be further metabolised endogenously by the plants.

Example 9

Dwarf Ylang Ylang Essential Oils are Quantitatively Dominated by Sesquiterpene Compounds Like jasmine and rose extracts, scent extracts derived ylang ylang flowers are widely used in the perfumery, cosmetic, and food industries. Plants use the vibrant colors and VOCs of flowers to attract pollinators. The chemical composition of floral VOCs produced by ylang ylang varieties has been previously reported (Gaydou et al, 1986; Benini et al., 2010, 2012; Brokl et al., 2013). These papers show the presence of volatile terpenes, benzenoid and phenylpropanoids in floral VOCs. A previous report described the composition of essential oils of ylang ylang flowers originating from Madagascar (*Cananga odorata* Hook Fil. et Thomson forma genuina) (Gaydou et al, 1986). These authors found that the primary component was the monoterpene linalool (19%), and the other major compounds were two sesquiterpenes, β-caryophyllene (10.7%) and germacrene D (10.3%) (Gaydou et al., 1986). Additionally, the variety of ylang ylang from Madagascar contained more than 20% of other aromatic compounds such as p-methylanisole, benzyl benzoate, methyl benzoate and benzyl salicylate (Gaydou et al., 1986). By contrast, our analysis on volatile essential oils of dwarf ylang ylang flowers (*C. odorata* var. *fruticosa*) showed that over 90% of it is composed of sesquiterpenes, such as α-farnesene (31.50%), α-bergamotene (26.79%), germacrene D (13.26%), β-caryophyllene (11.57%), humulene (1.63%), farnesol (0.75%), trans-β-farnesene (0.77%) and β-ylangen (0.63%) (FIGS. 1A and 1B and Table 2). In addition, we also detected other groups of aromatic compounds such as benzyl benzoate, benzyl salicylate and eugenol from the flowers of dwarf ylang ylang, but they constituted less than 3% (Table 2). In the variety studied here, a dominance of α-farnesene (31.50%) which was absent from Madagascar ylang ylang and α-bergamotene (26.79%) one of the main constituents of sandalwood oil (Jones et al., 2011) was found. The differences in the chemical composition of essential oils may be due to differences in genetic background, geographic location, growth conditions and extraction methods (Benini et al., 2012; Brokl et al., 2013). Fragrant flowers from champak (Michelia champaca L.), indian cork (*Millingtonia hortensis* L.), and jasmine (*Jasminum sambac* L.) produce high amounts of four sesquiterpenes, β-caryophyllene, β-bergamotene, α-cubebene and β-cubebene (Samakradhamrongthai et al, 2009). Therefore, these sesquiterpenes are important contributors to typical fragrances of these flowers. In addition to α-farnesene we detected high levels of β-caryophyllene and α-bergamotene in our ylang ylang variety as well.

Example 10

RNA-Seq Uncovers Terpene Synthase Genes from Dwarf Ylang Ylang

The RNA-seq approach provided a rich resource to identify and functionally characterize TPSs from the flowers of dwarf ylang ylang. Approximately 16 candidate TPS transcripts for various mono- and sesquiterpenes were found from the transcriptome data of dwarf ylang ylang flowers. However, many of the candidate TPS transcripts contained partial mRNA sequences from the RNA-seq data. Amongst the four CoTPSs transcripts studied, the expression level of CoTPS1 was the highest, followed by CoTPS2 and CoTPS3, with CoTPS4 being the lowest. However, the RNA-seq expression level of CoTPSs transcripts did not exactly correlate with the abundance of terpenes produced by these TPSs when analyzed by GC-MS. This may be due to post-translational modification or a reflection of different enzyme activities.

Example 11

Sequence Characteristics of CoTPSs

According to the phylogenetic analysis, CoTPS1 and CoTPS3 were grouped into TPS-b subfamily, which commonly represents angiosperm mono-TPSs. Generally, the TPS-b group contains two distinct structural domains, the plastid TP domain and the R(R)X$_8$W (SEQ B3 NO:1) motif for monoterpene cyclization located at N-terminal region of mature TPS (Bohlmann et al., 1998). CoTPS1 appears to be a typical member of TPS-b subfamily, and has both these mono-TPS characteristics. In vitro studies also showed that CoTPS1 catalyzed the formation of the monoterpene, β-thujene/sabinene/β-pinene/α-terpinene from GPP. In contrast to CoTPS1, CoTPS3 has a conserved R(R)X$_8$W (SEQ ID NO:1) motif, but no TP sequence for plastid targeting, which explains its cytosolic localization in transient expression assays (FIG. 5). Moreover, CoTPS3 used FPP to synthesize the sesquiterpene, α-bergamotene in vitro and produced same product in vivo (FIG. 7C and FIG. 8B). Hence it is a unique sesqui-TPS that contains not only monoterpene characteristic, R(R)X$_8$W (SEQ ID NO:1), but it also belongs to the TPS-b subfamily associated with mono-TPSs. The protein encoded by CoTPS3 has low level of sequence identity of 45% to the α-terpineol synthase from Magnolia flower (Magnolia grandiflora), which is a mono-TPS most similar to CoTPS3 (Lee and Charpell, 2008). Similar sesqui-TPSs that reside in the TPS-b phylogenetic clade have been reported in tomato (Solanum lycopersicum) and sandalwood (Santalum album) (Falara et al., 2011; Jones et al., 2011).

Conversely, the CoTPS4 contains N-terminal 35 amino acid residues of a putative plastid TP sequence, but lacks the R(R)X$_8$W (SEQ ID NO:1) motif, a characteristic feature of TPS-b mono-TPS. CoTPS4 was annotated as a plastid geraniol synthase through Blast X analysis since it closely resembled the geraniol synthase from Madagascar periwinkle (Catharanthus *roseus*), with an amino acid sequence identity of 84% (Simkin et al., 2013). As expected, this protein catalysed the synthesis of geraniol from GPP in vitro. Since the new TPS-g family lacking the R(R)X$_8$W (SEQ ID NO:1) motif was first defined from Snapdragon TPS genes related to floral scent biosynthesis (Dudareva et al., 2003), two additional TPS genes belonging to the TPS-g family were subsequently identified from *Arabidopsis* and rice. These TPSs produce an acyclic monoterpene linalool (Chen et al., 2011; Yuan et al., 2008), which eventually became a prominent feature for members of the TPS-g group. As expected from a member of TPS-g family CoTPS4 produced an acyclic geraniol and the protein sequence clustered closely with the grapevine geraniol synthases of the TPS-g subfamily (Martin et al., 2010) indicating these TPS functions are highly conserved among plants.

Example 12

CoTPS2 is a Multifunctional and Novel Sesquiterpene Synthase

Many TPSs are known to synthesize several products simultaneously. Typical multiproduct mono-TPSs such as cineole synthases, terpinene synthases, terpinolene synthases, bornyl diphosphate synthases, carene synthases and myrcene synthases additionally produce the same compounds such as sabinene, α/β-pinene (Fähnrich et al., 2011; Chen et al., 2003; Fäldt et al., 2003; Shimada et al., 2004; Lücker et al., 2002). Most of the multiproduct TPSs are likely to synthesize one or two compounds dominantly as major products and others as minor components. Interestingly, CoTPS1 was capable of producing all four monoterpenes, β-thujene, sabinene, β-pinene, and α-terpinene at similar levels, which was named as β-thujene/sabinene/β-pinene/α-terpinene synthase in this study. Monoterpene thujene, usually referred to as α-thujene, has two double-bond isomers known as β-thujene and sabinene. Since all thujene synthases identified catalyses the α form, CoTPS1 possessed the ability to cyclize GPP to β-thujene, found in dwarf ylang ylang flowers.

Some sesqui-TPSs belonging to the TPS-a subfamily from *Magnolia* and kiwifruit preserved the N-terminal R(R)X$_8$W (SEQ ID NO:1) motif (Lee and Chappell, 2008; Nieuwenhuizen et al., 2009). This is the case with CoTPS2 in this study. While CoTPS3 and CoTPS4 produced a single terpene product, α-bergamotene and geraniol, respectively, CoTPS2 was able to synthesize three kinds of sesquiterpenes, β-ylangene, β-copaene, and β-cubebene (FIGS. 7A-7D and FIGS. 8A and 8B). Similar to CoTPS2, many sesqui-TPSs derived from different plant species have been documented to produce multiple products which normally arise from enantiomers or common intermediates (Munck and Croteau, 1990, Steele et al, 1998, Mercke et al, 1999; Lee and Chappell, 2008).

Almost all the terpenes produced by the four CoTPSs are accounted for in the ylang ylang essential oils composition as shown in FIG. 1 and Table 2, as well from other sources (Gaydou et al, 1986; Brokl et al, 2013). The two undetectable compounds, geraniol and β-cubebene may be produced in extremely small quantities and possibly can be detected by improved analytical technology like two-dimensional GC coupled to time-of-flight MS. However, it remains to be clarified if these two compounds are indeed constituents of dwarf ylang ylang floral VOCs.

TPSs for α-bergamotene and geraniol have been reported in other plant species (Lu et al., 2002; Landmann et al, 2007; Iijima et al, 2004). However, exclusive β-ylangene/β-copaene/β-cubebene synthase has not yet been reported. β-cubebene synthase gene has been identified in *Magnolia grandiflora* (Lee and Chappell, 2008), as Mg25, sharing 55% amino acid sequence identity and 72% similarity to CoTPS2. β-ylangene/β-cubebene or β-copaene/β-cubebene were found as minor peaks out of total 52 or 15 sesquiterpenes synthesized in vitro assays in *Abies grandis* or *Medicago truncatula* (Steele et al., 1998; Arimura et al., 2008). Interestingly, a fungal (*Coprinus cinereus*) sesqui-TPS that synthesizes 10 different sesquiterpenes with δ-cadinene and β-copaene as the major products was capable of synthesizing β-ylangene, when the amino acid residues which presumably interact with a conserved Asp in the two metal-binding motifs were mutated (Lopez-Gallego et al, 2010). β-ylangene is a diastereomer of β-copaene, however it was not produced by the wild type sesqui-TPS (Lopez-Gallego et al., 2010). In conclusion, CoTPS2 is a multifunctional and novel TPS producing three sesquiterpenes, β-ylangene, β-copaene, and β-cubebene in vitro as well as in vivo. α-copaene, the isomer of β-copaene is a potent attractant for an agricultural pest, Mediterranean fruit flies, *Ceratitis capitata* (Nishida et al., 2000).

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

Arimura G, Garms S, Maffei M, Bossi S, Schulze B, Leitner M, Mithofer A, Boland W. 2008. Herbivore-induced terpenoid emission in *Medicago truncatula*: concerted action of jasmonate, ethylene and calcium signaling. *Planta* 227, 453-464.

Benini C, Danflous J P, Wathelet J P, du Jardin P, Fauconnier M L. 2010. Ylang-ylang [*Cananga odorata* (Lam.) Hook. f. & Thomson]: An unknown essential oil plant in an endangered sector. *Biotechnology, Agronomy, Society and Environment* 14, 693-705.

Benini C, Mahy G, Bizoux J P, Wathelet J P, du Jardin P, Brostaux Y, Fauconnier M L. 2012. Comparative chemical and molecular variability of *Cananga odorata* (Lam.) Hook.f. & Thomson forma genuina (ylang-ylang) in the Western Indian Ocean Islands: implication for valorization. *Chemistry & Biodiversity* 9, 1389-1402.

Bohlmann J, Meyer-Gauen G, Croteau R. 1998. Plant terpenoid synthases: molecular biology and phylogenetic analysis. *Proceedings of the National Academy of Sciences, USA* 95, 4126-4133.

Bonfim, K. et al. 2007. RNAi-mediated resistance to Bean golden mosaic virus in genetically engineered common bean (*Phaseolus vulgaris*). *Mol Plant Microbe Interact* 20:717-726.

Brokl M, Fauconnier M L, Benini C, Lognay G, du Jardin P, Focant J F. 2013. Improvement of Ylang-Ylang Essential Oil Characterization by GCXGC-TOFMS. *Molecules* 18, 1783-1797.

Burdock G A, Carabin L G. 2008. Safety assessment of ylang-ylang oil as a food ingredient. *Food and Chemical Toxicology* 46, 433-445.

Chang Y T, Chu F H. 2011. Molecular cloning and characterization of monoterpene synthases from *Litsea cubeba*. *Tree Genetics and Genomes* 7, 835-844.

Chen F, Tholl D, Bohlmann J, Pichersky E. 2011. The family of terpene synthases in plants: a mid-size family of genes for specialized metabolism that is highly diversified throughout the kingdom. *The Plant Journal* 66, 212-229.

Chiu, W. et al. 1996. Engineered GFP as a vital reporter in plants. *Current Biology* 6:325-330.

Christensen, A. H. and Quail, P. H. 1989. Sequence analysis and transcriptional regulation by heat shock of polyubiquitin transcripts from maize. *Plant Mol Biol* 12:619-632.

Christensen, A. H. et al. 1992. Maize polyubiquitin genes: structure, thermal perturbation of expression and transcript splicing, and promoter activity following transfer to protoplasts by electroporation. *Plant Mol Biol* 18:675-689.

Cordoba E, Porta H, Arroyo A, San Roman C, Medina L, Rodriguez-Concepcion M, Leon P. 2011. Functional characterization of the three genes encoding 1-deoxy-D-xylulose 5-phosphate synthase in maize. *Journal of Experimental Botany* 62, 2023-2038.

Degenhardt J, Köllner T G, Gershenzon J. 2009. Monoterpene and sesquiterpene synthases and the origin of terpene skeletal diversity in plants. *Phytochemistry* 70, 1621-1637.

De Wet, J. R. et al. 1987. Firefly luciferase gene: structure and expression in mammalian cells. *Mol Cell Biol* 7:725-737.

Dudareva N, Cseke L, Blanc V M, Pichersky E. 1996. Evolution of floral scent in *Clarkia*: novel patterns of S-linalool synthase gene expression in the *C. breweri* flower. The *Plant Cell* 8, 1137-1148.

Dudareva N, Murfitt L M, Mann C J, Gorenstein N, Kolosova N, Kish C M, Bonham C, Wood K. 2000. Developmental regulation of methyl benzoate biosynthesis and emission in snapdragon flowers. *The Plant Cell* 12, 949-961.\

Dudareva N, Martin D, Kish C M, Kolosova N, Gorenstein N, Faldt J, Miller B, Bohlmann J. 2003. (E)-β-Ocimene and myrcene synthase genes of floral scent biosynthesis in snapdragon: function and expression of three terpene synthase genes of a new terpene synthase subfamily. *The Plant Cell* 15, 1227-1241.

Dudareva N, Klempien A, Muhlemann J K, Kaplan I. 2013. Biosynthesis, function and metabolic engineering of plant volatile organic compounds. *New Phytologist* 198, 16-32.

Falara V, Akhtar T A, Nguyen T T, et al. 2011. The tomato terpene synthase gene family. *Plant Physiology* 157, 770-789.

Fuentes, A. et al. 2006. Intron-hairpin RNA derived from replication associated protein C1 gene confers immunity to tomato yellow leaf curl virus infection in transgenic tomato plants. *Transgenic Res* 15:291-304.

Gaydou E M, Randriamiharisoa R, Bianchini J P. 1986. Composition of the essential oil of Ylang-Ylang (*Cananga odorata* Hook Fil. et Thomson forma genuina) from Madagascar. *Journal of Agricultural and Food Chemistry* 34, 481-487.

Goff, S. A. et al. 1990. Transactivation of anthocyanin biosynthetic genes following transfer of B regulatory genes into maize tissues. *EMBO J* 9:2517-2522.

Grabherr M G, Haas B J, Yassour M, et al. 2011. Full-length transcriptome assembly from RNA-Seq data without a reference genome. *Nature Biotechnology* 29, 644-652.

Guo, H. S. et al. 2003. A chemical-regulated inducible RNAi system in plants. *Plant J* 34:383-392.

Harju A T, Pennanen S M, Liesivuori J. 2004. The efficacy of benzyl benzoate sprays in killing the storage mite Tyrophagus putrescentiae (Acari: Acaridae). *Annals of Agricultural and Environmental Medicine* 11, 115-119.

Hoballah M E, Stuurman J, Turlings T C, Guerin P M, Connëtable S, Kuhlemeier C. 2005. The composition and timing of flower odour emission by wild *Petunia axillaris* coincide with the antennal perception and nocturnal activity of the pollinator Manduca sexta. *Planta* 222, 141-150.

Huber F K, Kaiser R, Sauter W, Schiestl F P. 2005. Floral scent emission and pollinator attraction in two species of Gymnadenia (Orchidaceae). *Oecologia* 142, 564-575.

Iijima Y, Gang D R, Fridman E, Lewinsohn E, Pichersky E. 2004. Characterization of geraniol synthase from the peltate glands of sweet basil. *Plant Physiology* 134, 370-379.

Jang I C, Yang J Y, Seo H S, Chua N H. 2005. HFR1 is targeted by COP1 E3 ligase for post-translational proteolysis during phytochrome A signalling. *Genes and Development* 19, 593-602.

Jefferson R A, Kavanagh T A, Bevan M W. 1987. GUS fusion: β-glucuronidase as a sensitive and versatile gene fusion marker in higher plants. *EMBO J* 6, 3901-39.

Jin J, Panicker D, Wang Q, Kim M J, Liu J, Yin J-L, Wong L, Jang I C, Chua N H, Sarojam R. 2014. Next generation sequencing unravels the biosynthetic ability of Spearmint (*Mentha spicata*) peltate glandular trichomes through comparative transcriptomics. *BMC genomics* 14, 292

Jones C G, Moniodis J, Zulak K G, Scaffidi A, Plummer J A, Ghisalberti E L, Barbour E L, Bohlmann J. 2011. Sandalwood fragrance biosynthesis involves sesquiterpene synthases of both the terpene synthase (TPS)-a and TPS-b subfamilies, including santalene synthases. *Journal of Biological Chemistry* 286, 17445-17454.

Kain, S. R. et al. 1995. Green fluorescent protein as a reporter of gene expression and protein localization. *Biotechniques* 19:650-655.

Kessler A, Baldwin I T. 2001. Defensive function of herbivore-induced plant volatile emissions in nature. *Science* 291, 2104-2105.

Knudsen J T, Tollsten L, Bergström L G. 1993. Floral scents—a checklist of volatile compounds isolated by head-space techniques. *Phytochemistry* 33, 253-280.

Knudsen J T, Eriksson R, Gershenzon J, Stahl B. 2006. Diversity and distribution of floral scent. *The Botanical Review* 72, 1-120.

Kramer W, Fritz H J. 1987. Oligonucleotide-directed construction of mutations via gapped duplex DNA. *Methods Enzymology* 154, 350-367.

Landmann C, Fink B, Festner M, Dregus M, Engel K H, Schwab W. 2007. Cloning and functional characterization of three terpene synthases from lavender (*Lavandula angustifolia*). *Archives of Biochemistry and Biophysics* 465, 417-429.

Last, D. I. et al. 1991. pEmu: an improved promoter for gene expression in cereal cells. *Theor Appl Genet* 81:581-588.

Lee S, Chappell J. 2008. Biochemical and genomic characterization of terpene synthases in *Magnolia grandiflora*. *Plant Physiology*. 147, 1017-1033.

Lopez-Gallego F, Waerzyn G T, Schmidt-Dannert C. 2010. Selectivity of fungal seaquiterpene synthases: Role of the active site's H-1α Loop in Catalysis. *Applied Environmental Microbiology* 76, 7723-7733.

Martin D M, Fäldt J, Bohlmann J. 2004. Functional characterization of nine Norway Spruce TPS genes and evolution of gymnosperm terpene synthases of the TPS-d subfamily. *Plant Physiology* 135, 1908-1927.

Martin D M, Aubourg S, Schouwey M B, Daviet L, Schalk M, Toub O, Lund S T, Bohlmann, J. 2010. Functional annotation, genome organization and phylogeny of the grapevine (*Vitis vinifera*) terpene synthase gene family based on genome assembly, FLcDNA cloning, and enzyme assays. *BMC Plant Biology* 10, 226.

McElroy, D. et al. 1990. Isolation of an efficient actin promoter for use in rice transformation. *Plant Cell* 2:163-171.

McGarvey D J, Croteau R. 1995. Terpenoid metabolism. *The Plant Cell* 7, 1015-1026.

Mercke P, Crock J, Croteau R, Brodelius P E. 1999. Cloning expression, and characterization of epi-cedrol synthase, a sesquiterpene cyclase from *Artemisia annua* L. *Archives of Biochemistry and Biophysics* 369, 213-222.

Muhlemann J K, Klempien A, Dudareva N. 2014. Floral volatiles: from biosynthesis to function. *Plant, Cell & Environment* 37, 1936-1949.

Munck S L, Croteau R. 1990. Purification and characterization of the sesquiterpene cyclase patchoulol synthase from *Pogostemon cablin*. *Archives of Biochemistry and Biophysics* 282, 58-64.

Mysara, M. et al. 2011. MysiRNA-designer: a workflow for efficient siRNA design. *PLOS one* 6(10):e25642.

Nieuwenhuizen N J, Wang M Y, Matich A J, Green S A, Chen X, Yauk Y K, Beuning L L, Nagegowda D A, Dudareva N, Atkinson R G. 2009. Two terpene synthases are responsible for the major sesquiterpenes emitted from the flowers of kiwifruit (*Actinidia deliciosa*). *Journal of Experimental Botany* 60, 3203-3219.

Nishida R., Shelly T E, Whittier T S, Kaneshiro K Y. 2000. α-Copaene, A Potential Rendezvous Cue for the Mediterranean Fruit Fly, *Ceratitis Capitata*? *Journal of Chemical Ecology* 26, 87-100.

Odell, J. T. et al. 1985. Identification of DNA sequences required for activity of the cauliflower mosaic virus 35S promoter. *Nature* 313:810-812.

Orlova I, Marshall-Colon A, Schnepp J, et al. 2006. Reduction of benzenoid synthesis in petunia flowers reveals multiple pathways to benzoic acid and enhancement in auxin transport. *The Plant Cell* 18, 3458-3475.

Quevillon E, Silventoinen V, Pillai S, Harte N, Mulder N, Apweiler R, Lopez R. 2005. InterProScan: protein domains identifier. *Nucleic Acids Research* 33, W116-W120.

Phillips M A, Walter M H, Ralph S G, et al. 2007. Functional identification and differential expression of 1-deoxy-D-xylulose 5-phosphate synthase in induced terpenoid resin formation of Norway spruce (*Picea abies*). *Plant Molecular Biology* 65, 243-257.

Samakradhamrongthai R, Utama-Ang M, Thakeow P. 2009. Identification of volatile compounds released from dry scented Thai flowers and their potential application in flower-mixed tea. *Asian Journal of Food and Agro-Industry* 2, 525-534.

Simkin A J, Miettinen K, Claudel P, et al. 2013. Characterization of the plastidial geraniol synthase from Madagascar periwinkle which initiates the monoterpenoid branch of the alkaloid pathway in internal phloem associated parenchyma. *Phytochemistry* 85, 36-43.

Song A A, Abdullah J O, Abdullah M P, Shafee N, Othman R, Tan E F, Noor N M, Raha A R. 2012. Overexpressing 3-hydroxy-3-methylglutaryl coenzyme A reductase (HMGR) in the lactococcal mevalonate pathway for heterologous plant sesquiterpene production. *PLOS ONE* 7, e52444.

Steele C L, Crock J, Bohlmann J, Croteau R. 1998. Sesquiterpene synthases from grand fir (*Abies grandis*): Comparison of constitutive and wound-induced activities, and cDNA isolation, characterization, and bacterial expression of 5-selinene synthase and γ-humulene synthase. *Journal of Biological Chemistry* 273, 2078-2089.

Tamura K, Peterson D, Peterson N, Stecher G, Nei M, Kumar S. 2011. MEGA5: molecular evolutionary genetics analysis using maximum likelihood, evolutionary distance, and maximum parsimony methods. *Molecular Biology and Evolution* 28, 2731-2739.

Vanderschuren, H. et al. 2007a. Transgenic cassava resistance to African cassava mosaic virus is enhanced by viral DNA-A bidirectional promoter-derived siRNAs. *Plant Mol Biol* 64:549-557.

Vanderschuren, H. et al. 2007b. Engineering resistance to geminiviruses—review and perspectives. *Plant Biotechnology Journal* 5:207-220.

Vogt T. 2010. Phenylpropanoid biosynthesis. *Molecular Plant* 3, 2-20.

Velten, J. et al. 1984. Isolation of a dual plant promoter fragment from the Ti plasmid of *Agrobacterium tumefaciens*. *EMBO J* 3:2723-2730.

Voinnet O, Rivas S, Mestre P, Baulcombe D. 2003. An enhanced transient expression system in plants based on suppression of gene silencing by the p19 protein of tomato bushy stunt virus. *The Plant Journal* 9, 949-956.

Walter M, Hans J, Strack D. 2002. Two distantly-related genes encoding 1-deoxy-D-xylulose 5-phosphate synthases: differential regulation in shoots and apocarotenoid-accumulating mycorrhizal roots. *The Plant Journal* 31, 243-254.

Wang, M. B. et al. 2000. A single copy of a virus-derived transgene encoding hairpin RNA gives immunity to barley yellow dwarf virus. *Mol Plant Pathol* 1:347-356.

Wesley, S. V. et al. 2001. Construct design for efficient, effective and high-throughput gene silencing in plants. *Plant J* 27:581-590.

Yan, P. et al. 2012. High-throughput construction of intron-containing hairpin RNA vectors for RNAi in plants. *PLOS one* 7(5):e38186.

Yuan J S, Köllner T G, Wiggins G, Grant J, Degenhardt J, Chen F. 2008. Molecular and genomic basis of volatile-mediated indirect defense against insects in rice. *The Plant Journal* 55, 491-503.

Zhang X, Garreton V, Chua N H. 2005. The AIP2 E3 ligase acts as a novel negative regulator of ABA signaling by promoting ABI3 degradation. *Genes and Development* 19, 1532-1543.

Zrachya, A. et al. 2007. Production of siRNA targeted against TYLCV coat protein transcripts leads to silencing of its expression and resistance to the virus. *Transgenic Res* 16:385-398.

What is claimed is:

1. A cDNA encoding a *Cananga odorata* terpene synthase 2 protein (CoTPS2 protein) having the amino acid sequence set forth in SEQ ID NO:10 or a modified CoTPS2 protein, wherein the modified CoTPS2 protein has the amino acid sequence set forth in SEQ ID NO:10 with 1-10 conservative amino acid substitutions, wherein the modified CoTPS2 protein has the motifs R(R)X$_8$W SEQ ID NO:1), DDXXD (SEQ ID NO:2) and NSE/DTE (SEQ ID NO:3/SEQ ID NO:4) and wherein the modified CoTPS2 protein has terpene synthase activity.

2. The cDNA of claim 1, wherein the modified CoTPS2 protein has 1-6 conservative amino acid substitutions.

3. The cDNA of claim 1, wherein the cDNA has the nucleotide sequence set forth in SEQ ID NO:9.

4. A nucleic construct comprising the cDNA of claim 1 operably linked to a plant operable promoter.

5. An expression vector comprising the cDNA of claim 1.

6. A transgenic plant cell, plant or plant seed comprising cDNA of claim 1 stably integrated into its genome.

7. The transgenic plant cell, plant or plant seed of claim 6, wherein the plant is a member of the *Cananga* genus.

8. The transgenic plant cell, plant or plant seed of claim 7, wherein the plant is a ylang ylang (*Cananga odorata*) plant.

9. A method for producing a transgenic plant which comprises introducing the cDNA of claim 1 or an expression vector comprising the cDNA into a plant, wherein the transgenic plant has the cDNA stably integrated in its genome.

10. A method for producing a transgenic plant which comprises transfecting the cDNA of claim 1 or an expression vector comprising the cDNA into a plant cell or plant cells and regenerating a transgenic plant from the transfected plant cell or transfected plant cells, wherein the transgenic plant has the cDNA stably integrated in its genome.

11. The method of claim 9, wherein the plant is a member of the *Cananga* genus.

12. The method of claim 11, wherein the transgenic plant is a ylang ylang (*Cananga odorata*) plant.

13. A method of synthesizing at least one terpene or sesquiterpene in a plant which comprises introducing the cDNA of claim 1 or an expression vector comprising the cDNA into a plant, wherein the cDNA is expressed in the plant thereby synthesizing the at least one terpene or sesquiterpene.

14. A method of synthesizing at least one terpene or sesquiterpene in a plant comprising transfecting the cDNA of claim 1 or an expression vector comprising the cDNA into a plant cell or plant cells and growing a plant from the transfected plant cell or transfected plant cells, wherein the cDNA is expressed in the plant thereby synthesizing the at least one terpene or sesquiterpene.

15. The method of claim 13, wherein the at least one sesquiterpene is β-ylangene, β-copaene or β-cubebene.

16. The method of claim 13, wherein the plant is a member of the *Cananga* genus.

17. The method of claim 16, wherein the transgenic plant is a ylang ylang (*Canangga odorata*) plant.

18. The method of claim 13, wherein the cDNA is overexpressed.

19. A method of producing at least one terpene or sesquiterpene in a yeast cell, the method comprising exogenously expressing within the yeast cell the cDNA of claim 1, thereby producing the at least one sesquiterpene in the yeast cell.

20. The method of claim 19, wherein the at least one sesquiterpene is β-ylangene, β-copaene or β-cubebene.

21. The cDNA of claim 1, wherein the modified CoTPS2 protein has 1 or 2 conservative amino acid substitutions.

22. An expression vector comprising the nucleic acid construct of claim 4.

* * * * *